United States Patent
Jung et al.

(10) Patent No.: US 10,393,748 B2
(45) Date of Patent: Aug. 27, 2019

(54) METHOD FOR PREDICTING EFFICACY OF C-MET INHIBITOR

(71) Applicant: Samsung Electronics Co., Ltd., Suwon-si, Gyeonggi-do (KR)

(72) Inventors: Soo Yeon Jung, Seongnam-si (KR); Seon Hui Shim, Daejeon (KR); Yun Jeong Song, Seongnam-si (KR); Hyeon-seok Yoo, Gangwon-do (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 14/591,787

(22) Filed: Jan. 7, 2015

(65) Prior Publication Data

US 2015/0192588 A1    Jul. 9, 2015

(30) Foreign Application Priority Data

Jan. 7, 2014    (KR) ........................ 10-2014-0001799
Jan. 6, 2015    (KR) ........................ 10-2015-0000956

(51) Int. Cl.
| | |
|---|---|
| G01N 33/50 | (2006.01) |
| G01N 33/574 | (2006.01) |
| C07K 16/40 | (2006.01) |
| C12Q 1/6886 | (2018.01) |
| A61K 39/00 | (2006.01) |

(52) U.S. Cl.
CPC ....... *G01N 33/57488* (2013.01); *C07K 16/40* (2013.01); *C12Q 1/6886* (2013.01); *G01N 33/57419* (2013.01); *G01N 33/57423* (2013.01); *G01N 33/57446* (2013.01); *A61K 2039/505* (2013.01); *C07K 2317/24* (2013.01); *C07K 2317/53* (2013.01); *C07K 2317/565* (2013.01); *C07K 2317/622* (2013.01); *C07K 2317/76* (2013.01); *C12Q 2600/106* (2013.01); *C12Q 2600/158* (2013.01); *G01N 2333/495* (2013.01); *G01N 2333/5421* (2013.01); *G01N 2333/99* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 8,129,114 B2 | 3/2012 | Ford et al. | |
| 8,133,686 B2 | 3/2012 | Teh et al. | |
| 8,563,696 B2 | 10/2013 | Cheong et al. | |
| 9,394,367 B2 | 7/2016 | Cheong et al. | |
| 2006/0150260 A1 | 7/2006 | Levenson et al. | |
| 2009/0004687 A1 | 1/2009 | Mansfield et al. | |
| 2009/0075267 A1 | 3/2009 | Siena et al. | |
| 2009/0150315 A1 | 6/2009 | Wirtz et al. | |
| 2009/0305277 A1 | 12/2009 | Baker et al. | |
| 2011/0104176 A1* | 5/2011 | Cheong ............. C07K 16/2863 424/152.1 |
| 2011/0151470 A1 | 6/2011 | Connors | |
| 2011/0217309 A1 | 9/2011 | Buck et al. | |
| 2011/0262436 A1 | 10/2011 | Bender et al. | |
| 2012/0089541 A1 | 4/2012 | Patel et al. | |
| 2012/0288862 A1 | 11/2012 | Xu et al. | |
| 2012/0295258 A1 | 11/2012 | Hoon | |
| 2013/0089557 A1 | 4/2013 | Cheong et al. | |

FOREIGN PATENT DOCUMENTS

| | | |
|---|---|---|
| JP | 2010-178651 A | 8/2010 |
| KR | 2011-0047698 A | 5/2011 |
| KR | 2011-0110247 A | 10/2011 |
| KR | 2012-0056939 A | 6/2012 |
| WO | 2010/077722 A1 | 7/2010 |

OTHER PUBLICATIONS

Zhou et al. Sensitivity of selected human tumor models to PF-04217903, a novel selective c-Met kinase inhibitor. Mol Cancer Ther. Apr. 2012;11(4):1036-47.*
Brand et al. KRAS mutant colorectal tumors. Small GTPases. Jan. 1, 2012; 3(1): 34-39.*
Ma, Chaoyu et al., "Extracellular matrix protein bIG-H3/TGFBI promotes metastasis of colon cancer by enhancing cell extravasation," *Genes & Development*, 22:308-321 (2008).
European Search Report for EP Patent No. 15150360.4 dated May 28, 2015.
Scagliotti, Giorgio V. et al., "The emerging role of MET/HGF inhibitors in oncology," *Cancer Treatment Reviews*, vol. 39, No. 7, 793-801 (2013).
Torti, Davide et al., "A preclinical algorithm of soluble surrogate biomarkers that correlate with therapeutic inhibition of the MET oncogene in gastric tumors," *Int. J. Cancer*, 130, No. 6, 1357-1366 (2012).
Klotz Monika, et al., "Preclinical evaluation of biomarkers for response monitoring to the MET inhibitor BAY-853474," *Biomarkers*, vol. 17, No. 4, 325-335 (2012) (abstract only; abstr. No. XP 002739624).
European Patent Office Action for Application No. 15 150 360.4 dated Jul. 5. 2016 (4 pages).
European Search Report for Application No. 15 150 360.4 dated Sep. 15, 2015 (13 pages).

(Continued)

*Primary Examiner* — Dong Jiang
(74) *Attorney, Agent, or Firm* — Leydig, Voit & Mayer, Ltd.

(57) ABSTRACT

A biomarker for predicting and/or monitoring the efficacy of a c-Met inhibitor; a composition for predicting and/or monitoring the efficacy of a c-Met inhibitor, comprising a material detecting the biomarker; a composition for selecting a subject suitable for the application of a c-Met inhibitor, comprising a material detecting the biomarker; a method for predicting and/or monitoring the efficacy of a c-Met inhibitor using the biomarker; a method for selecting a subject suitable for the application of a c-Met inhibitor using the biomarker; and a method for preventing and/or treating cancer comprising administering a c-Met inhibitor to the selected subject.

6 Claims, 27 Drawing Sheets

Specification includes a Sequence Listing.

(56) References Cited

OTHER PUBLICATIONS

Torti, D., et al., "204 Identification and pre-clinical validation of surrogate soluble biomarkers correlating with therapeutic response to met inhibition," *European Journal of Cancer Supplement*, vol. 8, No. 5, pp. 53 (2010).
Japanese Office Action in 2015-001880 dated Feb. 6, 2018 (with English Translation).
Hurwitz et al., "The Clinical Benefit of Bevacizumab in Metastatic Colorectal Cancer Is Independent of K-ras Mutation Status: Analysis of a Phase III Study of Bevacizumab with Chemotherapy in Previously Untreated Metastatic Colorectal Cancer", *The Oncologist*, 14:22-28 (2009).
Ma et al., "Extracellular matrix protein ßig-h3/TGFBI promotes metastasis of colon cancer by enhancing cell extravasation", *Genes & Development*, 22: 308-321 (2008).

* cited by examiner

FIG. 3
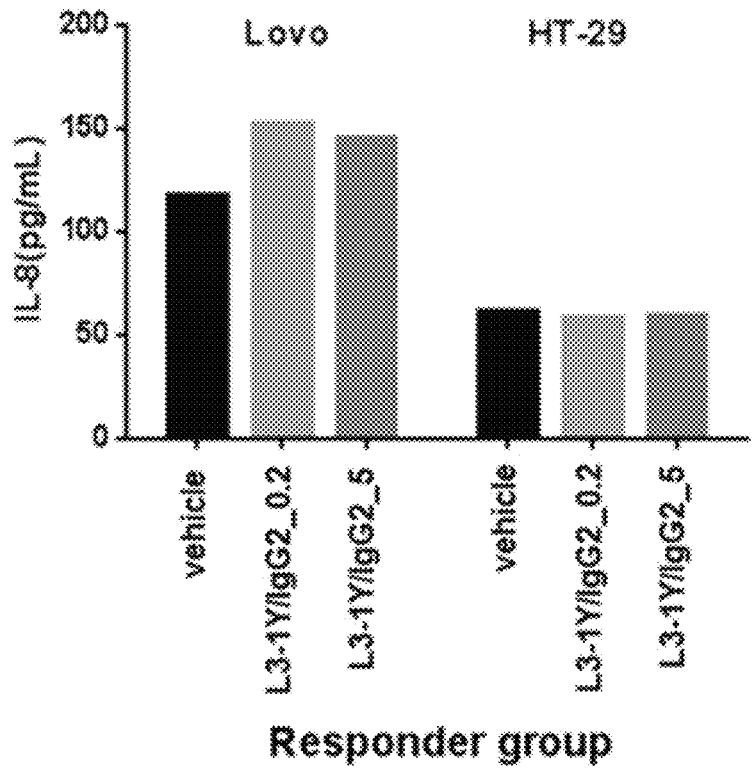
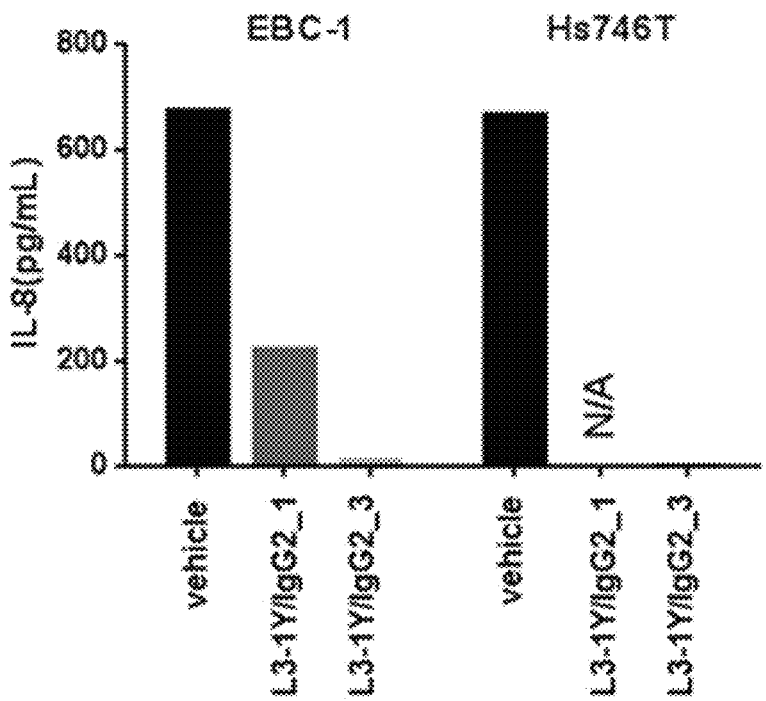

IL-8 CBA EBC-1

FIG. 15
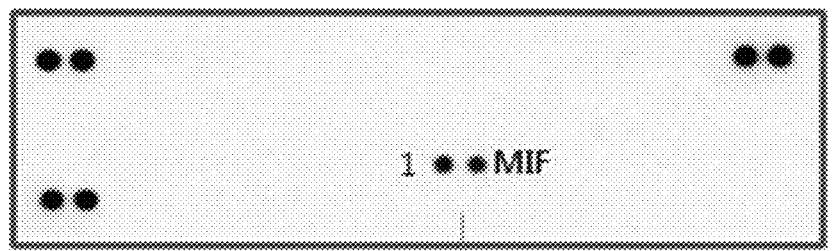
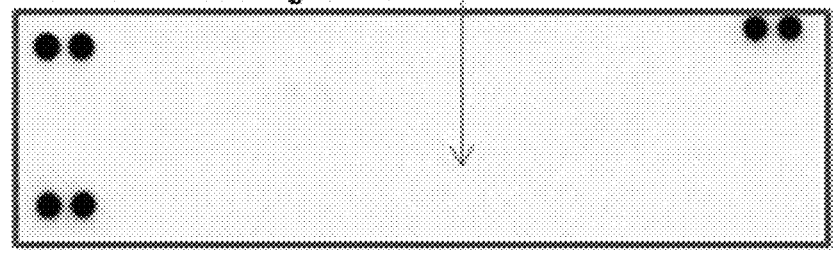

FIG. 19
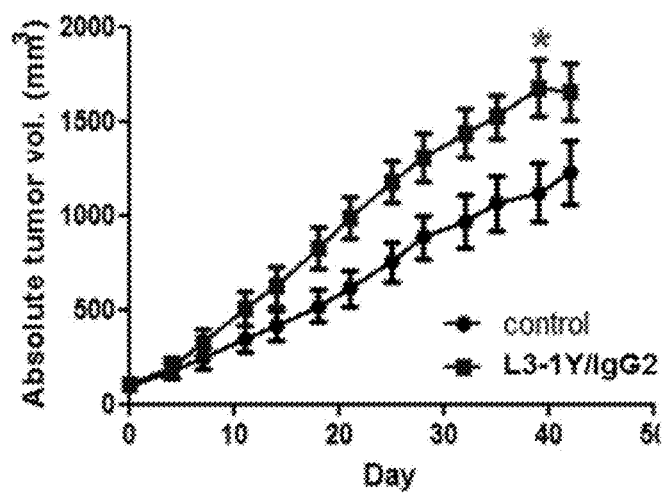
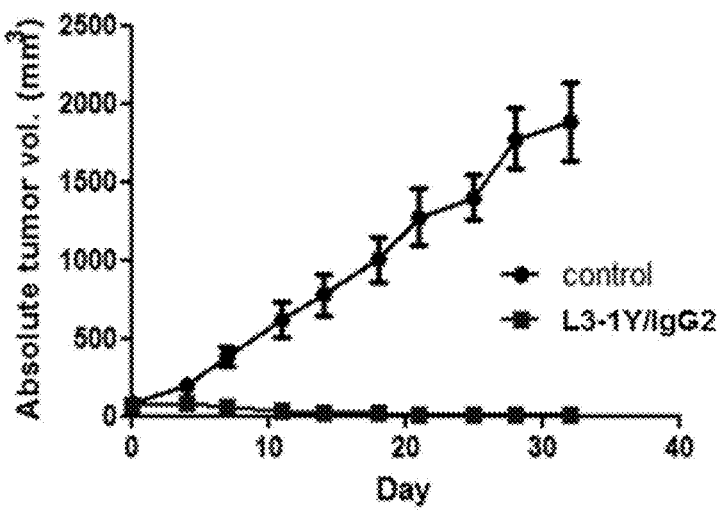

```
                         SEQUENCE LISTING

<160> NUMBER OF SEQ ID NOS: 115

<210> SEQ ID NO 1
<211> LENGTH: 5
<212> TYPE: PRT
<213> ORGANISM: Artificial Sequence
<220> FEATURE:
<223> OTHER INFORMATION: Synthetic heavy chain CDR1 of AbF46

<400> SEQUENCE: 1

Asp Tyr Tyr Met Ser
 1               5

<210> SEQ ID NO 2
<211> LENGTH: 19
<212> TYPE: PRT
<213> ORGANISM: Artificial Sequence
<220> FEATURE:
<223> OTHER INFORMATION: Synthetic heavy chain CDR2 of AbF46

<400> SEQUENCE: 2

Phe Ile Arg Asn Lys Ala Asn Gly Tyr Thr Thr Glu Tyr Ser Ala Ser
 1               5                  10                  15

Val Lys Gly

<210> SEQ ID NO 3
<211> LENGTH: 6
<212> TYPE: PRT
<213> ORGANISM: Artificial Sequence
<220> FEATURE:
<223> OTHER INFORMATION: Synthetic heavy chain CDR3 of AbF46

<400> SEQUENCE: 3

Asp Asn Trp Phe Ala Tyr
 1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic heavy chain CDR1 of c-Met antibody
<220> FEATURE:
<221> NAME/KEY: MOD_RES
<222> LOCATION: (1)
<223> OTHER INFORMATION: Xaa is Pro or Ser or absent
<220> FEATURE:
<221> NAME/KEY: MOD_RES
<222> LOCATION: (2)
<223> OTHER INFORMATION: Xaa is Glu or Asp

<400> SEQUENCE: 4

Xaa Xaa Tyr Tyr Met Ser
 1               5

<210> SEQ ID NO 5
<211> LENGTH: 8
```

```
<212> TYPE: PRT
<213> ORGANISM: Artificial Sequence
<220> FEATURE:
<223> OTHER INFORMATION: Synthetic heavy chain CDR2 of c-Met antibody
<220> FEATURE:
<221> NAME/KEY: MOD_RES
<222> LOCATION: (3)
<223> OTHER INFORMATION: Xaa is Asn or Lys
<220> FEATURE:
<221> NAME/KEY: MOD_RES
<222> LOCATION: (4)
<223> OTHER INFORMATION: Xaa is Ala or Val
<220> FEATURE:
<221> NAME/KEY: MOD_RES
<222> LOCATION: (7)
<223> OTHER INFORMATION: Xaa is Asn or Thr

<400> SEQUENCE: 5

Arg Asn Xaa Xaa Asn Gly Xaa Thr
 1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic heavy chain CDR3 of c-Met antibody
<220> FEATURE:
<221> NAME/KEY: MOD_RES
<222> LOCATION: (5)
<223> OTHER INFORMATION: Xaa is Ser or Thr

<400> SEQUENCE: 6

Asp Asn Trp Leu Xaa Tyr
 1               5

<210> SEQ ID NO 7
<211> LENGTH: 17
<212> TYPE: PRT
<213> ORGANISM: Artificial Sequence
<220> FEATURE:
<223> OTHER INFORMATION: Synthetic light chain CDR1 of c-Met antibody
<220> FEATURE:
<221> NAME/KEY: MOD_RES
<222> LOCATION: (4)
<223> OTHER INFORMATION: Xaa is His, Arg, Gln or Lys
<220> FEATURE:
<221> NAME/KEY: MOD_RES
<222> LOCATION: (9)
<223> OTHER INFORMATION: Xaa is Ser or Trp
<220> FEATURE:
<221> NAME/KEY: MOD_RES
<222> LOCATION: (12)
<223> OTHER INFORMATION: Xaa is His or Gln
<220> FEATURE:
<221> NAME/KEY: MOD_RES
<222> LOCATION: (13)
<223> OTHER INFORMATION: Xaa is Lys or Asn

<400> SEQUENCE: 7

Lys Ser Ser Xaa Ser Leu Leu Ala Xaa Gly Asn Xaa Xaa Asn Tyr Leu
 1               5                  10                  15

Ala

<210> SEQ ID NO 8
<211> LENGTH: 7
<212> TYPE: PRT
<213> ORGANISM: Artificial Sequence
<220> FEATURE:
<223> OTHER INFORMATION: Synthetic light chain CDR2 of c-Met antibody
<220> FEATURE:
<221> NAME/KEY: MOD_RES
```

```
<222> LOCATION: (2)
<223> OTHER INFORMATION: Xaa is Ala or Gly
<220> FEATURE:
<221> NAME/KEY: MOD_RES
<222> LOCATION: (4)
<223> OTHER INFORMATION: Xaa is Thr or Lys
<220> FEATURE:
<221> NAME/KEY: MOD_RES
<222> LOCATION: (7)
<223> OTHER INFORMATION: Xaa is Ser or Pro

<400> SEQUENCE: 8

Trp Xaa Ser Xaa Arg Val Xaa
  1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic light chain CDR3 of c-Met antibody
<220> FEATURE:
<221> NAME/KEY: MOD_RES
<222> LOCATION: (1)
<223> OTHER INFORMATION: Xaa is Gly, Ala or Gln
<220> FEATURE:
<221> NAME/KEY: MOD_RES
<222> LOCATION: (6)
<223> OTHER INFORMATION: Xaa is Arg, His, Ser, Ala, Gly or Lys
<220> FEATURE:
<221> NAME/KEY: MOD_RES
<222> LOCATION: (8)
<223> OTHER INFORMATION: Xaa is Leu, Tyr, Phe or Met

<400> SEQUENCE: 9

Xaa Gln Ser Tyr Ser Xaa Pro Xaa Thr
  1               5

<210> SEQ ID NO 10
<211> LENGTH: 17
<212> TYPE: PRT
<213> ORGANISM: Artificial Sequence
<220> FEATURE:
<223> OTHER INFORMATION: Synthetic light chain CDR1 of AbF46

<400> SEQUENCE: 10

Lys Ser Ser Gln Ser Leu Leu Ala Ser Gly Asn Gln Asn Asn Tyr Leu
  1               5                  10                  15

Ala

<210> SEQ ID NO 11
<211> LENGTH: 7
<212> TYPE: PRT
<213> ORGANISM: Artificial Sequence
<220> FEATURE:
<223> OTHER INFORMATION: Synthetic light chain CDR2 of AbF46

<400> SEQUENCE: 11

Trp Ala Ser Thr Arg Val Ser
  1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic light chain CDR3 of AbF46

<400> SEQUENCE: 12
```

Gln Gln Ser Tyr Ser Ala Pro Leu Thr
 1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic CDR-L3 derived from L3-1 clone

<400> SEQUENCE: 13

Gln Gln Ser Tyr Ser Arg Pro Tyr Thr
 1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic CDR-L3 derived from L3-2 clone

<400> SEQUENCE: 14

Gly Gln Ser Tyr Ser Arg Pro Leu Thr
 1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic CDR-L3 derived from L3-3 clone

<400> SEQUENCE: 15

Ala Gln Ser Tyr Ser His Pro Phe Ser
 1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic CDR-L3 derived from L3-5 clone

<400> SEQUENCE: 16

Gln Gln Ser Tyr Ser Arg Pro Phe Thr
 1               5

<210> SEQ ID NO 17
<211> LENGTH: 117
<212> TYPE: PRT
<213> ORGANISM: Artificial Sequence
<220> FEATURE:
<223> OTHER INFORMATION: Synthetic heavy chain variable region of anti
      c-Met humanized antibody(huAbF46-H4)

<400> SEQUENCE: 17

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Asp Tyr
                20                  25                  30

Tyr Met Ser Trp Val Arg Gln Ala Pro Gly Lys Gly Leu Glu Trp Leu
            35                  40                  45

Gly Phe Ile Arg Asn Lys Ala Asn Gly Tyr Thr Thr Glu Tyr Ser Ala
        50                  55                  60

Ser Val Lys Gly Arg Phe Thr Ile Ser Arg Asp Asn Ser Lys Asn Thr

```
                65                  70                  75                  80
Leu Tyr Leu Gln Met Asn Ser Leu Arg Ala Glu Asp Thr Ala Val Tyr
                    85                  90                  95

Tyr Cys Ala Arg Asp Asn Trp Phe Ala Tyr Trp Gly Gln Gly Thr Leu
                100                 105                 110

Val Thr Val Ser Ser
        115

<210> SEQ ID NO 18
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 18

Asp Ile Gln Met Thr Gln Ser Pro Ser Ser Leu Ser Ala Ser Val Gly
  1               5                  10                  15

Asp Arg Val Thr Ile Thr Cys Lys Ser Ser Gln Ser Leu Leu Ala Ser
                 20                  25                  30

Gly Asn Gln Asn Asn Tyr Leu Ala Trp His Gln Lys Pro Gly Lys
             35                  40                  45

Ala Pro Lys Met Leu Ile Ile Trp Ala Ser Thr Arg Val Ser Gly Val
         50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Ser Tyr Ser Arg Pro Tyr Thr Phe Gly Gln Gly Thr Lys Val Glu Ile
                100                 105                 110

Lys Arg

<210> SEQ ID NO 19
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 19

Asp Ile Gln Met Thr Gln Ser Pro Ser Ser Leu Ser Ala Ser Val Gly
  1               5                  10                  15

Asp Arg Val Thr Ile Thr Cys Lys Ser Ser Gln Ser Leu Leu Ala Ser
                 20                  25                  30

Gly Asn Gln Asn Asn Tyr Leu Ala Trp His Gln Lys Pro Gly Lys
             35                  40                  45

Ala Pro Lys Met Leu Ile Ile Trp Ala Ser Thr Arg Val Ser Gly Val
         50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gly Gln
                 85                  90                  95

Ser Tyr Ser Arg Pro Leu Thr Phe Gly Gln Gly Thr Lys Val Glu Ile
                100                 105                 110

Lys Arg
```

```
<210> SEQ ID NO 20
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 20

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
                20                  25                  30

Gly Asn Gln Asn Asn Tyr Leu Ala Trp His Gln Gln Lys Pro Gly Lys
            35                  40                  45

Ala Pro Lys Met Leu Ile Ile Trp Ala Ser Thr Arg Val Ser Gly Val
        50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Ala Gln
                85                  90                  95

Ser Tyr Ser His Pro Phe Ser Phe Gly Gln Gly Thr Lys Val Glu Ile
            100                 105                 110

Lys Arg

<210> SEQ ID NO 21
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 21

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
                20                  25                  30

Gly Asn Gln Asn Asn Tyr Leu Ala Trp His Gln Gln Lys Pro Gly Lys
            35                  40                  45

Ala Pro Lys Met Leu Ile Ile Trp Ala Ser Thr Arg Val Ser Gly Val
        50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                85                  90                  95

Ser Tyr Ser Arg Pro Phe Thr Phe Gly Gln Gly Thr Lys Val Glu Ile
            100                 105                 110

Lys Arg

<210> SEQ ID NO 22
<211> LENGTH: 6
<212> TYPE: PRT
<213> ORGANISM: Artificial Sequence
<220> FEATURE:
<223> OTHER INFORMATION: Synthetic CDR-H1 derived from H11-4 clone

<400> SEQUENCE: 22

Pro Glu Tyr Tyr Met Ser
```

<210> SEQ ID NO 23
<211> LENGTH: 6
<212> TYPE: PRT
<213> ORGANISM: Artificial Sequence
<220> FEATURE:
<223> OTHER INFORMATION: Synthetic CDR-H1 derived from YC151 clone

<400> SEQUENCE: 23

Pro Asp Tyr Tyr Met Ser
 1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic CDR-H1 derived from YC193 clone

<400> SEQUENCE: 24

Ser Asp Tyr Tyr Met Ser
 1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic CDR-H2 derived from YC244 clone

<400> SEQUENCE: 25

Arg Asn Asn Ala Asn Gly Asn Thr
 1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic CDR-H2 derived from YC321 clone

<400> SEQUENCE: 26

Arg Asn Lys Val Asn Gly Tyr Thr
 1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic CDR-H3 derived from YC354 clone

<400> SEQUENCE: 27

Asp Asn Trp Leu Ser Tyr
 1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic CDR-H3 derived from YC374 clone

<400> SEQUENCE: 28

Asp Asn Trp Leu Thr Tyr
 1               5

<210> SEQ ID NO 29
<211> LENGTH: 17
<212> TYPE: PRT
<213> ORGANISM: Artificial Sequence
<220> FEATURE:
<223> OTHER INFORMATION: Synthetic CDR-L1 derived from L1-1 clone

<400> SEQUENCE: 29

Lys Ser Ser His Ser Leu Leu Ala Ser Gly Asn Gln Asn Asn Tyr Leu
 1               5                  10                  15

Ala

<210> SEQ ID NO 30
<211> LENGTH: 17
<212> TYPE: PRT
<213> ORGANISM: Artificial Sequence
<220> FEATURE:
<223> OTHER INFORMATION: Synthetic CDR-L1 derived from L1-3 clone

<400> SEQUENCE: 30

Lys Ser Ser Arg Ser Leu Leu Ser Ser Gly Asn His Lys Asn Tyr Leu
 1               5                  10                  15

Ala

<210> SEQ ID NO 31
<211> LENGTH: 17
<212> TYPE: PRT
<213> ORGANISM: Artificial Sequence
<220> FEATURE:
<223> OTHER INFORMATION: Synthetic CDR-L1 derived from L1-4 clone

<400> SEQUENCE: 31

Lys Ser Ser Lys Ser Leu Leu Ala Ser Gly Asn Gln Asn Asn Tyr Leu
 1               5                  10                  15

Ala

<210> SEQ ID NO 32
<211> LENGTH: 17
<212> TYPE: PRT
<213> ORGANISM: Artificial Sequence
<220> FEATURE:
<223> OTHER INFORMATION: Synthetic CDR-L1 derived from L1-12 clone

<400> SEQUENCE: 32

Lys Ser Ser Arg Ser Leu Leu Ala Ser Gly Asn Gln Asn Asn Tyr Leu
 1               5                  10                  15

Ala

<210> SEQ ID NO 33
<211> LENGTH: 17
<212> TYPE: PRT
<213> ORGANISM: Artificial Sequence
<220> FEATURE:
<223> OTHER INFORMATION: Synthetic CDR-L1 derived from L1-22 clone

<400> SEQUENCE: 33

Lys Ser Ser His Ser Leu Leu Ala Ser Gly Asn Gln Asn Asn Tyr Leu
 1               5                  10                  15

Ala

<210> SEQ ID NO 34
<211> LENGTH: 7

```
<212> TYPE: PRT
<213> ORGANISM: Artificial Sequence
<220> FEATURE:
<223> OTHER INFORMATION: Synthetic CDR-L2 derived from L2-9 clone

<400> SEQUENCE: 34

Trp Ala Ser Lys Arg Val Ser
 1               5

<210> SEQ ID NO 35
<211> LENGTH: 7
<212> TYPE: PRT
<213> ORGANISM: Artificial Sequence
<220> FEATURE:
<223> OTHER INFORMATION: Synthetic CDR-L2 derived from L2-12 clone

<400> SEQUENCE: 35

Trp Gly Ser Thr Arg Val Ser
 1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic CDR-L2 derived from L2-16 clone

<400> SEQUENCE: 36

Trp Gly Ser Thr Arg Val Pro
 1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic CDR-L3 derived from L3-32 clone

<400> SEQUENCE: 37

Gln Gln Ser Tyr Ser Lys Pro Phe Thr
 1               5

<210> SEQ ID NO 38
<211> LENGTH: 1416
<212> TYPE: DNA
<213> ORGANISM: Artificial Sequence
<220> FEATURE:
<223> OTHER INFORMATION: Synthetic nucleotide sequence of heavy chain
      of chAbF46
<220> FEATURE:
<221> NAME/KEY: misc_feature
<222> LOCATION: (1)..(6)
<223> OTHER INFORMATION: EcoRI restriction site
<220> FEATURE:
<221> NAME/KEY: misc_feature
<222> LOCATION: (7)..(66)
<223> OTHER INFORMATION: signal sequence
<220> FEATURE:
<221> NAME/KEY: misc_feature
<222> LOCATION: (67)..(417)
<223> OTHER INFORMATION: VH - heavy chain variable region
<220> FEATURE:
<221> NAME/KEY: misc_feature
<222> LOCATION: (418)..(423)
<223> OTHER INFORMATION: NdeI restriction site
<220> FEATURE:
<221> NAME/KEY: misc_feature
<222> LOCATION: (418)..(1407)
<223> OTHER INFORMATION: CH - heavy chain constant region
<220> FEATURE:
<221> NAME/KEY: misc_feature
```

<222> LOCATION: (1408)..(1410)
<223> OTHER INFORMATION: TGA - stop codon
<220> FEATURE:
<221> NAME/KEY: misc_feature
<222> LOCATION: (1411)..(1416)
<223> OTHER INFORMATION: XhoI restriction site

<400> SEQUENCE: 38

```
gaattcgccg ccaccatgga atggagctgg gttttctcg taacactttt aaatggtatc      60
cagtgtgagg tgaagctggt ggagtctgga ggaggcttgg tacagcctgg gggttctctg    120
agactctcct gtgcaacttc tgggttcacc ttcactgatt actacatgag ctgggtccgc    180
cagcctccag aaaggcact tgagtggttg gtttttatta aaacaaagc taatggttac     240
acaacagagt acagtgcatc tgtgaagggt cggttcacca tctccagaga taattcccaa    300
agcatcctct atcttcaaat ggacaccctg agagctgagg acagtgccac ttattactgt    360
gcaagagata actggtttgc ttactgggc caagggactc tggtcactgt ctctgcagct    420
agcaccaagg gcccatcggt cttcccctg cacctcct ccaagagcac ctctggggc      480
acagcggccc tgggctgcct ggtcaaggac tacttcccg aaccggtgac ggtgtcgtgg    540
aactcaggcg ccctgaccag cggcgtgcac accttcccgg ctgtcctaca gtcctcagga    600
ctctactccc tcagcagcgt ggtgaccgtg ccctccagca gcttgggcac ccagacctac    660
atctgcaacg tgaatcacaa gcccagcaac accaaggtgg acaagaaagt tgagcccaaa    720
tcttgtgaca aaactcacac atgcccaccg tgcccagcac ctgaactcct ggggggaccg    780
tcagtcttcc tcttcccccc aaaacccaag gacaccctca tgatctcccg gacccctgag    840
gtcacatgcg tggtggtgga cgtgagccac gaagaccctg aggtcaagtt caactggtac    900
gtggacggcg tggaggtgca taatgccaag acaaagccgc gggaggagca gtacaacagc    960
acgtaccgtg tggtcagcgt cctcaccgtc ctgcaccagg actggctgaa tggcaaggag   1020
tacaagtgca aggtctccaa caaagccctc ccagccccca tcgagaaaac catctccaaa   1080
gccaaagggc agccccgaga accacaggtg tacaccctgc ccccatcccg ggaggagatg   1140
accaagaacc aggtcagcct gacctgcctg gtcaaaggct tctatcccag cgacatcgcc   1200
gtggagtggg agagcaatgg gcagccggag aacaactaca agaccacgcc tcccgtgctg   1260
gactccgacg gctccttctt cctctacagc aagctcaccg tggacaagag caggtggcag   1320
caggggaacg tcttctcatg ctccgtgatg catgaggctc tgcacaacca ctacacgcag   1380
aagagcctct ccctgtctcc gggtaaatga ctcgag                             1416
```

<210> SEQ ID NO 39
<211> LENGTH: 759
<212> TYPE: DNA
<213> ORGANISM: Artificial Sequence
<220> FEATURE:
<223> OTHER INFORMATION: Synthetic nucleotide sequence of light chain
      of chAbF46
<220> FEATURE:
<221> NAME/KEY: misc_difference
<222> LOCATION: (1)..(6)
<223> OTHER INFORMATION: EcoRI restriction site
<220> FEATURE:
<221> NAME/KEY: misc_difference
<222> LOCATION: (7)..(90)
<223> OTHER INFORMATION: signal sequence
<220> FEATURE:
<221> NAME/KEY: misc_difference
<222> LOCATION: (91)..(432)
<223> OTHER INFORMATION: VL - light chain variable region
<220> FEATURE:
<221> NAME/KEY: misc_difference

```
<222> LOCATION: (430)..(435)
<223> OTHER INFORMATION: BsiWI restriction site
<220> FEATURE:
<221> NAME/KEY: misc_difference
<222> LOCATION: (433)..(750)
<223> OTHER INFORMATION: CL - light chain constant region
<220> FEATURE:
<221> NAME/KEY: misc_difference
<222> LOCATION: (751)..(753)
<223> OTHER INFORMATION: stop codon
<220> FEATURE:
<221> NAME/KEY: misc_difference
<222> LOCATION: (754)..(759)
<223> OTHER INFORMATION: XhoI restriction site

<400> SEQUENCE: 39
gaattcacta gtgattaatt cgccgccacc atggattcac aggcccaggt cctcatgttg      60
ctgctgctat cggtatctgg tacctgtgga gacattttga tgacccagtc tccatcctcc     120
ctgactgtgt cagcaggaga aaggtcact atgagctgca agtccagtca gagtctttta      180
gctagtggca accaaaataa ctacttggcc tggcaccagc agaaaccagg acgatctcct     240
aaaatgctga taatttgggc atccactagg gtatctggag tccctgatcg cttcataggc     300
agtggatctg ggacggattt cactctgacc atcaacagtg tgcaggctga agatctggct     360
gtttattact gtcagcagtc ctacagcgct ccgctcacgt tcggtgctgg gaccaagctg     420
gagctgaaac gtacggtggc tgcaccatct gtcttcatct tcccgccatc tgatgagcag     480
ttgaaatctg gaactgcctc tgttgtgtgc ctgctgaata acttctatcc cagagaggcc     540
aaagtacagt ggaaggtgga taacgccctc caatcgggta actcccagga gagtgtcaca     600
gagcaggaca gcaaggacag cacctacagc ctcagcagca ccctgacgct gagcaaagca     660
gactacgaga aacacaaagt ctacgcctgc gaagtcaccc atcagggcct gagctcgccc     720
gtcacaaaga gcttcaacag gggagagtgt tgactcgag                           759

<210> SEQ ID NO 40
<211> LENGTH: 447
<212> TYPE: PRT
<213> ORGANISM: Artificial Sequence
<220> FEATURE:
<223> OTHER INFORMATION: Synthetic amino acid sequence of H1-heavy

<400> SEQUENCE: 40

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Thr Asp Tyr
             20                  25                  30

Tyr Met Ser Trp Val Arg Gln Ala Pro Gly Lys Gly Leu Glu Trp Leu
         35                  40                  45

Gly Phe Ile Arg Asn Lys Ala Asn Gly Tyr Thr Thr Glu Tyr Ser Ala
     50                  55                  60

Ser Val Lys Gly Arg Phe Thr Ile Ser Arg Asp Asn Ser Lys Asn Ser
 65                  70                  75                  80

Leu Tyr Leu Gln Met Asn Ser Leu Lys Thr Glu Asp Thr Ala Val Tyr
             85                  90                  95

Tyr Cys Ala Arg Asp Asn Trp Phe Ala Tyr Trp Gly Gln Gly Thr Leu
        100                 105                 110

Val Thr Val Ser Ser Ala Ser Thr Lys Gly Pro Ser Val Phe Pro Leu
    115                 120                 125

Ala Pro Ser Ser Lys Ser Thr Ser Gly Gly Thr Ala Ala Leu Gly Cys
130                 135                 140
```

```
Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 41
<211> LENGTH: 447
<212> TYPE: PRT
<213> ORGANISM: Artificial Sequence
<220> FEATURE:
<223> OTHER INFORMATION: Synthetic amino acid sequence of H3-heavy

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60
```

Ser Val Lys Gly Arg Phe Thr Ile Ser Arg Asp Asn Ser Lys Asn Ser
 65                  70                  75                  80

Leu Tyr Leu Gln Met Asn Ser Leu Arg Ala Glu Asp Thr Ala Val Tyr
             85                  90                  95

Tyr Cys Ala Arg Asp Asn Trp Phe Ala Tyr Trp Gly Gln Gly Thr Leu
        100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 42
<211> LENGTH: 447
<212> TYPE: PRT
<213> ORGANISM: Artificial Sequence
<220> FEATURE:

<223> OTHER INFORMATION: Synthetic amino acid sequence of H4-heavy

<400> SEQUENCE: 42

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Thr Asp Tyr
             20                  25                  30

Tyr Met Ser Trp Val Arg Gln Ala Pro Gly Lys Gly Leu Glu Trp Leu
         35                  40                  45

Gly Phe Ile Arg Asn Lys Ala Asn Gly Tyr Thr Thr Glu Tyr Ser Ala
     50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
             85                  90                  95

Tyr Cys Ala Arg Asp Asn Trp Phe Ala Tyr Trp Gly Gln Gly Thr Leu
        100                 105                 110

Val Thr Val Ser Ser Ala Ser Thr Lys Gly Pro Ser Val Phe Pro Leu
    115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
        180                 185                 190

Leu Gly Thr Gln Thr Tyr Ile Cys Asn Val Asn His Lys Pro Ser Asn
    195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
        260                 265                 270

Val Lys Phe Asn Trp Tyr Val Asp Gly Val Glu Val His Asn Ala Lys
    275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
            325                 330                 335

Ser Lys Ala Lys Gly Gln Pro Arg Glu Pro Gln Val Tyr Thr Leu Pro
        340                 345                 350

Pro Ser Arg Glu Glu Met Thr Lys Asn Gln Val Ser Leu Thr Cys Leu
    355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400
```

```
Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
        420                 425                 430

His Asn His Tyr Thr Gln Lys Ser Leu Ser Leu Ser Pro Gly Lys
        435                 440                 445

<210> SEQ ID NO 43
<211> LENGTH: 220
<212> TYPE: PRT
<213> ORGANISM: Artificial Sequence
<220> FEATURE:
<223> OTHER INFORMATION: Synthetic amino acid sequence of H1-light

<400> SEQUENCE: 43

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp His Gln Gln Lys Pro Gly Gln
        35                  40                  45

Pro Pro Lys Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 44
<211> LENGTH: 220
<212> TYPE: PRT
<213> ORGANISM: Artificial Sequence
<220> FEATURE:
<223> OTHER INFORMATION: Synthetic amino acid sequence of H2-light

<400> SEQUENCE: 44

Asp Ile Val Met Thr Gln Thr Pro Leu Ser Leu Pro Val Thr Pro Gly
 1               5                  10                  15

Glu Pro Ala Ser Ile Ser Cys Lys Ser Ser Gln Ser Leu Leu Ala Ser
            20                  25                  30

Gly Asn Gln Asn Asn Tyr Leu Ala Trp His Leu Gln Lys Pro Gly Gln
        35                  40                  45
```

Ser Pro Gln Met Leu Ile Ile Trp Ala Ser Thr Arg Val Ser Gly Val
         50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Val Tyr Tyr Cys Gln Gln
                 85                  90                  95

Ser Tyr Ser Ala Pro Leu Thr Phe Gly Gln Gly Thr Lys Leu Glu Leu
                100                 105                 110

Lys Arg Thr Val Ala Ala Pro Ser Val Phe Ile Phe Pro Pro Ser Asp
                115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
                195                 200                 205

Ser Pro Val Thr Lys Ser Phe Asn Arg Gly Glu Cys
                210                 215                 220

<210> SEQ ID NO 45
<211> LENGTH: 220
<212> TYPE: PRT
<213> ORGANISM: Artificial Sequence
<220> FEATURE:
<223> OTHER INFORMATION: Synthetic amino acid sequence of H3-light

<400> SEQUENCE: 45

Asp Ile Val Met Thr Gln Ser Pro Asp Ser Leu Ala Val Ser Leu Gly
  1               5                  10                  15

Glu Arg Ala Thr Ile Asn Cys Lys Ser Ser Gln Ser Leu Leu Ala Ser
                 20                  25                  30

Gly Asn Gln Asn Asn Tyr Leu Ala Trp Tyr Gln Gln Lys Pro Gly Gln
             35                  40                  45

Pro Pro Lys Leu Leu Ile Ile Trp Ala Ser Thr Arg Val Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Ser Tyr Ser Ala Pro Leu Thr Phe Gly Gly Gly Thr Lys Val Glu Ile
                100                 105                 110

Lys Arg Thr Val Ala Ala Pro Ser Val Phe Ile Phe Pro Pro Ser Asp
                115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

```
Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 46
<211> LENGTH: 219
<212> TYPE: PRT
<213> ORGANISM: Artificial Sequence
<220> FEATURE:
<223> OTHER INFORMATION: Synthetic amino acid sequence of H4-light

<400> SEQUENCE: 46

Asp Ile Gln Met Thr Gln Ser Pro Ser Ser Leu Ser Ala Ser Val Gly
  1               5                  10                  15

Asp Arg Val Thr Ile Thr Cys Lys Ser Ser Gln Ser Leu Leu Ala Ser
             20                  25                  30

Gly Asn Gln Asn Asn Tyr Leu Ala Trp His Gln Gln Lys Pro Gly Lys
         35                  40                  45

Ala Pro Lys Met Leu Ile Ile Trp Ala Ser Thr Arg Val Ser Gly Val
     50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Ser Tyr Ser Ala Pro Leu Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu
    210                 215

<210> SEQ ID NO 47
<211> LENGTH: 1350
<212> TYPE: DNA
<213> ORGANISM: Artificial Sequence
<220> FEATURE:
<223> OTHER INFORMATION: Synthetic nucleotide sequence of H1-heavy

<400> SEQUENCE: 47
gaggtgcagc tggtggagtc tgggggaggc ttggtccagc ctggagggtc cctgagactc      60
tcctgtgcag cctctggatt caccttcact gactactaca tgagctgggt ccgccaggct     120
ccagggaagg gctggagtg gttgggcttt attagaaaca agctaacgg ttacaccaca       180 gaatacagtg cgtctgtgaa aggcagattc accatctcaa gagataattc aaagaactca     240
ctgtatctgc aaatgaacag cctgaaaacc gaggacacgg ccgtgtatta ctgtgctaga     300
```

```
gataactggt ttgcttactg gggtcaagga accctggtca ccgtctcctc ggctagcacc        360
aagggcccat cggtcttccc cctggcaccc tcctccaaga gcacctctgg gggcacagcg        420
gccctgggct gcctggtcaa ggactacttc cccgaaccgg tgacggtgtc gtggaactca        480
ggcgccctga ccagcggcgt gcacaccttc ccggctgtcc tacagtcctc aggactctac        540
tccctcagca gcgtggtgac cgtgccctcc agcagcttgg gcacccagac ctacatctgc        600
aacgtgaatc acaagcccag caacaccaag gtggacaaga agttgagcc caaatcttgt         660 gacaaaactc acacatgccc accgtgccca gcacctgaac tcctgggggg accgtcagtc        720
ttcctcttcc cccaaaaacc caaggacacc ctcatgatct cccggacccc tgaggtcaca        780
tgcgtggtgg tggacgtgag ccacgaagac cctgaggtca agttcaactg gtacgtggac        840
ggcgtggagg tgcataatgc caagacaaag ccgcgggagg agcagtacaa cagcacgtac        900
cgtgtggtca gcgtcctcac cgtcctgcac caggactggc tgaatggcaa ggagtacaag        960
tgcaaggtct ccaacaaagc cctcccagcc cccatcgaga aaaccatctc caaagccaaa       1020
gggcagcccc gagaaccaca ggtgtacacc ctgcccccat cccgggagga gatgaccaag       1080
aaccaggtca gcctgacctg cctggtcaaa ggcttctatc ccagcgacat cgccgtggag       1140
tgggagagca atgggcagcc ggagaacaac tacaagacca cgcctcccgt gctggactcc       1200
gacggctcct tcttcctcta cagcaagctc accgtggaca agagcaggtg gcagcagggg       1260
aacgtcttct catgctccgt gatgcatgag gctctgcaca accactacac gcagaagagc       1320
ctctccctgt ctccgggtaa atgactcgag                                        1350
```

<210> SEQ ID NO 48
<211> LENGTH: 1350
<212> TYPE: DNA
<213> ORGANISM: Artificial Sequence
<220> FEATURE:
<223> OTHER INFORMATION: Synthetic nucleotide sequence of H3-heavy

<400> SEQUENCE: 48

```
gaggtgcagc tggtggagtc tgggggaggc ttggtccagc ctggagggtc cctgagactc         60
tcctgtgcag cctctggatt caccttcact gactactaca tgagctgggt ccgccaggct        120
ccagggaagg ggctggagtg gttgggcttt attagaaaca agctaacgg ttacaccaca         180 gaatacagtg cgtctgtgaa aggcagattc accatctcaa gagataattc aaagaactca        240
ctgtatctgc aaatgaacag cctgcgtgct gaggacacgg ccgtgtatta ctgtgctaga        300
gataactggt ttgcttactg gggtcaagga accctggtca ccgtctcctc ggctagcacc        360
aagggcccat cggtcttccc cctggcaccc tcctccaaga gcacctctgg gggcacagcg        420
gccctgggct gcctggtcaa ggactacttc cccgaaccgg tgacggtgtc gtggaactca        480
ggcgccctga ccagcggcgt gcacaccttc ccggctgtcc tacagtcctc aggactctac        540
tccctcagca gcgtggtgac cgtgccctcc agcagcttgg gcacccagac ctacatctgc        600
aacgtgaatc acaagcccag caacaccaag gtggacaaga agttgagcc caaatcttgt         660 gacaaaactc acacatgccc accgtgccca gcacctgaac tcctgggggg accgtcagtc        720
ttcctcttcc cccaaaaacc caaggacacc ctcatgatct cccggacccc tgaggtcaca        780
tgcgtggtgg tggacgtgag ccacgaagac cctgaggtca agttcaactg gtacgtggac        840
ggcgtggagg tgcataatgc caagacaaag ccgcgggagg agcagtacaa cagcacgtac        900
cgtgtggtca gcgtcctcac cgtcctgcac caggactggc tgaatggcaa ggagtacaag        960
tgcaaggtct ccaacaaagc cctcccagcc cccatcgaga aaaccatctc caaagccaaa       1020
```

```
gggcagcccc gagaaccaca ggtgtacacc ctgcccccat cccggga gga gatgaccaag    1080 aaccaggtca gcctgacctg cctggtcaaa ggcttctatc cagcgacat cgccgtggag     1140 tgggagagca atgggcagcc ggagaacaac tacaagacca cgcctcccgt gctggactcc    1200
gacggctcct tcttcctcta cagcaagctc accgtggaca gagcaggtg gcagcagggg    1260 aacgtcttct catgctccgt gatgcatgag gctctgcaca accactacac gcagaagagc    1320 ctctcccctgt ctccgggtaa atgactcgag                                     1350
```

<210> SEQ ID NO 49
<211> LENGTH: 1350
<212> TYPE: DNA
<213> ORGANISM: Artificial Sequence
<220> FEATURE:
<223> OTHER INFORMATION: Synthetic nucleotide sequence of H4-heavy

<400> SEQUENCE: 49

```
gaggttcagc tggtggagtc tggcggtggc ctggtgcagc cagggggctc actccgtttg      60
tcctgtgcag cttctggctt caccttcact gattactaca tgagctgggt gcgtcaggcc     120
ccgggtaagg gcctggaatg gttgggtttt attagaaaca aagctaatgg ttacacaaca     180
gagtacagtg catctgtgaa gggtcgtttc actataagca gagataattc caaaaacaca     240
ctgtacctgc agatgaacag cctgcgtgct gaggacactg ccgtctatta ttgtgctaga     300
gataactggt ttgcttactg gggccaaggg actctggtca ccgtctcctc ggctagcacc     360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
aacgtgaatc acaagcccag caacaccaag gtggacaaga aagttgagcc caaatcttgt     660
gacaaaactc acacatgccc accgtgccca gcacctgaac tcctgggggg accgtcagtc     720
ttcctcttcc ccccaaaacc caaggacacc ctcatgatct cccggacccc tgaggtcaca     780
tgcgtggtgg tggacgtgag ccacgaagac cctgaggtca agttcaactg gtacgtggac     840
ggcgtggagg tgcataatgc caagacaaag ccgcgggagg agcagtacaa cagcacgtac     900
cgtgtggtca gcgtcctcac cgtcctgcac caggactggc tgaatggcaa ggagtacaag     960
tgcaaggtct ccaacaaagc cctcccagcc cccatcgaga aaaccatctc caaagccaaa    1020
gggcagcccc gagaaccaca ggtgtacacc ctgcccccat cccgggagga gatgaccaag    1080
aaccaggtca gcctgacctg cctggtcaaa ggcttctatc cagcgacat cgccgtggag    1140 tgggagagca atgggcagcc ggagaacaac tacaagacca cgcctcccgt gctggactcc    1200
gacggctcct tcttcctcta cagcaagctc accgtggaca gagcaggtg gcagcagggg    1260 aacgtcttct catgctccgt gatgcatgag gctctgcaca accactacac gcagaagagc    1320 ctctcccctgt ctccgggtaa atgactcgag                                   1350
```

<210> SEQ ID NO 50
<211> LENGTH: 669
<212> TYPE: DNA
<213> ORGANISM: Artificial Sequence
<220> FEATURE:
<223> OTHER INFORMATION: Synthetic nucleotide sequence of H1-light

<400> SEQUENCE: 50

```
gacatcgtga tgacccagtc tccagactcc ctggctgtgt ctctgggcga gagggccacc    60
atcaactgca agtccagcca gagtctttta gctagcggca accaaaataa ctacttagct   120
tggcaccagc agaaaccagg acagcctcct aagatgctca ttatttgggc atctacccgg   180
gtatccgggg tccctgaccg attcagtggc agcgggtctg ggacagattt cactctcacc   240
atcagcagcc tgcaggctga agatgtggca gtttattact gtcagcaatc ctatagtgct   300
cctctcacgt tcggaggcgg taccaaggtg gagatcaaac gtacggtggc tgcaccatct   360
gtcttcatct tcccgccatc tgatgagcag ttgaaatctg gaactgcctc tgttgtgtgc   420
ctgctgaata acttctatcc cagagaggcc aaagtacagt ggaaggtgga taacgccctc   480
caatcgggta actcccagga gagtgtcaca gagcaggaca gcaaggacag cacctacagc   540
ctcagcagca ccctgacgct gagcaaagca gactacgaga aacacaaagt ctacgcctgc   600
gaagtcaccc atcagggcct gagctcgccc gtcacaaaga gcttcaacag gggagagtgt   660
tgactcgag                                                           669

<210> SEQ ID NO 51
<211> LENGTH: 669
<212> TYPE: DNA
<213> ORGANISM: Artificial Sequence
<220> FEATURE:
<223> OTHER INFORMATION: Synthetic nucleotide sequence of H2-light

<400> SEQUENCE: 51
gatattgtga tgacccagac tccactctcc ctgcccgtca cccctggaga gccggcctcc    60
atctcctgca agtccagtca gagtctttta gctagtggca accaaaataa ctacttggcc   120
tggcacctgc agaagccagg gcagtctcca cagatgctga tcatttgggc atccactagg   180
gtatctggag tcccagacag gttcagtggc agtgggtcag gcactgattt cacactgaaa   240
atcagcaggg tggaggctga ggatgttgga gtttattact gccagcagtc ctacagcgct   300
ccgctcacgt tcggacaggg taccaagctg gagctcaaac gtacggtggc tgcaccatct   360
gtcttcatct tcccgccatc tgatgagcag ttgaaatctg gaactgcctc tgttgtgtgc   420
ctgctgaata acttctatcc cagagaggcc aaagtacagt ggaaggtgga taacgccctc   480
caatcgggta actcccagga gagtgtcaca gagcaggaca gcaaggacag cacctacagc   540
ctcagcagca ccctgacgct gagcaaagca gactacgaga aacacaaagt ctacgcctgc   600
gaagtcaccc atcagggcct gagctcgccc gtcacaaaga gcttcaacag gggagagtgt   660
tgactcgag                                                           669

<210> SEQ ID NO 52
<211> LENGTH: 669
<212> TYPE: DNA
<213> ORGANISM: Artificial Sequence
<220> FEATURE:
<223> OTHER INFORMATION: Synthetic nucleotide sequence of H3-light

<400> SEQUENCE: 52
gacatcgtga tgacccagtc tccagactcc ctggctgtgt ctctgggcga gagggccacc    60
atcaactgca agtccagcca gagtctttta gctagcggca accaaaataa ctacttagct   120
tggtaccagc agaaaccagg acagcctcct aagctgctca ttatttgggc atctacccgg   180
gtatccgggg tccctgaccg attcagtggc agcgggtctg ggacagattt cactctcacc   240
atcagcagcc tgcaggctga agatgtggca gtttattact gtcagcaatc ctatagtgct   300
cctctcacgt tcggaggcgg taccaaggtg gagatcaaac gtacggtggc tgcaccatct   360
```

```
gtcttcatct tcccgccatc tgatgagcag ttgaaatctg gaactgcctc tgttgtgtgc      420
ctgctgaata acttctatcc cagagaggcc aaagtacagt ggaaggtgga taacgccctc      480
caatcgggta actcccagga gagtgtcaca gagcaggaca gcaaggacag cacctacagc      540
ctcagcagca ccctgacgct gagcaaagca gactacgaga aacacaaagt ctacgcctgc      600
gaagtcaccc atcagggcct gagctcgccc gtcacaaaga gcttcaacag gggagagtgt      660
tgactcgag                                                              669

<210> SEQ ID NO 53
<211> LENGTH: 669
<212> TYPE: DNA
<213> ORGANISM: Artificial Sequence
<220> FEATURE:
<223> OTHER INFORMATION: Synthetic nucleotide sequence of H4-light

<400> SEQUENCE: 53
gatatccaga tgacccagtc cccgagctcc ctgtccgcct ctgtgggcga tagggtcacc       60
atcacctgca gtccagtca gagtctttta gctagtggca accaaaataa ctacttggcc      120
tggcaccaac agaaaccagg aaaagctccg aaaatgctga ttatttgggc atccactagg      180
gtatctggag tcccttctcg cttctctgga tccgggtctg ggacggattt cactctgacc      240
atcagcagtc tgcagccgga agacttcgca acttattact gtcagcagtc ctacagcgct      300
ccgctcacgt tcggacaggg taccaaggtg gagatcaaac gtacggtggc tgcaccatct      360
gtcttcatct tcccgccatc tgatgagcag ttgaaatctg gaactgcctc tgttgtgtgc      420
ctgctgaata acttctatcc cagagaggcc aaagtacagt ggaaggtgga taacgccctc      480
caatcgggta actcccagga gagtgtcaca gagcaggaca gcaaggacag cacctacagc      540
ctcagcagca ccctgacgct gagcaaagca gactacgaga aacacaaagt ctacgcctgc      600
gaagtcaccc atcagggcct gagctcgccc gtcacaaaga gcttcaacag gggagagtgt      660
tgactcgag                                                              669

<210> SEQ ID NO 54
<211> LENGTH: 23
<212> TYPE: PRT
<213> ORGANISM: Artificial Sequence
<220> FEATURE:
<223> OTHER INFORMATION: Synthetic linker between VH and VL

<400> SEQUENCE: 54

Gly Leu Gly Gly Leu Gly Gly Gly Ser Gly Gly Gly Gly Ser Gly
 1               5                  10                  15

Gly Ser Ser Gly Val Gly Ser
            20

<210> SEQ ID NO 55
<211> LENGTH: 1088
<212> TYPE: DNA
<213> ORGANISM: Artificial Sequence
<220> FEATURE:
<223> OTHER INFORMATION: Synthetic polynucleotide encoding scFv of
      huAbF46 antibody

<400> SEQUENCE: 55
gctagcgttt tagcagaagt tcaattggtt gaatctggtg gtggtttggt tcaaccaggt       60
ggttctttga gattgtcttg tgctgcttct ggttttactt tcaccgatta ttacatgtcc      120
tgggttagac aagctccagg taaaggtttg gaatggttgg gtttcattag aaacaaggct      180
```

-continued

```
aacggttaca ctaccgaata ttctgcttct gttaagggta gattcaccat ttctagagac    240
aactctaaga acaccttgta cttgcaaatg aactccttga gagctgaaga tactgctgtt    300
tattactgcg ctagagataa ttggtttgct tattggggtc aaggtacttt ggttactgtt    360
tcttctggcc tcgggggcct cggaggagga ggtagtggcg gaggaggctc cggtggatcc    420
agcggtgtgg gttccgatat tcaaatgacc caatctccat cttctttgtc tgcttcagtt    480
ggtgatagag ttaccattac ttgtaagtcc tcccaatctt tgttggcttc tggtaatcag    540
aacaattact ggcttggca tcaacaaaaa ccaggtaaag ctccaaagat gttgattatt    600
tgggcttcta ccagagtttc tggtgttcca tctagatttt ctggttctgg ttccggtact    660
gattttactt tgaccatttc atccttgcaa ccagaagatt tcgctactta ctactgtcaa    720
caatcttact ctgctccatt gacttttggt caaggtacaa aggtcgaaat caagagagaa    780
ttcggtaagc ctatccctaa ccctctcctc ggtctcgatt ctacgggtgg tggtggatct    840
ggtggtggtg gttctggtgg tggtggttct caggaactga caactatatg cgagcaaatc    900
ccctcaccaa ctttagaatc gacgccgtac tctttgtcaa cgactactat tttggccaac    960
gggaaggcaa tgcaaggagt ttttgaatat tacaaatcag taacgtttgt cagtaattgc    1020
ggttctcacc cctcaacaac tagcaaaggc agccccataa acacacagta tgttttttga    1080
gtttaaac                                                             1088
```

```
<210> SEQ ID NO 56
<211> LENGTH: 5597
<212> TYPE: DNA
<213> ORGANISM: Artificial Sequence
<220> FEATURE:
<223> OTHER INFORMATION: Synthetic expression vector including
      polynucleotide encoding scFv of huAbF46 antibody
<220> FEATURE:
<221> NAME/KEY: misc_difference
<222> LOCATION: (573)..(578)
<223> OTHER INFORMATION: NheI restriction site
<220> FEATURE:
<221> NAME/KEY: misc_difference
<222> LOCATION: (588)..(938)
<223> OTHER INFORMATION: huAbF46 VH
<220> FEATURE:
<221> NAME/KEY: misc_difference
<222> LOCATION: (939)..(1007)
<223> OTHER INFORMATION: linker
<220> FEATURE:
<221> NAME/KEY: misc_difference
<222> LOCATION: (1008)..(1349)
<223> OTHER INFORMATION: huAbF46 VL
<220> FEATURE:
<221> NAME/KEY: misc_difference
<222> LOCATION: (1350)..(1355)
<223> OTHER INFORMATION: EcoRI restriction site
<220> FEATURE:
<221> NAME/KEY: misc_difference
<222> LOCATION: (1356)..(1397)
<223> OTHER INFORMATION: V5 epitope
<220> FEATURE:
<221> NAME/KEY: misc_difference
<222> LOCATION: (1398)..(1442)
<223> OTHER INFORMATION: (G4S)3 linker
<220> FEATURE:
<221> NAME/KEY: misc_difference
<222> LOCATION: (1443)..(1649)
<223> OTHER INFORMATION: Aga2
<220> FEATURE:
<221> NAME/KEY: misc_difference
<222> LOCATION: (1650)..(1652)
<223> OTHER INFORMATION: TGA(stop codon)
<220> FEATURE:
<221> NAME/KEY: misc_difference
```

<222> LOCATION: (1653)..(1660)
<223> OTHER INFORMATION: PmeI restriction site

<400> SEQUENCE: 56

| | | | | |
|---|---|---|---|---|
| acggattaga | agccgccgag | cgggtgacag | ccctccgaag | gaagactctc ctccgtgcgt | 60 |
| cctcgtcttc | accggtcgcg | ttcctgaaac | gcagatgtgc | ctcgcgccgc actgctccga | 120 |
| acaataaaga | ttctacaata | ctagctttta | tggttatgaa | gaggaaaaat tggcagtaac | 180 |
| ctggccccac | aaaccttcaa | atgaacgaat | caaattaaca | accataggat gataatgcga | 240 |
| ttagttttt | agccttattt | ctggggtaat | taatcagcga | agcgatgatt tttgatctat | 300 |
| taacagatat | ataaatgcaa | aaactgcata | accactttaa | ctaatacttt caacattttc | 360 |
| ggtttgtatt | acttcttatt | caaatgtaat | aaaagtatca | acaaaaaatt gttaatatac | 420 |
| ctctatactt | taacgtcaag | gagaaaaaac | cccggatcgg | actactagca gctgtaatac | 480 |
| gactcactat | agggaatatt | aagctaattc | tacttcatac | attttcaatt aagatgcagt | 540 |
| tacttcgctg | tttttcaata | ttttctgtta | ttgctagcgt | tttagcagaa gttcaattgg | 600 |
| ttgaatctgg | tggtggtttg | gttcaaccag | gtggttcttt | gagattgtct tgtgctgctt | 660 |
| ctggttttac | tttcaccgat | tattacatgt | cctgggttag | acaagctcca ggtaaaggtt | 720 |
| tggaatggtt | gggtttcatt | agaaacaagg | ctaacggtta | cactaccgaa tattctgctt | 780 |
| ctgttaaggg | tagattcacc | atttctagag | acaactctaa | gaacaccttg tacttgcaaa | 840 |
| tgaactcctt | gagagctgaa | gatactgctg | tttattactg | cgctagagat aattggtttg | 900 |
| cttattgggg | tcaaggtact | ttggttactg | tttcttctgg | cctcggggc ctcggaggag | 960 |
| gaggtagtgg | cggaggaggc | tccggtggat | ccagcggtgt | gggttccgat attcaaatga | 1020 |
| cccaatctcc | atcttctttg | tctgcttcag | ttggtgatag | agttaccatt acttgtaagt | 1080 |
| cctcccaatc | tttgttggct | tctggtaatc | agaacaatta | cttggcttgg catcaacaaa | 1140 |
| aaccaggtaa | agctccaaag | atgttgatta | tttgggcttc | taccagagtt tctggtgttc | 1200 |
| catctagatt | ttctggttct | ggttccggta | ctgatttac | tttgaccatt tcatccttgc | 1260 |
| aaccagaaga | tttcgctact | tactactgtc | aacaatctta | ctctgctcca ttgacttttg | 1320 |
| gtcaaggtac | aaaggtcgaa | atcaagagag | aattcggtaa | gcctatccct aaccctctcc | 1380 |
| tcggtctcga | ttctacgggt | ggtggtggat | ctggtggtgg | tggttctggt ggtggtggtt | 1440 |
| ctcaggaact | gacaactata | tgcgagcaaa | tcccctcacc | aactttagaa tcgacgccgt | 1500 |
| actctttgtc | aacgactact | attttggcca | acgggaaggc | aatgcaagga ttttttgaat | 1560 |
| attacaaatc | agtaacgttt | gtcagtaatt | gcggttctca | cccctcaaca actagcaaag | 1620 |
| gcagccccat | aaacacacag | tatgtttttt | gagtttaaac | ccgctgatct gataacaaca | 1680 |
| gtgtagatgt | aacaaaatcg | actttgttcc | cactgtactt | ttagctcgta caaaatacaa | 1740 |
| tatactttc | atttctccgt | aaacaacatg | ttttcccatg | taatatcctt ttctattttt | 1800 |
| cgttccgtta | ccaactttac | acatacttta | tatagctatt | cacttctata cactaaaaaa | 1860 |
| ctaagacaat | tttaattttg | ctgcctgcca | tatttcaatt | tgttataaat tcctataatt | 1920 |
| tatcctatta | gtagctaaaa | aaagatgaat | gtgaatcgaa | tcctaagaga attgggcaag | 1980 |
| tgcacaaaca | atacttaaat | aaatactact | cagtaataac | ctatttctta gcattttga | 2040 |
| cgaaatttgc | tattttgtta | gagtcttta | caccatttgt | ctccacacct ccgcttacat | 2100 |
| caacaccaat | aacgccattt | aatctaagcg | catcaccaac | attttctggc gtcagtccac | 2160 |
| cagctaacat | aaaatgtaag | ctctcggggc | tctcttgcct | tccaacccag tcagaaatcg | 2220 |

```
agttccaatc caaaagttca cctgtcccac ctgcttctga atcaaacaag ggaataaacg    2280
aatgaggttt ctgtgaagct gcactgagta gtatgttgca gtcttttgga aatacgagtc    2340
ttttaataac tggcaaaccg aggaactctt ggtattcttg ccacgactca tctccgtgca    2400
gttggacgat atcaatgccg taatcattga ccagagccaa acatcctcc ttaggttgat     2460
tacgaaacac gccaaccaag tatttcggag tgcctgaact atttttatat gcttttacaa    2520
gacttgaaat tttccttgca ataaccgggt caattgttct ctttctattg ggcacacata    2580
taatacccag caagtcagca tcggaatcta gagcacattc tgcggcctct gtgctctgca    2640
agccgcaaac tttcaccaat ggaccagaac tacctgtgaa attaataaca gacatactcc    2700
aagctgcctt tgtgtgctta atcacgtata ctcacgtgct caatagtcac caatgccctc    2760
cctcttggcc ctctccttt cttttttcga ccgaatttct tgaagacgaa agggcctcgt     2820
gatacgccta ttttatagg ttaatgtcat gataataatg gtttcttagg acggatcgct    2880
tgcctgtaac ttacgcgcgc ctcgtatctt ttaatgatgg aataatttgg gaatttactc    2940
tgtgtttatt tattttatg ttttgtattt ggattttaga aagtaaataa agaaggtaga     3000
agagttacgg aatgaagaaa aaaaaataaa caaaggttta aaaaatttca acaaaaagcg    3060
tactttacat atatatttat tagacaagaa aagcagatta aatagatata cattcgatta    3120
acgataagta aaatgtaaaa tcacaggatt ttcgtgtgtg gtcttctaca cagacaagat    3180
gaaacaattc ggcattaata cctgagagca ggaagagcaa gataaaaggt agtatttgtt    3240
ggcgatcccc ctagagtctt ttacatcttc ggaaaacaaa aactatttt tctttaattt     3300
cttttttac tttctatttt taatttatat atttatatta aaaatttaa attataatta      3360
tttttatagc acgtgatgaa aaggacccag gtggcacttt tcggggaaat gtgcgcggaa    3420
cccctatttg tttattttc taaatacatt caaatatgta tccgctcatg agacaataac     3480
cctgataaat gcttcaataa tattgaaaaa ggaagagtat gagtattcaa catttccgtg    3540
tcgcccttat tccctttttt gcggcatttt gccttcctgt ttttgctcac ccagaaacgc    3600
tggtgaaagt aaaagatgct gaagatcagt tgggtgcacg agtgggttac atcgaactgg    3660
atctcaacag cggtaagatc cttgagagtt ttcgccccga agaacgtttt ccaatgatga    3720
gcacttttaa agttctgcta tgtggcgcgg tattatcccg tgttgacgcc gggcaagagc    3780
aactcggtcg ccgcatacac tattctcaga atgacttggt tgagtactca ccagtcacag    3840
aaaagcatct tacggatggc atgacagtaa gagaattatg cagtgctgcc ataaccatga    3900
gtgataacac tgcggccaac ttacttctga caacgatcgg aggaccgaag gagctaaccg    3960
cttttttgca caacatgggg gatcatgtaa ctcgccttga tcgttgggaa ccggagctga    4020
atgaagccat accaaacgac gagcgtgaca ccacgatgcc tgtagcaatg gcaacaacgt    4080
tgcgcaaact attaactggc gaactactta ctctagcttc ccggcaacaa ttaatagact    4140
ggatggaggc ggataaagtt gcaggaccac ttctgcgctc ggcccttccg gctggctggt    4200
ttattgctga taaatctgga gccggtgagc gtgggtctcg cggtatcatt gcagcactgg    4260
ggccagatgg taagccctcc cgtatcgtag ttatctacac gacgggcagt caggcaacta    4320
tggatgaacg aaatagacag atcgctgaga taggtgcctc actgattaag cattggtaac    4380
tgtcagacca gtttactca tatatacttt agattgattt aaaacttcat ttttaattta     4440
aaaggatcta ggtgaagatc ctttttgata atctcatgac caaaatccct taacgtgagt    4500
tttcgttcca ctgagcgtca gacccgtag aaaagatcaa aggatcttct tgagatcctt     4560
ttttttctgcg cgtaatctgc tgcttgcaaa caaaaaaacc accgctacca gcggtggttt    4620
```

```
gtttgccgga tcaagagcta ccaactcttt ttccgaaggt aactggcttc agcagagcgc    4680
agataccaaa tactgtcctt ctagtgtagc cgtagttagg ccaccacttc aagaactctg    4740
tagcaccgcc tacatacctc gctctgctaa tcctgttacc agtggctgct gccagtggcg    4800
ataagtcgtg tcttaccggg ttggactcaa gacgatagtt accggataag gcgcagcggt    4860
cgggctgaac ggggggttcg tgcacacagc ccagcttgga gcgaacgacc tacaccgaac    4920
tgagatacct acagcgtgag cattgagaaa gcgccacgct tcccgaaggg agaaaggcgg    4980
acaggtatcc ggtaagcggc agggtcggaa caggagagcg cacgagggag cttccagggg    5040
ggaacgcctg gtatctttat agtcctgtcg ggtttcgcca cctctgactt gagcgtcgat    5100
ttttgtgatg ctcgtcaggg gggccgagcc tatggaaaaa cgccagcaac gcggcctttt    5160
tacggttcct ggccttttgc tggccttttg ctcacatgtt ctttcctgcg ttatcccctg    5220
attctgtgga taaccgtatt accgcctttg agtgagctga taccgctcgc cgcagccgaa    5280
cgaccgagcg cagcgagtca gtgagcgagg aagcggaaga gcgcccaata cgcaaaccgc    5340
ctctccccgc gcgttggccg attcattaat gcagctggca cgacaggttt cccgactgga    5400
aagcgggcag tgagcgcaac gcaattaatg tgagttacct cactcattag gcaccccagg    5460
ctttacactt tatgcttccg gctcctatgt tgtgtggaat tgtgagcgga taacaatttc    5520
acacaggaaa cagctatgac catgattacg ccaagctcgg aattaaccct cactaaaggg    5580
aacaaaagct ggctagt                                                  5597
```

<210> SEQ ID NO 57
<211> LENGTH: 13
<212> TYPE: PRT
<213> ORGANISM: Artificial Sequence
<220> FEATURE:
<223> OTHER INFORMATION: Synthetic U6-HC7 hinge

<400> SEQUENCE: 57

Glu Pro Lys Ser Cys Asp Cys His Cys Pro Pro Cys Pro
 1               5                  10

<210> SEQ ID NO 58
<211> LENGTH: 435
<212> TYPE: DNA
<213> ORGANISM: Artificial Sequence
<220> FEATURE:
<223> OTHER INFORMATION: Synthetic polynucleotide encoding CDR-L3
      derived from L3-1 clone

<400> SEQUENCE: 58

```
gaattcacta gtgattaatt cgccgccacc atggattcac aggcccaggt cctcatgttg     60
ctgctgctat cggtatctgg tacctgtgga gatatccaga tgacccagtc cccgagctcc    120
ctgtccgcct ctgtgggcga tagggtcacc atcacctgca gtccagtca gagtctttta    180 gctagtggca accaaaataa ctacttggcc tggcaccaac agaaaccagg aaaagctccg    240
aaaatgctga ttatttgggc atccactagg gtatctggag tcccttctcg cttctctgga    300
tccgggtctg gacggatttc actctgacc atcagcagtc tgcagccgga agacttcgca    360
acttattact gtcagcagtc ctacagccgc cgtacacgt cggacaggg taccaaggtg    420 gagatcaaac gtacg                                                    435
```

<210> SEQ ID NO 59
<211> LENGTH: 435
<212> TYPE: DNA

<213> ORGANISM: Artificial Sequence
<220> FEATURE:
<223> OTHER INFORMATION: Synthetic polynucleotide encoding CDR-L3 derived from L3-2 clone

<400> SEQUENCE: 59

| | |
|---|---:|
| gaattcacta gtgattaatt cgccgccacc atggattcac aggcccaggt cctcatgttg | 60 |
| ctgctgctat cggtatctgg tacctgtgga gatatccaga tgacccagtc cccgagctcc | 120 |
| ctgtccgcct ctgtgggcga tagggtcacc atcacctgca agtccagtca gagtcttta | 180 |
| gctagtggca accaaaataa ctacttggcc tggcaccaac agaaaccagg aaaagctccg | 240 |
| aaaatgctga ttatttgggc atccactagg gtatctggag tcccttctcg cttctctgga | 300 |
| tccgggtctg ggacggattt cactctgacc atcagcagtc tgcagccgga agacttcgca | 360 |
| acttattact gtgggcagtc ctacagccgt ccgctcacgt tcggacaggg taccaaggtg | 420 |
| gagatcaaac gtacg | 435 |

<210> SEQ ID NO 60
<211> LENGTH: 435
<212> TYPE: DNA
<213> ORGANISM: Artificial Sequence
<220> FEATURE:
<223> OTHER INFORMATION: Synthetic polynucleotide encoding CDR-L3 derived from L3-3 clone

<400> SEQUENCE: 60

| | |
|---|---:|
| gaattcacta gtgattaatt cgccgccacc atggattcac aggcccaggt cctcatgttg | 60 |
| ctgctgctat cggtatctgg tacctgtgga gatatccaga tgacccagtc cccgagctcc | 120 |
| ctgtccgcct ctgtgggcga tagggtcacc atcacctgca agtccagtca gagtcttta | 180 |
| gctagtggca accaaaataa ctacttggcc tggcaccaac agaaaccagg aaaagctccg | 240 |
| aaaatgctga ttatttgggc atccactagg gtatctggag tcccttctcg cttctctgga | 300 |
| tccgggtctg ggacggattt cactctgacc atcagcagtc tgcagccgga agacttcgca | 360 |
| acttattact gtgcacagtc ctacagccat ccgttctctt tcggacaggg taccaaggtg | 420 |
| gagatcaaac gtacg | 435 |

<210> SEQ ID NO 61
<211> LENGTH: 435
<212> TYPE: DNA
<213> ORGANISM: Artificial Sequence
<220> FEATURE:
<223> OTHER INFORMATION: Synthetic polynucleotide encoding CDR-L3 derived from L3-5 clone

<400> SEQUENCE: 61

| | |
|---|---:|
| gaattcacta gtgattaatt cgccgccacc atggattcac aggcccaggt cctcatgttg | 60 |
| ctgctgctat cggtatctgg tacctgtgga gatatccaga tgacccagtc cccgagctcc | 120 |
| ctgtccgcct ctgtgggcga tagggtcacc atcacctgca agtccagtca gagtcttta | 180 |
| gctagtggca accaaaataa ctacttggcc tggcaccaac agaaaccagg aaaagctccg | 240 |
| aaaatgctga ttatttgggc atccactagg gtatctggag tcccttctcg cttctctgga | 300 |
| tccgggtctg ggacggattt cactctgacc atcagcagtc tgcagccgga agacttcgca | 360 |
| acttattact gtcagcagtc ctacagccgc ccgtttacgt tcggacaggg taccaaggtg | 420 |
| gagatcaaac gtacg | 435 |

<210> SEQ ID NO 62

```
<211> LENGTH: 462
<212> TYPE: PRT
<213> ORGANISM: Artificial Sequence
<220> FEATURE:
<223> OTHER INFORMATION: Synthetic polypeptide consisting of heavy chain
      of huAbF46-H4-A1, U6-HC7 hinge and constant region of
      human IgG1

<400> SEQUENCE: 62
```

| | | | | | | | | | | | | | | | |
|---|---|---|---|---|---|---|---|---|---|---|---|---|---|---|---|
| Met | Glu | Trp | Ser | Trp | Val | Phe | Leu | Val | Thr | Leu | Leu | Asn | Gly | Ile | Gln |
| 1 | | | | 5 | | | | | 10 | | | | | 15 | |
| Cys | Glu | Val | Gln | Leu | Val | Glu | Ser | Gly | Gly | Gly | Leu | Val | Gln | Pro | Gly |
| | | | 20 | | | | | 25 | | | | | 30 | | |
| Gly | Ser | Leu | Arg | Leu | Ser | Cys | Ala | Ala | Ser | Gly | Phe | Thr | Phe | Thr | Asp |
| | | | 35 | | | | | 40 | | | | | 45 | | |
| Tyr | Tyr | Met | Ser | Trp | Val | Arg | Gln | Ala | Pro | Gly | Lys | Gly | Leu | Glu | Trp |
| | 50 | | | | | 55 | | | | | 60 | | | | |
| Leu | Gly | Phe | Ile | Arg | Asn | Lys | Ala | Asn | Gly | Tyr | Thr | Thr | Glu | Tyr | Ser |
| 65 | | | | | 70 | | | | | 75 | | | | | 80 |
| Ala | Ser | Val | Lys | Gly | Arg | Phe | Thr | Ile | Ser | Arg | Asp | Asn | Ser | Lys | Asn |
| | | | | 85 | | | | | 90 | | | | | 95 | |
| Thr | Leu | Tyr | Leu | Gln | Met | Asn | Ser | Leu | Arg | Ala | Glu | Asp | Thr | Ala | Val |
| | | | 100 | | | | | 105 | | | | | 110 | | |
| Tyr | Tyr | Cys | Ala | Arg | Asp | Asn | Trp | Phe | Ala | Tyr | Trp | Gly | Gln | Gly | Thr |
| | | 115 | | | | | 120 | | | | | 125 | | | |
| Leu | Val | Thr | Val | Ser | Ser | Ala | Ser | Thr | Lys | Gly | Pro | Ser | Val | Phe | Pro |
| 130 | | | | | 135 | | | | | 140 | | | | | |
| Leu | Ala | Pro | Ser | Ser | Lys | Ser | Thr | Ser | Gly | Gly | Thr | Ala | Ala | Leu | Gly |
| 145 | | | | | 150 | | | | | 155 | | | | | 160 |
| Cys | Leu | Val | Lys | Asp | Tyr | Phe | Pro | Glu | Pro | Val | Thr | Val | Ser | Trp | Asn |
| | | | | 165 | | | | | 170 | | | | | 175 | |
| Ser | Gly | Ala | Leu | Thr | Ser | Gly | Val | His | Thr | Phe | Pro | Ala | Val | Leu | Gln |
| | | | 180 | | | | | 185 | | | | | 190 | | |
| Ser | Ser | Gly | Leu | Tyr | Ser | Leu | Ser | Ser | Val | Val | Thr | Val | Pro | Ser | Ser |
| | | 195 | | | | | 200 | | | | | 205 | | | |
| Ser | Leu | Gly | Thr | Gln | Thr | Tyr | Ile | Cys | Asn | Val | Asn | His | Lys | Pro | Ser |
| 210 | | | | | 215 | | | | | 220 | | | | | |
| Asn | Thr | Lys | Val | Asp | Lys | Lys | Val | Glu | Pro | Lys | Ser | Cys | Asp | Cys | His |
| 225 | | | | | 230 | | | | | 235 | | | | | 240 |
| Cys | Pro | Pro | Cys | Pro | Ala | Pro | Glu | Leu | Leu | Gly | Gly | Pro | Ser | Val | Phe |
| | | | | 245 | | | | | 250 | | | | | 255 | |
| Leu | Phe | Pro | Pro | Lys | Pro | Lys | Asp | Thr | Leu | Met | Ile | Ser | Arg | Thr | Pro |
| | | | 260 | | | | | 265 | | | | | 270 | | |
| Glu | Val | Thr | Cys | Val | Val | Val | Asp | Val | Ser | His | Glu | Asp | Pro | Glu | Val |
| | | 275 | | | | | 280 | | | | | 285 | | | |
| Lys | Phe | Asn | Trp | Tyr | Val | Asp | Gly | Val | Glu | Val | His | Asn | Ala | Lys | Thr |
| | 290 | | | | | 295 | | | | | 300 | | | | |
| Lys | Pro | Arg | Glu | Glu | Gln | Tyr | Asn | Ser | Thr | Tyr | Arg | Val | Val | Ser | Val |
| 305 | | | | | 310 | | | | | 315 | | | | | 320 |
| Leu | Thr | Val | Leu | His | Gln | Asp | Trp | Leu | Asn | Gly | Lys | Glu | Tyr | Lys | Cys |
| | | | | 325 | | | | | 330 | | | | | 335 | |
| Lys | Val | Ser | Asn | Lys | Ala | Leu | Pro | Ala | Pro | Ile | Glu | Lys | Thr | Ile | Ser |
| | | | 340 | | | | | 345 | | | | | 350 | | |
| Lys | Ala | Lys | Gly | Gln | Pro | Arg | Glu | Pro | Gln | Val | Tyr | Thr | Leu | Pro | Pro |
| | | 355 | | | | | 360 | | | | | 365 | | | |

| Ser | Arg | Glu | Glu | Met | Thr | Lys | Asn | Gln | Val | Ser | Leu | Thr | Cys | Leu | Val |
|---|---|---|---|---|---|---|---|---|---|---|---|---|---|---|---|
| 370 | | | | | 375 | | | | | 380 | | | | | |

| Lys | Gly | Phe | Tyr | Pro | Ser | Asp | Ile | Ala | Val | Glu | Trp | Glu | Ser | Asn | Gly |
|---|---|---|---|---|---|---|---|---|---|---|---|---|---|---|---|
| 385 | | | | | 390 | | | | | 395 | | | | | 400 |

| Gln | Pro | Glu | Asn | Asn | Tyr | Lys | Thr | Thr | Pro | Pro | Val | Leu | Asp | Ser | Asp |
|---|---|---|---|---|---|---|---|---|---|---|---|---|---|---|---|
| | | | | 405 | | | | | 410 | | | | | 415 | |

| Gly | Ser | Phe | Phe | Leu | Tyr | Ser | Lys | Leu | Thr | Val | Asp | Lys | Ser | Arg | Trp |
|---|---|---|---|---|---|---|---|---|---|---|---|---|---|---|---|
| | | | 420 | | | | | 425 | | | | | 430 | | |

| Gln | Gln | Gly | Asn | Val | Phe | Ser | Cys | Ser | Val | Met | His | Glu | Ala | Leu | His |
|---|---|---|---|---|---|---|---|---|---|---|---|---|---|---|---|
| | | | 435 | | | | 440 | | | | | 445 | | | |

| Asn | His | Tyr | Thr | Gln | Lys | Ser | Leu | Ser | Leu | Ser | Pro | Gly | Lys |
|---|---|---|---|---|---|---|---|---|---|---|---|---|---|
| 450 | | | | | 455 | | | | | 460 | | | |

<210> SEQ ID NO 63
<211> LENGTH: 1410
<212> TYPE: DNA
<213> ORGANISM: Artificial Sequence
<220> FEATURE:
<223> OTHER INFORMATION: Synthetic polynucleotide encoding polypeptide
consisting of heavy chain of huAbF46-H4-A1, U6-HC7
hinge and constant region of human IgG1

<400> SEQUENCE: 63

```
gaattcgccg ccaccatgga atggagctgg gttttctcg taacactttt aaatggtatc      60
cagtgtgagg ttcagctggt ggagtctggc ggtggcctgg tgcagccagg gggctcactc     120
cgtttgtcct gtgcagcttc tggcttcacc ttcactgatt actacatgag ctgggtgcgt     180
caggccccgg gtaagggcct ggaatggttg ggttttatta gaaacaaagc taatggttac     240
acaacagagt acagtgcatc tgtgaagggt cgtttcacta agcagagat aattccaaa      300
aacacactgt acctgcagat gaacagcctg cgtgctgagg acactgccgt ctattattgt     360
gctagagata actggtttgc ttactgggc caagggactc tggtcaccgt ctcctcggct     420
agcaccaagg gcccatcggt cttccccctg gcaccctcct ccaagagcac ctctggggc      480
acagcggccc tgggctgcct ggtcaaggac tacttccccg aaccggtgac ggtgtcgtgg     540
aactcaggcg ccctgaccag cggcgtgcac accttcccgg ctgtcctaca gtcctcagga     600
ctctactccc tcagcagcgt ggtgaccgtg ccctccagca gcttgggcac ccagacctac     660
atctgcaacg tgaatcacaa gcccagcaac accaaggtgg acaagaaagt tgagcccaaa     720
agctgcgatt gccactgtcc tccatgtcca gcacctgaac tcctgggggg accgtcagtc     780
ttcctcttcc ccccaaaacc caaggacacc ctcatgatct cccggacccc tgaggtcaca     840
tgcgtggtgg tggacgtgag ccacgaagac cctgaggtca agttcaactg gtacgtggac     900
ggcgtggagg tgcataatgc caagacaaag ccgcgggagg agcagtacaa cagcacgtac     960
cgtgtggtca gcgtcctcac cgtcctgcac caggactggc tgaatggcaa ggagtacaag    1020
tgcaaggtct ccaacaaagc cctcccagcc ccatcgaga aaccatctc caaagccaaa      1080
gggcagcccc gagaaccaca ggtgtacacc ctgcccccat cccgggagga gatgaccaag    1140
aaccaggtca gcctgacctg cctggtcaaa ggcttctatc ccagcgacat cgccgtggag    1200
tgggagagca atgggcagcc ggagaacaac tacaagacca cgcctcccgt gctggactcc    1260
gacggctcct tcttcctcta cagcaagctc accgtggaca agagcaggtg gcagcagggg    1320
aacgtcttct catgctccgt gatgcatgag gctctgcaca accactacac gcagaagagc    1380
ctctccctgt ctccgggtaa atgactcgag                                      1410
```

<210> SEQ ID NO 64
<211> LENGTH: 461
<212> TYPE: PRT
<213> ORGANISM: Artificial Sequence
<220> FEATURE:
<223> OTHER INFORMATION: Synthetic polypeptide consisting of heavy chain of huAbF46-H4-A1, human IgG2 hinge and constant region of human IgG1

<400> SEQUENCE: 64

```
Met Glu Trp Ser Trp Val Phe Leu Val Thr Leu Leu Asn Gly Ile Gln
  1               5                  10                  15

Cys Glu Val Gln Leu Val Glu Ser Gly Gly Gly Leu Val Gln Pro Gly
                 20                  25                  30

Gly Ser Leu Arg Leu Ser Cys Ala Ala Ser Gly Phe Thr Phe Thr Asp
             35                  40                  45

Tyr Tyr Met Ser Trp Val Arg Gln Ala Pro Gly Lys Gly Leu Glu Trp
         50                  55                  60

Leu Gly Phe Ile Arg Asn Lys Ala Asn Gly Tyr Thr Thr Glu Tyr Ser
 65                  70                  75                  80

Ala Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
        115                 120                 125

Leu Val Thr Val Ser Ser Ala Ser Thr Lys Gly Pro Ser Val Phe Pro
130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Arg Lys Cys Cys Val Glu Cys
225                 230                 235                 240

Pro Pro Cys Pro Ala Pro Glu Leu Leu Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Lys
        275                 280                 285

Phe Asn Trp Tyr Val Asp Gly Val Glu Val His Asn Ala Lys Thr Lys
    290                 295                 300

Pro Arg Glu Glu Gln Tyr Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Ala Leu Pro Ala Pro Ile Glu Lys Thr Ile Ser Lys
            340                 345                 350

Ala Lys Gly Gln Pro Arg Glu Pro Gln Val Tyr Thr Leu Pro Pro Ser
        355                 360                 365
```

```
Arg Glu Glu Met Thr Lys Asn Gln Val Ser Leu Thr Cys Leu Val Lys
        370                 375                 380
Gly Phe Tyr Pro Ser Asp Ile Ala Val Glu Trp Glu Ser Asn Gly Gln
385                 390                 395                 400
Pro Glu Asn Asn Tyr Lys Thr Thr Pro Pro Val Leu Asp Ser Asp Gly
                405                 410                 415
Ser Phe Phe Leu Tyr Ser Lys Leu Thr Val Asp Lys Ser Arg Trp Gln
            420                 425                 430
Gln Gly Asn Val Phe Ser Cys Ser Val Met His Glu Ala Leu His Asn
        435                 440                 445
His Tyr Thr Gln Lys Ser Leu Ser Leu Ser Pro Gly Lys
        450                 455                 460
```

<210> SEQ ID NO 65
<211> LENGTH: 1407
<212> TYPE: DNA
<213> ORGANISM: Artificial Sequence
<220> FEATURE:
<223> OTHER INFORMATION: Synthetic polynucleotide encoding polypeptide
      consisting of heavy chain of huAbF46-H4-A1, human IgG2
      hinge and constant region of human IgG1

<400> SEQUENCE: 65

| | | | | | |
|---|---|---|---|---|---|
| gaattcgccg | ccaccatgga | atggagctgg | gttttttctcg | taacactttt | aaatggtatc | 60 |
| cagtgtgagg | ttcagctggt | ggagtctggc | ggtggcctgg | tgcagccagg | gggctcactc | 120 |
| cgtttgtcct | gtgcagcttc | tggcttcacc | ttcactgatt | actacatgag | ctgggtgcgt | 180 |
| caggccccgg | gtaagggcct | ggaatggttg | ggttttatta | gaaacaaagc | taatggttac | 240 |
| acaacagagt | acagtgcatc | tgtgaagggt | cgtttcacta | taagcagaga | taattccaaa | 300 |
| aacacactgt | acctgcagat | gaacagcctg | cgtgctgagg | acactgccgt | ctattattgt | 360 |
| gctagagata | actggtttgc | ttactggggc | caagggactc | tggtcaccgt | ctcctcggct | 420 |
| agcaccaagg | gcccatcggt | cttccccctg | gcaccctcct | ccaagagcac | ctctgggggc | 480 |
| acagcggccc | tgggctgcct | ggtcaaggac | tacttccccg | aaccggtgac | ggtgtcgtgg | 540 |
| aactcaggcg | ccctgaccag | cggcgtgcac | accttcccgg | ctgtcctaca | gtcctcagga | 600 |
| ctctactccc | tcagcagcgt | ggtgaccgtg | ccctccagca | gcttgggcac | ccagacctac | 660 |
| atctgcaacg | tgaatcacaa | gcccagcaac | accaaggtgg | acaagaaagt | tgagaggaag | 720 |
| tgctgtgtgg | agtgcccccc | ctgcccagca | cctgaactcc | tggggggacc | gtcagtcttc | 780 |
| ctcttccccc | caaaacccaa | ggacaccctc | atgatctccc | ggaccccctga | ggtcacatgc | 840 |
| gtggtggtgg | acgtgagcca | cgaagaccct | gaggtcaagt | tcaactggta | cgtggacggc | 900 |
| gtggaggtgc | ataatgccaa | gacaaagccg | cgggaggagc | agtacaacag | cacgtaccgt | 960 |
| gtggtcagcg | tcctcaccgt | cctgcaccag | gactggctga | atggcaagga | gtacaagtgc | 1020 |
| aaggtctcca | acaaagccct | cccagccccc | atcgagaaaa | ccatctccaa | agccaaaggg | 1080 |
| cagccccgag | aaccacaggt | gtacaccctg | cccccatccc | gggaggagat | gaccaagaac | 1140 |
| caggtcagcc | tgacctgcct | ggtcaaaggc | ttctatccca | gcgacatcgc | cgtggagtgg | 1200 |
| gagagcaatg | ggcagccgga | gaacaactac | aagaccacgc | ctcccgtgct | ggactccgac | 1260 |
| ggctccttct | tcctctacag | caagctcacc | gtggacaaga | gcaggtggca | gcaggggaac | 1320 |
| gtcttctcat | gctccgtgat | gcatgaggct | ctgcacaacc | actacacgca | gaagagcctc | 1380 |
| tccctgtctc | cgggtaaatg | actcgag | | | | 1407 |

<210> SEQ ID NO 66
<211> LENGTH: 460
<212> TYPE: PRT
<213> ORGANISM: Artificial Sequence
<220> FEATURE:
<223> OTHER INFORMATION: Synthetic polypeptide consisting of heavy chain of huAbF46-H4-A1, human IgG2 hinge and constant region of human IgG2

<400> SEQUENCE: 66

```
Met Glu Trp Ser Trp Val Phe Leu Val Thr Leu Leu Asn Gly Ile Gln
 1               5                  10                  15
Cys Glu Val Gln Leu Val Glu Ser Gly Gly Gly Leu Val Gln Pro Gly
            20                  25                  30
Gly Ser Leu Arg Leu Ser Cys Ala Ala Ser Gly Phe Thr Phe Thr Asp
        35                  40                  45
Tyr Tyr Met Ser Trp Val Arg Gln Ala Pro Gly Lys Gly Leu Glu Trp
    50                  55                  60
Leu Gly Phe Ile Arg Asn Lys Ala Asn Gly Tyr Thr Thr Glu Tyr Ser
65                  70                  75                  80
Ala Ser Val Lys Gly Arg Phe Thr Ile Ser Arg Asp Asn Ser Lys Asn
                85                  90                  95
Thr Leu Tyr Leu Gln Met Asn Ser Leu Arg Ala Glu Asp Thr Ala Val
            100                 105                 110
Tyr Tyr Cys Ala Arg Asp Asn Trp Phe Ala Tyr Trp Gly Gln Gly Thr
        115                 120                 125
Leu Val Thr Val Ser Ser Ala Ser Thr Lys Gly Pro Ser Val Phe Pro
    130                 135                 140
Leu Ala Pro Cys Ser Arg Ser Thr Ser Glu Ser Thr Ala Ala Leu Gly
145                 150                 155                 160
Cys Leu Val Lys Asp Tyr Phe Pro Glu Pro Val Thr Val Ser Trp Asn
                165                 170                 175
Ser Gly Ala Leu Thr Ser Gly Val His Thr Phe Pro Ala Val Leu Gln
            180                 185                 190
Ser Ser Gly Leu Tyr Ser Leu Ser Ser Val Val Thr Val Pro Ser Ser
        195                 200                 205
Asn Phe Gly Thr Gln Thr Tyr Thr Cys Asn Val Asp His Lys Pro Ser
    210                 215                 220
Asn Thr Lys Val Asp Lys Thr Val Glu Arg Lys Cys Cys Val Glu Cys
225                 230                 235                 240
Pro Pro Cys Pro Ala Pro Pro Val Ala Gly Pro Ser Val Phe Leu Phe
                245                 250                 255
Pro Pro Lys Pro Lys Asp Thr Leu Met Ile Ser Arg Thr Pro Glu Val
            260                 265                 270
Thr Cys Val Val Val Asp Val Ser His Glu Asp Pro Glu Val Gln Phe
        275                 280                 285
Asn Trp Tyr Val Asp Gly Val Glu Val His Asn Ala Lys Thr Lys Pro
    290                 295                 300
Arg Glu Glu Gln Phe Asn Ser Thr Phe Arg Val Val Ser Val Leu Thr
305                 310                 315                 320
Val Val His Gln Asp Trp Leu Asn Gly Lys Glu Tyr Lys Cys Lys Val
                325                 330                 335
Ser Asn Lys Gly Leu Pro Ala Pro Ile Glu Lys Thr Ile Ser Lys Thr
            340                 345                 350
Lys Gly Gln Pro Arg Glu Pro Gln Val Tyr Thr Leu Pro Pro Ser Arg
```

```
                355                 360                 365
Glu Glu Met Thr Lys Asn Gln Val Ser Leu Thr Cys Leu Val Lys Gly
        370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Met Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
        435                 440                 445

Tyr Thr Gln Lys Ser Leu Ser Leu Ser Pro Gly Lys
450                 455                 460

<210> SEQ ID NO 67
<211> LENGTH: 1404
<212> TYPE: DNA
<213> ORGANISM: Artificial Sequence
<220> FEATURE:
<223> OTHER INFORMATION: Synthetic polynucleotide encoding polypeptide
      consisting of heavy chain of huAbF46-H4-A1, human
      IgG2 hinge and constant region of human IgG2

<400> SEQUENCE: 67
```

| | | | | | |
|---|---|---|---|---|---|
| gaattcgccg | ccaccatgga | atggagctgg | gttttttctcg | taacactttt | aaatggtatc | 60 |
| cagtgtgagg | ttcagctggt | ggagtctggc | ggtggcctgg | tgcagccagg | gggctcactc | 120 |
| cgtttgtcct | gtcagcttc | tggcttcacc | ttcactgatt | actacatgag | ctgggtgcgt | 180 |
| caggccccgg | gtaagggcct | ggaatggttg | ggttttatta | gaaacaaagc | taatggttac | 240 |
| acaacagagt | acagtgcatc | tgtgaagggt | cgtttcacta | taagcagaga | taattccaaa | 300 |
| aacacactgt | acctgcagat | gaacagcctg | cgtgctgagg | acactgccgt | ctattattgt | 360 |
| gctagagata | actggtttgc | ttactggggc | caagggactc | tggtcaccgt | ctcctcggct | 420 |
| agcaccaagg | gcccatcggt | cttccccctg | gcgccctgct | ccaggagcac | ctccgagagc | 480 |
| acagcggccc | tgggctgcct | ggtcaaggac | tacttccccg | aaccggtgac | ggtgtcgtgg | 540 |
| aactcaggcg | ctctgaccag | cggcgtgcac | accttcccag | ctgtcctaca | gtcctcagga | 600 |
| ctctactccc | tcagcagcgt | ggtgaccgtg | ccctccagca | acttcggcac | ccagacctac | 660 |
| acctgcaacg | tagatcacaa | gcccagcaac | accaaggtgg | acaagacagt | tgagcgcaaa | 720 |
| tgttgtgtcg | agtgcccacc | gtgcccagca | ccacctgtgg | caggaccgtc | agtcttcctc | 780 |
| ttccccccaa | aacccaagga | caccctcatg | atctcccgga | ccctgaggt | cacgtgcgtg | 840 |
| gtggtggacg | tgagccacga | agaccccgag | gtccagttca | actggtacgt | ggacggcgtg | 900 |
| gaggtgcata | atgccaagac | aaagccacgg | gaggagcagt | tcaacagcac | gttccgtgtg | 960 |
| gtcagcgtcc | tcaccgttgt | gcaccaggac | tggctgaacg | gcaaggagta | caagtgcaag | 1020 |
| gtctccaaca | aaggcctccc | agcccccatc | gagaaaacca | tctccaaaac | caaagggcag | 1080 |
| ccccgagaac | cacaggtgta | caccctgccc | ccatcccggg | aggagatgac | caagaaccag | 1140 |
| gtcagcctga | cctgcctggt | caaaggcttc | taccccagcg | acatcgccgt | ggagtgggag | 1200 |
| agcaatgggc | agccggagaa | caactacaag | accacgcctc | ccatgctgga | ctccgacggc | 1260 |
| tccttcttcc | tctacagcaa | gctcaccgtg | gacaagagca | ggtggcagca | ggggaacgtc | 1320 |
| ttctcatgct | ccgtgatgca | tgaggctctg | cacaaccact | acacgcagaa | gagcctctcc | 1380 |
| ctgtctccgg | gtaaatgact | cgag | | | | 1404 |

<210> SEQ ID NO 68
<211> LENGTH: 240
<212> TYPE: PRT
<213> ORGANISM: Artificial Sequence
<220> FEATURE:
<223> OTHER INFORMATION: Synthetic polypeptide consisting of light chain
of huAbF46-H4-A1(H36Y) and human kappa constant
region

<400> SEQUENCE: 68

```
Met Asp Ser Gln Ala Gln Val Leu Met Leu Leu Leu Leu Ser Val Ser
  1               5                  10                  15

Gly Thr Cys Gly Asp Ile Gln Met Thr Gln Ser Pro Ser Ser Leu Ser
             20                  25                  30

Ala Ser Val Gly Asp Arg Val Thr Ile Thr Cys Lys Ser Ser Gln Ser
         35                  40                  45

Leu Leu Ala Ser Gly Asn Gln Asn Asn Tyr Leu Ala Trp Tyr Gln Gln
     50                  55                  60

Lys Pro Gly Lys Ala Pro Lys Met Leu Ile Ile Trp Ala Ser Thr Arg
 65                  70                  75                  80

Val Ser Gly Val Pro Ser Arg Phe Ser Gly Ser Gly Ser Gly Thr Asp
                 85                  90                  95

Phe Thr Leu Thr Ile Ser Ser Leu Gln Pro Glu Asp Phe Ala Thr Tyr
            100                 105                 110

Tyr Cys Gln Gln Ser Tyr Ser Arg Pro Tyr Thr Phe Gly Gln Gly Thr
        115                 120                 125

Lys Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240
```

<210> SEQ ID NO 69
<211> LENGTH: 758
<212> TYPE: DNA
<213> ORGANISM: Artificial Sequence
<220> FEATURE:
<223> OTHER INFORMATION: Synthetic polynucleotide encoding polypeptide
consisting of light chain of huAbF46-H4-A1(H36Y)
and human kappa constant region

<400> SEQUENCE: 69

```
aattcactag tgattaattc gccgccacca tggattcaca ggcccaggtc ctcatgttgc     60
tgctgctatc ggtatctggt acctgtggag atatccagat gacccagtcc ccgagctccc    120
tgtccgcctc tgtgggcgat agggtcacca tcacctgcaa gtccagtcag agtcttttag    180
ctagtggcaa ccaaaataac tacttggcct ggtaccaaca gaaaccagga aaagctccga    240
aaatgctgat tatttgggca tccactaggg tatctggagt cccttctcgc ttctctggat    300
```

```
ccgggtctgg gacggatttc actctgacca tcagcagtct gcagccggaa gacttcgcaa    360
cttattactg tcagcagtcc tacagccgcc cgtacacgtt cggacagggt accaaggtgg    420
agatcaaacg tacggtggct gcaccatctg tcttcatctt cccgccatct gatgagcagt    480
tgaaatctgg aactgcctct gttgtgtgcc tgctgaataa cttctatccc agagaggcca    540
aagtacagtg gaaggtggat aacgccctcc aatcgggtaa ctcccaggag agtgtcacag    600
agcaggacag caaggacagc acctacagcc tcagcagcac cctgacgctg agcaaagcag    660
actacgagaa acacaaagtc tacgcctgcg aagtcaccca tcagggcctg agctcgcccg    720
tcacaaagag cttcaacagg ggagagtgtt gactcgag                            758
```

<210> SEQ ID NO 70
<211> LENGTH: 240
<212> TYPE: PRT
<213> ORGANISM: Artificial Sequence
<220> FEATURE:
<223> OTHER INFORMATION: Synthetic polypeptide consisting of light chain
    of huAbF46-H4-A1 and human kappa constant region

<400> SEQUENCE: 70

```
Met Asp Ser Gln Ala Gln Val Leu Met Leu Leu Leu Leu Ser Val Ser
1               5                   10                  15

Gly Thr Cys Gly Asp Ile Gln Met Thr Gln Ser Pro Ser Ser Leu Ser
                20                  25                  30

Ala Ser Val Gly Asp Arg Val Thr Ile Thr Cys Lys Ser Ser Gln Ser
            35                  40                  45

Leu Leu Ala Ser Gly Asn Gln Asn Asn Tyr Leu Ala Trp His Gln Gln
        50                  55                  60

Lys Pro Gly Lys Ala Pro Lys Met Leu Ile Ile Trp Ala Ser Thr Arg
65                  70                  75                  80

Val Ser Gly Val Pro Ser Arg Phe Ser Gly Ser Gly Ser Gly Thr Asp
                85                  90                  95

Phe Thr Leu Thr Ile Ser Ser Leu Gln Pro Glu Asp Phe Ala Thr Tyr
                100                 105                 110

Tyr Cys Gln Gln Ser Tyr Ser Arg Pro Tyr Thr Phe Gly Gln Gly Thr
            115                 120                 125

Lys Val Glu Ile Lys Arg Thr Val Ala Ala Pro Ser Val Phe Ile Phe
130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240
```

<210> SEQ ID NO 71
<211> LENGTH: 19
<212> TYPE: PRT
<213> ORGANISM: Artificial Sequence
<220> FEATURE:

```
<223> OTHER INFORMATION: Synthetic epitope in SEMA domain of c-Met

<400> SEQUENCE: 71

Phe Ser Pro Gln Ile Glu Glu Pro Ser Gln Cys Pro Asp Cys Val Val
 1               5                  10                  15

Ser Ala Leu

<210> SEQ ID NO 72
<211> LENGTH: 10
<212> TYPE: PRT
<213> ORGANISM: Artificial Sequence
<220> FEATURE:
<223> OTHER INFORMATION: Synthetic epitope in SEMA domain of c-Met

<400> SEQUENCE: 72

Pro Gln Ile Glu Glu Pro Ser Gln Cys Pro
 1               5                  10

<210> SEQ ID NO 73
<211> LENGTH: 5
<212> TYPE: PRT
<213> ORGANISM: Artificial Sequence
<220> FEATURE:
<223> OTHER INFORMATION: Synthetic epitope in SEMA domain of c-Met

<400> SEQUENCE: 73

Glu Glu Pro Ser Gln
 1               5

<210> SEQ ID NO 74
<211> LENGTH: 117
<212> TYPE: PRT
<213> ORGANISM: Artificial Sequence
<220> FEATURE:
<223> OTHER INFORMATION: Synthetic heavy chain variable region of
      anti-c-Met antibody (AbF46 or huAbF46-H1)

<400> SEQUENCE: 74

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Asp Tyr
             20                  25                  30

Tyr Met Ser Trp Val Arg Gln Ala Pro Gly Lys Gly Leu Glu Trp Leu
         35                  40                  45

Gly Phe Ile Arg Asn Lys Ala Asn Gly Tyr Thr Thr Glu Tyr Ser Ala
     50                  55                  60

Ser Val Lys Gly Arg Phe Thr Ile Ser Arg Asp Asn Ser Lys Asn Ser
 65                  70                  75                  80

Leu Tyr Leu Gln Met Asn Ser Leu Lys Thr Glu Asp Thr Ala Val Tyr
                 85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 75
<211> LENGTH: 114
<212> TYPE: PRT
<213> ORGANISM: Artificial Sequence
<220> FEATURE:
<223> OTHER INFORMATION: Synthetic light chain variable region of
      anti-c-Met antibody (AbF46 or huAbF46-H1)
```

<400> SEQUENCE: 75

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
                20                  25                  30

Gly Asn Gln Asn Asn Tyr Leu Ala Trp His Gln Lys Pro Gly Gln
            35                  40                  45

Pro Pro Lys Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gly Gly Thr Lys Val Glu Ile
            100                 105                 110

Lys Arg

<210> SEQ ID NO 76
<211> LENGTH: 1416
<212> TYPE: DNA
<213> ORGANISM: Artificial Sequence
<220> FEATURE:
<223> OTHER INFORMATION: Synthetic nucleotide sequence of heavy chain of
      anti-c-Met antibody (AbF46 or huAbF46-H1)
<220> FEATURE:
<221> NAME/KEY: misc_feature
<222> LOCATION: (1)..(6)
<223> OTHER INFORMATION: EcoRI restriction site
<220> FEATURE:
<221> NAME/KEY: misc_feature
<222> LOCATION: (7)..(66)
<223> OTHER INFORMATION: signal sequence
<220> FEATURE:
<221> NAME/KEY: misc_feature
<222> LOCATION: (67)..(417)
<223> OTHER INFORMATION: VH - heavy chain variable region
<220> FEATURE:
<221> NAME/KEY: misc_feature
<222> LOCATION: (418)..(423)
<223> OTHER INFORMATION: NdeI restriction site
<220> FEATURE:
<221> NAME/KEY: misc_feature
<222> LOCATION: (418)..(1407)
<223> OTHER INFORMATION: CH - heavy chain constant region
<220> FEATURE:
<221> NAME/KEY: misc_feature
<222> LOCATION: (1408)..(1410)
<223> OTHER INFORMATION: TGA - stop codon
<220> FEATURE:
<221> NAME/KEY: misc_feature
<222> LOCATION: (1411)..(1416)
<223> OTHER INFORMATION: XhoI restriction site

<400> SEQUENCE: 76
gaattcgccg ccaccatgga atggagctgg gttttctcg taacactttt aaatggtatc      60
cagtgtgagg tgaagctggt ggagtctgga ggaggcttgg tacagcctgg ggttctctg    120 agactctcct gtgcaacttc tgggttcacc ttcactgatt actacatgag ctgggtccgc    180
cagcctccag aaaggcact tgagtggttg ggttttatta aaacaaagc taatggttac     240 acaacagagt acagtgcatc tgtgaagggt cggttcacca tctccagaga taattcccaa    300
agcatcctct atcttcaaat ggacaccctg agagctgagg acagtgccac ttattactgt    360
gcaagagata actggtttgc ttactggggc caagggactc tggtcactgt ctctgcagct    420
agcaccaagg gcccatcggt cttccccctg gcaccctcct ccaagagcac ctctgggggc    480

-continued

```
acagcggccc tgggctgcct ggtcaaggac tacttcccg aaccggtgac ggtgtcgtgg      540
aactcaggcg ccctgaccag cggcgtgcac accttcccgg ctgtcctaca gtcctcagga      600
ctctactccc tcagcagcgt ggtgaccgtg ccctccagca gcttgggcac ccagacctac      660
atctgcaacg tgaatcacaa gcccagcaac accaaggtgg acaagaaagt tgagcccaaa      720
tcttgtgaca aaactcacac atgcccaccg tgcccagcac ctgaactcct ggggggaccg      780
tcagtcttcc tcttcccccc aaaacccaag gacaccctca tgatctcccg gacccctgag      840
gtcacatgcg tggtggtgga cgtgagccac gaagaccctg aggtcaagtt caactggtac      900
gtggacggcg tggaggtgca taatgccaag acaaagccgc gggaggagca gtacaacagc      960
acgtaccgtg tggtcagcgt cctcaccgtc ctgcaccagg actggctgaa tggcaaggag     1020
tacaagtgca aggtctccaa caaagccctc ccagccccca tcgagaaaac catctccaaa     1080
gccaaagggc agccccgaga accacaggtg tacaccctgc ccccatcccg ggaggagatg     1140
accaagaacc aggtcagcct gacctgcctg gtcaaaggct tctatcccag cgacatcgcc     1200
gtggagtggg agagcaatgg gcagccggag aacaactaca agaccacgcc tcccgtgctg     1260
gactccgacg gctccttctt cctctacagc aagctcaccg tggacaagag caggtggcag     1320
caggggaacg tcttctcatg ctccgtgatg catgaggctc tgcacaacca ctacacgcag     1380
aagagcctct ccctgtctcc gggtaaatga ctcgag                               1416
```

<210> SEQ ID NO 77
<211> LENGTH: 759
<212> TYPE: DNA
<213> ORGANISM: Artificial Sequence
<220> FEATURE:
<223> OTHER INFORMATION: Synthetic nucleotide sequence of light chain of
      anti-c-Met antibody (AbF46 or huAbF46-H1)
<220> FEATURE:
<221> NAME/KEY: misc_difference
<222> LOCATION: (1)..(6)
<223> OTHER INFORMATION: EcoRI restriction site
<220> FEATURE:
<221> NAME/KEY: misc_difference
<222> LOCATION: (7)..(90)
<223> OTHER INFORMATION: signal sequence
<220> FEATURE:
<221> NAME/KEY: misc_difference
<222> LOCATION: (91)..(432)
<223> OTHER INFORMATION: VL - light chain variable region
<220> FEATURE:
<221> NAME/KEY: misc_difference
<222> LOCATION: (430)..(435)
<223> OTHER INFORMATION: BsiWI restriction site
<220> FEATURE:
<221> NAME/KEY: misc_difference
<222> LOCATION: (433)..(750)
<223> OTHER INFORMATION: CL - light chain constant region
<220> FEATURE:
<221> NAME/KEY: misc_difference
<222> LOCATION: (751)..(753)
<223> OTHER INFORMATION: stop codon
<220> FEATURE:
<221> NAME/KEY: misc_difference
<222> LOCATION: (754)..(759)
<223> OTHER INFORMATION: XhoI restriction site

<400> SEQUENCE: 77

```
gaattcacta gtgattaatt cgccgccacc atggattcac aggcccaggt cctcatgttg       60
ctgctgctat cggtatctgg tacctgtgga gacattttga tgacccagtc tccatcctcc      120
ctgactgtgt cagcaggaga gaaggtcact atgagctgca gtccagtcaa gagtcttta      180 gctagtggca accaaaataa ctacttggcc tggcaccagc agaaaccagg acgatctcct      240
```

| | |
|---|---:|
| aaaatgctga taatttgggc atccactagg gtatctggag tccctgatcg cttcataggc | 300 |
| agtggatctg ggacggattt cactctgacc atcaacagtg tgcaggctga agatctggct | 360 |
| gtttattact gtcagcagtc ctacagcgct ccgctcacgt tcggtgctgg gaccaagctg | 420 |
| gagctgaaac gtacggtggc tgcaccatct gtcttcatct tcccgccatc tgatgagcag | 480 |
| ttgaaatctg gaactgcctc tgttgtgtgc ctgctgaata acttctatcc cagagaggcc | 540 |
| aaagtacagt ggaaggtgga taacgccctc caatcgggta actcccagga gagtgtcaca | 600 |
| gagcaggaca gcaaggacag cacctacagc ctcagcagca ccctgacgct gagcaaagca | 660 |
| gactacgaga aacacaaagt ctacgcctgc gaagtcaccc atcagggcct gagctcgccc | 720 |
| gtcacaaaga gcttcaacag gggagagtgt tgactcgag | 759 |

<210> SEQ ID NO 78
<211> LENGTH: 4170
<212> TYPE: DNA
<213> ORGANISM: Artificial Sequence
<220> FEATURE:
<223> OTHER INFORMATION: Synthetic polynucleotide encoding c-Met protein

<400> SEQUENCE: 78

| | |
|---|---:|
| atgaaggccc ccgctgtgct tgcacctggc atcctcgtgc tcctgtttac cttggtgcag | 60 |
| aggagcaatg gggagtgtaa agaggcacta gcaaagtccg agatgaatgt gaatatgaag | 120 |
| tatcagcttc ccaacttcac cgcggaaaca cccatccaga atgtcattct acatgagcat | 180 |
| cacattttcc ttggtgccac taactacatt tatgttttaa atgaggaaga ccttcagaag | 240 |
| gttgctgagt acaagactgg gcctgtgctg gaacacccag attgtttccc atgtcaggac | 300 |
| tgcagcagca agccaatttt atcaggaggt gtttggaaag ataacatcaa catggctcta | 360 |
| gttgtcgaca cctactatga tgatcaactc attagctgtg gcagcgtcaa cagagggacc | 420 |
| tgccagcgac atgtctttcc ccacaatcat actgctgaca tacagtcgga ggttcactgc | 480 |
| atattctccc cacagataga agagcccagc cagtgtcctg actgtgtggt gagcgccctg | 540 |
| ggagccaaag tcctttcatc tgtaaaggac cggttcatca acttctttgt aggcaatacc | 600 |
| ataaattctt cttatttccc agatcatcca ttgcattcga tatcagtgag aaggctaaag | 660 |
| gaaacgaaag atggttttat gttttttgacg gaccagtcct acattgatgt tttacctgag | 720 |
| ttcagagatt cttaccccat taagtatgtc catgcctttg aaagcaacaa ttttatttac | 780 |
| ttcttgacgg tccaaaggga aactctagat gctcagactt tcacacaag aataatcagg | 840 |
| ttctgttcca taaactctgg attgcattcc tacatggaaa tgcctctgga gtgtattctc | 900 |
| acagaaaaga gaaaaagag atccacaaag aaggaagtgt taatatact tcaggctgcg | 960 |
| tatgtcagca agcctggggc ccagcttgct agacaaatag gagccagcct gaatgatgac | 1020 |
| attcttttcg gggtgttcgc acaaagcaag ccagattctg ccgaaccaat ggatcgatct | 1080 |
| gccatgtgtg cattccctat caaatatgtc aacgacttct tcaacaagat cgtcaacaaa | 1140 |
| aacaatgtga atgtctcca gcatttttac ggacccaatc atgagcactg ctttaatagg | 1200 |
| acacttctga aaattcatc aggctgtgaa gcgcgccgtg atgaatatcg aacagagttt | 1260 |
| accacagctt tgcagcgcgt tgacttattc atgggtcaat tcagcgaagt cctcttaaca | 1320 |
| tctatatcca ccttcattaa aggagacctc accatagcta atcttgggac atcagagggt | 1380 |
| cgcttcatgc aggttgtggt ttctcgatca ggaccatcaa cccctcatgt gaattttctc | 1440 |
| ctggactccca atccagtgtc tccagaagtg attgtggagc atacattaaa ccaaaatggc | 1500 |

```
tacacactgg ttatcactgg gaagaagatc acgaagatcc cattgaatgg cttgggctgc    1560
agacatttcc agtcctgcag tcaatgcctc tctgccccac cctttgttca gtgtggctgg    1620
tgccacgaca aatgtgtgcg atcggaggaa tgcctgagcg ggacatggac tcaacagatc    1680
tgtctgcctg caatctacaa ggttttccca aatagtgcac cccttgaagg agggacaagg    1740
ctgaccatat gtggctggga ctttggattt cggaggaata ataaatttga tttaaagaaa    1800
actagagttc tccttggaaa tgagagctgc accttgactt taagtgagag cacgatgaat    1860
acattgaaat gcacagttgg tcctgccatg aataagcatt tcaatatgtc cataattatt    1920
tcaaatggcc acgggacaac acaatacagt acattctcct atgtggatcc tgtaataaca    1980
agtatttcgc cgaaatacgg tcctatggct ggtggcactt tacttacttt aactggaaat    2040
tacctaaaca gtgggaattc tagacacatt tcaattggtg aaaaacatg tactttaaaa    2100
agtgtgtcaa acagtattct tgaatgttat accccagccc aaaccatttc aactgagttt    2160
gctgttaaat tgaaaattga cttagccaac cgagagacaa gcatcttcag ttaccgtgaa    2220
gatcccattg tctatgaaat tcatccaacc aaatctttta ttagtggtgg gagcacaata    2280
acaggtgttg ggaaaaacct gaattcagtt agtgtcccga gaatggtcat aaatgtgcat    2340
gaagcaggaa ggaactttac agtggcatgt caacatcgct ctaattcaga gataatctgt    2400
tgtaccactc cttccctgca acagctgaat ctgcaactcc ccctgaaaac caaagccttt    2460
ttcatgttag atgggatcct ttccaaatac tttgatctca tttatgtaca taatcctgtg    2520
tttaagcctt tgaaaagcc agtgatgatc tcaatgggca atgaaaatgt actggaaatt    2580
aagggaaatg atattgaccc tgaagcagtt aaaggtgaag tgttaaaagt tggaaataag    2640
agctgtgaga atatacactt acattctgaa gccgttttat gcacggtccc caatgacctg    2700
ctgaaattga acagcgagct aaatatagag tggaagcaag caatttcttc aaccgtcctt    2760
ggaaaagtaa tagttcaacc agatcagaat ttcacaggat tgattgctgg tgttgtctca    2820
atatcaacag cactgttatt actacttggg tttttcctgt ggctgaaaaa gagaaagcaa    2880
attaaagatc tgggcagtga attagttcgc tacgatgcaa gagtacacac tcctcatttg    2940
gataggcttg taagtgcccg aagtgtaagc ccaactacag aaatggtttc aaatgaatct    3000
gtagactacc gagctacttt tccagaagat cagtttccta attcatctca gaacggttca    3060
tgccgacaag tgcagtatcc tctgacagac atgtccccca tcctaactag tggggactct    3120
gatatatcca gtccattact gcaaaatact gtccacattg acctcagtgc tctaaatcca    3180
gagctggtcc aggcagtgca gcatgtagtg attgggccca gtagcctgat tgtgcatttc    3240
aatgaagtca taggaagagg gcattttggt tgtgtatatc atgggacttt gttggacaat    3300
gatggcaaga aaattcactg tgctgtgaaa tccttgaaca gaatcactga cataggagaa    3360
gtttcccaat ttctgaccga gggaatcatc atgaaagatt ttagtcatcc caatgtcctc    3420
tcgctcctgg gaatctgcct gcgaagtgaa gggtctccgc tggtggtcct accatacatg    3480
aaacatggag atcttcgaaa tttcattcga atgagactc ataatccaac tgtaaaagat    3540
cttattggct ttggtcttca agtagccaaa ggcatgaaat atcttgcaag caaaaagttt    3600
gtccacagag acttggctgc aagaaactgt atgctggatg aaaaattcac agtcaaggtt    3660
gctgattttg gtcttgccag agacatgtat gataaagaat actatagtgt acacaacaaa    3720
acaggtgcaa agctgccagt gaagtggatg gctttggaaa gtctgcaaac tcaaaagttt    3780
accaccaagt cagatgtgtg gtcctttggc gtgctcctct gggagctgat gacaagagga    3840
gccccacctt atcctgacgt aaacacctt gatataactg tttacttgtt gcaagggaga    3900
```

```
agactcctac aacccgaata ctgcccagac cccttatatg aagtaatgct aaaatgctgg    3960
caccctaaag ccgaaatgcg cccatccttt tctgaactgg tgtcccggat atcagcgatc    4020
ttctctactt tcattgggga gcactatgtc catgtgaacg ctacttatgt gaacgtaaaa    4080
tgtgtcgctc cgtatccttc tctgttgtca tcagaagata cgctgatga tgaggtggac    4140 acacgaccag cctccttctg ggagacatca                                    4170
```

<210> SEQ ID NO 79
<211> LENGTH: 444
<212> TYPE: PRT
<213> ORGANISM: Artificial Sequence
<220> FEATURE:
<223> OTHER INFORMATION: Synthetic SEMA domain of c-Met

<400> SEQUENCE: 79

```
Leu His Glu His His Ile Phe Leu Gly Ala Thr Asn Tyr Ile Tyr Val
  1               5                  10                  15

Leu Asn Glu Glu Asp Leu Gln Lys Val Ala Glu Tyr Lys Thr Gly Pro
             20                  25                  30

Val Leu Glu His Pro Asp Cys Phe Pro Cys Gln Asp Cys Ser Ser Lys
         35                  40                  45

Ala Asn Leu Ser Gly Gly Val Trp Lys Asp Asn Ile Asn Met Ala Leu
     50                  55                  60

Val Val Asp Thr Tyr Tyr Asp Asp Gln Leu Ile Ser Cys Gly Ser Val
 65                  70                  75                  80

Asn Arg Gly Thr Cys Gln Arg His Val Phe Pro His Asn His Thr Ala
                 85                  90                  95

Asp Ile Gln Ser Glu Val His Cys Ile Phe Ser Pro Gln Ile Glu Glu
            100                 105                 110

Pro Ser Gln Cys Pro Asp Cys Val Val Ser Ala Leu Gly Ala Lys Val
        115                 120                 125

Leu Ser Ser Val Lys Asp Arg Phe Ile Asn Phe Val Gly Asn Thr
    130                 135                 140

Ile Asn Ser Ser Tyr Phe Pro Asp His Pro Leu His Ser Ile Ser Val
145                 150                 155                 160

Arg Arg Leu Lys Glu Thr Lys Asp Gly Phe Met Phe Leu Thr Asp Gln
                165                 170                 175

Ser Tyr Ile Asp Val Leu Pro Glu Phe Arg Asp Ser Tyr Pro Ile Lys
            180                 185                 190

Tyr Val His Ala Phe Glu Ser Asn Asn Phe Ile Tyr Phe Leu Thr Val
        195                 200                 205

Gln Arg Glu Thr Leu Asp Ala Gln Thr Phe His Thr Arg Ile Ile Arg
    210                 215                 220

Phe Cys Ser Ile Asn Ser Gly Leu His Ser Tyr Met Glu Met Pro Leu
225                 230                 235                 240

Glu Cys Ile Leu Thr Glu Lys Arg Lys Lys Arg Ser Thr Lys Lys Glu
                245                 250                 255

Val Phe Asn Ile Leu Gln Ala Ala Tyr Val Ser Lys Pro Gly Ala Gln
            260                 265                 270

Leu Ala Arg Gln Ile Gly Ala Ser Leu Asn Asp Asp Ile Leu Phe Gly
        275                 280                 285

Val Phe Ala Gln Ser Lys Pro Asp Ser Ala Glu Pro Met Asp Arg Ser
    290                 295                 300

Ala Met Cys Ala Phe Pro Ile Lys Tyr Val Asn Asp Phe Phe Asn Lys
```

```
                305                 310                 315                 320
Ile Val Asn Lys Asn Asn Val Arg Cys Leu Gln His Phe Tyr Gly Pro
                    325                 330                 335

Asn His Glu His Cys Phe Asn Arg Thr Leu Leu Arg Asn Ser Ser Gly
                340                 345                 350

Cys Glu Ala Arg Arg Asp Glu Tyr Arg Thr Glu Phe Thr Thr Ala Leu
            355                 360                 365

Gln Arg Val Asp Leu Phe Met Gly Gln Phe Ser Glu Val Leu Leu Thr
        370                 375                 380

Ser Ile Ser Thr Phe Ile Lys Gly Asp Leu Thr Ile Ala Asn Leu Gly
385                 390                 395                 400

Thr Ser Glu Gly Arg Phe Met Gln Val Val Ser Arg Ser Gly Pro
                405                 410                 415

Ser Thr Pro His Val Asn Phe Leu Leu Asp Ser His Pro Val Ser Pro
                420                 425                 430

Glu Val Ile Val Glu His Thr Leu Asn Gln Asn Gly
            435                 440

<210> SEQ ID NO 80
<211> LENGTH: 451
<212> TYPE: PRT
<213> ORGANISM: Artificial Sequence
<220> FEATURE:
<223> OTHER INFORMATION: Synthetic PSI-IPT domain of c-Met

<400> SEQUENCE: 80

Tyr Thr Leu Val Ile Thr Gly Lys Lys Ile Thr Lys Ile Pro Leu Asn
 1               5                  10                  15

Gly Leu Gly Cys Arg His Phe Gln Ser Cys Ser Gln Cys Leu Ser Ala
                20                  25                  30

Pro Pro Phe Val Gln Cys Gly Trp Cys His Asp Lys Cys Val Arg Ser
            35                  40                  45

Glu Glu Cys Leu Ser Gly Thr Trp Thr Gln Gln Ile Cys Leu Pro Ala
    50                  55                  60

Ile Tyr Lys Val Phe Pro Asn Ser Ala Pro Leu Glu Gly Gly Thr Arg
65                  70                  75                  80

Leu Thr Ile Cys Gly Trp Asp Phe Gly Phe Arg Arg Asn Asn Lys Phe
                85                  90                  95

Asp Leu Lys Lys Thr Arg Val Leu Leu Gly Asn Glu Ser Cys Thr Leu
            100                 105                 110

Thr Leu Ser Glu Ser Thr Met Asn Thr Leu Lys Cys Thr Val Gly Pro
        115                 120                 125

Ala Met Asn Lys His Phe Asn Met Ser Ile Ile Ile Ser Asn Gly His
    130                 135                 140

Gly Thr Thr Gln Tyr Ser Thr Phe Ser Tyr Val Asp Pro Val Ile Thr
145                 150                 155                 160

Ser Ile Ser Pro Lys Tyr Gly Pro Met Ala Gly Gly Thr Leu Leu Thr
                165                 170                 175

Leu Thr Gly Asn Tyr Leu Asn Ser Gly Asn Ser Arg His Ile Ser Ile
            180                 185                 190

Gly Gly Lys Thr Cys Thr Leu Lys Ser Val Ser Asn Ser Ile Leu Glu
        195                 200                 205

Cys Tyr Thr Pro Ala Gln Thr Ile Ser Thr Glu Phe Ala Val Lys Leu
    210                 215                 220

Lys Ile Asp Leu Ala Asn Arg Glu Thr Ser Ile Phe Ser Tyr Arg Glu
```

-continued

```
                225                 230                 235                 240
Asp Pro Ile Val Tyr Glu Ile His Pro Thr Lys Ser Phe Ile Ser Thr
                    245                 250                 255

Trp Trp Lys Glu Pro Leu Asn Ile Val Ser Phe Leu Phe Cys Phe Ala
                    260                 265                 270

Ser Gly Gly Ser Thr Ile Thr Gly Val Gly Lys Asn Leu Asn Ser Val
                    275                 280                 285

Ser Val Pro Arg Met Val Ile Asn Val His Glu Ala Gly Arg Asn Phe
                    290                 295                 300

Thr Val Ala Cys Gln His Arg Ser Asn Ser Glu Ile Ile Cys Cys Thr
305                 310                 315                 320

Thr Pro Ser Leu Gln Gln Leu Asn Leu Gln Leu Pro Leu Lys Thr Lys
                    325                 330                 335

Ala Phe Phe Met Leu Asp Gly Ile Leu Ser Lys Tyr Phe Asp Leu Ile
                    340                 345                 350

Tyr Val His Asn Pro Val Phe Lys Pro Phe Glu Lys Pro Val Met Ile
                    355                 360                 365

Ser Met Gly Asn Glu Asn Val Leu Glu Ile Lys Gly Asn Asp Ile Asp
                370                 375                 380

Pro Glu Ala Val Lys Gly Glu Val Leu Lys Val Gly Asn Lys Ser Cys
385                 390                 395                 400

Glu Asn Ile His Leu His Ser Glu Ala Val Leu Cys Thr Val Pro Asn
                    405                 410                 415

Asp Leu Leu Lys Leu Asn Ser Glu Leu Asn Ile Glu Trp Lys Gln Ala
                    420                 425                 430

Ile Ser Ser Thr Val Leu Gly Lys Val Ile Val Gln Pro Asp Gln Asn
                    435                 440                 445

Phe Thr Gly
        450

<210> SEQ ID NO 81
<211> LENGTH: 313
<212> TYPE: PRT
<213> ORGANISM: Artificial Sequence
<220> FEATURE:
<223> OTHER INFORMATION: Synthetic TyrKc domain of c-Met

<400> SEQUENCE: 81

Val His Phe Asn Glu Val Ile Gly Arg Gly His Phe Gly Cys Val Tyr
1               5                   10                  15

His Gly Thr Leu Leu Asp Asn Asp Gly Lys Lys Ile His Cys Ala Val
                    20                  25                  30

Lys Ser Leu Asn Arg Ile Thr Asp Ile Gly Glu Val Ser Gln Phe Leu
                    35                  40                  45

Thr Glu Gly Ile Ile Met Lys Asp Phe Ser His Pro Asn Val Leu Ser
                50                  55                  60

Leu Leu Gly Ile Cys Leu Arg Ser Glu Gly Ser Pro Leu Val Val Leu
65                  70                  75                  80

Pro Tyr Met Lys His Gly Asp Leu Arg Asn Phe Ile Arg Asn Glu Thr
                    85                  90                  95

His Asn Pro Thr Val Lys Asp Leu Ile Gly Phe Gly Leu Gln Val Ala
                    100                 105                 110

Lys Gly Met Lys Tyr Leu Ala Ser Lys Lys Phe Val His Arg Asp Leu
                    115                 120                 125

Ala Ala Arg Asn Cys Met Leu Asp Glu Lys Phe Thr Val Lys Val Ala
```

```
                130                 135                 140
Asp Phe Gly Leu Ala Arg Asp Met Tyr Asp Lys Glu Tyr Tyr Ser Val
145                 150                 155                 160

His Asn Lys Thr Gly Ala Lys Leu Pro Val Lys Trp Met Ala Leu Glu
                165                 170                 175

Ser Leu Gln Thr Gln Lys Phe Thr Thr Lys Ser Asp Val Trp Ser Phe
            180                 185                 190

Gly Val Leu Leu Trp Glu Leu Met Thr Arg Gly Ala Pro Pro Tyr Pro
        195                 200                 205

Asp Val Asn Thr Phe Asp Ile Thr Val Tyr Leu Leu Gln Gly Arg Arg
    210                 215                 220

Leu Leu Gln Pro Glu Tyr Cys Pro Asp Pro Leu Tyr Glu Val Met Leu
225                 230                 235                 240

Lys Cys Trp His Pro Lys Ala Glu Met Arg Pro Ser Phe Ser Glu Leu
                245                 250                 255

Val Ser Arg Ile Ser Ala Ile Phe Ser Thr Phe Ile Gly Glu His Tyr
            260                 265                 270

Val His Val Asn Ala Thr Tyr Val Asn Val Lys Cys Val Ala Pro Tyr
        275                 280                 285

Pro Ser Leu Leu Ser Ser Glu Asp Asn Ala Asp Asp Glu Val Asp Thr
    290                 295                 300

Arg Pro Ala Ser Phe Trp Glu Thr Ser
305                 310

<210> SEQ ID NO 82
<211> LENGTH: 1332
<212> TYPE: DNA
<213> ORGANISM: Artificial Sequence
<220> FEATURE:
<223> OTHER INFORMATION: Synthetic polynucleotide encoding SEMA domain
      of c-Met

<400> SEQUENCE: 82
ctacatgagc atcacatttt ccttggtgcc actaactaca tttatgtttt aaatgaggaa      60
gaccttcaga aggttgctga gtacaagact gggcctgtgc tggaacaccc agattgtttc     120
ccatgtcagg actgcagcag caaagccaat ttatcaggag gtgtttggaa agataacatc     180
aacatggctc tagttgtcga cacctactat gatgatcaac tcattagctg tggcagcgtc     240
aacagaggga cctgccagcg acatgtcttt ccccacaatc atactgctga catacagtcg     300
gaggttcact gcatattctc cccacagata gaagagccca gccagtgtcc tgactgtgtg     360
gtgagcgccc tgggagccaa agtcctttca tctgtaaagg accggttcat caacttcttt     420
gtaggcaata ccataaattc ttcttatttc ccagatcatc cattgcattc gatatcagtg     480
agaaggctaa aggaaacgaa gatggttttt atgttttga cggaccagtc ctacattgat     540
gttttacctg agttcagaga ttcttacccc attaagtatg tccatgcctt gaaaagcaac     600
aattttattt acttcttgac ggtccaaagg gaaactctag atgctcagac ttttcacaca     660
agaataatca ggttctgttc cataaactct ggattgcatt cctacatgga aatgcctctg     720
gagtgtattc tcacagaaaa agagaaaaag agatccacaa gaaggaagt gtttaatata     780 cttcaggctg cgtatgtcag caagcctggg gcccagcttg ctagacaaat aggagccagc     840
ctgaatgatg acattctttt cggggtgttc gcacaaagca agccagattc tgccgaacca     900
atggatcgat ctgccatgtg tgcattccct atcaaatatg tcaacgactt cttcaacaag     960
atcgtcaaca aaaacaatgt gagatgtctc cagcattttt acggacccaa tcatgagcac    1020
```

```
tgctttaata ggacacttct gagaaattca tcaggctgtg aagcgcgccg tgatgaatat    1080
cgaacagagt ttaccacagc tttgcagcgc gttgacttat tcatgggtca attcagcgaa    1140
gtcctcttaa catctatatc caccttcatt aaaggagacc tcaccatagc taatcttggg    1200
acatcagagg gtcgcttcat gcaggttgtg gtttctcgat caggaccatc aaccctcat    1260 gtgaattttc tcctggactc ccatccagtg tctccagaag tgattgtgga gcatacatta    1320
aaccaaaatg gc                                                         1332

<210> SEQ ID NO 83
<211> LENGTH: 1299
<212> TYPE: DNA
<213> ORGANISM: Artificial Sequence
<220> FEATURE:
<223> OTHER INFORMATION: Synthetic polynucleotide encoding PSI-IPT
      domain of c-Met

<400> SEQUENCE: 83
tacacactgg ttatcactgg gaagaagatc acgaagatcc cattgaatgg cttgggctgc      60
agacatttcc agtcctgcag tcaatgcctc tctgccccac cctttgttca gtgtggctgg    120
tgccacgaca aatgtgtgcg atcggaggaa tgcctgagcg ggacatggac tcaacagatc    180
tgtctgcctg caatctacaa ggttttccca aatagtgcac cccttgaagg agggacaagg    240
ctgaccatat gtggctggga cttggatttt cggaggaata taaatttga tttaaagaaa      300 actagagttc tccttggaaa tgagagctgc accttgactt taagtgagag cacgatgaat    360
acattgaaat gcacagttgg tcctgccatg aataagcatt tcaatatgtc cataattatt    420
tcaaatgggc acgggacaac acaatacagt acattctcct atgtggatcc tgtaataaca    480
agtatttcgc cgaaatacgg tcctatggct ggtggcactt tacttacttt aactggaaat    540
tacctaaaca gtgggaattc tagacacatt tcaattggtg aaaaacatg tactttaaaa    600 agtgtgtcaa acagtattct tgaatgttat accccagccc aaaccatttc aactgagttt    660
gctgttaaat tgaaaattga cttagccaac cgagagacaa gcatcttcag ttaccgtgaa    720
gatcccattg tctatgaaat tcatccaacc aaatctttta ttagtggtgg agcacaata    780 acaggtgttg ggaaaaacct gaattcagtt agtgtcccga gaatggtcat aaatgtgcat    840
gaagcaggaa ggaactttac agtggcatgt caacatcgct ctaattcaga gataatctgt    900
tgtaccactc cttccctgca acagctgaat ctgcaactcc cctgaaaac caaagccttt    960 ttcatgttag atgggatcct ttccaaatac tttgatctca tttatgtaca taatcctgtg   1020
tttaagcctt tgaaaagcc agtgatgatc tcaatgggca atgaaaatgt actggaaatt    1080
aagggaaatg atattgaccc tgaagcagtt aaaggtgaag tgttaaaagt tggaaataag   1140
agctgtgaga atatacactt acattctgaa gccgttttat gcacggtccc caatgacctg   1200
ctgaaattga acagcgagct aaatatagag tggaagcaag caatttcttc aaccgtcctt    1260
ggaaaagtaa tagttcaacc agatcagaat ttcacagga                          1299

<210> SEQ ID NO 84
<211> LENGTH: 939
<212> TYPE: DNA
<213> ORGANISM: Artificial Sequence
<220> FEATURE:
<223> OTHER INFORMATION: Synthetic polynucleotide encoding TyrKc domain
      of c-Met

<400> SEQUENCE: 84
```

```
gtgcatttca atgaagtcat aggaagaggg catttggtt gtgtatatca tgggactttg      60
ttggacaatg atgcaagaa aattcactgt gctgtgaaat ccttgaacag aatcactgac     120
ataggagaag tttcccaatt tctgaccgag ggaatcatca tgaaagattt tagtcatccc     180
aatgtcctct cgctcctggg aatctgcctg cgaagtgaag ggtctccgct ggtggtccta     240
ccatacatga acatggaga tcttcgaaat tcattcgaa atgagactca taatccaact       300
gtaaaagatc ttattggctt tggtcttcaa gtagccaaag catgaaata tcttgcaagc     360 aaaaagtttg tccacagaga cttggctgca agaaactgta tgctggatga aaaattcaca     420
gtcaaggttg ctgattttgg tcttgccaga gacatgtatg ataaagaata ctatagtgta     480
cacaacaaaa caggtgcaaa gctgccagtg aagtggatgg ctttggaaag tctgcaaact     540
caaaagttta ccaccaagtc agatgtgtgg tcctttggcg tgctcctctg ggagctgatg     600
acaagaggag ccccaccttt tcctgacgta aacacctttg atataactgt ttacttgttg     660
caagggagaa gactcctaca acccgaatac tgcccagacc ccttatatga agtaatgcta     720
aaatgctggc accctaaagc cgaaatgcgc ccatcctttt ctgaactggt gtcccggata     780
tcagcgatct tctctacttt cattggggag cactatgtcc atgtgaacgc tacttatgtg     840
aacgtaaaat gtgtcgctcc gtatccttct ctgttgtcat cagaagataa cgctgatgat     900
gaggtggaca cacgaccagc ctccttctgg gagacatca                            939
```

<210> SEQ ID NO 85
<211> LENGTH: 13
<212> TYPE: PRT
<213> ORGANISM: Artificial Sequence
<220> FEATURE:
<223> OTHER INFORMATION: Synthetic heavy chain CDR3 of anti-c-Met
      antibody

<400> SEQUENCE: 85

Asp Asn Trp Phe Ala Tyr Trp Gly Gln Gly Thr Leu Val
  1               5                  10

<210> SEQ ID NO 86
<211> LENGTH: 10
<212> TYPE: PRT
<213> ORGANISM: Artificial Sequence
<220> FEATURE:
<223> OTHER INFORMATION: Synthetic light chain CDR3 of anti-c-Met
      antibody

<400> SEQUENCE: 86

Leu Thr Phe Gly Ala Gly Thr Lys Leu Glu
  1               5                  10

<210> SEQ ID NO 87
<211> LENGTH: 117
<212> TYPE: PRT
<213> ORGANISM: Artificial Sequence
<220> FEATURE:
<223> OTHER INFORMATION: Synthetic heavy chain variable region of
      monoclonal antibody AbF46

<400> SEQUENCE: 87

Glu Val Lys Leu Val Glu Ser Gly Gly Gly Leu Val Gln Pro Gly Gly
  1               5                  10                  15

Ser Leu Arg Leu Ser Cys Ala Thr Ser Gly Phe Thr Phe Thr Asp Tyr
             20                  25                  30

Tyr Met Ser Trp Val Arg Gln Pro Pro Gly Lys Ala Leu Glu Trp Leu
         35                  40                  45

Gly Phe Ile Arg Asn Lys Ala Asn Gly Tyr Thr Thr Glu Tyr Ser Ala
            50                  55                  60

Ser Val Lys Gly Arg Phe Thr Ile Ser Arg Asp Asn Ser Gln Ser Ile
 65                  70                  75                  80

Leu Tyr Leu Gln Met Asp Thr Leu Arg Ala Glu Asp Ser Ala Thr Tyr
                 85                  90                  95

Tyr Cys Ala Arg Asp Asn Trp Phe Ala Tyr Trp Gly Gln Gly Thr Leu
                100                 105                 110

Val Thr Val Ser Ala
            115

<210> SEQ ID NO 88
<211> LENGTH: 114
<212> TYPE: PRT
<213> ORGANISM: Artificial Sequence
<220> FEATURE:
<223> OTHER INFORMATION: Synthetic light chain variable region of
      anti-c-Met antibody

<400> SEQUENCE: 88

Asp Ile Leu Met Thr Gln Ser Pro Ser Ser Leu Thr Val Ser Ala Gly
 1               5                  10                  15

Glu Lys Val Thr Met Ser Cys Lys Ser Ser Gln Ser Leu Leu Ala Ser
                20                  25                  30

Gly Asn Gln Asn Asn Tyr Leu Ala Trp His Gln Gln Lys Pro Gly Arg
            35                  40                  45

Ser Pro Lys Met Leu Ile Ile Trp Ala Ser Thr Arg Val Ser Gly Val
 50                  55                  60

Pro Asp Arg Phe Ile Gly Ser Gly Ser Gly Thr Asp Phe Thr Leu Thr
 65                  70                  75                  80

Ile Asn Ser Val Gln Ala Glu Asp Leu Ala Val Tyr Tyr Cys Gln Gln
                 85                  90                  95

Ser Tyr Ser Ala Pro Leu Thr Phe Gly Ala Gly Thr Lys Leu Glu Leu
                100                 105                 110

Lys Arg

<210> SEQ ID NO 89
<211> LENGTH: 17
<212> TYPE: PRT
<213> ORGANISM: Artificial Sequence
<220> FEATURE:
<223> OTHER INFORMATION: Synthetic light chain CDR3 of anti-c-Met
      antibody

<400> SEQUENCE: 89

Gln Gln Ser Tyr Ser Ala Pro Leu Thr Phe Gly Ala Gly Thr Lys Leu
 1               5                  10                  15

Glu

<210> SEQ ID NO 90
<211> LENGTH: 117
<212> TYPE: PRT
<213> ORGANISM: Artificial Sequence
<220> FEATURE:
<223> OTHER INFORMATION: Synthetic heavy chain variable region of AT-VH1

<400> SEQUENCE: 90

Glu Val Lys Leu Val Glu Ser Gly Gly Gly Leu Val Gln Pro Gly Gly
 1               5                  10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Ser Thr
65                  70                  75                  80

Leu Tyr Leu Gln Met Asn Ser Leu Arg Ala Glu Asp Ser Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 91
<211> LENGTH: 117
<212> TYPE: PRT
<213> ORGANISM: Artificial Sequence
<220> FEATURE:
<223> OTHER INFORMATION: Synthetic heavy chain variable region of AT-VH2

<400> SEQUENCE: 91

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Ser Thr
65                  70                  75                  80

Leu Tyr Leu Gln Met Asn Ser Leu Arg Ala Glu Asp Thr Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 92
<211> LENGTH: 117
<212> TYPE: PRT
<213> ORGANISM: Artificial Sequence
<220> FEATURE:
<223> OTHER INFORMATION: Synthetic heavy chain variable region of AT-VH3

<400> SEQUENCE: 92

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Ser Thr
65                  70                  75                  80

```
Leu Tyr Leu Gln Met Asn Ser Leu Arg Ala Glu Asp Thr Ala Thr Tyr
             85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 93
<211> LENGTH: 117
<212> TYPE: PRT
<213> ORGANISM: Artificial Sequence
<220> FEATURE:
<223> OTHER INFORMATION: Synthetic heavy chain variable region of AT-VH4

<400> SEQUENCE: 93

Glu Val Gln Leu Val Glu Ser Gly Gly Gly Leu Val Gln Pro Gly Gly
  1               5                  10                  15

Ser Leu Arg Leu Ser Cys Ala Thr Ser Gly Phe Thr Phe Thr Asp Tyr
             20                  25                  30

Tyr Met Ser Trp Val Arg Gln Pro Pro Gly Lys Gly Leu Glu Trp Leu
         35                  40                  45

Gly Phe Ile Arg Asn Lys Ala Asn Gly Tyr Thr Thr Glu Tyr Ser Ala
     50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Thr Tyr
             85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 94
<211> LENGTH: 117
<212> TYPE: PRT
<213> ORGANISM: Artificial Sequence
<220> FEATURE:
<223> OTHER INFORMATION: Synthetic heavy chain variable region of AT-VH5

<400> SEQUENCE: 94

Glu Val Gln Leu Val Glu Ser Gly Gly Gly Leu Val Gln Pro Gly Gly
  1               5                  10                  15

Ser Leu Arg Leu Ser Cys Ala Thr Ser Gly Phe Thr Phe Thr Asp Tyr
             20                  25                  30

Tyr Met Ser Trp Val Arg Gln Pro Pro Gly Lys Gly Leu Glu Trp Leu
         35                  40                  45

Gly Phe Ile Arg Asn Lys Ala Asn Gly Tyr Thr Thr Glu Tyr Ser Ala
     50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
             85                  90                  95

Tyr Cys Ala Arg Asp Asn Trp Phe Ala Tyr Trp Gly Gln Gly Thr Leu
            100                 105                 110

Val Thr Val Ser Ser
        115
```

```
<210> SEQ ID NO 95
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 95

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
                20                  25                  30

Gly Asn Gln Asn Asn Tyr Leu Ala Trp His Gln Lys Pro Gly Lys
            35                  40                  45

Ala Pro Lys Met Leu Ile Ile Trp Ala Ser Thr Arg Val Ser Gly Val
        50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                85                  90                  95

Ser Tyr Ser Ala Pro Leu Thr Phe Gly Gln Gly Thr Lys Val Glu Ile
            100                 105                 110

Lys Arg

<210> SEQ ID NO 96
<211> LENGTH: 113
<212> TYPE: PRT
<213> ORGANISM: Artificial Sequence
<220> FEATURE:
<223> OTHER INFORMATION: Synthetic light chain variable region of AT-Vk1

<400> SEQUENCE: 96

Asp Ile Leu Met Thr Gln Ser Pro Ser Ser Leu Thr Ala Ser Val Gly
 1               5                  10                  15

Asp Arg Val Thr Met Thr Cys Lys Ser Ser Gln Ser Leu Leu Ala Ser
                20                  25                  30

Gly Asn Gln Asn Asn Tyr Leu Ala Trp His Gln Lys Pro Gly Lys
            35                  40                  45

Ala Pro Lys Met Leu Ile Ile Trp Ala Ser Thr Arg Val Ser Gly Val
        50                  55                  60

Pro Asp Arg Phe Ile Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110

Lys

<210> SEQ ID NO 97
<211> LENGTH: 113
<212> TYPE: PRT
<213> ORGANISM: Artificial Sequence
<220> FEATURE:
<223> OTHER INFORMATION: Synthetic light chain variable region of AT-Vk2

<400> SEQUENCE: 97

Asp Ile Leu Met Thr Gln Ser Pro Ser Ser Leu Ser Ala Ser Val Gly
 1               5                  10                  15
```

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Asp Arg Phe Ile Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110

Lys

<210> SEQ ID NO 98
<211> LENGTH: 113
<212> TYPE: PRT
<213> ORGANISM: Artificial Sequence
<220> FEATURE:
<223> OTHER INFORMATION: Synthetic light chain variable region of AT-Vk3

<400> SEQUENCE: 98

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Asp Arg Phe Ile Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110

Lys

<210> SEQ ID NO 99
<211> LENGTH: 113
<212> TYPE: PRT
<213> ORGANISM: Artificial Sequence
<220> FEATURE:
<223> OTHER INFORMATION: Synthetic light chain variable region of AT-Vk4

<400> SEQUENCE: 99

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln

```
                        85                  90                  95
Ser Tyr Ser Ala Pro Leu Thr Phe Gly Gln Gly Thr Lys Leu Glu Ile
                100                 105                 110
Lys

<210> SEQ ID NO 100
<211> LENGTH: 13
<212> TYPE: PRT
<213> ORGANISM: Artificial Sequence
<220> FEATURE:
<223> OTHER INFORMATION: Synthetic modified hinge region(U7-HC6)

<400> SEQUENCE: 100

Glu Pro Ser Cys Asp Lys His Cys Cys Pro Pro Cys Pro
 1               5                  10

<210> SEQ ID NO 101
<211> LENGTH: 13
<212> TYPE: PRT
<213> ORGANISM: Artificial Sequence
<220> FEATURE:
<223> OTHER INFORMATION: Synthetic modified hinge region(U6-HC7)

<400> SEQUENCE: 101

Glu Pro Lys Ser Cys Asp Cys His Cys Pro Pro Cys Pro
 1               5                  10

<210> SEQ ID NO 102
<211> LENGTH: 12
<212> TYPE: PRT
<213> ORGANISM: Artificial Sequence
<220> FEATURE:
<223> OTHER INFORMATION: Synthetic modified hinge region(U3-HC9)

<400> SEQUENCE: 102

Glu Arg Lys Cys Cys Val Glu Cys Pro Pro Cys Pro
 1               5                  10

<210> SEQ ID NO 103
<211> LENGTH: 14
<212> TYPE: PRT
<213> ORGANISM: Artificial Sequence
<220> FEATURE:
<223> OTHER INFORMATION: Synthetic modified hinge region(U6-HC8)

<400> SEQUENCE: 103

Glu Pro Arg Asp Cys Gly Cys Lys Pro Cys Pro Pro Cys Pro
 1               5                  10

<210> SEQ ID NO 104
<211> LENGTH: 13
<212> TYPE: PRT
<213> ORGANISM: Artificial Sequence
<220> FEATURE:
<223> OTHER INFORMATION: Synthetic modified hinge region(U8-HC5)

<400> SEQUENCE: 104

Glu Lys Cys Asp Lys Thr His Thr Cys Pro Pro Cys Pro
 1               5                  10

<210> SEQ ID NO 105
<211> LENGTH: 15
<212> TYPE: PRT
<213> ORGANISM: Artificial Sequence
<220> FEATURE:
<223> OTHER INFORMATION: Synthetic human hinge region
```

<400> SEQUENCE: 105

Glu Pro Lys Ser Cys Asp Lys Thr His Thr Cys Pro Pro Cys Pro
1               5                   10                  15

<210> SEQ ID NO 106
<211> LENGTH: 17
<212> TYPE: PRT
<213> ORGANISM: Artificial Sequence
<220> FEATURE:
<223> OTHER INFORMATION: Synthetic CDR-L1 of antibody L3-11Y

<400> SEQUENCE: 106

Lys Ser Ser Gln Ser Leu Leu Ala Trp Gly Asn Gln Asn Asn Tyr Leu
1               5                   10                  15

Ala

<210> SEQ ID NO 107
<211> LENGTH: 114
<212> TYPE: PRT
<213> ORGANISM: Artificial Sequence
<220> FEATURE:
<223> OTHER INFORMATION: Synthetic amino acid sequence of light chain
      variable region of antibody L3-11Y

<400> SEQUENCE: 107

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Trp
            20                  25                  30

Gly Asn Gln Asn Asn Tyr Leu Ala Trp Tyr Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Tyr Thr Phe Gly Gln Gly Thr Lys Val Glu Ile
            100                 105                 110

Lys Arg

<210> SEQ ID NO 108
<211> LENGTH: 220
<212> TYPE: PRT
<213> ORGANISM: Artificial Sequence
<220> FEATURE:
<223> OTHER INFORMATION: Synthetic amino acid sequence of light chain of
      antibody L3-11Y

<400> SEQUENCE: 108

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Trp
            20                  25                  30

Gly Asn Gln Asn Asn Tyr Leu Ala Trp Tyr Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr

```
            65                  70                  75                  80
Ile Ser Ser Leu Gln Pro Glu Asp Phe Ala Thr Tyr Tyr Cys Gln Gln
                    85                  90                  95

Ser Tyr Ser Arg Pro Tyr Thr Phe Gly Gln Gly Thr Lys Val Glu Ile
                100                 105                 110

Lys Arg Thr Val Ala Ala Pro Ser Val Phe Ile Phe Pro Pro Ser Asp
                115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
                195                 200                 205

Ser Pro Val Thr Lys Ser Phe Asn Arg Gly Glu Cys
        210                 215                 220
```

<210> SEQ ID NO 109
<211> LENGTH: 188
<212> TYPE: PRT
<213> ORGANISM: Artificial Sequence
<220> FEATURE:
<223> OTHER INFORMATION: Synthetic wild type KRAS
      (accession number NP_004976)

<400> SEQUENCE: 109

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
        50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
                100                 105                 110

Leu Val Gly Asn Lys Cys Asp Leu Pro Ser Arg Thr Val Asp Thr Lys
            115                 120                 125

Gln Ala Gln Asp Leu Ala Arg Ser Tyr Gly Ile Pro Phe Ile Glu Thr
        130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
                180                 185
```

<210> SEQ ID NO 110
<211> LENGTH: 766

<212> TYPE: PRT
<213> ORGANISM: Artificial Sequence
<220> FEATURE:
<223> OTHER INFORMATION: Synthetic wild type BRAF
      (accession number NP_004324)

<400> SEQUENCE: 110

```
Met Ala Ala Leu Ser Gly Gly Gly Gly Gly Ala Glu Pro Gly Gln
 1               5                  10                  15

Ala Leu Phe Asn Gly Asp Met Glu Pro Glu Ala Gly Ala Gly Ala
             20                  25                  30

Gly Ala Ala Ala Ser Ser Ala Ala Asp Pro Ala Ile Pro Glu Glu Val Trp
             35                  40                  45

Asn Ile Lys Gln Met Ile Lys Leu Thr Gln Glu His Ile Glu Ala Leu
         50                  55                  60

Leu Asp Lys Phe Gly Gly Glu His Asn Pro Pro Ser Ile Tyr Leu Glu
 65                  70                  75                  80

Ala Tyr Glu Glu Tyr Thr Ser Lys Leu Asp Ala Leu Gln Gln Arg Glu
                 85                  90                  95

Gln Gln Leu Leu Glu Ser Leu Gly Asn Gly Thr Asp Phe Ser Val Ser
                100                 105                 110

Ser Ser Ala Ser Met Asp Thr Val Thr Ser Ser Ser Ser Ser Ser Leu
                115                 120                 125

Ser Val Leu Pro Ser Ser Leu Ser Val Phe Gln Asn Pro Thr Asp Val
    130                 135                 140

Ala Arg Ser Asn Pro Lys Ser Pro Gln Lys Pro Ile Val Arg Val Phe
145                 150                 155                 160

Leu Pro Asn Lys Gln Arg Thr Val Val Pro Ala Arg Cys Gly Val Thr
                165                 170                 175

Val Arg Asp Ser Leu Lys Lys Ala Leu Met Met Arg Gly Leu Ile Pro
                180                 185                 190

Glu Cys Cys Ala Val Tyr Arg Ile Gln Asp Gly Glu Lys Lys Pro Ile
                195                 200                 205

Gly Trp Asp Thr Asp Ile Ser Trp Leu Thr Gly Glu Glu Leu His Val
    210                 215                 220

Glu Val Leu Glu Asn Val Pro Leu Thr Thr His Asn Phe Val Arg Lys
225                 230                 235                 240

Thr Phe Phe Thr Leu Ala Phe Cys Asp Phe Cys Arg Lys Leu Leu Phe
                245                 250                 255

Gln Gly Phe Arg Cys Gln Thr Cys Gly Tyr Lys Phe His Gln Arg Cys
                260                 265                 270

Ser Thr Glu Val Pro Leu Met Cys Val Asn Tyr Asp Gln Leu Asp Leu
    275                 280                 285

Leu Phe Val Ser Lys Phe Phe Glu His His Pro Ile Pro Gln Glu Glu
    290                 295                 300

Ala Ser Leu Ala Glu Thr Ala Leu Thr Ser Gly Ser Ser Pro Ser Ala
305                 310                 315                 320

Pro Ala Ser Asp Ser Ile Gly Pro Gln Ile Leu Thr Ser Pro Ser Pro
                325                 330                 335

Ser Lys Ser Ile Pro Ile Pro Gln Pro Phe Arg Pro Ala Asp Glu Asp
                340                 345                 350

His Arg Asn Gln Phe Gly Gln Arg Asp Arg Ser Ser Ser Ala Pro Asn
    355                 360                 365

Val His Ile Asn Thr Ile Glu Pro Val Asn Ile Asp Asp Leu Ile Arg
    370                 375                 380
```

```
Asp Gln Gly Phe Arg Gly Asp Gly Gly Ser Thr Thr Gly Leu Ser Ala
385                 390                 395                 400

Thr Pro Pro Ala Ser Leu Pro Gly Ser Leu Thr Asn Val Lys Ala Leu
            405                 410                 415

Gln Lys Ser Pro Gly Pro Gln Arg Glu Arg Lys Ser Ser Ser Ser Ser
        420                 425                 430

Glu Asp Arg Asn Arg Met Lys Thr Leu Gly Arg Arg Asp Ser Ser Asp
            435                 440                 445

Asp Trp Glu Ile Pro Asp Gly Gln Ile Thr Val Gly Gln Arg Ile Gly
        450                 455                 460

Ser Gly Ser Phe Gly Thr Val Tyr Lys Gly Lys Trp His Gly Asp Val
465                 470                 475                 480

Ala Val Lys Met Leu Asn Val Thr Ala Pro Thr Pro Gln Gln Leu Gln
            485                 490                 495

Ala Phe Lys Asn Glu Val Gly Val Leu Arg Lys Thr Arg His Val Asn
        500                 505                 510

Ile Leu Leu Phe Met Gly Tyr Ser Thr Lys Pro Gln Leu Ala Ile Val
            515                 520                 525

Thr Gln Trp Cys Glu Gly Ser Ser Leu Tyr His His Leu His Ile Ile
530                 535                 540

Glu Thr Lys Phe Glu Met Ile Lys Leu Ile Asp Ile Ala Arg Gln Thr
545                 550                 555                 560

Ala Gln Gly Met Asp Tyr Leu His Ala Lys Ser Ile Ile His Arg Asp
            565                 570                 575

Leu Lys Ser Asn Asn Ile Phe Leu His Glu Asp Leu Thr Val Lys Ile
        580                 585                 590

Gly Asp Phe Gly Leu Ala Thr Val Lys Ser Arg Trp Ser Gly Ser His
    595                 600                 605

Gln Phe Glu Gln Leu Ser Gly Ser Ile Leu Trp Met Ala Pro Glu Val
        610                 615                 620

Ile Arg Met Gln Asp Lys Asn Pro Tyr Ser Phe Gln Ser Asp Val Tyr
625                 630                 635                 640

Ala Phe Gly Ile Val Leu Tyr Glu Leu Met Thr Gly Gln Leu Pro Tyr
            645                 650                 655

Ser Asn Ile Asn Asn Arg Asp Gln Ile Ile Phe Met Val Gly Arg Gly
        660                 665                 670

Tyr Leu Ser Pro Asp Leu Ser Lys Val Arg Ser Asn Cys Pro Lys Ala
    675                 680                 685

Met Lys Arg Leu Met Ala Glu Cys Leu Lys Lys Lys Arg Asp Glu Arg
    690                 695                 700

Pro Leu Phe Pro Gln Ile Leu Ala Ser Ile Glu Leu Leu Ala Arg Ser
705                 710                 715                 720

Leu Pro Lys Ile His Arg Ser Ala Ser Glu Pro Ser Leu Asn Arg Ala
            725                 730                 735

Gly Phe Gln Thr Glu Asp Phe Ser Leu Tyr Ala Cys Ala Ser Pro Lys
        740                 745                 750

Thr Pro Ile Gln Ala Gly Gly Tyr Gly Ala Phe Pro Val His
        755                 760                 765
```

<210> SEQ ID NO 111
<211> LENGTH: 442
<212> TYPE: PRT
<213> ORGANISM: Artificial Sequence
<220> FEATURE:

<223> OTHER INFORMATION: Synthetic Heavy chain of anti-c-Met antibody LY2875358

<400> SEQUENCE: 111

| | | | | | | | | | | | | | | | |
|---|---|---|---|---|---|---|---|---|---|---|---|---|---|---|---|
| Gln | Val | Gln | Leu | Val | Gln | Ser | Gly | Ala | Glu | Val | Lys | Pro | Gly | Ala |
| 1 | | | | 5 | | | | | 10 | | | | | 15 |
| Ser | Val | Lys | Val | Ser | Cys | Lys | Ala | Ser | Gly | Tyr | Thr | Phe | Thr | Asp | Tyr |
| | | | 20 | | | | | 25 | | | | | 30 | | |
| Tyr | Met | His | Trp | Val | Arg | Gln | Ala | Pro | Gly | Gln | Gly | Leu | Glu | Trp | Met |
| | | 35 | | | | | 40 | | | | | 45 | | | |
| Gly | Arg | Val | Asn | Pro | Asn | Arg | Gly | Thr | Thr | Tyr | Asn | Gln | Lys | Phe |
| 50 | | | | | 55 | | | | | 60 | | | | |
| Glu | Gly | Arg | Val | Thr | Met | Thr | Thr | Asp | Thr | Ser | Thr | Ser | Thr | Ala | Tyr |
| 65 | | | | | 70 | | | | | 75 | | | | | 80 |
| Met | Glu | Leu | Arg | Ser | Leu | Arg | Ser | Asp | Asp | Thr | Ala | Val | Tyr | Tyr | Cys |
| | | | | 85 | | | | | 90 | | | | | 95 | |
| Ala | Arg | Ala | Asn | Trp | Leu | Asp | Tyr | Trp | Gly | Gln | Gly | Thr | Thr | Val | Thr |
| | | | 100 | | | | | 105 | | | | | 110 | | |
| Val | Ser | Ser | Ala | Ser | Thr | Lys | Gly | Pro | Ser | Val | Phe | Pro | Leu | Ala | Pro |
| | | 115 | | | | | 120 | | | | | 125 | | | |
| Cys | Ser | Arg | Ser | Thr | Ser | Glu | Ser | Thr | Ala | Ala | Leu | Gly | Cys | Leu | Val |
| 130 | | | | | 135 | | | | | 140 | | | | | |
| Lys | Asp | Tyr | Phe | Pro | Glu | Pro | Val | Thr | Val | Ser | Trp | Asn | Ser | Gly | Ala |
| 145 | | | | | 150 | | | | | 155 | | | | | 160 |
| Leu | Thr | Ser | Gly | Val | His | Thr | Phe | Pro | Ala | Val | Leu | Gln | Ser | Ser | Gly |
| | | | | 165 | | | | | 170 | | | | | 175 | |
| Leu | Tyr | Ser | Leu | Ser | Ser | Val | Val | Thr | Val | Pro | Ser | Ser | Ser | Leu | Gly |
| | | | 180 | | | | | 185 | | | | | 190 | | |
| Thr | Lys | Thr | Tyr | Thr | Cys | Asn | Val | Asp | His | Lys | Pro | Ser | Asn | Thr | Lys |
| | | | | 195 | | | | | 200 | | | | | 205 | |
| Val | Asp | Lys | Arg | Val | Glu | Ser | Lys | Tyr | Gly | Pro | Pro | Cys | Pro | Pro | Cys |
| 210 | | | | | 215 | | | | | 220 | | | | | |
| Pro | Ala | Pro | Glu | Ala | Ala | Gly | Gly | Pro | Ser | Val | Phe | Leu | Phe | Pro | Pro |
| 225 | | | | | 230 | | | | | 235 | | | | | 240 |
| Lys | Pro | Lys | Asp | Thr | Leu | Met | Ile | Ser | Arg | Thr | Pro | Glu | Val | Thr | Cys |
| | | | | 245 | | | | | 250 | | | | | 255 | |
| Val | Val | Val | Asp | Val | Ser | Gln | Glu | Asp | Pro | Glu | Val | Gln | Phe | Asn | Trp |
| | | | 260 | | | | | 265 | | | | | 270 | | |
| Tyr | Val | Asp | Gly | Val | Glu | Val | His | Asn | Ala | Lys | Thr | Lys | Pro | Arg | Glu |
| | | 275 | | | | | 280 | | | | | 285 | | | |
| Glu | Gln | Phe | Asn | Ser | Thr | Tyr | Arg | Val | Val | Ser | Val | Leu | Thr | Val | Leu |
| 290 | | | | | 295 | | | | | 300 | | | | | |
| His | Gln | Asp | Trp | Leu | Asn | Gly | Lys | Glu | Tyr | Lys | Cys | Lys | Val | Ser | Asn |
| 305 | | | | | 310 | | | | | 315 | | | | | 320 |
| Lys | Gly | Leu | Pro | Ser | Ser | Ile | Glu | Lys | Thr | Ile | Ser | Lys | Ala | Lys | Gly |
| | | | | 325 | | | | | 330 | | | | | 335 | |
| Gln | Pro | Arg | Glu | Pro | Gln | Val | Tyr | Thr | Leu | Pro | Pro | Ser | Gln | Glu | Glu |
| | | | 340 | | | | | 345 | | | | | 350 | | |
| Met | Thr | Lys | Asn | Gln | Val | Ser | Leu | Thr | Cys | Leu | Val | Lys | Gly | Phe | Tyr |
| | | 355 | | | | | 360 | | | | | 365 | | | |
| Pro | Ser | Asp | Ile | Ala | Val | Glu | Trp | Glu | Ser | Asn | Gly | Gln | Pro | Glu | Asn |
| 370 | | | | | 375 | | | | | 380 | | | | | |
| Asn | Tyr | Lys | Thr | Thr | Pro | Pro | Val | Leu | Asp | Ser | Asp | Gly | Ser | Phe | Phe |
| 385 | | | | | 390 | | | | | 395 | | | | | 400 |

Leu Tyr Ser Arg Leu Thr Val Asp Lys Ser Arg Trp Gln Glu Gly Asn
                405                 410                 415

Val Phe Ser Cys Ser Val Met His Glu Ala Leu His Asn His Tyr Thr
            420                 425                 430

Gln Lys Ser Leu Ser Leu Ser Leu Gly Lys
        435                 440

<210> SEQ ID NO 112
<211> LENGTH: 215
<212> TYPE: PRT
<213> ORGANISM: Artificial Sequence
<220> FEATURE:
<223> OTHER INFORMATION: Synthetic Light chain of anti-c-Met antibody
      LY2875358

<400> SEQUENCE: 112

Asp Ile Gln Met Thr Gln Ser Pro Ser Ser Leu Ser Ala Ser Val Gly
 1               5                  10                  15

Asp Arg Val Thr Ile Thr Cys Ser Val Ser Ser Val Ser Ser Ile
             20                  25                  30

Tyr Leu His Trp Tyr Gln Gln Lys Pro Gly Lys Ala Pro Lys Leu Leu
         35                  40                  45

Ile Tyr Ser Thr Ser Asn Leu Ala Ser Gly Val Pro Ser Arg Phe Ser
     50                  55                  60

Gly Ser Gly Ser Gly Thr Asp Phe Thr Leu Thr Ile Ser Ser Leu Gln
 65                  70                  75                  80

Pro Glu Asp Phe Ala Thr Tyr Tyr Cys Gln Val Tyr Ser Gly Tyr Pro
                 85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Asp Cys
    210                 215

<210> SEQ ID NO 113
<211> LENGTH: 24
<212> TYPE: DNA
<213> ORGANISM: Artificial Sequence
<220> FEATURE:
<223> OTHER INFORMATION: Synthetic Forward primer for IL-8 gene
      (ACCESSION NO: BC013615.1)

<400> SEQUENCE: 113
atgacttcca agctggccgt ggct                                      24

<210> SEQ ID NO 114
<211> LENGTH: 24

-continued

```
<212> TYPE: DNA
<213> ORGANISM: Artificial Sequence
<220> FEATURE:
<223> OTHER INFORMATION: Synthetic Reverse primer for IL-8 gene
      (ACCESSION NO: BC013615.1)

<400> SEQUENCE: 114
tctcagccct cttcaaaaac ttct                                          24

<210> SEQ ID NO 115
<211> LENGTH: 114
<212> TYPE: PRT
<213> ORGANISM: Artificial Sequence
<220> FEATURE:
<223> OTHER INFORMATION: Synthetic (light chain variable region of anti
      c-Met antibody)

<400> SEQUENCE: 115

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp Tyr Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Tyr Thr Phe Gly Gln Gly Thr Lys Val Glu Ile
            100                 105                 110

Lys Arg
```

METHOD FOR PREDICTING EFFICACY OF C-MET INHIBITOR

CROSS-REFERENCE TO RELATED APPLICATIONS

This application claims the benefit of Korean Patent Application No. 10-2014-0001799 filed on Jan. 7, 2014, and Korean Patent Application No. 10-2015-0000956 filed on Jan. 6, 2015, the entire disclosures of which are hereby incorporated by reference.

INCORPORATION-BY-REFERENCE OF MATERIAL ELECTRONICALLY SUBMITTED

Incorporated by reference in its entirety herein is a computer-readable nucleotide/amino acid sequence listing submitted herewith and identified as follows: One 146,702 bytes ASCII (Text) file named "719114 ST25-Revised" created Feb. 1, 2016.

BACKGROUND OF THE INVENTION

1. Field

Provided are methods for predicting and/or monitoring the effect of a c-Met inhibitor by analyzing one or more biomarkers; a composition for predicting and/or monitoring the effect of a c-Met inhibitor, comprising a material detecting the biomarker; a composition for selecting a subject suitable for the application of a c-Met inhibitor, comprising a material detecting the biomarker; a method for predicting and/or monitoring the effect of a c-Met inhibitor using one or more biomarkers; a method for selecting a subject suitable for the application of a c-Met inhibitor using one or more biomarkers; and a method for preventing and/or treating cancer comprising administering a c-Met inhibitor to the selected subject.

2. Description of the Related Art

A biomarker generally refers to a measured characteristic (e.g., a naturally occurring protein) which may be used as an indicator of some change caused in an organism by an external factor (e.g., injury). Active studies have recently been made to apply biomarkers to the diagnosis of various diseases, such as cancer, stroke, dementia, etc., and the prediction or monitoring of therapeutic effects of some agents. Among biomarkers relevant to drug development are pharmacodynamic markers (PD markers) for indicating whether drugs are functionally effective in vivo, and predictive markers for indicating the most likely response to particular drugs before administration. The use of such markers is helpful in establishing the clinical strategy of drugs. For example, a predictive marker, designed to indicate sensitivity or resistance to drug action, may be applied to the selection of patients to allow for more effective drug therapy while the activity of a drug in individual patients can be monitored with a pharmacodynamic marker, which together can lead to the establishment of effective therapeutic strategies. Further, even in the absence of a predictive marker, a pharmacodynamic marker permits the early monitoring of responses to a drug, thus allowing one to identify drug-effective groups from drug-ineffective groups at an early stage. Consequentially, more effective and successful drug therapies can be developed. In addition, when applied to the monitoring of responses to a drug as a function of concentrations, a pharmacodynamic marker can be an index for calculating suitable doses of the drug.

To date, cancer is one of the leading causes of death. Although the development of medical techniques has brought about a remarkable progress in cancer therapy, the 5-year survival rate of all cancers has only improved by 10% over the past two decades. This is because cancer characteristics, such as rapid growth, metastasis, etc., make it difficult to diagnose and treat within a suitable time. The identification of suitable biomarkers that provide information regarding the efficacy of a cancer therapy can greatly impact the ability to provide the most suitable cancer therapies at the most optimal times. For example, patients with lung cancer may differ from each other in cancer classification, genotype, and protein secretion, and thus must be treated with different, proper therapeutics. For chemotherapy using a specific drug, a corresponding biomarker, if present, would reduce the number of erroneous trials and increase possibility of success. In this regard, it is very important to explore biomarkers for predicting or monitoring the effect of anti-cancer therapeutics. A proper biomarker, if successfully exploited, can make a great contribution to the utility and value of anti-cancer drugs and the success rate of treatment with them.

c-Met is a hepatocyte growth factor (HGF) receptor. Hepatocyte growth factor (HGF) acts as a multi-functional cytokine which binds to the extracellular domain of the c-Met receptor to regulate cell division, cell motility, and morphogenesis in various normal and tumor cells. The c-Met receptor is a membrane receptor that possesses tyrosine kinase activity. c-Met is a proto-oncogene, that encodes the representative receptor tyrosine kinase. Occasionally, it takes part in a variety of mechanisms responsible for the development of cancer such as oncogenesis, metastasis, migration, angiogenesis, and invasion of cancer cells, etc., irrespectively of the ligand HGF, and thus has attracted intensive attention as a target for anti-cancer therapy. Thus targeted therapies, such as antibodies against c-Met, have been developed.

A therapy with a developed c-Met targeting drug might be more effective treating cancer, with an elevated probability of success if there is a biomarker that is capable of predicting and monitoring the therapeutic effect of the drug to select patients suitable for the drug therapy and to monitor patient responses to the drug. Thus, the use of biomarkers could be applied to the establishment of effective therapeutic strategies.

BRIEF SUMMARY OF THE INVENTION

Provided is a method for predicting and/or monitoring the effect of a c-Met inhibitor, including measuring the existence (presence/absence), the level, and/or the mutation of at least one selected from the group consisting of IL-8, b-IG-H3, MIF, KRAS/BRAF, and nucleic acids encoding the proteins, in a biological sample.

Also provided is a method for selecting a subject suitable for the application of a c-Met inhibitor, including measuring the existence, the level, and/or the mutation of at least one selected from the group consisting of IL-8, b-IG-H3, MIF, KRAS/BRAF, and nucleic acids encoding the proteins, in a biological sample.

Another embodiment provides a method for inhibiting c-Met, and a method of preventing and/or treating a cancer, which methods including administering a c-Met inhibitor to the selected subject selected by the disclosed methods as being suitable for application of the c-Met inhibitor.

BRIEF DESCRIPTION OF THE DRAWINGS

FIG. 3 contains graphs showing the serum level changes of IL-8 in response to the different doses of the anti-c-Met antibody in responder and non-responder groups of the human cancer cell-implanted mouse models.

FIG. 15 shows a change in protein expression pattern in a patient-derived tumor tissue-implanted mouse model (LXFA623), as measured by a chemiluminescence immunoassay using protein array kit.

FIG. 19 contains graphs illustrating the change of tumor sizes after treatment of the anti-c-Met antibody in the presence or absence of K-RAS and B-RAF mutations in patient-derived tumor tissue-implanted mouse models.

DETAILED DESCRIPTION OF THE INVENTION

Figure 1A:
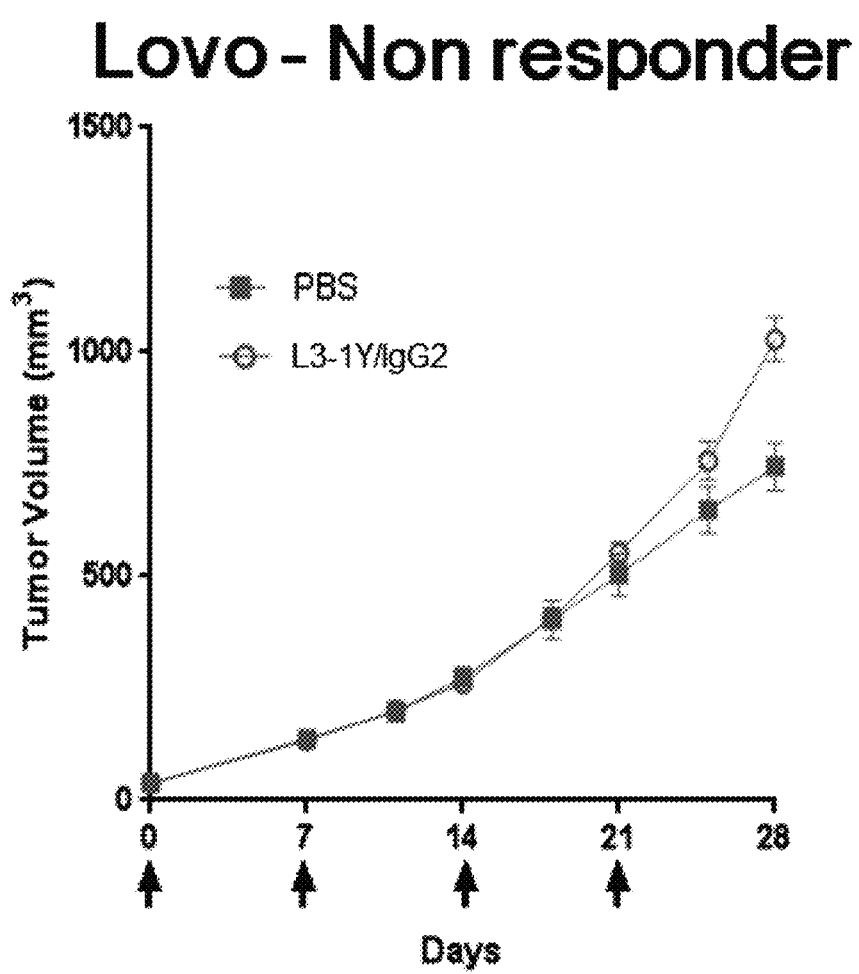
FIGS. 1A, 1B, 1C, 1D, and 1E are graphs showing the anticancer activity of an anti-c-Met antibody in terms of changes in tumor size with treatment with the anti-c-Met antibody in mouse models implanted with Lovo cells (FIG. 1A), HT29 cells (FIG. 1B), EBC-1 cells (FIG. 1C), Hs746T cells (FIG. 1D), and MKN45 cells (FIG. 1E).
Figure 1B:
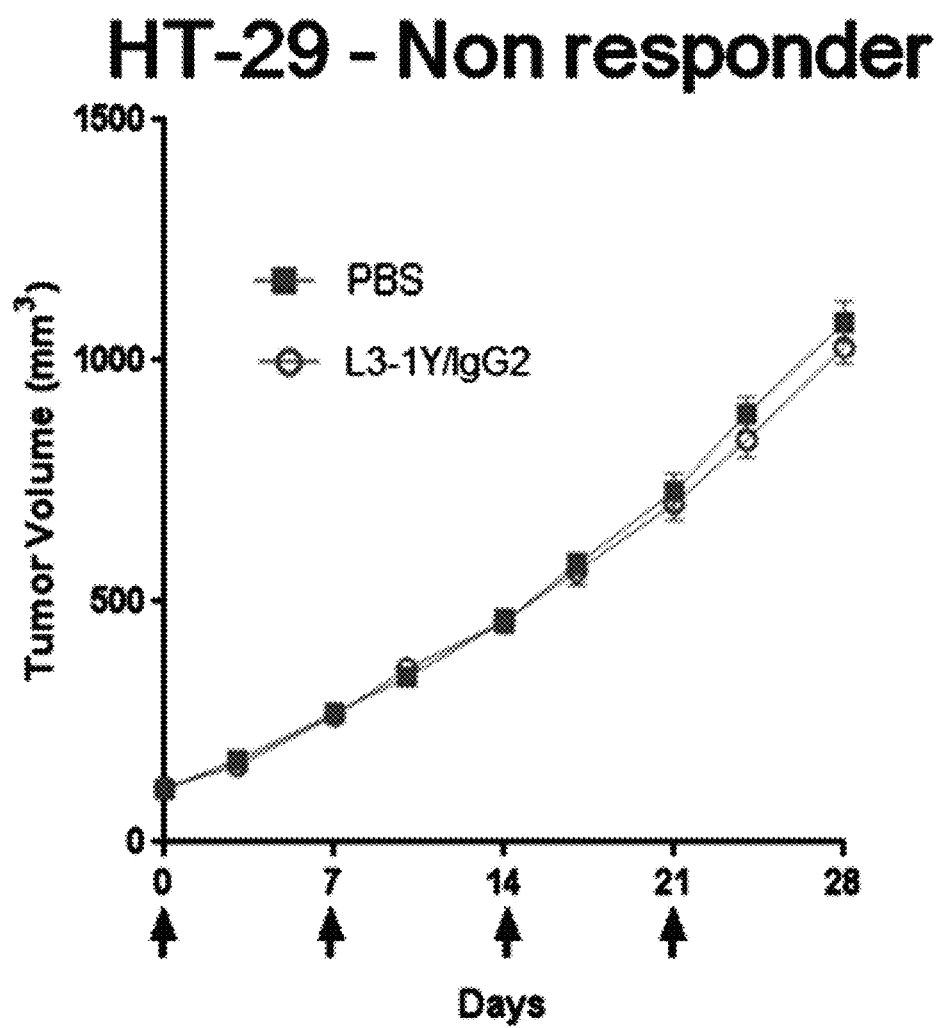
Figure 1C:
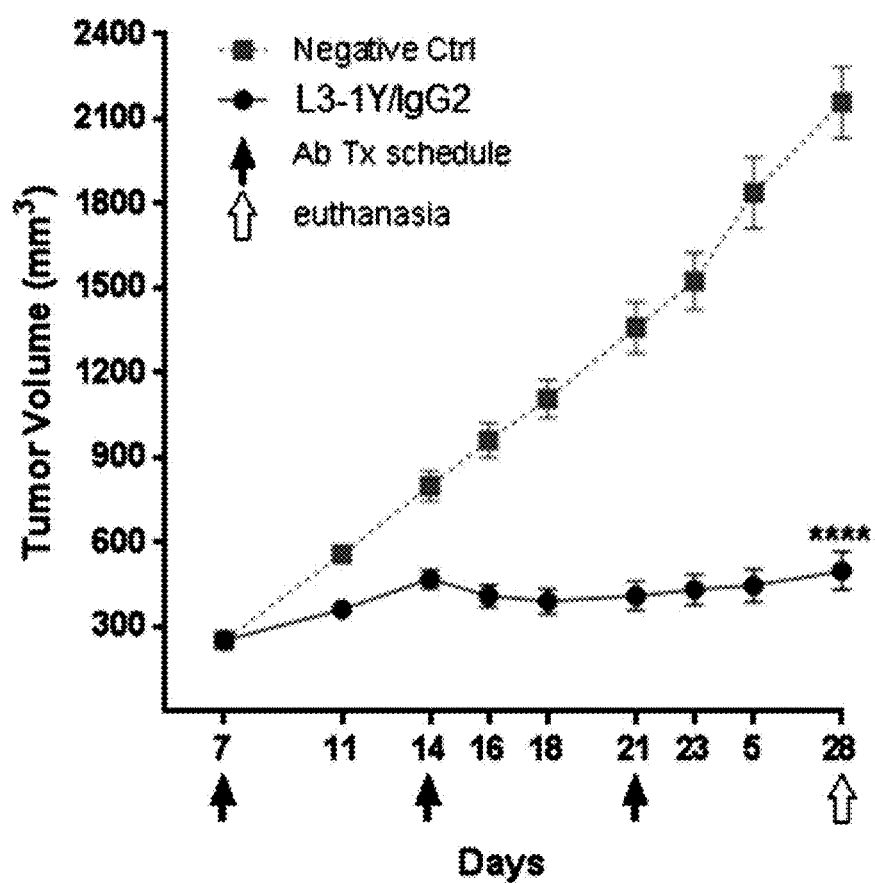
Figure 1D:
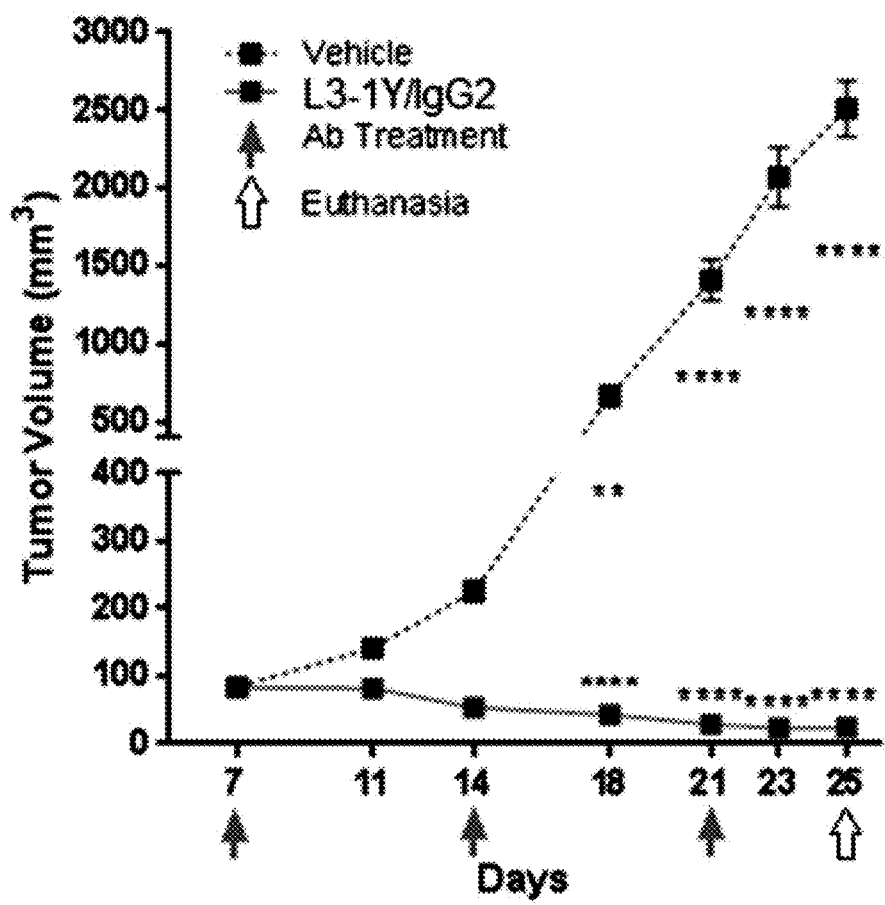
Figure 1E:
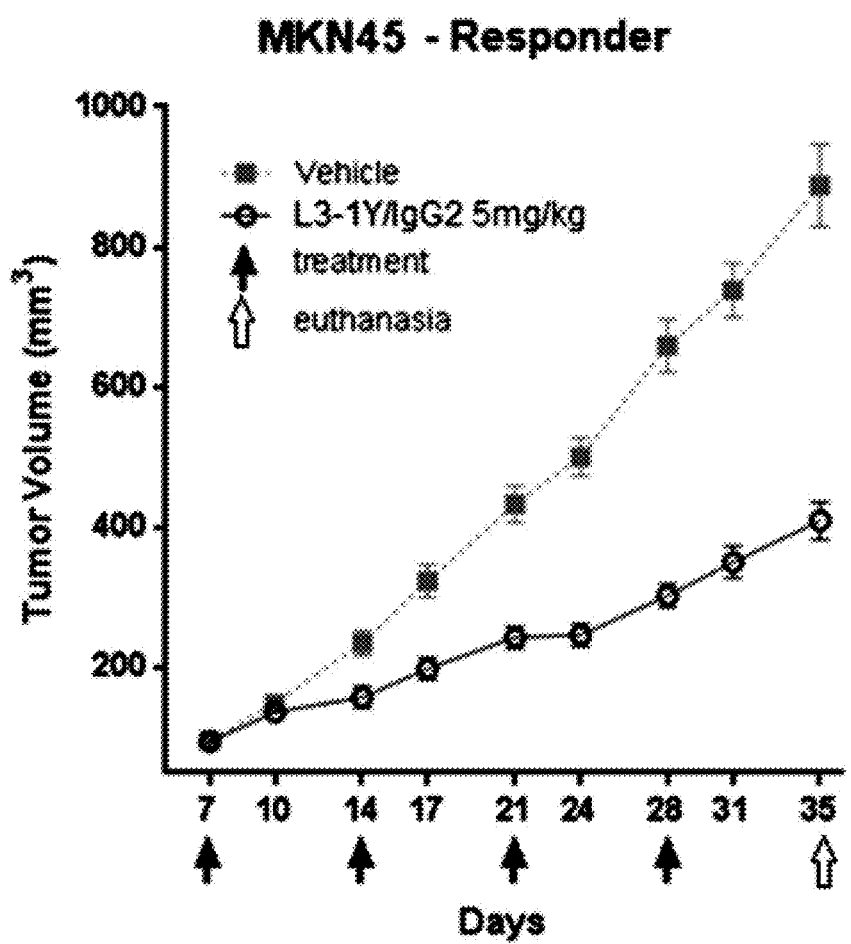

Provided is the use of at least one of selected from the group consisting of IL-8, b-IG-H3, MIF, KRAS/BRAF, and nucleic acids encoding the proteins in predicting the effect of a c-Met inhibitor and/or monitoring the effect of administered c-Met inhibitors.

One embodiment provides a method for predicting and/or monitoring the effect of a c-Met inhibitor, comprising the analysis of at least one biomarker selected from the group consisting of IL-8, b-IG-H3, MIF, KRAS/BRAF, and nucleic acids encoding the proteins.

Another embodiment provides a method for selecting a subject to which a c-Met inhibitor is applicable (i.e., will exhibit efficacy), comprising the analysis of at least one biomarker selected from the group consisting of IL-8, b-IG-H3, MIF, KRAS/BRAF, and nucleic acids encoding the proteins.

Another embodiment provides a composition and a kit for predicting and/or monitoring the effect of a c-Met inhibitor, comprising a material interacting with at least one selected from the group consisting of IL-8, b-IG-H3, MIF, KRAS/BRAF, and nucleic acids encoding the proteins.

Another embodiment provides a composition and a kit for selecting a subject to which a c-Met inhibitor is applicable, comprising a material interacting with at least one selected from the group consisting of IL-8, b-IG-H3, MIF, KRAS/BRAF, and nucleic acids encoding the proteins.

Another embodiment provides a method for predicting and/or monitoring the efficacy of c-Met inhibitor or for providing information on the prediction and/or monitoring of the efficacy of a c-Met inhibitor, comprising measuring existence, level, and/or mutation of at least one selected from the group consisting of IL-8, b-IG-H3, MIF, KRAS/BRAF, and nucleic acids encoding the proteins, in a biological sample.

Another embodiment provides a method for selecting a subject suitable for the application of a c-Met inhibitor, comprising measuring for existence, level and/or mutation of at least one selected from the group consisting of IL-8, b-IG-H3, MIF, KRAS/BRAF, and nucleic acids encoding the proteins, in a biological sample obtained from a subject.

Another embodiment provides a method for preventing and/or treating cancer, comprising administering a c-Met inhibitor to a subject, wherein the subject has a high level of IL-8 or a nucleic acid encoding IL-8 compared to a reference sample in which a c-Met inhibitor is not effective, as defined below; shows a decreased level of IL-8, bIG-H3, MIF, and/or nucleic acids encoding them after administering a c-Met inhibitor (compared to that of before the administration); and/or has a mutation of KRAS, BRAF, and/or nucleic acids encoding them. For example, the subject may be selected by the above method for selecting a subject suitable for the application of a c-Met inhibitor. This preventing or treating method may further comprise selecting a subject suitable for the application of the c-Met inhibitor, prior to the administration.

Another embodiment provides a method for inhibiting c-Met, comprising administering a c-Met inhibitor to a subject, wherein the subject has a high level of IL-8 or a nucleic acid encoding IL-8 compared to a reference sample in which a c-Met inhibitor is not effective, as defined below; shows a decreased level of IL-8, bIG-H3, MIF, and/or nucleic acids encoding them after administering a c-Met inhibitor (compared to that of before the administration); and/or has a mutation of KRAS, BRAF, and/or nucleic acids encoding them. For example, the subject may be selected by the above method for selecting a subject suitable for the application of a c-Met inhibitor. This inhibiting method may further comprise selecting a subject suitable for the application of the c-Met inhibitor, prior to the administration.

As used herein, the term "efficacy" of a c-Met inhibitor refers to a c-Met inhibitory effect and/or the pharmaceutical activity of a c-Met inhibitor resulting in the prevention, amelioration, reduction or treatment of a c-Met-related disease, for instance, a cancer. As regards cancer the efficacy refers to an anticancer effect, for example, an ability to induce the reduction or death of cancer cells or tissues, and the suppression of cancer cell migration and/or invasion responsible for cancer metastasis. In other word, the efficacy may refer to responsiveness of a subject, who is administered with a c-Met inhibitor, to the c-Met inhibitor.

As used herein, the term "predicting an efficacy of a c-Met inhibitor" may refer to determining whether or not or how much the c-Met inhibitor exhibits its desired efficacy (e.g., an antitumor or anticancer efficacy) on a subject who is treated therewith.

As used herein, the wording "a subject suitable for the application of the c-Met inhibitor" may refer to "a subject suitable for administration, treatment with a c-Met inhibitor", "a subject with a disease (e.g., cancer) that is likely to respond to a c-Met inhibitor", or an individual that is likely to respond to a c-Met inhibitor.

The expression level of a certain protein may be determined by quantitatively analyzing the protein or the gene (nucleic acid) encoding it, such as DNA, cDNA or mRNA. As used herein, the term "gene" refers to any nucleic acid encoding the protein, whether genomic DNA, cDNA, or RNA (mRNA). The determination of KRAS and/or BRAF mutations may be achieved at a gene level or a protein level.

IL-8 (Interleukin 8) is a chemokine functioning as an important mediator of immune responses. IL-8, also known as neutrophil chemotactic factor, has two primary functions: it induces chemotaxis in target cells, primarily neutrophils but also other granulocytes, causing them to migrate toward the site of infection; and also phagocytosis once they have arrived. IL-8 is also known to be a potent promoter of angiogenesis contributing to the proliferation and metastasis of tumor cells. In one exemplary embodiment of the present invention, a response to a c-Met inhibitor varies depending on the expression level of IL-8, and a difference in the expression level of IL-8 between biological samples before and after treatment with an c-Met inhibitor is dependent on the response to the c-Met inhibitor (see Example 1). Briefly, a higher level of IL-8 or its gene in a biological sample indicates that a c-Met inhibitor, e.g., an anti-c-Met antibody, more efficiently exerts its function on the biological sample or a patient from which the biological sample is sourced. In addition, a biological sample in which a c-Met inhibitor, for example, an anti-c-Met antibody, functions well (drug response group), a decrease in the level of IL-8 or its gene after the application of the c-Met inhibitor, compared to before the application, is typically observed.

That is, an expression level of IL-8 can be used to predict the efficacy of an c-Met inhibitor and thus to select a subject suitable for treatment with the c-Met inhibitor, or a change in the expression level of IL-8 according to, or before and after treatment with a c-Met inhibitor allows for the evaluation (identification) or monitoring of the efficacy of the c-Met inhibitor, thereby being useful in determining whether the c-Met inhibitor should continue to be applied, or in establishing the therapeutic strategy of the c-Met inhibitor with regard to dose, dosing interval, and dosing number. Based on this finding, the use of IL-8 as a marker for indicating and/or monitoring the efficacy of a c-Met inhibitor is suggested.

The IL-8 may originate from vertebrates including mammals, such as rodents, e.g., mice, rat, etc., and primates, e.g., humans, monkeys, etc., birds, reptiles, amphibians, and fishes. For example, the IL-8 may be selected from the group consisting of NP_000575.1, AAH13615.1, AAA59158.1, NP_001028137.1, AAA80141.2, and AAA86711.1. An IL-8-encoding gene (cDNA or mRNA) may be selected from among NM_000584.3, BC013615.1 (from 41 to 340 positions), NC_000004, NG_029889, NC_018915.2, AC_000136, M28130.1, NM_001032965.1, S78555.1, and U19849.1.

One embodiment is directed to the analysis of a biomarker for the prediction and/or monitoring of the efficacy of a c-Met inhibitor comprising the analysis of (e.g., measuring the level of) at least one selected from the group consisting of IL-8 and a nucleic acid (e.g., gene) encoding IL-8.

Another embodiment is directed to the analysis of a biomarker for the selection of a subject suitable to the application of a c-Met inhibitor, comprising the analysis of (e.g., measuring the level of) at least one selected from the group consisting of IL-8 and a nucleic acid (e.g., gene) encoding IL-8.

A further is directed to a composition and a kit for the prediction and/or monitoring of the efficacy of a c-Met inhibitor, comprising a material capable of interacting with at least one selected from the group consisting of IL-8 and a nucleic acid (e.g., gene) encoding IL-8.

A further embodiment addresses a composition and a kit for the selection of a subject suitable to the application of a c-Met inhibitor, comprising a material interacting with at least one selected from the group consisting of IL-8 and a nucleic acid (e.g., gene) encoding IL-8.

Another embodiment is a method for predicting and/or monitoring the efficacy of a c-Met inhibitor or for offering information on the prediction and/or monitoring of the efficacy of a c-Met inhibitor, comprising measuring a biological sample for a level of at least one selected from the group consisting of IL-8 and a nucleic acid (e.g., gene) encoding IL-8.

Another embodiment provides a method for selecting a subject suitable to the application of a c-Met inhibitor or for offering information on the selection of a subject suitable to the application of a c-Met inhibitor, comprising measuring a biological sample for a level of at least one selected from the group consisting of IL-8 and a nucleic acid (e.g., gene) encoding IL-8.

Provided according to one embodiment is a method for predicting the efficacy of a c-Met inhibitor, for offering information on the prediction of the efficacy of a c-Met inhibitor, for selecting a subject suitable to the application of a c-Met inhibitor, or for offering information of the selection of a subject suitable to the application of a c-Met inhibitor, comprising measuring a level of at least one selected from the group consisting of IL-8 and a nucleic acid (e.g., gene) encoding IL-8 in a biological sample. In the method for predicting the efficacy of a c-Met inhibitor or for offering information on the efficacy of a c-Met inhibitor, when a biological sample is measured to have a high level of at least one selected from the group consisting of IL-8 and a nucleic acid (e.g., gene) encoding IL-8, the biological sample or a patient from which the biological sample is originated can be predicted to allow the c-Met inhibitor to effectively exert its activity or may be considered to be suitable for the application of the c-Met inhibitor. Hence, the method for predicting the efficacy of a c-Met inhibitor or for offering information on the efficacy of a c-Met inhibitor may further comprise determining that the c-Met inhibitor exhibits its efficacy in the biological sample or the patient when the biological sample is observed to have a high level of at least one selected from the group IL-8 or a nucleic acid (e.g., gene) encoding IL-8 after the measurement. In addition, the method for selecting a subject suitable to the application of a c-Met inhibitor or for offering information on the selection may further comprise determining the biological sample or the patient as a subject suitable for the application of the c-Met inhibitor when the biological sample is observed to have a high level of at least one selected from the group IL-8 or a nucleic acid (e.g., gene) encoding IL-8 after the measurement.

"A high level of at least one selected from the group consisting of IL-8 and a nucleic acid (e.g., gene) encoding IL-8" may refer to a large amount of IL-8 protein and/or a nucleic acid (e.g., gene) encoding IL-8 (DNA, cDNA or mRNA), compared to a biological sample (reference sample) from a patient in which a c-Met inhibitor to be applied does not exert therapeutic activity. For example, when the level of at least one selected from IL-8 and a nucleic acid (e.g., gene) encoding IL-8 in a test biological sample from a test patient is at least about 1.5-, about 2-, about 3-, about 4-, or about 5-fold, for example, about 1.5- to about 100-fold, about 2- to about 100-fold, about 3- to about 100-fold, about 4- to about 100-fold, or about 5- to about 100-fold greater in weight than that in a reference biological sample on which the c-Met inhibitor to be applied does not exert its efficacy (e.g., a c-Met inhibitory efficacy or an anticancer efficacy), the c-Met inhibitor is predicted to effectively exert its efficacy (e.g., a c-Met inhibitory efficacy or an anticancer efficacy) in the test biological sample or the test patient, or the test biological sample or the test patient can be considered as a subject suitable to the application of the c-Met inhibitor. The c-Met inhibitor may be, for example, an anti-c-Met antibody. The reference biological sample can be any sample useful for comparing the expression of the c-Met biomarker and/or c-Met inhibitor efficacy, such as a biological sample comprising cells, such as a mammalian cancer cell, in which the c-Met inhibitor does not have its efficacy (e.g., a c-Met inhibitory and/or anticancer efficacy). Examples of the reference biological sample on which the c-Met inhibitor does not exert its efficacy include, but are not limited to, the Lovo cell line (CCL-229, ATCC), and the HT-29 cell line (HTB-38, ATCC). Therefore, the method for predicting the efficacy of a c-Met inhibitor (or for offering information on the prediction of the efficacy of a c-Met inhibitor) or for selecting a subject suitable to the application of a c-Met inhibitor (or for offering information of the selection of a subject suitable to the application of a c-Met inhibitor) may further comprise a step of measuring a level of at least one selected from the group consisting of IL-8 and a nucleic acid (e.g., gene) encoding IL-8 in a reference biological sample. The measurement of the level of IL-8 and/or a nucleic acid (e.g., gene) encoding IL-8 (e.g., quantitative analysis) may be performed by the same method in both the test biological sample and the reference biological sample.

Measuring the biological sample for a level of at least one selected from among IL-8 and a nucleic acid (e.g., gene) encoding IL-8 may comprise i) treating (reacting or contacting) the biological sample with a material interacting with at least one selected from the group consisting of IL-8 and a nucleic acid (e.g., gene) encoding IL-8; and ii) quantitatively analyzing the reaction mixture to determine the level of at least one selected from IL-8 and a nucleic acid (e.g., gene) encoding IL-8. In an embodiment, prior to step i), a step of preparing a biological sample may be further performed, wherein the preparation step may comprise obtaining (isolating) a biological sample from a patient or obtaining a biological sample which has been isolated from a patient. In step i), the interacting material may be at least one selected from the group consisting of compounds (a small molecular chemical; including any general label such as a fluorescent, a dye, etc.), proteins (antibodies, aptamers, etc.), nucleic acids (DNA, RNA, etc.), and the like, which bind to IL-8 or IL-8 gene, and for example, the interacting material may be a compound (a small molecular chemical; e.g., general label such as a fluorescent, a dye, etc.), an antibody, or an aptamer, all binding (e.g., specifically binding) to IL-8, a polynucleotide (e.g., a primer, a probe, an aptamer) binding to a part or entirety of a nucleic acid (e.g., gene) encoding IL-8, or any combination thereof; and optionally, may be conjugated with a general label, such as a fluorescent, a secondary antibody, a bead (e.g., a magnetic bead or polystyrene bead), a dye, or any combination thereof. The step i) may be configured to form a complex by adding the interacting material to the biological sample. In step ii), the reaction mixture may be the complex resulting from interaction (binding) between at least one selected from the group consisting of IL-8 and a nucleic acid (e.g., gene) encoding IL-band the interacting material, which can be obtained in step i). Quantitatively analyzing may comprise quantifying the complex, the label conjugated to the complex, or the IL-8 or nucleic acid (e.g., gene) encoding IL-8 segregated from the complex after the isolation of the complex from the biological sample.

Provided in accordance with another embodiment is a method for monitoring (evaluating or identifying) the efficacy of a c-Met inhibitor or for offering information on the monitoring (evaluation or identification) of the efficacy of a c-Met inhibitor, comprising measuring a level of at least one selected from the group consisting of IL-8 and a nucleic acid (e.g., gene) encoding IL-8 in a biological sample. In the method for monitoring the efficacy of a c-Met inhibitor or for offering information on the monitoring of the efficacy of a c-Met inhibitor, levels of at least one selected from the group consisting of IL-8 and a nucleic acid (e.g., gene) encoding IL-8 in biological samples from a patient before and after treatment with the c-Met inhibitor (or in a c-Met inhibitor-untreated biological sample and a c-Met inhibitor-treated biological sample) may be measured and compared to each other. When the post-treatment level of at least one selected from the group consisting of IL-8 and a nucleic acid (e.g., gene) encoding IL-8 is lower (decreased) compared to the pre-treatment level, the c-Met inhibitor is determined to exert its efficacy in the patient from which the biological sample is sourced (obtained), or when the post-treatment level of at least one selected from the group consisting of IL-8 and a nucleic acid (e.g., gene) encoding IL-8 is the same with or higher (increased) compared to the pre-treatment level, it is determined that the c-Met inhibitor does not exert its efficacy or a resistance to the c-Met inhibitor occurs in the patient from which the biological sample is sourced (obtained). Therefore, the method for monitoring the efficacy of a c-Met inhibitor or for offering information on the monitoring of the efficacy of a c-Met inhibitor may further comprise 1) comparing the levels of at least one selected from the group consisting of IL-8 and a nucleic acid (e.g., gene) encoding IL-8 in a biological sample from the c-Met inhibitor-treated group with that in a biological sample from the untreated group, and/or 2) determining that the c-Met inhibitor exerts its efficacy in the biological sample-derived patient when the level of at least one selected from the group consisting of IL-8 and a nucleic acid (e.g., gene) encoding IL-8 in the biological sample of the c-Met inhibitor-treated group is reduced, compared to that of the untreated group (in this case, it may be determined to maintain (continue) the administration of a c-Met inhibitor to the subject), and/or 3) determining that the c-Met inhibitor does not exert its efficacy or a resistance to the c-Met inhibitor occurs in the biological sample-derived patient when the level of at least one selected from the group consisting of IL-8 and a nucleic acid (e.g., gene) encoding IL-8 in the biological sample of the c-Met inhibitor-treated group is maintained or increased (in this case, it may be determined to stop the administration of a c-Met inhibitor to the subject). The c-Met inhibitor may be an anti-c-Met antibody. The c-Met inhibitor-treated group and the untreated group mean the same biological sample after and before treatment with a c-Met inhibitor, respectively, or aliquots of the same biological sample which are treated with and are not treated with a c-Met inhibitor (for example, treated only with a vehicle), respectively. Unless stated otherwise, the terms "c-Met inhibitor-untreated group (or biological sample)" and "biological sample before treatment with a c-Met inhibitor" or "pre-treatment biological sample" are identical to each other while the terms "c-Met inhibitor-treated group (or biological sample)" and "biological sample after treatment with a c-Met inhibitor" or "post-treatment biological sample" share the same meaning.

The level of at least one selected from the group consisting of IL-8 and a nucleic acid (e.g., gene) encoding IL-8 may be measured by quantifying an IL-8 protein and/or a nucleic acid (e.g., gene) encoding IL-8 (DNA, cDNA or mRNA). For example, when the level of at least one selected from the group consisting of IL-8 and a nucleic acid (e.g., gene) encoding IL-8 in the c-Met inhibitor-treated group or in the biological sample after treatment with a c-Met inhibitor is about 0 to about 80 wt %, about 0 to about 70 wt %, about 0 to about 60 wt %, about 0 to about 50 wt %, about 0 to about 40 wt %, about 0 to about 30 wt %, about 0 to about 20 wt %, or about 0 to about 10 wt % compared to that (considering 100 wt %) of the c-Met inhibitor-untreated group or the pre-treatment biological sample, the c-Met inhibitor-treated group, or the post-treatment sample biological, is determined to decrease in the level of at least one selected from the group consisting of IL-8 and a nucleic acid (e.g., gene) encoding IL-8, compared to the c-Met inhibitor-untreated or the pre-treatment biological sample. When the level of IL-8 and a nucleic acid (e.g., gene) encoding IL-8 in the c-Met inhibitor-treated group or the post-treatment biological sample is about 0 wt % of that in the c-Met inhibitor-untreated group or the pre-treatment biological sample there is no detection (absence) of at least one selected from the IL-8 and a nucleic acid (e.g., gene) encoding IL-8 in the c-Met inhibitor-treated group or the post-treatment biological sample. Levels of IL-8 and/or a nucleic acid (e.g., gene) encoding IL-8 in the c-Met inhibitor-untreated group (or pre-treatment) and the c-Met inhibitor-treated group (or post-treatment) may be measured by conducting the same procedure on sample samples from the same patient.

Monitoring the efficacy of an c-Met inhibitor, IL-8 and/or a nucleic acid (e.g., gene) encoding IL-8 may be quantitatively analyzed within a relatively short period of time, for example, a week, 5 days, 3 days, 2 days or 1 day after administration of the c-Met inhibitor, and comparison between levels of the marker before and after administration thereof can evaluate the efficacy of c-Met inhibitor. Henceforth, the advantage of establishing a more effective therapeutic strategy can be achieved, since it is possible to evaluate the efficacy of the c-Met inhibitor in an early stage of therapy.

In one embodiment, the measuring of a level of at least one selected from the group consisting of IL-8 and a nucleic acid (e.g., gene) encoding IL-8 in a biological sample may comprise 1) determining a level of at least one selected from the group consisting of IL-8 and a nucleic acid (e.g., gene) encoding IL-8 in a biological sample from a patient prior to treatment with a c-Met inhibitor (or a c-Met inhibitor untreated biological sample which is a part of biological sample from a patient) and 2) determining a level of at least one selected from the group consisting of IL-8 and a nucleic acid (e.g., gene) encoding IL-8 in a biological sample from the patient after treatment with a c-Met inhibitor (or a c-Met inhibitor treated biological sample which is the other part of biological sample from a patient). Each of the steps 1) and 2) may comprise i) applying (adding) a material interacting with at least one selected from the group consisting of IL-8 and a nucleic acid (e.g., gene) encoding IL-8 to the biological sample, and ii) quantitatively analyzing the resulting reaction mixture to determine a level of at least one selected from the group consisting of IL-8 and a nucleic acid (e.g., gene) encoding IL-8. In an embodiment, prior to the step i), a step of preparing a biological sample may be further performed, wherein the preparation step may comprise obtaining (isolating) a biological sample from the patient or obtaining a biological sample which has been isolated from a patient. In step i), as will be further elucidated below, the interacting material may be at least one selected from the group consisting of compounds (a small molecular chemical; e.g., general label such as a fluorescent, a dye, etc.), proteins (antibodies, aptamers, etc.) nucleic acid (DNA, RNA, etc.), and the like, binding to IL-8 or IL-8 gene, and for example, the interacting material may be at least one selected from the group consisting of a compound, an antibody (e.g., antibodies for Intracellular staining (Human CXCL8/IL-8 Phycoerythrin MAb; #IC208P; R&D systems), etc.), an aptamer, all specifically binding to IL-8, and a polynucleotide (e.g., a primer (e.g., a primer set used in RT-PCR for IL-8 gene (ACCESSION NO: BC013615.1; Forward primer: 5'-ATG ACT TCC AAG CTG GCC GTG GCT-3' (SEQ ID NO: 113) and Reverse primer: 5'-TCT CAG CCC TCT TCA AAA ACT TCT-3' (SEQ ID NO: 114), etc.), a probe, an aptamer) binding to a part or entirety of a gene encoding IL-8, and optionally, may be conjugated with a label, such as a fluorescent or a dye. The step i) may be configured to form a complex by applying (adding) the interacting material to the biological sample. In step ii), the reaction mixture may be a complex resulting from interaction (binding) between at least one selected from the group consisting of IL-8 and a nucleic acid (e.g., gene) encoding IL-8 and the interacting material, which can be obtained in step i). The quantitatively analyzing step may comprise quantifying the complex, the marker conjugated to the complex, or the IL-8 or the gene segregated from the complex after the isolation of the complex from the biological sample. The quantitative analysis of IL-8 may be performed by any general quantifying means of proteins, such as immunochromatography, immunohistochemistry, immunohistochemical staining, enzyme linked immunosorbent assay (ELISA; e.g., Platinum ELISA Human IL-8/NAP-1 (#BMS204/3, eBioscience), etc.), radioimmunoassay (RIA), enzyme immunoassay (EIA), fluorescence immunoassay (FIA), luminescence immunoassay (LIA), Western blotting, microarray, surface plasmon resonance (SPR), flow cytometry assay (e.g., Cytometric Bead Array (CBA) assay (e.g., IL-8 flex set (#558277), human inflammatory cytokine kit (#551811); BD biosciences), Intracellular staining (e.g., using antibodies such as Human CXCL8/IL-8 Phycoerythrin MAb (#IC208P; R&D systems)), etc.), Luminex assay, and the like, and the quantitative analysis of IL-8 gene may be performed by any general quantifying means of genes (DNA or RNA), such as PCR (e.g., qPCR, RT-PCR, etc.), mRNA microarray, and the like, but not limited thereto.

The monitoring method may be useful in determining whether the c-Met inhibitor continues to be used, and/or suitable dosing conditions of the c-Met inhibitor (dose, dosing interval, number of doses, etc.). For example, when the level of at least one selected from the group consisting of IL-8 and a nucleic acid (e.g., gene) encoding IL-8 in the c-Met inhibitor-treated group or in the post-treatment biological sample is reduced, compared to the c-Met inhibitor-untreated group or the pre-treatment biological sample, for example, when the level of at least one selected from the group consisting of IL-8 and a nucleic acid (e.g., gene) encoding IL-8 in the c-Met inhibitor-treated group or in the post-treatment biological sample is about 0 to about 80 wt %, about 0 to about 70 wt %, about 0 to about 60 wt %, about 0 to about 50 wt %, about 0 to about 40 wt %, about 0 to about 30 wt %, about 0 to about 20 wt %, or about 0 to about 10 wt % of that of the c-Met inhibitor-untreated group or the pre-treatment biological sample, the use of c-Met inhibitor may be determined to be continued. In addition, when the level of at least one selected from the group consisting of IL-8 and a nucleic acid (e.g., gene) encoding IL-8 in the c-Met inhibitor-treated group or in the post-treatment biological sample is reduced, compared to the c-Met inhibitor-untreated group or the pre-treatment biological sample, for example, when the level of at least one selected from the group consisting of IL-8 and a nucleic acid (e.g., gene) encoding IL-8 in the c-Met inhibitor-treated group or in the post-treatment biological sample is about 0 to about 80 wt %, about 0 to about 70 wt %, about 0 to about 60 wt %, about 0 to about 50 wt %, about 0 to about 40 wt %, about 0 to about 30 wt %, about 0 to about 20 wt %, or about 0 to about 10 wt %, of that of the c-Met inhibitor-untreated group or the pre-treatment biological sample, the dosing condition of the c-Met inhibitor may be determined to be suitable. The dosing condition may be at least one selected from the group consisting of a dose, a dosing interval, and a number of doses.

Another embodiment provides a method for inhibiting c-Met, comprising administering a c-Met inhibitor to a subject who has a high level of IL-8 and/or a nucleic acid encoding IL-8 (wherein the high level is defined above) and/or shows a decreased level of IL-8 and/or a nucleic acid encoding IL-8 after administration of a c-Met inhibitor (compared to before administration of the c-Met inhibitor). The subject may be 1) selected by the above method for selecting a subject suitable for the application of a c-Met inhibitor or 2) determined by the above method of monitoring efficacy of a c-Met inhibitor as a subject wherein a c-Met inhibitor exerts its efficacy thereon.

Another embodiment provides a method for preventing and/or treating cancer, comprising administering a c-Met inhibitor to a subject who has a high level of IL-8 or a nucleic acid encoding IL-8 (wherein the high level is defined above) and/or shows a decreased level of IL-8 and/or a nucleic acid encoding IL-8 after administration of a c-Met inhibitor (compared to before administration of the c-Met inhibitor). The subject may be 1) selected by the above method for selecting a subject suitable for the application of a c-Met inhibitor or 2) determined by the above method of monitoring efficacy of a c-Met inhibitor as a subject wherein a c-Met inhibitor exert its efficacy thereon.

The method for inhibiting c-Met or the method for preventing and/or treating cancer may further comprise selecting a subject to which the c-Met inhibitor is applicable, prior to the administering step. Details of the selection are as described above. The c-Met inhibitor may be an anti-c-Met antibody.

In an embodiment, the method for inhibiting c-Met or for preventing and/or treating cancer may comprise:
identifying a subject to which a c-Met inhibitor is applicable; and
administering a pharmaceutically effective amount of the c-Met inhibitor to the subject.

In another embodiment, the method for inhibiting c-Met or for preventing and/or treating cancer may comprise:
measuring a level of IL-8 and/or a nucleic acid (e.g., gene) encoding IL-8 in a biological sample to select a c-Met inhibitor-applicable subject; and
administering a pharmaceutically effective amount of the c-Met inhibitor to the subject.

With regard to dosing conditions of the c-Met inhibitor, such as doses, dosing intervals and/or number of doses, they may be determined in the method for monitoring a c-Met inhibitor for efficacy.

Some anti-cancer agents such as sunitinib, cis-platin, paclitaxel, etc. often cannot exert their anticancer effects in individuals with a high level of IL-8 because they provoke resistance. In contrast, c-Met inhibitors, for example, anti-c-Met antibodies, particularly, those described below, can exhibit high anticancer activity in individuals with a high level of IL-8, thereby allowing for the suggestion of more effective therapeutic strategies.

bIG-H3, also known as TGFBI (transforming growth factor beta-induced), is RGD-containing protein that binds to type I, II and IV collagens. The RGD motif is found in ECM (extracellular matrix). Serves as a ligand binding to a3b1 integrin, bIG-H3 is involved in cell adhesion, and migration. bIG-H3 is a soluble protein and plays a role in cancer metastasis and angiogenesis in the tumor microenvironment. No reports have been made on a relationship between c-Met and bIG-H3, so far.

MIF (Macrophage migration inhibitory factor) is an important regulator of innate immunity and is classified as an inflammatory cytokine.

In the Example section of the specification, a difference in the expression level of bIG-H3 and/or MIF between c-Met inhibitor-treated groups and untreated groups or between a post-treatment group and a pre-treatment group was observed to vary depending in response to the c-Met inhibitor (refer to Examples 2 and 3). In detail, when a c-Met inhibitor, e.g., an anti-c-Met antibody functions well (drug responsive group), the level of at least one selected from the group consisting of bIG-H3, MIF and nucleic acids encoding the proteins is lower after application of the c-Met inhibitor than before the application.

In other words, expression levels of at least one selected from the group consisting of bIG-H3, MIF, and nucleic acids encoding the proteins before or after the application of a c-Met inhibitor are measured to assay (identify) or monitor the effect of the c-Met inhibitor, so that the measurements can be effectively used to determine whether the c-Met inhibitor should continue to be applied or not, or to establish a therapeutic strategy with regard to, for example, doses, dosing intervals, dose numbers of the c-Met inhibitor. Based on this finding, bIG-H3 and/or MIF as appear to be viable pharmacodynamic markers for c-Met inhibitors.

The bIG-H3 may originate from vertebrates including mammals, such as rodents, e.g., mice, rat, etc., and primates, e.g., humans, monkeys, etc., birds, reptiles, amphibians, and fishes. For example, the bIG-H3 may be selected from the group consisting of, but not limited to, human bIG-H3 (NP_000349.1, AAC24944.1, AAC08449.1, AAH00097.1, etc.), mouse bIG-H3 (NP_033395.1, AAI29901.1, AAI29902.1, etc.), rat bIG-H3 (NP_446254.1, etc.), and zebrafish bIG-H3 (NP_878282.1, etc.). A bIG-H3 encoding gene (cDNA or mRNA) may be selected from the group consisting of but not limited to, NM_000358.2, NM_009369.4, NM_053802.1, and NM_182862.1.

MIF may originate from vertebrates including mammals, birds, reptiles, amphibians, and fishes. For example, the MIF may be selected from the group consisting of, but not limited to, human MIF (NP_002406.1, etc.), monkey MIF (e.g., NP_001028087.1, etc.), sheep MIF (NP_001072123.1, etc.), rodent MIF (e.g., mouse MIF (NP_034928.1, etc.), rat MIF (NP_112313.1, etc.), NP_001266756.1, etc.), cow MIF (NP_001028780.1, etc.), zebrafish MIF (NP_001036786.1, etc.), pig MIF (NP_001070681.1, etc.), frog MIF (NP_001083650.1, NP_001107147.1, etc.), and fish MIF (e.g., NP_001118053.1, NP_001135019.1, NP_001027889.1). An MIF-encoding gene (cDNA or mRNA) may be selected from among, but not limited to, NM_002415.1, NM_001032915.1, NM_001078655.1, NM_010798.2, NM_031051.1, NM_001279827.1, NM_001033608.1, NM_001043321.1, NM_001077213.2, NM_001090181.1, NM_001113675.1, NM_001124581.1, NM_001141547.1, and NM_001032717.1.

An embodiment provides a biomarker for evaluating the effect of a c-Met inhibitor, comprising at least one selected from the group consisting of bIG-H3, MIF, and nucleic acids encoding the proteins.

Another embodiment provides a composition and a kit for evaluating the effect of a c-Met inhibitor, comprising at least one selected from the group consisting of bIG-H3, MIF, and nucleic acids encoding the proteins.

Another embodiment provides a method for evaluating (or identifying or monitoring) the efficacy of a c-Met inhibitor or for offering information on the evaluation (or identifying or monitoring) of the efficacy of a c-Met inhibitor, comprising measuring a level of at least one selected from the group consisting of bIG-H3, MIF, and nucleic acids encoding the proteins in a biological sample.

In the method for monitoring the efficacy of a c-Met inhibitor or for offering information on the monitoring of the efficacy of a c-Met inhibitor, levels of at least one selected from the group consisting of bIG-H3, MIF and nucleic acids encoding the proteins in biological samples from a patient before and after treatment with the c-Met inhibitor (or in a c-Met inhibitor treated group biological sample and a c-Met inhibitor untreated biological sample) are measured and compared. When the post-treatment level of at least one selected from the group consisting of bIG-H3, MIF, and nucleic acids encoding the proteins is lower (decreased) compared to the pre-treatment level, the c-Met inhibitor is determined to exert its activity in the patient from which the biological sample is sourced (obtained), whereas when the post-treatment level of at least one selected from the group consisting of bIG-H3, MIF, and nucleic acids encoding the proteins is the same with or higher (increase) compared to the pre-treatment level, it is determined that the c-Met inhibitor does not exert its efficacy or a resistance to the c-Met inhibitor occurs in the patient from which the biological sample is sourced (obtained). Therefore, the method for monitoring the efficacy of a c-Met inhibitor or for offering information on the monitoring of the efficacy of a c-Met inhibitor may further comprise 1) comparing the level of at least one selected from the group consisting of bIG-H3, MIF, and nucleic acids encoding the proteins in a biological sample from the c-Met inhibitor-treated group with that in a biological sample from the untreated group, and/or 2) determining that the c-Met inhibitor exerts its efficacy in the biological sample-derived patient when the level of at least one selected from the group consisting of bIG-H3 or MIF and a nucleic acid (e.g., gene) encoding bIG-H3 or MIF in the biological sample of the c-Met inhibitor-treated group is reduced, compared to that of the untreated group (in this case, it may be determined to maintain (continue) the administration of a c-Met inhibitor to the subject), and/or 3) determining that the c-Met inhibitor does not exert its efficacy or a resistance to the c-Met inhibitor occurs in the biological sample-derived patient when the level of at least one selected from the group consisting of bIG-H3, MIF, and nucleic acids encoding the proteins in the biological sample of the c-Met inhibitor-treated group is maintained or increased (in this case, it may be determined to stop the administration of a c-Met inhibitor to the subject). The c-Met inhibitor may be an anti-c-Met antibody.

The level of at least one selected from the group consisting of bIG-H3, MIF and nucleic acids encoding the proteins may be measured by quantifying an bIG-H3 protein, an MIF protein and nucleic acids (DNA, cDNA or mRNA) encoding the proteins using the quantification techniques described, above. For example, when the level of at least one selected from the group consisting of bIG-H3, MIF and nucleic acids encoding the proteins in the c-Met inhibitor-treated group or in the biological sample after treatment with a c-Met inhibitor is about 0 to about 80 wt %, about 0 to about 70 wt %, about 0 to about 60 wt %, about 0 to about 50 wt %, about 0 to about 40 wt %, about 0 to about 30 wt %, about 0 to about 20 wt %, or about 0 to about 10 wt % of that of the c-Met inhibitor-untreated group or the pre-treatment biological sample," the c-Met inhibitor-treated group, or the post-treatment sample biological is determined to decrease in the level of at least one selected from the group consisting of bIG-H3, MIF and nucleic acids encoding the proteins, compared to the c-Met inhibitor-untreated or the pre-treatment biological sample. When the level of at least one selected from the group consisting of bIG-H3, MIF and nucleic acids encoding the proteins in the c-Met inhibitor-treated group or the post-treatment biological sample is about 0 wt % of that in the c-Met inhibitor-untreated group or the pre-treatment biological sample, there is no detection (absence) of at least one selected from the bIG-H3, MIF and nucleic acids encoding the proteins in the c-Met inhibitor-treated group or the post-treatment biological sample. Levels of bIG-H3, MIF and nucleic acids encoding the proteins in the c-Met inhibitor-untreated group (or pre-treatment) and the c-Met inhibitor-treated group (or post-treatment) may be measured by conducting the same procedure on sample samples from the same patient.

bIG-H3, MIF and nucleic acids encoding the proteins may be quantitatively analyzed within a relatively short period of time, for example, one month, two weeks, a week, 5 days, 3 days, 2 days or 1 day after administration of the c-Met inhibitor, and comparison between levels of the marker after and before administration thereof can evaluate the efficacy of c-Met inhibitor. Henceforth, the advantage of establishing a more effective therapeutic strategy can be achieved, since it makes it possible to evaluate the efficacy of the c-Met inhibitor in an early stage of therapy.

In one embodiment, the measuring of a level of at least one selected from the group consisting of bIG-H3, MIF and nucleic acids encoding the proteins in a biological sample may comprise 1) determining a level of at least one selected from the group consisting of bIG-H3, MIF and nucleic acids encoding the proteins in a biological sample from a patient prior to treatment with a c-Met inhibitor (or in a c-Met inhibitor untreated biological sample which is a part of biological sample from a patient) and 2) determining a level of at least one selected from the group consisting of bIG-H3, MIF and nucleic acids encoding the proteins in a biological sample from the patient after treatment with a c-Met inhibitor (or in a c-Met inhibitor treated biological sample which is a part of biological sample from a patient). Each of the steps 1) and 2) may comprise i) applying (adding) a material interacting with at least one selected from the group consisting of bIG-H3, MIF and nucleic acids encoding the proteins to the biological sample; and ii) quantitatively analyzing the resulting reaction mixture to determine a level of at least one selected from the group consisting of bIG-H3, MIF and nucleic acids encoding the proteins. In an embodiment, prior to the step i), a step of preparing a biological sample may be further performed, wherein the preparation step may comprise obtaining (isolating) a biological sample from the patient or obtained a biological sample which has been isolated from a patient. In step i), as will be further elucidated below, the interacting material may be at least one selected from the group consisting of compounds (a small molecular chemical; e.g., general label such as a fluorescent, a dye, etc.), proteins (antibodies, aptamers, etc.) nucleic acid (DNA, RNA, etc.), and the like, binding to bIG-H3, MIF, bIG-H3 gene or MIF gene, and for example, the interacting material may be at least one selected from the group consisting of a compound, an antibody, an aptamer, all specifically binding to bIG-H3 or MIF, and a polynucleotide (e.g., a primer, a probe, an aptamer) binding to a part or entirety of a gene encoding bIG-H3 or MIF, and optionally, may be conjugated with a label, such as a fluorescent, a secondary antibody, a bead (e.g., a magnetic or polystyrene bead), or a dye. The step i) may be configured to form a complex by applying (adding) the interacting material to the biological sample. In step ii), the reaction mixture may be a complex resulting from interaction (binding) between at least one selected from the group consisting of bIG-H3, MIF and nucleic acids encoding the proteins and the interacting material, which can be obtained in step i). The quantitative analysis step may comprise quantifying the complex, the label conjugated to the complex, or the bIG-H3 or the MIF, or the nucleic acid encoding same segregated from the complex after the isolation of the complex from the biological sample. The quantitative analysis of bIG-H3 or MIF may be performed by any general quantifying means of proteins, such as immunochromatography, immunohistochemistry, immunohistochemical staining, enzyme linked immunosorbent assay (ELISA), radioimmunoassay (RIA), enzyme immunoassay (EIA), fluorescence immunoassay (FIA), luminescence immunoassay (LIA), Western blotting, microchip, surface plasmon resonance (SPR), flow cytometry assay (e.g., Cytometric Bead Array (CBA) assay, human inflammatory cytokine kit; BD biosciences), Intracellular staining, Luminex assay, and the like, and the quantitative analysis of IL-8 gene may be performed by any general quantifying means of genes (DNA or RNA), such as PCR, (e.g., qPCR, RT-PCR, etc.), mRNA microarray, and the like, but not limited thereto.

The evaluating method may be useful in determining whether the c-Met inhibitor continues to be used, and/or suitable dosing conditions of the c-Met inhibitor (dose, dosing interval, and number of dosing). For example, when the level of at least one selected from the group consisting of bIG-H3, MIF and genes in the c-Met inhibitor-treated group or in the post-treatment biological sample is reduced, compared to the c-Met inhibitor-untreated group or the pre-treatment biological sample, e.g., when the level of at least one selected from the group consisting of bIG-H3, MIF and genes in the c-Met inhibitor-treated group or in the post-treatment biological sample is about 0 to about 80 wt %, about 0 to about 70 wt %, about 0 to about 60 wt %, about 0 to about 50 wt %, about 0 to about 40 wt %, about 0 to about 30 wt %, about 0 to about 20 wt %, or about 0 to about 10 wt % of that of the c-Met inhibitor-untreated group or the pre-treatment biological sample, the use of c-Met inhibitor may be determined to be continued. In addition, when the level of at least one selected from the group consisting of bIG-H3, MIF and genes in the c-Met inhibitor-treated group or in the post-treatment biological sample is reduced, compared to the c-Met inhibitor-untreated group or the pre-treatment biological sample, e.g., when the level of at least one selected from the group consisting of bIG-H3, MIF and genes in the c-Met inhibitor-treated group or in the post-treatment biological sample is about 0 to about 80 wt %, about 0 to about 70 wt %, about 0 to about 60 wt %, about 0 to about 50 wt %, about 0 to about 40 wt %, about 0 to about 30 wt %, about 0 to about 20 wt %, or about 0 to about 10 wt % of that of the c-Met inhibitor-untreated group or the pre-treatment biological sample, the dosing condition of the c-Met inhibitor may be determined to be suitable. The dosing condition may be at least one selected from the group consisting of a dose, a dosing interval, and a number of doses. The dosing condition may be determined using the techniques described, above.

Another embodiment provides a method for inhibiting c-Met, comprising administering a c-Met inhibitor to a subject in need thereof. Another embodiment provides a method for preventing and/or treating cancer, comprising administering a c-Met inhibitor to a subject in need thereof. In the method for inhibiting c-Met or for preventing and/or treating cancer, the subject may be one showing a decreased level of bIG-H3, MIF, and/or nucleic acids encoding them after administering the c-Met inhibitor (compared to before the administration). For example, the subject may be 1) selected by the above method for selecting a subject suitable for the application of a c-Met inhibitor or 2) determined by the above method of monitoring efficacy of a c-Met inhibitor as a subject wherein a c-Met inhibitor exert its efficacy thereon.

In the method for inhibiting c-Met or for preventing and/or treating cancer, the administration of the c-Met inhibitor may be conducted according to the suitable dosing conditions determined by the evaluating method, such as a dose, a dosing interval, and/or a number of doses.

Levels of IL-8, bIG-H3, MIF, and nucleic acids (e.g., genes) encoding them can be measured by any general protein or gene assay method using a material interacting with the proteins or the genes. The material interacting with any of the proteins or the genes may be a compound, an antibody, or an aptamer, all specifically binding to IL-8, bIG-H3, or MIF 8 proteins, or a polynucleotide (e.g., a primer, a probe, an aptamer) binding to a part or entirety of a gene encoding IL-8, bIG-H3, or MIF proteins. For example, the levels of IL-8, bIG-H3, or MIF protein may be measured by detecting enzymatic reactions, fluorescence, luminescence and/or radioactivity using a compound (a small molecular chemical; e.g., general label such as a fluorescent, a dye, etc.), an antibody and/or an aptamer, which binds (e.g., specifically binds) to IL-8, bIG-H3, or MIF proteins. In detail, the level of the proteins may be determined using an analysis technique selected from among, but not limited to, immunochromatography, immunohistochemistry (IHC), immunohistochemical staining, enzyme linked immunosorbent assay (ELISA), radioimmunoassay (RIA), enzyme immunoassay (ETA), fluorescence immunoassay (FIA), luminescence immunoassay (LIA), Western blotting, microarray, surface plasmon resonance (SPR), flow cytometry assay (e.g., Cytometric Bead Array (CBA) assay (BD biosciences), Intracellular staining, etc.), Luminex assay, and the like. In addition, the level of a gene encoding IL-8, bIG-H3 or MIF may be measured by a typical gene assay method using a primer, probe or aptamer hybridizable with the gene, for example, by polymerase chain reaction (PCR; e.g., qPCR, RT-PCR), FISH (fluorescent in situ hybridization), or microarray assay. In one embodiment, the primer is designed to detect a fragment of successive base pairs out of the gene encoding IL-8, bIG-H3 or MIF5 (full-length DNA, cDNA or mRNA), for example, a fragment of about 5 bp to about 2000 bp or 5 to 1000 bp, e.g., about 10 bp to about 1500 bp, about 10 bp to about 1000 bp, about 10 to about 500 bp, about 20 to about 200 bp, or about 50 to about 200 bp, and may be a pair of primers having nucleotide sequences which are respectively hybridizable with (e.g., complementary to) 3'- and 5'-terminal regions ranging in size from about 5 to about 100 bp, e.g., about 5 to about 50 bp, about 5 to about 30 bp, or about 10 to about 25 bp. The probe or the aptamer hybridizable with the gene may have a nucleotide sequence with a size of from about 5 bp to about 2000 bp, from about 5 bp to about 1500 bp, from about 5 bp to about 1000 bp, from about 5 bp to about 500 bp, from about 5 bp to about 100 bp, from about 5 to about 50 bp, from about 5 to about 30 bp, or from about 5 to about 25 bp, which is hybridizable with (or complementary to) a fragment of the IL-8, bIG-H3 or MIF-encoding gene (full-length DNA, cDNA or mRNA). As used herein, the term "hybridizable" means pertaining to complementarily binding to a specific region of the gene, with a sequence complementarity of 80% or higher, e.g., 90% or higher, 95% or higher, 98% or higher, 99% or higher, or 100% between the primer, probe or aptamer and the gene region.

The RAS-RAF pathway is a representative cell proliferation signaling pathway of which cancer cells take advantage in their growth. For this reason, the RAS-RAF pathway is a main target of anticancer drugs. Hence, a mutation of the RAS-RAF pathway may be an important factor that can affect the efficacy of a drug targeting the pathway. No reports have been made on a relationship between c-Met and RAS-RAF mutation, so far.

In one exemplary embodiment of the present invention, a response to a c-Met inhibitor varies depending on the mutation of RAS and/or RAF (see Example 4). In greater detail, when a biological sample is observed to have a RAS and/or RAF mutation, a c-Met inhibitor, e.g., an anti-c-Met antibody does not work in the biological sample or the patient from which the biological sample originates.

In other words, detection of the mutation of RAS and/or RAF may be effectively used to predict the efficacy of a c-Met inhibitor or to select a subject to which a c-Met inhibitor is applicable. Based on this finding, RAS-RAF is first suggested as a predictive maker for c-Met inhibitors.

RAS, a member of the GTPase superfamily, may be selected from the group consisting of KRAS, NRAS, and HRAS, all of which originate from vertebrates including mammals, such as rodents, e.g., mice, rat, etc., and primates, e.g., humans, monkeys, etc., birds, reptiles, amphibians, and fishes. For example, KRAS may be selected from the group consisting of, but not limited to, human KRAS (NP_004976.2, NP_203524.1, etc.), mouse KRAS (NP_067259.4, etc.), zebrafish KRAS (NP_001003744.1, etc.), frog KRAS (NP_001095209.1, etc.), cow KRAS (NP_001103471.1, etc.), chicken KRAS (NP_001243091.1, etc.), monkey KRAS (NP_001248441.1, etc.), NP_001028153.1, NP_113703.1, and NP_001008034.1. A KRAS-encoding gene (cDNA or mRNA) may be selected from among, but not limited to, NM_004985.4, NM_033360.3, NM_021284.6, NM_001003744.1, NM_001101739.1, NM_001110001.1, NM_001256162.1, NM_001261512.2, NM_001032981.2, NM_031515.3, and NM_001008033.1.

The mutation of KRAS connected with the prediction of the effect of c-Met inhibitors may be a substitution on the codon 12 GGT (corresponding to Gly at position 12 of the amino acid sequence NP_004976) of wild-type KRAS (accession number: NM_004985) and/or on the codon 13 GGC (corresponding to Gly at position 13 of the amino acid sequence NP_004976), as shown in Table 1, below.

TABLE 1

| Examples of amino acid modification of NP_004976 | | |
|---|---|---|
| Co-don # | Base substitution | Amino acid substitution (in NP_004976) |
| 12 | GGT→GCT | Gly→Ala (G12A) |
| 12 | GGT→GAT | Gly→Asp (G12D) |
| 12 | GGT→CGT | Gly→Arg (G12R) |
| 12 | GGT→TGT | Gly→Cys (G12C) |
| 12 | GGT→AGT | Gly→Ser (G12S) |
| 12 | GGT→GTT | Gly→Val (G12V) |
| 13 | GGC→GAC | Gly→Asp (G13D) |
| 13 | | Gly→Asn (G13N) |
| 13 | | Gly→Cys (G13C) |
| 23 | | Leu→Arg (L23R) |
| 24 | | Ile→Phe (I24F) |

TABLE 1-continued

Examples of amino acid modification of NP_004976

| Codon # | Base substitution | Amino acid substitution (in NP_004976) |
|---|---|---|
| 59 | | Ala→Thr (A59T) |
| 61 | | Gln→Leu (Q61L) |
| 61 | | Gln→His (Q61H) |
| 61 | | Gln→Lys (Q61K) |
| 146 | | Ala→Thr (A146T) |

In addition, the mutation may be a substitution for at least one amino acid residue selected from the group consisting of Gly at position 13, Ile at position 24, Ala at position 59, Gln at position 61, and Ala at position 146 on the amino acid sequence of NP_004976, and/or a mutation in a KRAS coding nucleic acid inducing the amino acid mutation described above. For example, the mutation of KRAS may comprise at least one selected from the group consisting of G12A, G12D, G12R, G12C, G12S, G12V, A146T, A59T, L23R, G13N, G13D, I24F, Q61L, Q61H, G13C, and Q61K on the amino acid sequence of NP_004976, mutations in a KRAS coding nucleic acid inducing the amino acid mutation described above, or a combination thereof.

```
Amino acid sequence of NP_004976
                              (188 a.a.: SEQ ID NO: 109)
MTEYKLVVVG AGGVGKSALT IQLIQNHFVD EYDPTIEDSY

RKQVVIDGET CLLDILDTAG QEEYSAMRDQ YMRTGEGFLC

VFAINNTKSF EDIHHYREQI KRVKDSEDVP

MVLVGNKCDLPSRTVDTKQA QDLARSYGIP FIETSAKTRQ

GVDDAFYTLV REIRKHKEKM SKDGKKKKKKSKTKCVIM
```

RAF may be selected from the group consisting of BRAF, c-RAF A-RAF, V-RAF, KSR1, and KSR2, all of which originate from vertebrates including mammals, such as rodents, e.g., mice, rats, etc., and primates, e.g., humans, monkeys, etc., birds, reptiles, amphibians, and fishes. For example, BRAF may be selected from the group consisting of, but not limited to, human BRAF (NP_004324.2, etc.), mouse BRAF (NP_647455.3, etc.), frog BRAF (NP_001083526.1, etc.), zebrafish BRAF (NP_991307.2, etc.), rat BRAF (NP_579817.1, etc.), and chicken KRAS (NP_990633.1, etc.). The BRAF-encoding gene (cDNA or mRNA) may be selected from the group consisting of but not limited to, NM_004333.4, NM_139294.5, NM_001090057.1, NM_205744.3, NM_133283.1, and NM_205302.1.

The mutation of BRAF connected with the prediction of the effect of c-Met inhibitors may be a substitution of at least one selected from the group consisting of the amino acids at positions 596 (G), 600 (V), 601 (K), 469 (G), 466 (G), 581 (N), 597 (L), 464 (G), and the like, mutations in a BRAF coding nucleic acid inducing the amino acid mutation described above, or a combination thereof. For example, the mutation of BRAF connected with the prediction of the effect of c-Met inhibitors may comprise at least one following mutation on the basis of wild-type BRAF (accession number NP_004324): G596R (base G at position 596 substituted by R), V600E, V600K, V600R, K601E, K601E, G469A, V600M, G469A, V600L, G466V, V600D, G469V, D594G, D594N, N581S, L597V, L597S, L597Q, K601N, G466V, G466E, G464V, G469E, etc.; mutations in a BRAF coding nucleic acid inducing the amino acid mutation described above; or a combination thereof.

```
Amino Acid Sequence of NP_004324
                              (766 a.a.: SEQ ID NO: 110)
MAALSGGGGG GAEPGQALFN GDMEPEAGAG AGAAASSAAD

PAIPEEVWNI KQMIKLTQEHIEALLDKFGG EHNPPSIYLE AYEEYTSKLD

ALQQREQQLL ESLGNGTDFS VSSSASMDTVTSSSSSSLSV LPSSLSVFQN

PTDVARSNPK SPQKPIVRVF LPNKQRTVVP ARCGVTVRDSLKKALMMRGL

IPECCAVYRI QDGEKKPIGW DTDISWLTGE ELHVEVLENV

PLTTHNFVRKTFFTLAFCDF CRKLLFQGFR CQTCGYKFHQ RCSTEVPLMC

VNYDQLDLLF VSKFFEHHPIPQEEASLAET ALTSGSSPSA PASDSIGPQI

LTSPSPSKSI PIPQPFRPAD EHRNQFGQRDRSSSAPNVH INTIEPVNID

DLIRDQGFRG DGGSTTGLSA TPPASLPGSL TNVKALQKSPGPQRERKSSS

SSEDRNRMKT LGRRDSSDDW EIPDGQITVG QRIGSGSFGT

VYKGKWHGDVAVKMLNVTAP TPQQLQAFKN EVGVLRKTRH VNILLFMGYS

TKPQLAIVTQ WCEGSSLYHHLHIIETKFEM IKLIDIARQT AQGMDYLHAK

SIIHRDLKSN NIFLHEDLTV KIGDFGLATVKSRWSGSHQF EQLSGSILWM

APEVIRMQDK NPYSFQSDVY AFGIVLYELM TGQLPYSNINNRDQIIFMVG

RGYLSPDLSK VRSNCPKAMK RLMAECLKKK RDERPLFPQI

LASIELLARSLPKIHRSASE PSLNRAGFQT EDFSLYACAS PKTPIQAGGY GAFPVH
```

An embodiment provides a composition and a kit for the prediction of the efficacy of a c-Met inhibitor, comprising a material detecting a mutation of at least one selected from the group consisting of KRAS protein, BRAF protein and nucleic acids encoding the proteins.

Another embodiment provides a composition and a kit for the selection of a subject suitable to the application of a c-Met inhibitor, comprising a material detecting a mutation of at least one selected from the group consisting of KRAS protein, BRAF protein and nucleic acids encoding the proteins.

Also, provided according to another embodiment is a method for predicting the efficacy of a c-Met inhibitor, for offering information on the prediction of the efficacy of a c-Met inhibitor, for selecting a subject suitable to the application of a c-Met inhibitor, or for offering information of the selection of a subject suitable to the application of a c-Met inhibitor, comprising detecting a mutation of at least one selected from the group consisting of KRAS protein, BRAF protein and nucleic acids encoding the proteins in a biological sample. In the method for predicting the efficacy of a c-Met inhibitor or for offering information on the efficacy of a c-Met inhibitor, when a mutation of at least one selected from the group consisting of KRAS protein, BRAF protein and nucleic acids encoding the proteins is not detected in a biological sample, the biological sample or a patient from which the biological sample is originated can be predicted to allow the c-Met inhibitor to effectively exert its activity or may be considered to be suitable for the application of the c-Met inhibitor. Hence, the method for predicting the efficacy of a c-Met inhibitor or for offering information on the efficacy of a c-Met inhibitor may further comprise estimating that when a mutation of at least one selected from the group consisting of KRAS protein, BRAF protein and nucleic acids encoding the proteins in a biological sample, the c-Met inhibitor would exert its efficacy in the biological sample or the patient. In addition, the method for selecting a subject suitable to the application of a c-Met inhibitor or for offering information on the selection may further comprise determining the biological sample or the patient as a subject suitable for the application of the c-Met inhibitor when a mutation of at least one selected from the group consisting of KRAS protein, BRAF protein and nucleic acids encoding the proteins is not detected biological sample.

Detecting a mutation of at least one selected from the group consisting of KRAS protein, BRAF protein and nucleic acids encoding the proteins in the biological sample may comprise i) treating the biological sample with a material detecting a mutation of at least one selected from the group consisting of KRAS protein, BRAF protein and nucleic acids encoding the proteins; and ii) analyzing the reaction mixture to determine the presence or absence of the mutation. In an embodiment, prior to the preparing step i), a step of preparing a biological sample may be further performed, wherein the preparation step may comprise obtaining (isolating) a biological sample from a patient or obtaining a biological sample which has been isolated from a patient. In step i), the detective material may be at least one selected from the group consisting of 1) a polynucleotide (e.g., a probe or aptamer) comprising a nucleotide sequence hybridizable with (e.g., complementary to) a mutation-containing fragment of a KRAS gene and/or BRAF gene (full-length DNA, cDNA or mRNA) ranging in size from about 5 bp to about 2000 bp, from about 5 bp to about 1500 bp, from about 5 bp to about 1000 bp, from about 5 bp to about 500 bp, from about 5 bp to about 100 bp, from about 5 bp to about 50 bp, from about 5 bp to about 30 bp, or from about 5 bp to about 25 bp, and a pair of primers having nucleotide sequences which are respectively hybridizable with (e.g., complementary to) 3'- and 5'-terminal regions ranging in size from about 5 bp to about 100 bp, from about 5 bp to about 50 bp, from about 5 bp to about 30 bp, or from about 5 bp to about 25 bp, out of the gene fragment with a size of about 5 bp to about 2000 bp or about 5 bp to about 1000 bp, e.g., from about 10 bp to about 1500 bp, from about 10 bp to about 1000 bp, from about 10 bp to about 500 bp, from about 20 to about 200 bp, or from about 50 to about 200 bp; 2) a compound (a small molecular chemical; e.g., general label such as a fluorescent, a dye, etc.), an antibody, or an aptamer, all binding (e.g., specifically binding) to the KRAS or BRAF protein having the amino acid mutation. Optionally, the detective material may be conjugated with a label, such as a fluorescent, a secondary antibody, a bead (e.g., a magnetic bead or a polystyrene bead), a dye or a combination thereof. As used herein, the term "hybridizable" means pertaining to complementarily binding to a specific region of the gene, with a sequence homology of 80% or higher, e.g., 90% or higher, 95% or higher, 98% or higher, 99% or higher, or 100% between the primer, probe or aptamer and the gene region. The step i) may be configured to form a complex by adding (applying) the detective material to the biological sample.

In step ii), the reaction mixture may be the complex resulting from hybridization between a gene selected from a KRAS gene and a BRAF gene (which is mutated) and the detective material or resulting from an interaction between a compound (a small molecular chemical; e.g., general label such as a fluorescent, a dye, etc.), an antibody, or an aptamer, and a KRAS or BRAF protein having the amino acid mutation (e.g., substitution), which can be obtained in step i). The analyzing may comprise detecting the presence of the complex or the label conjugated to the complex, or base or amino acid sequencing the KRAS, BRAF, KRAS gene and/or BRAF gene fragment segregated from the complex after the isolation of the complex from the biological sample.

Another embodiment provides a method for inhibiting c-Met, comprising administering a c-Met inhibitor to a subject who has a mutation of at least one of KRAS, BRAF, and nucleic acids encoding them. For example, the subject may be selected by the above method for selecting a subject suitable for the application of a c-Met inhibitor.

Another embodiment provides a method for preventing and/or treating cancer, comprising administering a c-Met inhibitor to a subject who has a mutation of at least one of KRAS, BRAF, and nucleic acids encoding them. For example, the subject may be selected by the above method for selecting a subject suitable for the application of a c-Met inhibitor.

The method for inhibiting c-Met or the method for preventing and/treating cancer may further comprise selecting a subject to which the c-Met inhibitor is applicable, prior to the administering step. Details of the selection are as described above. The c-Met inhibitor may be an anti-c-Met antibody.

In an embodiment, the method for inhibiting c-Met or for preventing and/or treating cancer may comprise:
identifying a subject to which a c-Met inhibitor is applicable; and
administering a pharmaceutically effective amount of the c-Met inhibitor to the subject.

In another embodiment, the method for inhibiting c-Met or for preventing and/or treating cancer may comprise:

detecting a mutation on KRAS, BRAF, or nucleic acid encoding them in a biological sample to select a c-Met inhibitor-applicable subject; and administering a pharmaceutically effective amount of the c-Met inhibitor to the selected c-Met inhibitor-applicable subject. As used herein, the mutation of KRAS or BRAF protein may refer to the above described amino acid mutation (e.g., substitution), and the mutation of a nucleic acid encoding KRAS or BRAF protein may refer to a mutation (e.g., substitution) in the nucleic acid which induce the mutation of KRAS or BRAF protein as described above.

From the point of view of using a c-Met inhibitor such as an anti-c-Met antibody, a certain expression level of c-Met in cancer cells is prerequisite for the c-Met inhibitor therapy.

Accordingly, the composition and/or kit for predicting an efficacy of a c-Met inhibitor, selecting a subject for applying a c-Met inhibitor, or monitoring an efficacy of a c-Met inhibitor may further comprise a substance interacting with at least one selected from the group consisting of c-Met and c-Met coding gene, in addition to a substance interacting with at least one selected from the group consisting of IL-8, bIG-H3, MIF, KRAS/BRAF, and coding genes thereof. The interacting substance with c-Met and/or c-Met coding gene may be at least one selected from the group consisting of chemicals (small molecules; e.g., general label such as a fluorescent, a dye, etc.), proteins, peptides, nucleic acids (polynucleotides, oligonucleotides, etc.), and the like, which are specifically interact with (or bind to) c-Met and/or c-Met coding gene. For example, the substance interacting with c-Met and/or c-Met coding gene may be at least one selected from the group consisting of chemicals, antibodies, and aptamers, which specifically bind to c-Met, and nucleic acids (e.g., primers, probes, aptamers, etc.) which bind to an whole or a part (e.g., about 5 to about 100 bp, about 5 to about 50 bp, about 5 to about 30 bp, or about 5 to about 25 bp) of c-Met coding gene, which may be labeled with a general labeling material, such as a florescence, a secondary antibody, beads (e.g., a magnetic bead or polystyrene bead), a coloring material, and the like.

In addition, the method for predicting the efficacy of a c-Met inhibitor (or for offering information on the prediction of the efficacy of a c-Met inhibitor) or the method for selecting a subject suitable to the application of a c-Met inhibitor (or for offering information of the selection of a subject suitable to the application of a c-Met inhibitor) may further comprise measuring a level of c-Met protein or a gene thereof (e.g., full-length DNA, cDNA, mRNA) in the biological sample from the patient. The steps of measuring the level of c-Met and/or c-Met coding gene and measuring the level of at least one selected from the group consisting of IL-8, bIG-H3, MIF, KRAS/BRAF, and coding genes thereof may be performed simultaneously or sequentially in any order. Details of the measuring step are as described above. For example, a western blotting technique may be employed. In this regard, when a predetermined amount (e.g., about 10 μg) of proteins obtained from a biological sample (e.g., cancer cells or tissues) is loaded on SDS PAGE gel, transferred onto the membrane, and reacted with an anti-c-Met antibody, and then, exposed on ECL reaction for a certain time (e.g., about 30 sec), the detection of a band may indicate that a prerequisite for the c-Met inhibitor therapy is established. In another embodiment, if the c-Met level, which is determined by immunohistochemistry (IHC) using a tissue section (e.g., (Formalin-fixed paraffin-embedded tissues (FFPE), etc.) of a tumor tissue, is +2 or more, the tumor tissue can be determined that a c-Met inhibitor can exhibit its therapeutic efficacy thereon. In another embodiment, when a biological sample is found to have a c-Met mRNA level of about 12,000 or higher, about 13,000 or higher, or about 14,000 or higher, as measured by Affymetrix array (Affymetrix GeneChip Human Genome U133 Plus 2.0 array; using the primer set "203510_at"), a prerequisite for the c-Met inhibitor therapy may be established. Cancer cells characterized by a high expression level of c-Met include cells from lung cancer, breast cancer, brain cancer, stomach cancer, liver cancer, and kidney cancer. However, any cancer cell, although derived from different kinds, may be a target of the c-Met inhibitor therapy if it expresses a high level of c-Met according to personal characteristics of patients.

In another embodiment, a biological sample used in the method for predicting the efficacy of a c-Met inhibitor (or for offering information on the prediction of the efficacy of a c-Met inhibitor) or the method for selecting a subject suitable to the application of a c-Met inhibitor (or for offering information of the selection of a subject suitable to the application of a c-Met inhibitor) may be a tissue, a cell or body fluid (blood, serum, urine, saliva, etc.) which shows a high expression level of c-Met, for example, a c-Met level of about 12,000 or higher, about 13,000 or higher, or about 14,000 or higher, as measured by Affymetrix array (Affymetrix GeneChip Human Genome U133 Plus 2.0 array; using the primer set "203510_at").

The method of predicting, monitoring, or selecting may further comprising administering a c-Met inhibitor to a subject, who is selected by the selecting method, or who is predicted or monitored that a c-Met inhibitor exerts its efficacy therein.

The method of predicting, monitoring, or selecting may further comprise optimizing the application of a c-Met inhibitor or a therapy with a c-Met inhibitor by 1) determining whether or not a c-Met inhibitor is administered to a subject according to the determination of the determining step of the predicting or selecting method (e.g., determining to administer a c-Met inhibitor to the subject when the level of IL-8 and/or a nucleic acid encoding IL-8 in a biological sample obtained (separated) from the subject is higher than that of a reference sample or when a mutation of at least one of KRAS, BRAF, and nucleic acids encoding the proteins is not present in the biological sample, or determining not to administer a c-Met inhibitor to the subject when the level of IL-8 and/or a nucleic acid encoding IL-8 in a biological sample obtained (separated) from the subject is equal to or lower than that of a reference sample or when a mutation of at least one of KRAS, BRAF, and nucleic acids encoding the proteins is present in the biological sample, or 2) determining whether the administration of a c-Met inhibitor to the subject is maintained (continued) or stopped according to the determination of the determining step of the monitoring method (e.g., determining to maintain the administration of c-Met inhibitor to the subject, when the level of IL-8, bIG-H3, MIF, and/or nucleic acids encoding the proteins in the biological sample after the administration of a c-Met inhibitor is decreased compared to before the administration, or determining to stop the administration of a c-Met inhibitor, when the level of IL-8, bIG-H3, MIF, and/or nucleic acids encoding the proteins in the biological sample after the administration of a c-Met inhibitor is equal to or increased compared to before the administration.

As used herein, the term "c-Met inhibitor-applicable subject" or "subject suitable for the application of the c-Met inhibitor" means a patient to which a c-Met inhibitor therapy is applicable suitably, and the term "subject" may be selected from the group consisting of mammals, such as rodents, e.g., mice, rats, etc., and primates, e.g., humans, monkeys, etc., e.g., a cancer patient. The biological sample may be a patient itself (mammals, such as primates, e.g., humans, monkeys, etc., or rodents, e.g., mice, rats, etc.) or a cell, a tissue or body fluid (e.g., blood, serum, urine, saliva, etc.) isolated from the patient or artificially an artificial culture thereof. The biological sample may be blood or a serum. The reference sample may be selected from the group consisting of mammal, mammalian cells or tissues (including tumor (e.g., cancer) cells or tissues), and the like, on which a c-Met inhibitor has no efficacy (e.g., a c-Met inhibitory efficacy or an anti-cancer efficacy).

As used herein, the term "c-Met inhibitor" may refer to any agent capable of inhibiting activity and/or expression of c-Met, or blocking c-Met signaling by inhibiting a ligand of c-Met. In an particular embodiment, the c-Met inhibitor may be at least one selected from the group consisting of an anti-c-Met antibody or an antigen-binding fragment thereof, crizotinib (PF-02341066; 3-((R)-1-(2,6-dichloro-3-fluorophenyl)ethoxy)-5-(1-(piperidin-4-yl)-1H-pyrazol-4-yl)pyridin-2-amine), cabozantinib (XL-184; N-(4-(6,7-dimethoxyquinolin-4-yloxy)phenyl)-N-(4-fluorophenyl)cyclopropane-1,1-dicarboxamide), foretinib (N-(3-fluoro-4-(6-methoxy-7-(3-morpholinopropoxyl)quinolin-4-yloxy)phenyl)-N-(4-fluorophenyl)cyclopropane-1,1-dicarboxamide), PHA-665752((R,Z)-5-(2,6-dichlorobenzylsulfonyl)-3-((3,5-dimethyl-4-(2-(pyrrolidin-1-ylmethyl)pyrrolidine-1-carbonyl)-1H-pyrrol-2-yl)methylene)indolin-2-one), SU11274((Z)—N-(3-chlorophenyl)-3-((3,5-dimethyl-4-(1-methylpiperazine-4-carbonyl)-1H-pyrrol-2-yl)methylene)-N-methyl-2-oxoindoline-5-sulfonamide), SGX-523(6-(6-(1-methyl-1H-pyrazol-4-yl)-[1,2,4]triazolo[4,3-b]pyridazin-3-ylthio)quinoline), PF-04217903(24443-(quinolin-6-ylmethyl)-3H-[1,2,3]triazolo[4,5-b]pyrazin-5-yl)-1H-pyrazol-1-yl)ethanol), EMD 1214063(Benzonitrile, 3-[1,6-Dihydro-1-[[3-[5-[(1-Methyl-4-Piperidinyl)Methoxy]-2-PyriMidinyl]Phenyl]Methyl]-6-Oxo-3-Pyridazinyl]), golvatinib (N-(2-fluoro-4-((2-(4-(4-methylpiperazin-1-yl) piperidine-1-carboxamido)pyridin-4-yl)oxy)phenyl)-N-(4-fluorophenyl)cyclopropane-1,1-dicarboxamide), INCB28060(2-fluoro-N-methyl-4-(7-(quinolin-6-ylmethyl) imidazo[1,2-b][1,2,4]triazin-2-yl)benzamide), MK-2461(N-((2R)-1,4-Dioxan-2-ylmethyl)-N-methyl-N'-[3-(1-methyl-1H-pyrazol-4-yl)-5-oxo-5H-benzo[4,5]cyclohepta[1,2-b] pyridin-7-yl]sulfamide), tivantinib (ARQ 197; (3R,4R)-3-(5,6-Dihydro-4H-pyrrolo[3,2,1-ij]quinolin-1-yl)-4-(1H-indol-3-yl)pyrrolidine-2,5-dione), NVP-BVU972(6-[[6-(1-Methyl-1H-pyrazol-4-yl)imidazo[1,2-b]pyridazin-3-yl] methyl]quinoline), AMG458({1-(2-hydroxy-2-methylpropyl)-N-[5-(7-methoxyquinolin-4-yloxy)pyridin-2-yl]-5-methyl-3-oxo-2-phenyl-2,3-dihydro-1H-pyrazole-4-carboxamide}), BMS 794833(N-(4-((2-amino-3-chloropyridin-4-yl)oxy)-3-fluorophenyl)-5-(4-fluorophenyl)-4-oxo-1,4-dihydropyridine-3-carboxamide), BMS 777607(N-[4-[(2-Amino-3-chloropyridin-4-yl)oxy]-3-fluorophenyl]-4-ethoxy-1-(4-fluorophenyl)-2-oxo-1,2-dihydropyridine-3-carboxamide), MGCD-265(N-(3-Fluoro-4-(2-(1-methyl-1H-imidazol-4-yl)thieno[3,2-b]pyridin-7-yloxy)phenylcarbamothioyl)-2-phenylacetamide), AMG-208(7-Methoxy-4-[(6-phenyl-1,2,4-triazolo[4,3-b] pyridazin-3-yl)methoxy]quinoline), BMS-754807((2S)-1-[4-[(5-Cyclopropyl-1H-pyrazol-3-yl)amino]pyrrolo[2,1-f] [1,2,4]triazin-2-yl]-N-(6-fluoro-3-pyridinyl)-2-methyl-2-pyrrolidinecarboxamide), JNJ-38877605(6-[Difluoro[6-(1-methyl-1H-pyrazol-4-yl)-1,2,4-triazolo[4,3-b]pyridazin-3-yl]methyl]quinoline), and pharmaceutically acceptable salts thereof; or any combination thereof.

The anti-c-Met antibody or an antigen-binding fragment thereof may be any antibody which specifically recognizes c-Met as an antigen and/or specifically binds to c-Met, or an antigen-binding fragment thereof. For example, the anti-c-Met antibody may be any antibody that acts on c-Met to induce intracellular internalization and degradation of c-Met, or antigen-binding fragment thereof. The anti-c-Met antibody may recognize any specific region of c-Met, e.g., a specific region in the SEMA domain, as an epitope.

Herein, unless stated otherwise, the term "anti-c-Met antibody" may be intended to cover not only an anti-c-Met antibody in a complete form (e.g., an IgG form) but also its antigen-binding fragment. The antigen-binding fragment thereof may be at least one selected from the group consisting of scFv, (scFv)2, scFv-Fc, Fab, Fab', and F(ab')2 of an anti-c-Met antibody.

"c-Met" or "c-Met protein" refers to a receptor tyrosine kinase (RTK) which binds hepatocyte growth factor (HGF). c-Met may be derived (obtained) from any species, particularly a mammal, for instance, primates such as human c-Met (e.g., GenBank Accession No. NP_000236.2), monkey c-Met (e.g., Macaca mulatta, GenBank Accession No. NP_001162100), or rodents such as mouse c-Met (e.g., GenBank Accession No. NP_032617.2), rat c-Met (e.g., GenBank Accession No. NP_113705.1), and the like. The c-Met protein may include a polypeptide encoded by the nucleotide sequence identified as GenBank Accession No. NM_000245.2, a polypeptide having the amino acid sequence identified as GenBank Accession No. NP_000236.2 or extracellular domains thereof. The receptor tyrosine kinase c-Met participates in various mechanisms, such as cancer incidence, metastasis, migration of cancer cells, invasion of cancer cells, angiogenesis, and the like.

c-Met, a receptor for hepatocyte growth factor (HGF), may be divided into three portions: extracellular, transmembrane, and intracellular. The extracellular portion is composed of an α-subunit and a β-subunit which are linked to each other through a disulfide bond, and includes a SEMA domain responsible for binding HGF, a PSI domain (plexin-semaphorins-integrin identity/homology domain) and an IPT domain (immunoglobulin-like fold shared by plexins and transcriptional factors domain). The SEMA domain of c-Met protein may have the amino acid sequence of SEQ ID NO: 79, and is an extracellular domain that functions to bind HGF. A specific region of the SEMA domain, that is, a region having the amino acid sequence of SEQ ID NO: 71, which corresponds to a range from amino acid residues 106 to 124 of the amino acid sequence of the SEMA domain (SEQ ID NO: 79), is a loop region between the second and the third beta propellers within the epitopes of the SEMA domain. This region acts as an epitope for the anti-c-Met antibody.

The term "epitope," as used herein, refers to an antigenic determinant, a part of an antigen recognized by an antibody. In one embodiment, the epitope may be a region including about 5 or more contiguous (consecutive on primary, secondary (two-dimensional), or tertiary (three-dimensional) structure) amino acid residues within the SEMA domain (SEQ ID NO: 79) of c-Met protein, for instance, about 5 to about 19 contiguous amino acid residues within the amino acid sequence of SEQ ID NO: 71. For example, the epitope may be a polypeptide having about 5 to about 19 contiguous amino acids selected from among partial combinations of the amino acid sequence of SEQ ID NO: 71, wherein the polypeptide includes at least the amino sequence of SEQ ID NO: 73 (EEPSQ) which serves as an essential element for the epitope. For example, the epitope may be a polypeptide including, consisting essentially of, or consisting of the amino acid sequence of SEQ ID NO: 71, SEQ ID NO: 72, or SEQ ID NO: 73.

The epitope having the amino acid sequence of SEQ ID NO: 72 corresponds to the outermost part of the loop between the second and third beta propellers within the SEMA domain of a c-Met protein. The epitope having the amino acid sequence of SEQ ID NO: 73 is a site to which the antibody or antigen-binding fragment according to one embodiment most specifically binds.

Thus, the anti-c-Met antibody may specifically bind to an epitope which includes about 5 to about 19 contiguous amino acids selected from among partial combinations of the amino acid sequence of SEQ ID NO: 71, including SEQ ID NO: 73 as an essential element. For example, the anti-c-Met antibody may specifically bind to an epitope comprising the amino acid sequence of SEQ ID NO: 71, SEQ ID NO: 72, or SEQ ID NO: 73.

In one embodiment, the anti-c-Met antibody or an antigen-binding fragment thereof may comprise or consist essentially of:

(i) at least one heavy chain complementarity determining region (CDR) selected from the group consisting of (a) a CDR-H1 comprising the amino acid sequence of SEQ ID NO: 4; (b) a CDR-H2 comprising the amino acid sequence of SEQ ID NO: 5, the amino acid sequence of SEQ ID NO: 2, or an amino acid sequence comprising 8-19 consecutive amino acids within the amino acid sequence of SEQ ID NO: 2 comprising amino acid residues from the $3^{rd}$ to $10^{th}$ positions of the amino acid sequence of SEQ ID NO: 2; and (c) a CDR-H3 comprising the amino acid sequence of SEQ ID NO: 6, the amino acid sequence of SEQ ID NO: 85, or an amino acid sequence comprising 6-13 consecutive amino acids within the amino acid sequence of SEQ ID NO: 85 comprising amino acid residues from the $1^{st}$ to $6^{th}$ positions of the amino acid sequence of SEQ ID NO: 85, or a heavy chain variable region comprising the at least one heavy chain complementarity determining region;

(ii) at least one light chain complementarity determining region (CDR) selected from the group consisting of (a) a CDR-L1 comprising the amino acid sequence of SEQ ID NO: 7, (b) a CDR-L2 comprising the amino acid sequence of SEQ ID NO: 8, and (c) a CDR-L3 comprising the amino acid sequence of SEQ ID NO: 9, the amino acid sequence of SEQ ID NO: 15, the amino acid sequence of SEQ ID NO: 86, or an amino acid sequence comprising 9-17 consecutive amino acids within the amino acid sequence of SEQ ID NO: 89 comprising amino acid residues from the $1^{st}$ to $9^{th}$ positions of the amino acid sequence of SEQ ID NO: 89, or a light chain variable region including the at least one light chain complementarity determining region;

(iii) a combination of the at least one heavy chain complementarity determining region and at least one light chain complementarity determining region; or (iv) a combination of the heavy chain variable region and the light chain variable region.

Herein, the amino acid sequences of SEQ ID NOS: 4 to 9 are respectively represented by following Formulas I to VI, below:

Formula I: $Xaa_1$-$Xaa_2$-Tyr-Tyr-Met-Ser (SEQ ID NO: 4), wherein $Xaa_1$ is absent or Pro or Ser, and $Xaa_2$ is Glu or Asp, Formula II: Arg-Asn-$Xaa_3$-$Xaa_4$-Asn-Gly-$Xaa_5$-Thr (SEQ ID NO: 5), wherein $Xaa_3$ is Asn or Lys, $Xaa_4$ is Ala or Val, and $Xaa_5$ is Asn or Thr, Formula III: Asp-Asn-Trp-Leu-$Xaa_6$-Tyr (SEQ ID NO: 6), wherein $Xaa_6$ is Ser or Thr, Formula IV: Lys-Ser-Ser-$Xaa_7$-Ser-Leu-Leu-Ala-$Xaa_8$-Gly-Asn-$Xaa_9$-$Xaa_{10}$-Asn-Tyr-Leu-Ala (SEQ ID NO: 7), wherein $Xaa_7$ is His, Arg, Gln, or Lys, $Xaa_8$ is Ser or Trp, $Xaa_9$ is His or Gln, and $Xaa_{10}$ is Lys or Asn, Formula V: Trp-$Xaa_{11}$-Ser-$Xaa_{12}$-Arg-Val-$Xaa_{13}$ (SEQ ID NO: 8), wherein $Xaa_{11}$ is Ala or Gly, $Xaa_{12}$ is Thr or Lys, and $Xaa_{13}$ is Ser or Pro, and Formula VI: $Xaa_{14}$-Gln-Ser-Tyr-Ser-$Xaa_{15}$-Pro-$Xaa_{16}$-Thr (SEQ ID NO: 9), wherein $Xaa_{14}$ is Gly, Ala, or Gln, $Xaa_{15}$ is Arg, His, Ser, Ala, Gly, or Lys, and $Xaa_{16}$ is Leu, Tyr, Phe, or Met.

In one embodiment, the CDR-H1 may comprise an amino acid sequence selected from the group consisting of SEQ ID NO: 1, SEQ ID NO: 22, SEQ ID NO: 23, and SEQ ID NO: 24. The CDR-H2 may comprise an amino acid sequence selected from the group consisting of SEQ ID NO: 2, SEQ ID NO: 25, and SEQ ID NO: 26. The CDR-H3 may comprise an amino acid sequence selected from the group consisting of SEQ ID NO: 3, SEQ ID NO: 27, SEQ ID NO: 28, and SEQ ID NO: 85.

The CDR-L1 may comprise an amino acid sequence selected from the group consisting of SEQ ID NO: 10, SEQ ID NO: 29, SEQ ID NO: 30, SEQ ID NO: 31, SEQ ID NO: 32, SEQ ID NO: 33, and SEQ ID NO: 106. The CDR-L2 may comprise an amino acid sequence selected from the group consisting of SEQ ID NO: 11, SEQ ID NO: 34, SEQ ID NO: 35, and SEQ ID NO: 36. The CDR-L3 may comprise an amino acid sequence selected from the group consisting of SEQ ID NO: 12, SEQ ID NO: 13, SEQ ID NO: 14, SEQ ID NO: 15, SEQ ID NO: 16, SEQ ID NO: 37, SEQ ID NO: 86, and SEQ ID NO: 89.

In another embodiment, the anti-c-Met antibody or an antigen-binding fragment thereof may comprise or consisting essentially of:

a heavy variable region comprising or consisting essentially of a polypeptide (CDR-H1) comprising an amino acid sequence selected from the group consisting of SEQ ID NO: 1, SEQ ID NO: 22, SEQ ID NO: 23, and SEQ ID NO: 24, a polypeptide (CDR-H2) comprising an amino acid sequence selected from the group consisting of SEQ ID NO: 2, SEQ ID NO: 25, and SEQ ID NO: 26, and a polypeptide (CDR-H3) comprising an amino acid sequence selected from the group consisting of SEQ ID NO: 3, SEQ ID NO: 27, SEQ ID NO: 28, and SEQ ID NO: 85; and a light variable region comprising or consisting essentially of a polypeptide (CDR-L1) comprising an amino acid sequence selected from the group consisting of SEQ ID NO: 10, SEQ ID NO: 29, SEQ ID NO: 30, SEQ ID NO: 31, SEQ ID NO: 32, SEQ ID NO: 33, and SEQ ID NO: 106, a polypeptide (CDR-L2) comprising an amino acid sequence selected from the group consisting of SEQ ID NO: 11, SEQ ID NO: 34, SEQ ID NO: 35, and SEQ ID NO: 36, and a polypeptide (CDR-L3) comprising an amino acid sequence selected from the group consisting of SEQ ID NO: 12, SEQ ID NO: 13, SEQ ID NO: 14, SEQ ID NO: 15, SEQ ID NO: 16, SEQ ID NO: 37, SEQ ID NO: 86, and SEQ ID NO: 89.

In an embodiment, the anti-c-Met antibody or an antigen-binding fragment thereof may comprise or consist essentially of a heavy variable region comprising the amino acid sequence of SEQ ID NO: 17, SEQ ID NO: 74, SEQ ID NO: 87, SEQ ID NO: 90, SEQ ID NO: 91, SEQ ID NO: 92, SEQ ID NO: 93, or SEQ ID NO: 94, and a light variable region comprising the amino acid sequence of SEQ ID NO: 18, SEQ ID NO: 19, SEQ ID NO: 20, SEQ ID NO: 21, SEQ ID NO: 75, SEQ ID NO: 88, SEQ ID NO: 95, SEQ ID NO: 96, SEQ ID NO: 97, SEQ ID NO: 98, SEQ ID NO: 99, or SEQ ID NO: 107.

In another embodiment, the anti-c-Met antibody or an antigen-binding fragment may be Onartuzumab (MetMab), LY2875358 (Heavy chain: SEQ ID NO: 111; Light chain: SEQ ID NO: 112), Rilotumumab (AMG102), or an antigen-binding fragment thereof, and the like.

Animal-derived antibodies produced by immunizing non-immune animals with a desired antigen generally invoke immunogenicity when injected into humans for the purpose of medical treatment, and thus chimeric antibodies have been developed to inhibit such immunogenicity. Chimeric antibodies are prepared by replacing constant regions of animal-derived antibodies that cause an anti-isotype response with constant regions of human antibodies by genetic engineering. Chimeric antibodies are considerably improved in an anti-isotype response compared to animal-derived antibodies, but animal-derived amino acids still have variable regions, so that chimeric antibodies have side effects with respect to a potential anti-idiotype response. Humanized antibodies have been developed to reduce such side effects. Humanized antibodies are produced by grafting complementarity determining regions (CDR) which serve an important role in antigen binding in variable regions of chimeric antibodies into a human antibody framework.

The most important thing in CDR grafting to produce humanized antibodies is choosing the optimized human antibodies for accepting CDRs of animal-derived antibodies. Antibody databases, analysis of a crystal structure, and technology for molecule modeling are used. However, even when the CDRs of animal-derived antibodies are grafted to the most optimized human antibody framework, amino acids positioned in a framework of the animal-derived CDRs affecting antigen binding are present. Therefore, in many cases, antigen binding affinity is not maintained, and thus application of additional antibody engineering technology for recovering the antigen binding affinity is necessary.

The anti c-Met antibodies may be mouse-derived antibodies, mouse-human chimeric antibodies, humanized antibodies, or human antibodies. The antibodies or antigen-binding fragments thereof may be isolated from a living body or non-naturally occurring. The antibodies or antigen-binding fragments thereof may be recombinant or synthetic. The antibody may be monoclonal.

An intact antibody includes two full-length light chains and two full-length heavy chains, in which each light chain is linked to a heavy chain by disulfide bonds. The antibody includes a heavy chain constant region and a light chain constant region. The heavy chain constant region is of a gamma (γ), mu (μ), alpha (α), delta (δ), or epsilon (ε) type, which may be further categorized as gamma 1 (γ1), gamma 2 (γ2), gamma 3 (γ3), gamma 4 (γ4), alpha 1 (α1), or alpha 2 (α2). The light chain constant region is of either a kappa (κ) or lambda (λ) type.

As used herein, the term "heavy chain" refers to full-length heavy chain, and fragments thereof, including a variable region $V_H$ that includes amino acid sequences sufficient to provide specificity to antigens, and three constant regions, $C_{H1}$, $C_{H2}$, and $C_{H3}$, and a hinge. The term "light chain" refers to a full-length light chain and fragments thereof, including a variable region $V_L$ that includes amino acid sequences sufficient to provide specificity to antigens, and a constant region $C_L$.

The term "complementarity determining region (CDR)" refers to an amino acid sequence found in a hyper variable region of a heavy chain or a light chain of immunoglobulin. The heavy and light chains may respectively include three CDRs (CDRH1, CDRH2, and CDRH3; and CDRL1, CDRL2, and CDRL3). The CDRs may provide contact residues that play an important role in the binding of antibodies to antigens or epitopes. The terms "specifically binding" and "specifically recognized" are well known to one of ordinary skill in the art, and indicate that an antibody and an antigen specifically interact with each other to lead to an immunological activity.

The term "antigen-binding fragment" used herein refers to fragments of an intact immunoglobulin including portions of a polypeptide including antigen-binding regions having the ability to specifically bind to the antigen. In one embodiment, the antigen-binding fragment may be selected from the group consisting of scFv, (scFv)$_2$, Fab, Fab', and F(ab')$_2$, but not be limited thereto.

Among the antigen-binding fragments, Fab that includes light chain and heavy chain variable regions, a light chain constant region, and a first heavy chain constant region $C_{H1}$, includes one antigen-binding site.

The Fab' fragment is different from the Fab fragment, in that Fab' includes a hinge region with at least one cysteine residue at the C-terminal of $C_{H1}$.

The F(ab')$_2$ antibody is formed through disulfide bridging of the cysteine residues in the hinge region of the Fab' fragment. Fv is the smallest antibody fragment with only a heavy chain variable region and a light chain variable region. Recombination techniques of generating the Fv fragment are widely known in the art.

Two-chain Fv includes a heavy chain variable region and a light chain region which are linked by a non-covalent bond. Single-chain Fv generally includes a heavy chain variable region and a light chain variable region which are linked by a covalent bond via a peptide linker or linked at the C-terminals to have a dimer structure like the two-chain Fv. The peptide linker may be a polypeptide comprising about 1 to about 100 or about 2 to about 50 amino acids, wherein the amino acids may be selected from any amino acids without limitation.

The antigen-binding fragments may be attainable using protease (for example, the Fab fragment may be obtained by restricted cleavage of a whole antibody with papain, and the F(ab')$_2$ fragment may be obtained by cleavage with pepsin), or may be prepared by using a genetic recombination technique.

The term "hinge region," as used herein, refers to a region between CH1 and CH2 domains within the heavy chain of an antibody which functions to provide flexibility for the antigen-binding site.

When an animal antibody undergoes a chimerization process, the IgG1 hinge of animal origin may be replaced with a human IgG1 hinge or IgG2 hinge while the disulfide bridges between two heavy chains are reduced from three to two in number. In addition, an animal-derived IgG1 hinge is shorter than a human IgG1 hinge. Accordingly, the rigidity of the hinge is changed. Thus, a modification of the hinge region may bring about an improvement in the antigen binding efficiency of the humanized antibody. The modification of the hinge region through amino acid deletion, addition, or substitution is well-known to those skilled in the art.

In one embodiment, the anti-c-Met antibody or an antigen-binding fragment thereof may be modified by the deletion, insertion, addition, or substitution of at least one (e.g., two, three, four, five, six, seven, eight, nine, or ten) amino acid residue of the amino acid sequence of the hinge region so that it exhibits enhanced antigen-binding efficiency. For example, the antibody may include a hinge region including the amino acid sequence of SEQ ID NO: 100 (U7-HC6), 101 (U6-HC7), 102 (U3-HC9), 103 (U6-HC8), or 104 (U8-

HC5), or a hinge region including the amino acid sequence of SEQ ID NO: 105 (non-modified human hinge). Preferably, the hinge region includes the amino acid sequence of SEQ ID NO: 100 or 101.

In one embodiment, the anti-c-Met antibody may be a monoclonal antibody. The monoclonal antibody may be produced by the hybridoma cell line deposited with the Korean Cell Line Research Foundation, an international depository authority located at Yungun-Dong, Jongno-Gu, Seoul, Korea, on Oct. 6, 2009, under Accession No. KCLRF-BP-00220, which binds specifically to the extracellular region of c-Met protein (refer to Korean Patent Publication No. 2011-0047698, the entire disclosure of which is incorporated herein by reference). The anti-c-Met antibody may include all the antibodies defined in Korean Patent Publication No. 2011-0047698.

In the anti-c-Met antibody, the rest portion of the light chain and the heavy chain portion other than the CDRs, the light chain variable region, and the heavy chain variable region, e.g., a light chain constant region and/or a heavy chain constant region, may be from any subtype of immunoglobulin (e.g., IgA, IgD, IgE, IgG (IgG1, IgG2, IgG3, IgG4), IgM, etc.).

By way of further example, the anti-c-Met antibody may comprise or consist essentially of:

(a) a heavy chain comprising an amino acid sequence selected from the group consisting of the amino acid sequence of SEQ ID NO: 62 (wherein the amino acid sequence from amino acid residues from the $1^{st}$ to $17^{th}$ positions is a signal peptide), the amino acid sequence from the $18^{th}$ to $462^{nd}$ positions of SEQ ID NO: 62, the amino acid sequence of SEQ ID NO: 64 (wherein the amino acid sequence from the $1^{st}$ to $17^{th}$ positions is a signal peptide), the amino acid sequence from the $18^{th}$ to $461^{st}$ positions of SEQ ID NO: 64, the amino acid sequence of SEQ ID NO: 66 (wherein the amino acid sequence from the $1^{st}$ to $17^{th}$ positions is a signal peptide), and the amino acid sequence from the $18^{th}$ to $460^{th}$ positions of SEQ ID NO: 66; and (b) a light chain comprising an amino acid sequence selected from the group consisting of the amino acid sequence of SEQ ID NO: 68 (wherein the amino acid sequence from the $1^{st}$ to $20^{th}$ positions is a signal peptide), the amino acid sequence from the $21^{st}$ to $240^{th}$ positions of SEQ ID NO: 68, the amino acid sequence of SEQ ID NO: 70 (wherein the amino acid sequence from the $1^{st}$ to $20^{th}$ positions is a signal peptide), the amino acid sequence from the $21^{st}$ to $240^{th}$ positions of SEQ ID NO: 70, and the amino acid sequence of SEQ ID NO: 108.

For example, the anti-c-Met antibody may be selected from the group consisting of:

(i) an antibody comprising (a) a heavy chain comprising the amino acid sequence of SEQ ID NO: 62 or the amino acid sequence from the $18^{th}$ to $462^{nd}$ positions of SEQ ID NO: 62 and (b) a light chain comprising the amino acid sequence of SEQ ID NO: 68 or the amino acid sequence from the $21^{st}$ to $240^{th}$ positions of SEQ ID NO: 68;

(ii) an antibody comprising (a) a heavy chain comprising the amino acid sequence of SEQ ID NO: 64 or the amino acid sequence from the $18^{th}$ to $461^{st}$ positions of SEQ ID NO: 64 and (b) a light chain including the amino acid sequence of SEQ ID NO: 68 or the amino acid sequence from the $21^{st}$ to $240^{th}$ positions of SEQ ID NO: 68;

(iii) an antibody comprising (a) a heavy chain comprising the amino acid sequence of SEQ ID NO: 66 or the amino acid sequence from the $18^{th}$ to $460^{th}$ positions of SEQ ID NO: 66 and (b) a light chain comprising the amino acid sequence of SEQ ID NO: 68 or the amino acid sequence from the $21^{st}$ to $240^{th}$ positions of SEQ ID NO: 68;

(iv) an antibody comprising (a) a heavy chain comprising the amino acid sequence of SEQ ID NO: 62 or the amino acid sequence from the $18^{th}$ to $462^{nd}$ positions of SEQ ID NO: 62 and (b) a light chain including the amino acid sequence of SEQ ID NO: 70 or the amino acid sequence from the $21^{st}$ to $240^{th}$ positions of SEQ ID NO: 70;

(v) an antibody comprising a heavy chain comprising (a) the amino acid sequence of SEQ ID NO: 64 or the amino acid sequence from the $18^{th}$ to $461^{st}$ positions of SEQ ID NO: 64 and (b) a light chain comprising the amino acid sequence of SEQ ID NO: 70 or the amino acid sequence from the $21^{st}$ to $240^{th}$ positions of SEQ ID NO: 70;

(v) an antibody comprising (a) a heavy chain comprising the amino acid sequence of SEQ ID NO: 66 or the amino acid sequence from the $18^{th}$ to $460^{th}$ positions of SEQ ID NO: 66 and (b) a light chain comprising the amino acid sequence of SEQ ID NO: 70 or the amino acid sequence from the $21^{st}$ to $240^{th}$ positions of SEQ ID NO: 70;

(vi) an antibody comprising (a) a heavy chain comprising the amino acid sequence of SEQ ID NO: 62 or the amino acid sequence from the $18^{th}$ to $462^{nd}$ positions of SEQ ID NO: 62 and (b) a light chain comprising the amino acid sequence of SEQ ID NO: 108;

(vii) an antibody comprising (a) a heavy chain comprising the amino acid sequence of SEQ ID NO: 64 or the amino acid sequence from the $18^{th}$ to $461^{st}$ positions of SEQ ID NO: 64 and (b) a light chain comprising the amino acid sequence of SEQ ID NO: 108; and (viii) an antibody comprising (a) a heavy chain comprising the amino acid sequence of SEQ ID NO: 66 or the amino acid sequence from the $18^{th}$ to $460^{th}$ positions of SEQ ID NO: 66 and (b) a light chain comprising the amino acid sequence of SEQ ID NO: 108.

The polypeptide comprising the amino acid sequence of SEQ ID NO: 70 is a light chain including human kappa (κ) constant region, and the polypeptide comprising the amino acid sequence of SEQ ID NO: 68 is a polypeptide obtained by replacing histidine at position 62 (corresponding to position 36 of SEQ ID NO: 68 according to kabat numbering) of the polypeptide comprising the amino acid sequence of SEQ ID NO: 70 with tyrosine. The production yield of the antibodies may be increased by the replacement. The polypeptide comprising the amino acid sequence of SEQ ID NO: 108 is a polypeptide obtained by replacing serine at position 32 (position 27e according to kabat numbering in the amino acid sequence from amino acid residues 21 to 240 of SEQ ID NO: 68; positioned within CDR-L1) of SEQ ID NO: 108 with tryptophan. By such replacement, antibodies and antibody fragments including such sequences exhibit increased activities, such as c-Met biding affinity, c-Met degradation activity, Akt phosphorylation inhibition, and the like.

In another embodiment, the anti c-Met antibody may comprising a light chain complementarity determining region comprising the amino acid sequence of SEQ ID NO: 106, a light chain variable region comprising the amino acid sequence of SEQ ID NO: 107, or a light chain comprising the amino acid sequence of SEQ ID NO: 108.

The c-Met inhibitor may be applied (administered) together with a pharmaceutically acceptable carrier. The pharmaceutically acceptable carrier may be those commonly used for the formulation of the inhibitor (e.g., antibodies), which may be one or more selected from the group consisting of lactose, dextrose, sucrose, sorbitol, mannitol, starch, gum acacia, calcium phosphate, alginates, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate, and mineral oil, but are not limited thereto. The c-Met inhibitor may further comprise one or more selected from the group consisting of a lubricant, a wetting agent, a sweetener, a flavor enhancer, an emulsifying agent, a suspension agent, and preservative.

The c-Met inhibitor may be administered orally or parenterally. The parenteral administration may selected from the group consisting of intravenous injection, subcutaneous injection, muscular injection, intraperitoneal injection, endothelial administration, local administration, intranasal administration, intrapulmonary administration, and rectal administration. Since oral administration leads to digestion of proteins or peptides, the c-Met inhibitor for oral administration must be coated or formulated to prevent digestion in stomach. In addition, the c-Met inhibitor may be administered using an optional device that enables an active substance to be delivered to target cells.

The term "the pharmaceutically effective amount" as used herein may refer to an amount of which the active ingredient can exert pharmaceutically significant effects. The pharmaceutically effective amount of the c-Met inhibitor for a single dose may be prescribed in a variety of ways, depending on factors such as formulation methods, administration manners, age of patients, body weight of patients, gender of patients, pathologic conditions of patients, diets, administration time, administration interval, administration mute, excretion speed, and reaction sensitivity. For example, the pharmaceutically effective amount of the c-Met inhibitor for a single dose may be in ranges of 0.001 to 100 mg/kg, or 0.02 to 10 mg/kg, but not limited thereto. The pharmaceutically effective amount for the single dose may be formulated into a single formulation in a unit dosage form or formulated in suitably divided dosage forms, or it may be manufactured to be contained in a multiple dosage container.

The c-Met inhibitor may be used in the prevention and/or treatment of a cancer. The cancer may be associated with over-expression and/or abnormal activation of c-Met. The cancer may be a solid cancer or a blood cancer. The cancer may be, but not limited to, one or more selected from the group consisting of squamous cell carcinoma, small-cell lung cancer, non-small-cell lung cancer, adenocarcinoma of the lung, squamous cell carcinoma of the lung, peritoneal carcinoma, skin cancer, melanoma in the skin or eyeball, rectal cancer, cancer near the anus, esophagus cancer, small intestinal tumor, endocrine gland cancer, parathyroid cancer, adrenal cancer, soft-tissue sarcoma, urethral cancer, chronic or acute leukemia, lymphocytic lymphoma, hepatoma, gastric cancer, gastrointestinal cancer, pancreatic cancer, glioblastoma, cervical cancer, ovarian cancer, liver cancer, bladder cancer, hepatocellular adenoma, breast cancer, colon cancer, large intestine cancer, endometrial carcinoma or uterine carcinoma, salivary gland tumor, kidney cancer, prostate cancer, vulvar cancer, thyroid cancer, head or neck cancer, brain cancer, osteosarcoma, and the like. The cancer may be a primary cancer or a metastatic cancer. The cancer may be a c-Met inhibitor (e.g., an anti-c-Met antibody) resistant cancer.

The prevention and/or treatment of cancer may be achieved by at least one effect of the c-Met inhibitor selected from cancer cell death, inhibition of cancer cell proliferation, inhibition of migration, invasion, or metastasis of cancer, improvement of symptoms associated with cancer, etc.

Biomarkers capable of predicting and/or monitoring an efficacy of a c-Met inhibitor may lead to improvement of the therapeutic effect of the c-Met inhibitor, and making it possible to provide a patient-tailored treatment which is optimized for individual patient, thereby increasing the therapeutic efficacy.

EXAMPLES

Hereafter, the present invention will be described in detail by examples.

The following examples are intended merely to illustrate the invention and are not construed to restrict the invention.

Reference Example: Construction of Anti-c-Met Antibody 1.1. Production of "AbF46", a Mouse Antibody to c-Met 1.1.1. Immunization of Mice To obtain immunized mice necessary for the development of a hybridoma cell line, each of five BALB/c mice (Japan SLC, Inc.), 4 to 6 weeks old, was intraperitoneally injected with a mixture of 100 µg of human c-Met/Fc fusion protein (R&D Systems) and one volume of complete Freund's adjuvant. Two weeks after the injection, a second intraperitoneal injection was conducted on the same mice with a mixture of 50 µg of human c-Met/Fc protein and one volume of incomplete Freund's adjuvant. One week after the second immunization, the immune response was finally boosted. Three days later, blood was taken from the tails of the mice and the sera were 1/1000 diluted in PBS and used to examine a titer of antibody to c-Met by ELISA. Mice found to have a sufficient antibody titer were selected for use in the cell fusion process.

1.1.2. Cell Fusion and Production of a Hybridoma

Three days before cell fusion, BALB/c mice (Japan SLC, Inc.) were immunized with an intraperitoneal injection of a mixture of 50 µg of human c-Met/Fc fusion protein and one volume of PBS. The immunized mice were anesthetized before excising the spleen from the left half of the body. The spleen was meshed to separate splenocytes which were then suspended in a culture medium (DMEM, GIBCO, Invitrogen). The cell suspension was centrifuged to recover the cell layer. The splenocytes thus obtained ($1 \times 10^8$ cells) were mixed with myeloma cells (Sp2/0) ($1 \times 10^8$ cells), followed by spinning to yield a cell pellet. The cell pellet was slowly suspended, treated with 45% polyethylene glycol (PEG) (1 mL) in DMEM for 1 min at 37° C., and supplemented with 1 mL of DMEM. To the cells was added 10 mL of DMEM over 10 min, after which incubation was conducted in a water bath at 37° C. for 5 min. Then the cell volume was adjusted to 50 mL before centrifugation. The cell pellet thus formed was resuspended at a density of $1 \sim 2 \times 10^5$ cells/mL in a selection medium (HAT medium). 0.1 mL of the cell suspension was allocated to each well of 96-well plates which were then incubated at 37° C. in a $CO_2$ incubator to establish a hybridoma cell population.

1.1.3. Selection of Hybridoma Cells Producing Monoclonal Antibodies to c-Met Protein From the hybridoma cell population established in Reference Example 1.1.2, hybridoma cells which showed a specific response to c-Met protein were screened by ELISA using human c-Met/Fc fusion protein and human Fc protein as antigens.

Human c-Met/Fc fusion protein was seeded in an amount of 50 µL (2 µg/mL)/well to microtiter plates and allowed to adhere to the surface of each well. The antibody that remained unbound was removed by washing. For use in selecting the antibodies that do not bind c-Met but recognize Fc, human Fc protein was attached to the plate surface in the same manner.

The hybridoma cell culture obtained in Reference Example 1.1.2 was added in an amount of 50 μL to each well of the plates and incubated for 1 hour. The cells remaining unreacted were washed out with a sufficient amount of Tris-buffered saline and Tween 20 (TBST). Goat anti-mouse IgG-horseradish peroxidase (HRP) was added to the plates and incubated for 1 hour at room temperature. The plates were washed with a sufficient amount of TBST, followed by reacting the peroxidase with a substrate (OPD). Absorbance at 450 nm was measured on an ELISA reader.

Hybridoma cell lines which secrete antibodies that specifically and strongly bind to human c-Met but not human Fc were selected repeatedly. From the hybridoma cell lines obtained by repeated selection, a single clone producing a monoclonal antibody was finally separated by limiting dilution. The single clone of the hybridoma cell line producing the monoclonal antibody was deposited with the Korean Cell Line Research Foundation, an international depository authority located at Yungun-Dong, Jongno-Gu, Seoul, Korea, on Oct. 6, 2009, with Accession No. KCLRF-BP-00220 according to the Budapest Treaty (refer to Korean Patent Laid-Open Publication No. 2011-0047698).

1.1.4. Production and Purification of a Monoclonal Antibody

The hybridoma cell line obtained in Reference Example 1.1.3 was cultured in a serum-free medium, and the monoclonal antibody (AbF46) was produced and purified from the cell culture.

First, the hybridoma cells cultured in 50 mL of a medium (DMEM) supplemented with 10% (v/v) FBS (fetal bovine serum) were centrifuged and the cell pellet was washed twice or more with 20 mL of PBS to remove the FBS therefrom. Then, the cells were resuspended in 50 mL of DMEM and incubated for 3 days at 37° C. in a $CO_2$ incubator.

After the cells were removed by centrifugation, the supernatant was stored at 4° C. before use or immediately used for the separation and purification of the antibody. An AKTA system (GE Healthcare) equipped with an affinity column (Protein G agarose column; Pharmacia, USA) was used to purify the antibody from 50 to 300 mL of the supernatant, followed by concentration with a filter (Amicon). The antibody was stored in PBS before use in the following examples.

1.2. Construction of chAbF46, a Chimeric Antibody to c-Met

A mouse antibody is apt to elicit immunogenicity in humans. To solve this problem, chAbF46, a chimeric antibody, was constructed from the mouse antibody AbF46 produced in Reference Example 1.1.4 by replacing the constant region, but not the variable region responsible for antibody specificity, with an amino sequence of the human IgG1 antibody.

In this regard, a gene was designed to include the nucleotide sequence of "EcoRI-signal sequence-VH-NheI-CH-TGA-XhoI" (SEQ ID NO: 38) for a heavy chain and the nucleotide sequence of "EcoRI-signal sequence-VL-BsiWI-CL-TGA-XhoI" (SEQ ID NO: 39) for a light chain and synthesized. Then, a DNA fragment having the heavy chain nucleotide sequence (SEQ ID NO: 38) and a DNA fragment having the light chain nucleotide sequence (SEQ ID NO: 39) were digested with EcoRI (NEB, R0101S) and XhoI (NEB, R0146S) before cloning into a vector from the pOptiVEC™-TOPO TA Cloning Kit enclosed in an OptiCHO™ Antibody Express Kit (Cat no. 12762-019, Invitrogen), and a vector from the pcDNA™ 3.3-TOPO TA Cloning Kit (Cat no. 8300-01), respectively.

Each of the constructed vectors was amplified using Qiagen Maxiprep kit (Cat no. 12662), and a transient expression was performed using Freestyle™ MAX 293 Expression System (Invitrogen). 293 F cells were used for the expression and cultured in FreeStyle™ 293 Expression Medium in a suspension culture manner. At one day before the transient expression, the cells were provided in the concentration of $5 \times 10^5$ cells/mL. After 24 hours, when the cell number reached to $1 \times 10^6$ cells/mL, the transient expression was performed. A transfection was performed by a liposomal reagent method using Freestyle™ MAX reagent (Invitrogen), wherein in a 15 mL tube, the DNA was provided in the mixture ratio of 1:1 (heavy chain DNA:light chain DNA) and mixed with 2 mL of OptiPro™ SFM (Invitrogen) (A). In another 15 mL tube, 100 μL of Freestyle™ MAX reagent and 2 mL of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

Afterwards, the cells were incubated in DMEM supplemented with 10% (v/v) FBS for 5 hours at 37° C. under a 5% $CO_2$ condition and then in FBS-free DMEM for 48 hours at 37° C. under a 5% $CO_2$ condition.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE Healthcare, 17-0405-03), followed by elution with an IgG elution buffer (Thermo Scientific, 21004). The buffer was exchanged with PBS to purify a chimeric antibody AbF46 (hereinafter referred to as "chAbF46").

1.3. Construction of Humanized Antibody huAbF46 from Chimeric Antibody chAbF46

1.3.1. Heavy Chain Humanization

To design two domains H1-heavy and H3-heavy, human germline genes which share the highest identity/homology with the VH gene of the mouse antibody AbF46 purified in Reference Example 1.2 were analyzed. An Ig BLAST search (www.ncbi.nlm.nih.gov/igblast/) result revealed that VH3-71 has an identity/identity/homology of 83% at the amino acid level. CDR-H1, CDR-H2, and CDR-H3 of the mouse antibody AbF46 were defined according to Kabat numbering. A design was made to introduce the CDR of the mouse antibody AbF46 into the framework of VH3-71. Hereupon, back mutations to the amino acid sequence of the mouse AbF46 were conducted at positions 30 (S→T), 48 (V→L), 73 (D→N), and 78 (T→L). Then, H1 was further mutated at positions 83 (R→K) and 84 (A→T) to finally establish H1-heavy (SEQ ID NO: 40) and H3-heavy (SEQ ID NO: 41).

For use in designing H4-heavy, human antibody frameworks were analyzed by a BLAST search. The result revealed that the VH3 subtype, known to be most stable, is very similar in framework and sequence to the mouse antibody AbF46. CDR-H1, CDR-H2, and CDR-H3 of the mouse antibody AbF46 were defined according to Kabat numbering and introduced into the VH3 subtype to construct H4-heavy (SEQ ID NO: 42).

1.3.2. Light Chain Humanization

To design two domains H1-light (SEQ ID NO: 43) and H2-light (SEQ ID NO: 44), human germline genes which share the highest identity/homology with the VH gene of the mouse antibody AbF46 were analyzed. An Ig BLAST search result revealed that VK4-1 has an identity/homology of 75% at the amino acid level. CDR-L1, CDR-L2, and CDR-L3 of the mouse antibody AbF46 were defined according to Kabat numbering. A design was made to introduce the CDR of the mouse antibody AbF46 into the framework of VK4-1. Hereupon, back mutations to the amino acid sequence of the mouse AbF46 were conducted at positions 36 (Y→H), 46 (L→M), and 49 (Y→I). Only one back mutation was conducted at position 49 (Y→I) on H2-light.

To design H3-light (SEQ ID NO: 45), human germline genes which share the highest identity/homology with the VL gene of the mouse antibody AbF46 were analyzed by a BLAST search. As a result, VK2-40 was selected. VL and VK2-40 of the mouse antibody AbF46 were found to have a identity/homology of 61% at an amino acid level. CDR-L1, CDR-L2, and CDR-L3 of the mouse antibody were defined according to Kabat numbering and introduced into the framework of VK4-1. Back mutations were conducted at positions 36 (Y→H), 46 (L→M), and 49 (Y→I) on H3-light.

For use in designing H4-light (SEQ ID NO: 46), human antibody frameworks were analyzed. A BLAST search revealed that the Vk1 subtype, known to be the most stable, is very similar in framework and sequence to the mouse antibody AbF46. CDR-L1, CDR-L2, and CDR-L3 of the mouse antibody AbF46 were defined according to Kabat numbering and introduced into the Vk1 subtype. Hereupon, back mutations were conducted at positions 36 (Y→H), 46 (L→M), and 49 (Y→I) on H4-light.

Thereafter, DNA fragments having the heavy chain nucleotide sequences (H1-heavy: SEQ ID NO: 47, H3-heavy: SEQ ID NO: 48, H4-heavy: SEQ ID NO: 49) and DNA fragments having the light chain nucleotide sequences (H1-light: SEQ ID NO: 50, H2-light: SEQ ID NO: 51, H3-light: SEQ ID NO: 52, H4-light: SEQ ID NO: 53) were digested with EcoRI (NEB, R0101S) and XhoI (NEB, R0146S) before cloning into a vector from the pOptiVEC™-TOPO TA Cloning Kit enclosed in an OptiCHO™ Antibody Express Kit (Cat no. 12762-019, Invitrogen) and a vector from the pcDNA™ 3.3-TOPO TA Cloning Kit (Cat no. 8300-01), respectively, so as to construct recombinant vectors for expressing a humanized antibody.

Each of the constructed vectors was amplified using Qiagen Maxiprep kit (Cat no. 12662), and a transient expression was performed using Freestyle™ MAX 293 Expression System (invitrogen). 293 F cells were used for the expression and cultured in FreeStyle™ 293 Expression Medium in a suspension culture manner. At one day before the transient expression, the cells were provided in the concentration of 5×10⁵ cells/ml, and after 24 hours, when the cell number reached to 1×10⁶ cells/mL, the transient expression was performed. A transfection was performed by a liposomal reagent method using Freestyle™ MAX reagent (Invitrogen), wherein in a 15 mL tube, the DNA was provided in the mixture ratio of 1:1 (heavy chain DNA:light chain DNA) and mixed with 2 mL of OptiPro™ SFM (invtrogen) (A). In another 15 mL tube, 100 μL of Freestyle™ MAX reagent and 2 mL of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE Healthcare, 17-0405-03), followed by elution with an IgG elution buffer (Thermo Scientific, 21004). The buffer was exchanged with PBS to purify a humanized antibody AbF46 (hereinafter referred to as "huAbF46"). The humanized antibody huAbF46 used in the following examples comprised a combination of H4-heavy (SEQ ID NO: 42) and H4-light (SEQ ID NO: 46).

1.4. Construction of scFV Library of huAbF46 Antibody

For use in constructing an scFv of the huAbF46 antibody from the heavy and light chain variable regions of the huAbF46 antibody, a gene was designed to have the structure of "VH-linker-VL" for each of the heavy and the light chain variable region, with the linker comprising the amino acid sequence "GLGGLGGGGSGGGGSGGSSGVGS" (SEQ ID NO: 54). A polynucleotide sequence (SEQ ID NO: 55) encoding the designed scFv of huAbF46 was synthesized in Bioneer and an expression vector for the polynucleotide had the nucleotide sequence of SEQ ID NO: 56.

After expression, the product was found to exhibit specificity to c-Met.

1.5. Construction of Library Genes for Affinity Maturation 1.5.1. Selection of Target CDRs and Synthesis of Primers The affinity maturation of huAbF46 was achieved. First, six complementary determining regions (CDRs) were defined according to Kabat numbering. The CDRs are given in Table 2 below.

TABLE 2

| CDR | Amino Acid Sequence |
| --- | --- |
| CDR-H1 | DYYMS (SEQ ID NO: 1) |
| CDR-H2 | FIRNKANGYTTEYSASVKG (SEQ ID NO: 2) |
| CDR-H3 | DNWFAY (SEQ ID NO: 3) |
| CDR-L1 | KSSQSLLASGNQNNYLA (SEQ ID NO: 10) |
| CDR-L2 | WASTRVS (SEQ ID NO: 11) |
| CDR-L3 | QQSYSAPLT (SEQ ID NO: 12) |

For use in the introduction of random sequences into the CDRs of the antibody, primers were designed as follows. Conventionally, N codons were utilized to introduce bases at the same ratio (25% A, 25% G, 25% C, 25% T) into desired sites of mutation. In this experiment, the introduction of random bases into the CDRs of huAbF46 was conducted in such a manner that, of the three nucleotides per codon in the wild-type polynucleotide encoding each CDR, the first and second nucleotides conserved over 85% of the entire sequence while the other three nucleotides were introduced at the same percentage (each 5%) and that the same possibility was imparted to the third nucleotide (33% G, 33% C, 33% T).

1.5.2. Construction of a Library of huAbF46 Antibodies and Affinity for c-Met

The construction of antibody gene libraries through the introduction of random sequences was carried out using the primers synthesized in the same manner as in Reference Example 1.5.1. Two PCR products were obtained using a polynucleotide covering the scFV of huAbF46 as a template, and were subjected to overlap extension PCR to give scFv library genes for huAbF46 antibodies in which only desired CDRs were mutated. Libraries targeting each of the six CDRs prepared from the scFV library genes were constructed.

The affinity for c-Met of each library was compared to that of the wildtype. Most libraries were lower in affinity for c-Met, compared to the wild-type. The affinity for c-Met was retained in some mutants.

1.6. Selection of Antibody with Improved Affinity from Libraries

After maturation of the affinity of the constructed libraries for c-Met, the nucleotide sequence of scFv from each clone was analyzed. The nucleotide sequences thus obtained are summarized in Table 3 and were converted into IgG forms. Four antibodies which were respectively produced from clones L3-1, L3-2, L3-3, and L3-5 were used in the subsequent experiments.

TABLE 3

| Clone | Library constructed | CDR Sequence |
|---|---|---|
| H11-4 | CDR-H1 | PEYYMS (SEQ ID NO: 22) |
| YC151 | CDR-H1 | PDYYMS (SEQ ID NO: 23) |
| YC193 | CDR-H1 | SDYYMS (SEQ ID NO: 24) |
| YC244 | CDR-H2 | RNNANGNT (SEQ ID NO: 25) |
| YC321 | CDR-H2 | RNKVNGYT (SEQ ID NO: 26) |
| YC354 | CDR-H3 | DNWLSY (SEQ ID NO: 27) |
| YC374 | CDR-H3 | DNWLTY (SEQ ID NO: 28) |
| L1-1 | CDR-L1 | KSSHSLLASGNQNNYLA (SEQ ID NO: 29) |
| L1-3 | CDR-L1 | KSSRSLLSSGNHKNYLA (SEQ ID NO: 30) |
| L1-4 | CDR-L1 | KSSKSLLASGNQNNYLA (SEQ ID NO: 31) |
| L1-12 | CDR-L1 | KSSRSLLASGNQNNYLA (SEQ ID NO: 32) |
| L1-22 | CDR-L1 | KSSHSLLASGNQNNYLA (SEQ ID NO: 33) |
| L2-9 | CDR-L2 | WASKRVS (SEQ ID NO: 34) |
| L2-12 | CDR-L2 | WGSTRVS (SEQ ID NO: 35) |
| L2-16 | CDR-L2 | WGSTRVP (SEQ ID NO: 36) |
| L3-1 | CDR-L3 | QQSYSRPYT (SEQ ID NO: 13) |
| L3-2 | CDR-L3 | GQSYSRPLT (SEQ ID NO: 14) |
| L3-3 | CDR-L3 | AQSYSHPFS (SEQ ID NO: 15) |
| L3-5 | CDR-L3 | QQSYSRPFT (SEQ ID NO: 16) |
| L3-32 | CDR-L3 | QQSYSKPFT (SEQ ID NO: 37) |

1.7. Conversion of Selected Antibodies into IgG

Respective polynucleotides encoding heavy chains of the four selected antibodies were designed to have the structure of "EcoRI-signal sequence-VH-NheI-CH-XhoI" (SEQ ID NO: 38). The heavy chains of huAbF46 antibodies were used as they were because their amino acids were not changed during affinity maturation. In the case of the hinge region, however, the U6-HC7 hinge (SEQ ID NO: 57) was employed instead of the hinge of human IgG1. Genes were also designed to have the structure of "EcoRI-signal sequence-VL-BsiWI-CL-XhoI" for the light chain. Polypeptides encoding light chain variable regions of the four antibodies which were selected after the affinity maturation were synthesized in Bioneer. Then, a DNA fragment having the heavy chain nucleotide sequence (SEQ ID NO: 38) and DNA fragments having the light chain nucleotide sequences (DNA fragment comprising L3-1-derived CDR-L3: SEQ ID NO: 58, DNA fragment comprising L3-2-derived CDR-L3: SEQ ID NO: 59, DNA fragment comprising L3-3-derived CDR-L3: SEQ ID NO: 60, and DNA fragment comprising L3-5-derived CDR-L3: SEQ ID NO: 61) were digested with EcoRI (NEB, R0101S) and XhoI (NEB, R0146S) before cloning into a vector from the pOptiVEC™-TOPO TA Cloning Kit enclosed in an OptiCHO™ Antibody Express Kit (Cat no. 12762-019, Invitrogen) and a vector from the pcDNA™3.3-TOPO TA Cloning Kit (Cat no. 8300-01), respectively, so as to construct recombinant vectors for expressing affinity-matured antibodies.

Each of the constructed vectors was amplified using Qiagen Maxiprep kit (Cat no. 12662), and a transient expression was performed using Freestyle™ MAX 293 Expression System (invitrogen). 293 F cells were used for the expression and cultured in FreeStyle™ 293 Expression Medium in a suspension culture manner. At one day before the transient expression, the cells were provided in the concentration of $5 \times 10^5$ cells/mL. After 24 hours, when the cell number reached to $1 \times 10^6$ cells/mL, the transient expression was performed. A transfection was performed by a liposomal reagent method using Freestyle™ MAX reagent (Invitrogen), wherein in a 15 mL tube, the DNA was provided in the mixture ratio of 1:1 (heavy chain DNA:light chain DNA) and mixed with 2 mL of OptiPro™ SFM (Invitrogen) (A). I In another 15 mL tube, 100 µL of Freestyle™ MAX reagent and 2 mL of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE Healthcare, 17-0405-03), followed by elution with an IgG elution buffer (Thermo Scientific, 21004). The buffer was exchanged with PBS to purify four affinity-matured antibodies (hereinafter referred to as "huAbF46-H4-A1 (L3-1 origin), huAbF46-H4-A2 (L3-2 origin), huAbF46-H4-A3 (L3-3 origin), and huAbF46-H4-A5 (L3-5 origin)," respectively).

1.8. Construction of Constant Region- and/or Hinge Region-Substituted huAbF46-H4-A1

Among the four antibodies selected in Reference Example 1.7, huAbF46-H4-A1 was found to be the highest in affinity for c-Met and the lowest in Akt phosphorylation and c-Met degradation degree. In the antibody, the hinge region, or the constant region and the hinge region, were substituted.

The antibody huAbF46-H4-A1 (U6-HC7) was composed of a heavy chain comprising the heavy chain variable region of huAbF46-H4-A1, U6-HC7 hinge, and the constant region of human IgG1 constant region, and a light chain comprising the light chain variable region of huAbF46-H4-A1 and human kappa constant region. The antibody huAbF46-H4-A1 (IgG2 hinge) was composed of a heavy chain comprising a heavy chain variable region, a human IgG2 hinge region, and a human IgG1 constant region, and a light chain comprising the light chain variable region of huAbF46-H4-A1 and a human kappa constant region. The antibody huAbF46-H4-A1 (IgG2 Fc) was composed of the heavy chain variable region of huAbF46-H4-A1, a human IgG2 hinge region, and a human IgG2 constant region, and a light chain comprising the light variable region of huAbF46-H4-A1 and a human kappa constant region. Hereupon, the histidine residue at position 36 on the human kappa constant region of the light chain was changed to tyrosine in all of the three antibodies to increase antibody production.

For use in constructing the three antibodies, a polynucleotide (SEQ ID NO: 63) encoding a polypeptide (SEQ ID NO: 62) composed of the heavy chain variable region of huAbF46-H4-A1, a U6-HC7 hinge region, and a human IgG1 constant region, a polynucleotide (SEQ ID NO: 65) encoding a polypeptide (SEQ ID NO: 64) composed of the heavy chain variable region of huAbF46-H4-A1, a human IgG2 hinge region, and a human IgG1 region, a polynucleotide (SEQ ID NO: 67) encoding a polypeptide (SEQ ID NO: 66) composed of the heavy chain variable region of huAbF46-H4-A1, a human IgG2 region, and a human IgG2 constant region, and a polynucleotide (SEQ ID NO: 69) encoding a polypeptide (SEQ ID NO: 68) composed of the light chain variable region of huAbF46-H4-A1, with a tyrosine residue instead of histidine at position 36, and a human kappa constant region were synthesized in Bioneer. Then, the DNA fragments having heavy chain nucleotide sequences were inserted into a vector from the pOptiVEC™-TOPO TA Cloning Kit enclosed in an OptiCHO™ Antibody Express Kit (Cat no. 12762-019, Invitrogen) while DNA fragments having light chain nucleotide sequences were inserted into a vector from the pcDNA™3.3-TOPO TA Cloning Kit (Cat no. 8300-01) so as to construct vectors for expressing the antibodies.

Each of the constructed vectors was amplified using Qiagen Maxiprep kit (Cat no. 12662), and a transient expression was performed using Freestyle™ MAX 293 Expression System (Invitrogen). 293 F cells were used for the expression and cultured in FreeStyle™ 293 Expression Medium in a suspension culture manner. At one day before the transient expression, the cells were provided in the concentration of $5 \times 10^5$ cells/mL. After 24 hours, when the cell number reached to $1 \times 10^6$ cells/mL, the transient expression was performed. A transfection was performed by a liposomal reagent method using Freestyle™ MAX reagent (Invitrogen), wherein in a 15 mL tube, the DNA was provided in the mixture ratio of 1:1 (heavy chain DNA:light chain DNA) and mixed with 2 mL of OptiPro™ SFM (Invitrogen) (A). In another 15 mL tube, 100 μL of Freestyle™ MAX reagent and 2 mL of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE Healthcare, 17-0405-03), followed by elution with IgG elution buffer (Thermo Scientific, 21004). The buffer was exchanged with PBS to finally purify three antibodies (huAbF46-H4-A1 (U6-HC7), huAbF46-H4-A1 (IgG2 hinge), and huAbF46-H4-A1 (IgG2 Fc)). Among the three antibodies, huAbF46-H4-A1 (U6-HC7) and huAbF46-H4-A1 (IgG2 Fc) were representatively selected for the following examples, and referred as anti-c-Met antibody L3-1Y and L3-1Y/IgG2, respectively.

Example 1: Prediction and Evaluation of Efficacy of Anti-c-Met Antibody Using IL-8

1.1. Assay for Predicting and Evaluating Efficacy of Anti-c-Met Antibody in Cancer Cell-Implanted Mouse Model Using IL-8

1.1.1. Construction of Cancer Cell-Implanted Mouse Model

For use in assays for predicting and evaluating the efficacy of an anti-c-Met antibody, xenograft mouse models were prepared by implanting various conventional cancer cell lines (Lovo, HT-29, EBC-1, MKN45, and Hs746T) to mice.

Briefly, the human colorectal cancer cell line HT29 (ATCC HTB-38) or Lovo (ATCC CCL-229) were injected s.c. at a dose of $5 \times 10^6$ cells into BALB/C nude mice (4-5 week old, male; Shanghai SLAC Laboratory Animal Co. Ltd.) to construct xenograft mouse models. For modeling, 15 mice were allocated to each group. Also, the human stomach cancer cell lines Hs746T (ATCC HTB-135) and MKN45 (ATCC RCB1001), and the human non-small cell lung cancer cell line EBC-1 (ATCC JCRB0820) were used in the same manner to construct xenograft mouse models.

That is, mouse models implanted, respectively, with Lovo, HT-29, EBC-1, Hs746T, and MKN45 were constructed, and used in the following experiments.

1.1.2. Prediction of the Efficacy of Anti-c-Met Antibody in Cancer Cell-Implanted Mouse Model Using IL-8

After the anti-c-Met antibody L3-1Y/IgG2 prepared in Reference Example 1 was administered to Lovo-, HT-29-, EBC-1-, MKN45-, or Hs746T-implanted mouse models constructed in Example 1.1.1, tumor sizes were measured to identify groups which were responsive to L3-1Y/IgG2 (responder; effective anticancer activity) and were not responsive (non-responder; no anticancer activity).

Briefly, the anti-c-Met antibody was injected to each group of the mouse models constructed in Example 1.1.1 from 7-10 days after implantation. The injection was conducted at regular intervals of 7 days for 4 weeks via an intravenous route. Tumor volumes were measured and recorded twice a week. For a control, PBS was injected. The anti-c-Met antibody was injected at a dose of 0.2, 1, 5, or 10 mg/kg to HT29- or Lovo-implanted groups, and at a dose of 0.03, 0.1, 0.3, 1.0, 3.0, or 10.0 mg/kg to EBC-1-, MKN45-, or Hs746T-implanted groups. Results are depicted in FIGS. 1A to 1E (1a: Lovo, 1b: HT29, 1c: EBC-1, 1d: Hs746T, 1e: MKN45). FIGS. 1A to 1E show results of the control PBS group and representative anti-c-Met antibody groups (HT29, Lovo, MKN45, EBC-1 and Hs746T models, the first three were injected at a dose of 5 mg/kg while the remaining two injected at a dose of 3 mg/kg) only. Points of time of antibody injection or euthanasia are indicated by arrows. As can be seen in FIGS. 1A to 1E, the anticancer efficacy of L3-1Y/IgG2 was not detected in the Lovo- or the HT-29-implanted mouse models, but was apparent in EBC-1-, Hs746T- or MKN45-implanted mouse models. So, the Lovo- and the HT-29-implanted mouse models were determined to not be responsive to L3-1Y/IgG2 (non-responder group) while the EBC-1-, the Hs746T- and the MKN45-implanted mouse models were classified as responder groups.

An examination was made of a difference in serum IL-8 levels between the responder and the non-responder groups. Serum IL-8 levels of the Lovo-, the HT-29-, the EBC-1- and the Hs746T-implanted mouse models were compared to those of the control mice (injected with PBS only; at a dose of 100 μL every 7 days for 4 weeks), and relationship between serum IL-8 level and responsiveness to L3-1Y/IgG2 was investigated.

Briefly, sera from the control of each model were analyzed using a BD Cytometric Bead Array kit. Whole blood was collected from the mouse models in a BD vacutainer SST™ tube. After collection of the whole blood, the tube was mixed by gently inverting for 5 times, and then, allowed to clot for 30 minutes at room temperature. After the incubation, the clot was removed by centrifuge the tube at 1500×g for 10 minutes in a refrigerated centrifuge. The serum sample is obtained by transfer the supernatant into a new tube. Experiments were performed with a human inflammatory cytokine kit. According to the manufacture's guideline, mouse serum was diluted 1/4 (v/v) in the assay diluent buffer and incubated for 1.5 hrs with biotinylated anti-human IL-8 antibody-coated beads (BD Cytometric Bead Array (CBA) Human inflammatory cytokines kit, #551811, BD biosciences). Thereafter, the sample was mixed with 1 mL of the wash buffer containing in the BD Cytometric Bead Array (CBA) Human inflammatory cytokines kit, and centrifuged. After removal of the supernatant, the residue was incubated for 1.5 hrs with the streptavidin-PE of the kit, mixed with 1 mL of the wash buffer. After centrifugation (200 g, 5 min), the supernatant containing unreacted materials was discarded. The precipitate was suspended in 200 μL of wash buffer before FACS analysis (BD FACS CantoII flow cytometer, BD Bioscience). From the data thus obtained, serum IL-8 concentrations were calculated using the FCAP array program (BD Biosciences), and quantified by multiplication by the dilution factor.

Figure 2:
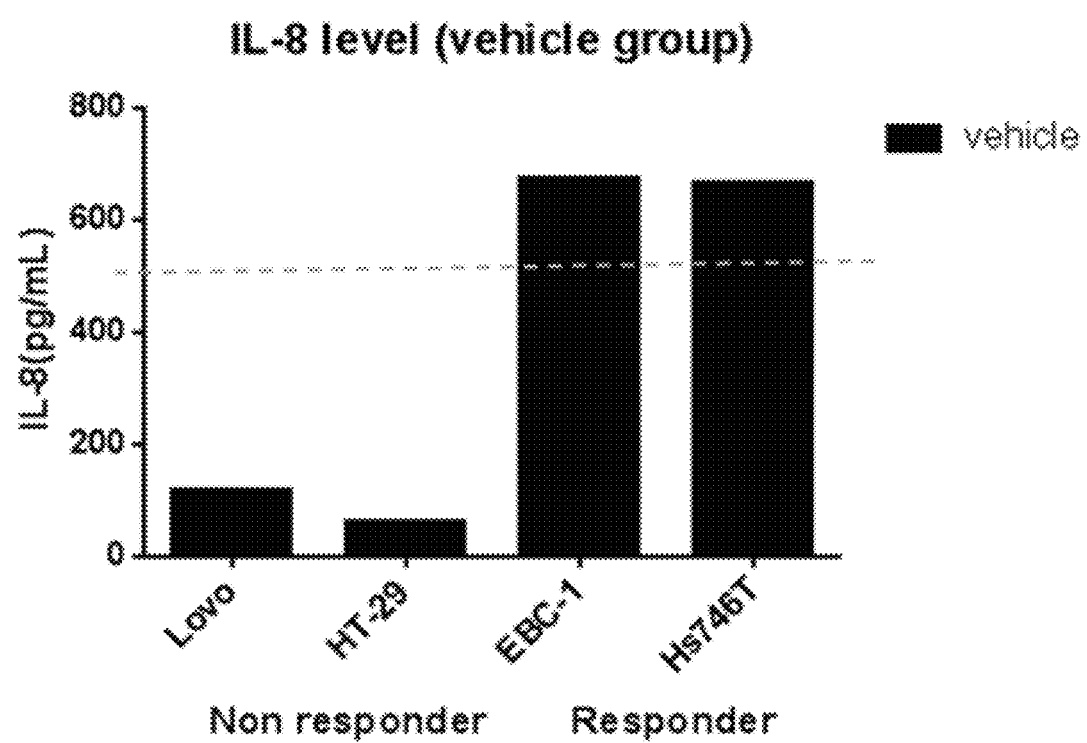
FIG. 2 is a graph of IL-8 levels in cancer cell-implanted mouse models showing relationship between IL-8 level and responsiveness to an anti-c-Met antibody.

The results are shown in FIG. 2. As can be seen in FIG. 2, the IL-8 level was measured about 500 pg/mL or higher in both the responder groups, but decreased to about 50-150 pg/ml in the non-responder groups. The serum IL-8 level of the responder groups was observed to be at least 3-fold higher than that of the non-responder. Accordingly, the cancer cells with high IL-8 levels are expected to allow L3-1Y/IgG2 to exert its anticancer activity more effectively.

1.1.3. Evaluation of the Efficacy of Anti-c-Met Antibody in Cancer Cell-Implanted Mouse Model Using IL-8

To examine the relationship between the level of IL-8 level and the responsiveness to an anti-c-Met antibody, the changes of serum IL-8 levels after treatment of the anti-c-Met antibody in cancer cell-implanted mouse models were monitored.

Briefly, among the serum samples obtained from the mouse xenograft models of Example 1.1.2, the vehicle-treated sample (PBS-treated, control) and the anti-c-Met antibody treated samples with high and low doses were prepared. To this end, serum samples were taken from HT29 and Lovo models (non-responder groups) injected at doses of 0.2 mg/kg and 5 mg/kg and from EBC-1 and Hs746T models (responder groups) injected at doses of 1 mg/kg and 3 mg/kg, and examined for the relationship between the anticancer efficacy of the anti-c-Met antibody and the change of IL-8 level after anti-c-Met antibody treatment. Serum IL-8 levels were analyzed with reference to Example 1.1.2.

Results are depicted in FIG. 3. As is understood from the data of FIG. 3, the non-responder groups showed no significant differences or an increase in the IL-8 level upon treatment with L3-1Y/IgG2 compared to the non-treated group ("vehicle-treated"; injected with vehicle only, PBS) whereas the responder groups showed a significant decrease in IL-8 level compared to the untreated group. These data imply that a patient can be monitored for responsiveness to L3-1Y/IgG2, that is, the efficacy of L3-1Y/IgG2 by measuring the expression level of IL-8 in the patient treated with L3-1Y/IgG2.

1.2. Assay for Predicting and Evaluating Efficacy of Anti-c-Met Antibody in Mouse Model Implanted with Patient-Derived Tumor Tissues by Measuring the Serum Level of IL-8.

1.2.1. Construction of Mouse Model Implanted with Patient-Derived Tumor Tissues.

For use in examining whether IL-8 can be used as a reliable biomarker in predicting or evaluating the efficacy of an anti-c-Met antibody when it is applied to patients, mouse models implanted with patient-derived tumor tissue suffering from cancer (lung cancer) were constructed.

This experiment was performed in the special company Oncotest (Oncotest GmbH, Freibrug Germany). Briefly, patient-derived lung cancer cell lines (non-small cell lung cancer (NSCLC)) LXFA297, 526, 623, 983, 1041 and 1647 were cultured and injected s.c. into NMRI nude mice (4-6 week old, female; Harlan) to construct xenograft mouse models. The construction was carried out according to the Oncotest SOP "Subcutaneous implantation" guideline. 10 mice were allocated to each group. After implantation, the mouse models were randomized to reduce measurement deviations of average tumor volumes between groups, and then injected with the drug. Experiments using patient-derived gastric cancer cell lines, GXF214 and GXF251, and patient-derived renal cancer cell lines, RXF488, RXF1114 and RXF1220 were performed referring to the above method.

The mouse models implanted with patient-derived tumor tissues were tested for responsiveness to an anti-c-Met antibody while L3-1Y/IgG2 was injected thereto.

Briefly, to monitor the anticancer efficacy of the antibody, the tumor volumes were regularly measured. Anticancer efficacy was calculated by dividing tumor volumes of each antibody-treated group (5 mg/kg, iv) by those of the control group (PBS injected) after completion of the injection (% inhibition=100−(tumor volume of test group/tumor volume of control*100)). The results are summarized in Tables 4 and 5.

A reduction of tumor volume by 30% or greater upon treatment with L3-1Y/IgG2 was considered statistically significant, which led to determining the antibody as being efficacious, and the group as a responder.

TABLE 4

| | NSCLC | | | | | |
|---|---|---|---|---|---|---|
| Model | LXFA297 | LXFA526 | LXFA623 | LXFA983 | LXFA1041 | LXFA1647 |
| % inhibition | −57.12 | 63.95 | 99.99 | 20.05 | −35.5 | 90.61 |
| Result | no efficacy | efficacy | efficacy | no efficacy | no efficacy | efficacy |

In Table 4, % inhibition = 100 − (tumor volume of test group/tumor volume of control *100)

TABLE 5

| | Gastric | | Renal | | |
|---|---|---|---|---|---|
| Model | GXF214 | GXF251 | RXF488 | RXF1114 | RXF1220 |
| % inhibition | 8.96 | −20.77 | 24.82 | 92.56 | 6.79 |
| Result | no efficacy | no efficacy | no efficacy | efficacy | no efficacy |

As is understood from data of Tables 4 and 5, the lung cancer cell-implanted mouse models LXFA526, LXFA623, and LXFA1647, and the kidney cancer cell-implanted mouse model RXF1114 were found to respond to L3-1Y/IgG2 (responder) while the other mouse models implanted with patient-derived tumor tissue were not responsive to the antibody (non-responder)

1.2.2. Prediction of the Efficacy of Anti-c-Met Antibody in Mouse Model Implanted with Patient-Derived Tumor Tissues Using Measurement of the Serum Level of IL-8

Differences in the basal level of serum IL-8 between the responders and the non-responders were examined. In this regard, serum samples were taken from the vehicle groups of mouse models constructed in Example 1.2.1 and the IL-8 levels in the serum samples were used to examine relationship with responsiveness to L3-1Y/IgG2.

Briefly, serum samples taken from the mouse models implanted with patient-derived tumor tissues were classified according to test group. IL-8 levels were measured in vehicle treated groups from the 6 samples of lung cancer models, 2 samples of stomach cancer models, 3 samples of kidney cancer models. Measurement of the IL-8 levels was carried out in the same manner as in Example 1.1.2.

Figure 4:
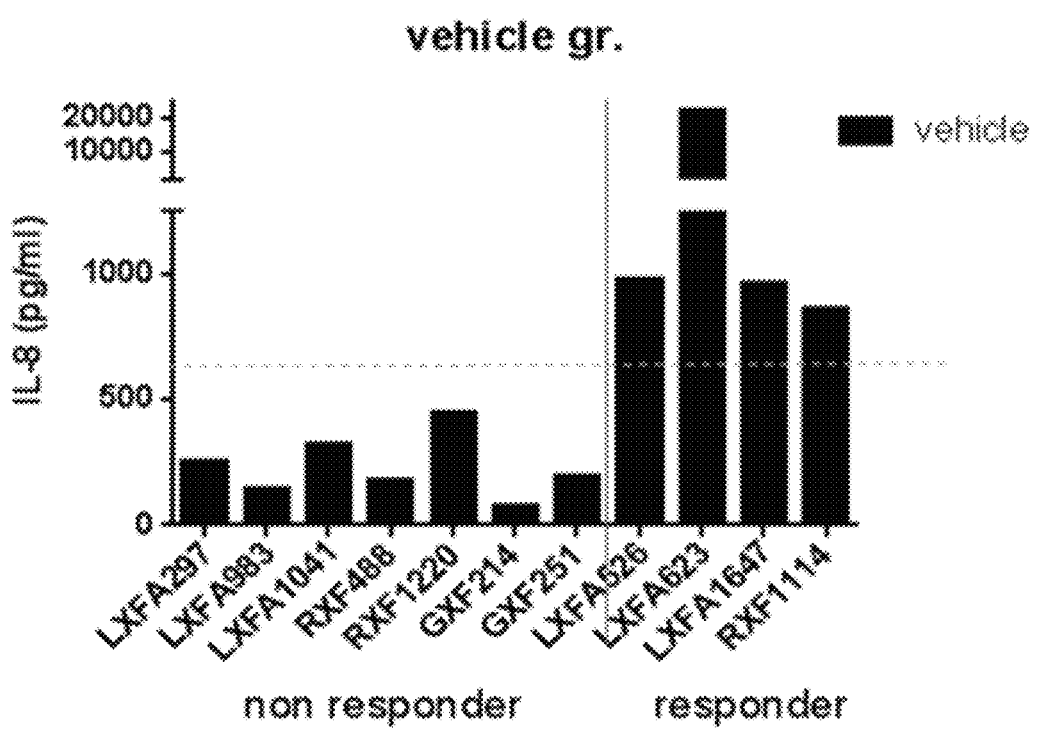
FIG. 4 is a graph showing IL-8 levels in serum samples from the control (vehicle (PBS) treated) of mouse models implanted with patient-derived tumor tissues.

The results are shown in FIG. 4. As is apparent from FIG. 4, the serum IL-8 levels were higher than 750 pg/mL in the responder groups but the levels were lower than about 500 pg/ml in the non-responder groups. The serum IL-8 level of the responder groups was observed to be at least 1.5-fold higher than that of the non-responder. Accordingly, the human cancer cells with high IL-8 levels are expected to allow L3-1Y/IgG2 to exert its anticancer activity more effectively.

1.2.3. Evaluation of the Efficacy of Anti-c-Met Antibody in Mouse Model Implanted with Patient-Derived Tumor Tissues Using Measurement of the Serum Level of IL-8

To examine the relationship between IL-8 level and responsiveness to an anti-c-Met antibody, changes of serum IL-8 levels after treatment of an anti-c-Met antibody in mouse models implanted with patient-derived tumor tissues were monitored.

Briefly, serum samples taken from the mouse models implanted with patient-derived tumor tissues were classified according to test group. IL-8 levels were measured in 6 samples of lung cancer models, 2 samples of stomach cancer models, 3 samples of kidney cancer models after injection of the anti-c-Met antibody (5 mg/kg, iv) and in samples of the control (PBS injected), and examined for relationship between the anticancer efficacy of the anti-c-Met antibody and the change of IL-8 level after the anti-c-Met antibody treatment. Measurement of the IL-8 levels was carried out in the same manner as in Example 1.1.2.

Figure 5:
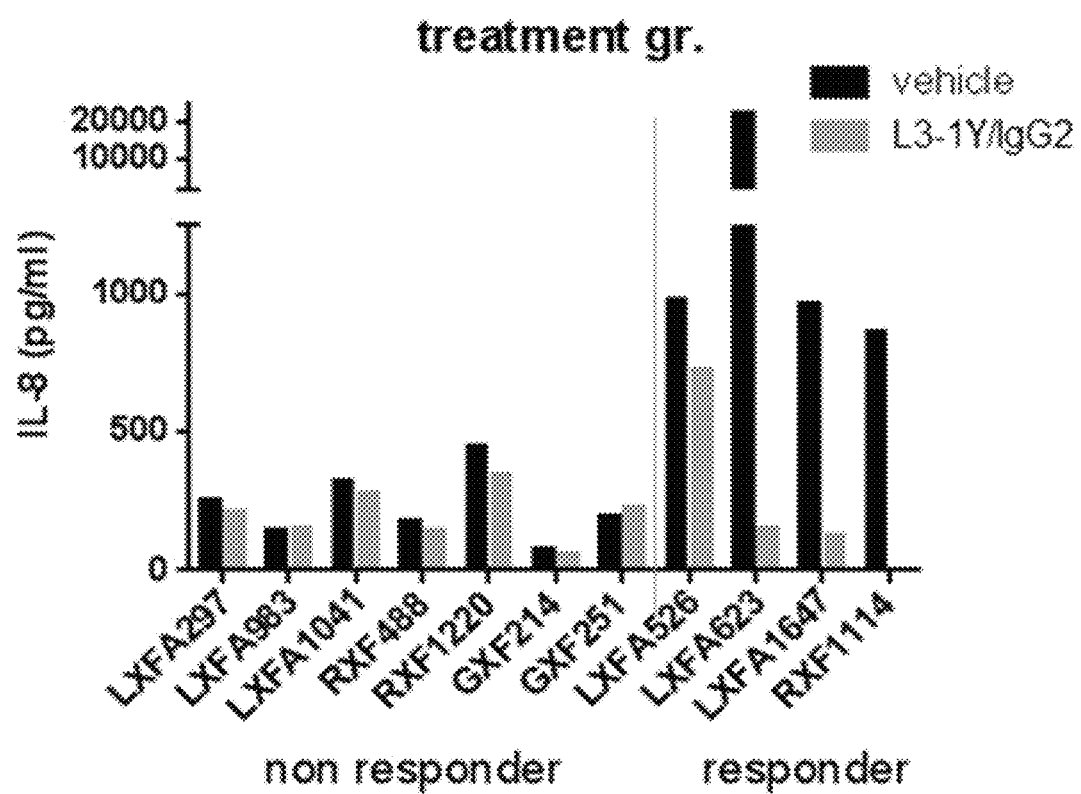
FIG. 5 is a graph of IL-8 levels in serum samples from anti-c-Met antibody-treated and untreated (control PBS treated) groups of mouse models implanted with patient-derived tumor tissues, showing relationship between the anticancer efficacy of the anti-c-Met antibody and the change of IL-8 level after treatment of anti-c-Met antibody.

Results are depicted in FIG. 5. As is understood from the data of FIG. 5, there are no significant differences in serum IL-8 levels between vehicle and L3-1Y/IgG2 treatment samples of non-responder group whereas the responder group showed significant decrease in serum IL-8 levels after treatment of L3-1Y/IgG2. These data imply that a patient can be monitored for responsiveness to L3-1Y/IgG2, that is, the efficacy of L3-1Y/IgG2 by measuring the expression level of IL-8 in the patient treated with L3-1Y/IgG2.

1.3. Change in IL-8 Level with Time after Anti-c-Met Antibody Injection 1.3.1. Construction of Cancer Cell-Implanted Mouse Model and Assay for Anticancer Activity of Anti-c-Met Antibody in the Mouse Model The role of IL-8 as a pharmcodynamic marker of anti-c-Met antibodies was confirmed in xengraft mouse models which were prepared by implanting cancer cell lines known to be responsive to the antibody.

As opposed to Example 1.1, this experiment was configured to examine the responsiveness in a condition under which tumor volumes were little changed. After implantation, tumors were increased to a size of 1000 mm$^3$ and, then, the antibody was injected in various doses to the mice models. According time after injection, serum samples and tumor tissues were taken from three mice per group. In addition, tumor volumes were measured at regular intervals of time.

Briefly, xenograft mouse models implanted with the human stomach cell line Hs746T (Accession No. HTB-135) or human non-small cell lung cancer line EBC-1 (Accession No. JCRB0820) were employed. Each cancer cell line was injected s.c. at a dose of $5 \times 10^6$ cells to 150 Balb/c nude mice (Shanghai SLAC Laboratory Animal Co. Ltd.). All of the experimental animals were male and 5-6 weeks old upon the implantation, and bred in an SPF condition. In order to increase the tumor to a predetermined size, the mice implanted with the cancer cells were treated with the drug (antibody) only 16-20 days after the implantation. When the tumor grew to a size of about 1000 mm$^3$, the mice were randomly divided into groups of 30: PBS-treated group (Group 1) and anti-c-Met antibody-treated groups (Groups 2, 3, and 4). The treated groups were classified according to the dose of the antibody: 1 mg/kg (Group 2), 3 mg/kg (Group 3) and 10 mg/kg (Group 4). The antibody and the vehicle were administered twice at regular intervals of 7 days. Each sample was withdrawn 1 hr, 1 day (24 hrs), 2 days (48 hrs), 3 days (72 hrs), and 7 days (168 hrs) after the first injection. The same sampling time schedule was repeated after the second injection: 1 hr (169 hrs), 1 day (192 hrs), 2 days (216 hrs), 3 days (240 hrs), and 7 days (336 hrs). With regard to sampling, serum and tissues were taken from three mice which were sacrificed at each time point. Tumor volumes were also measured upon sampling to monitor the anticancer activity of the antibody (PharmaLegacy Laboratories Vivarium).

Figure 6:
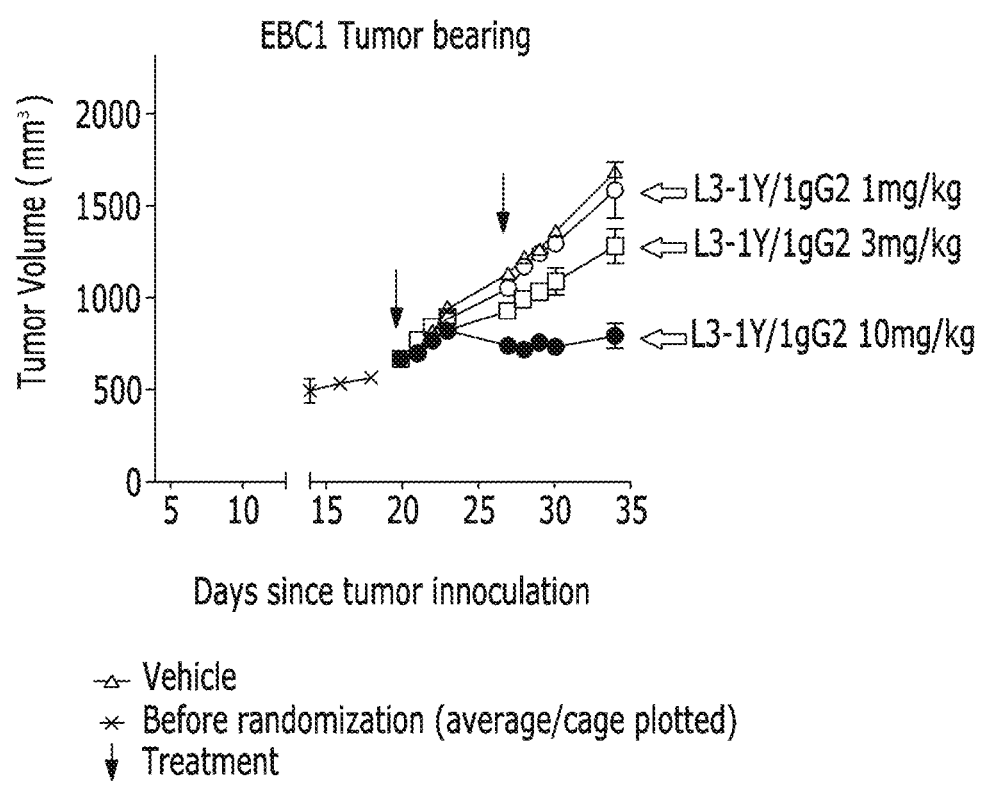
FIG. 6 is a graph showing a change in tumor size after treatment of the anti-c-Met antibody in conventional cancer cell line (EBC-1)-implanted mouse models.
Figure 7:
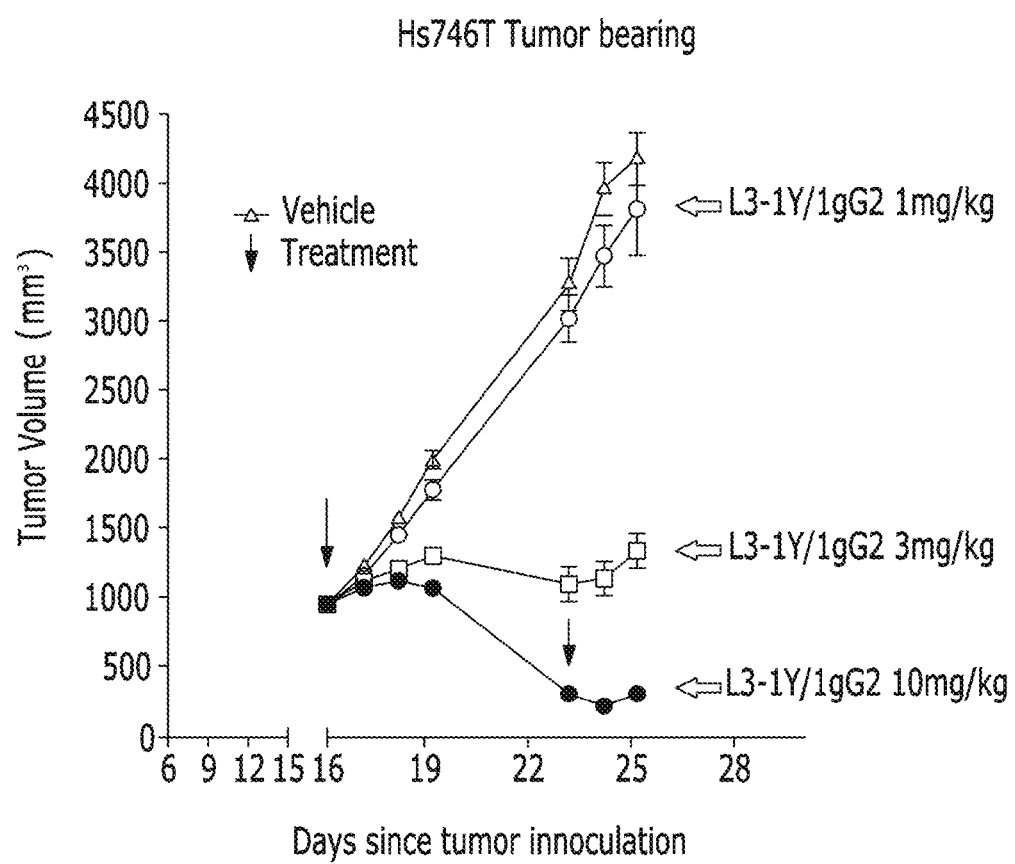
FIG. 7 is a graph showing a change in tumor size after treatment of the anti-c-Met antibody in conventional cancer cell line (Hs746T)-implanted mouse models.

Anticancer activity data obtained above are depicted in FIG. 6 (EBC-1 implanted) and FIG. 7 (Hs746T implanted).

As is apparent from the data of FIGS. 6 and 7, the anti-c-Met antibody exhibited anticancer activity in mice bearing tumors of EBC-1 and Hs746T, as well, and the anticancer activity was dose-dependent.

1.3.2 Evaluation of the Efficacy of Anti-c-Met Antibody in Cancer Cell-Implanted Mouse Model Using Measurement of the Serum Level of IL-8

The following experiments were conducted with samples taken from the EBC-1- or Hs746T-implanted mouse models prepared in Example 1.3.1. To examine whether the anti-c-Met antibody-induced responsiveness of IL-8 is simply reflect the shrunken tumor size as a result from the efficacy of anti-cMet Ab, time course serum samples were analyzed from the EBC-1- or Hs746T-implanted mouse models to measure the short-term response to L3-1Y/IgG2.

Figure 8:
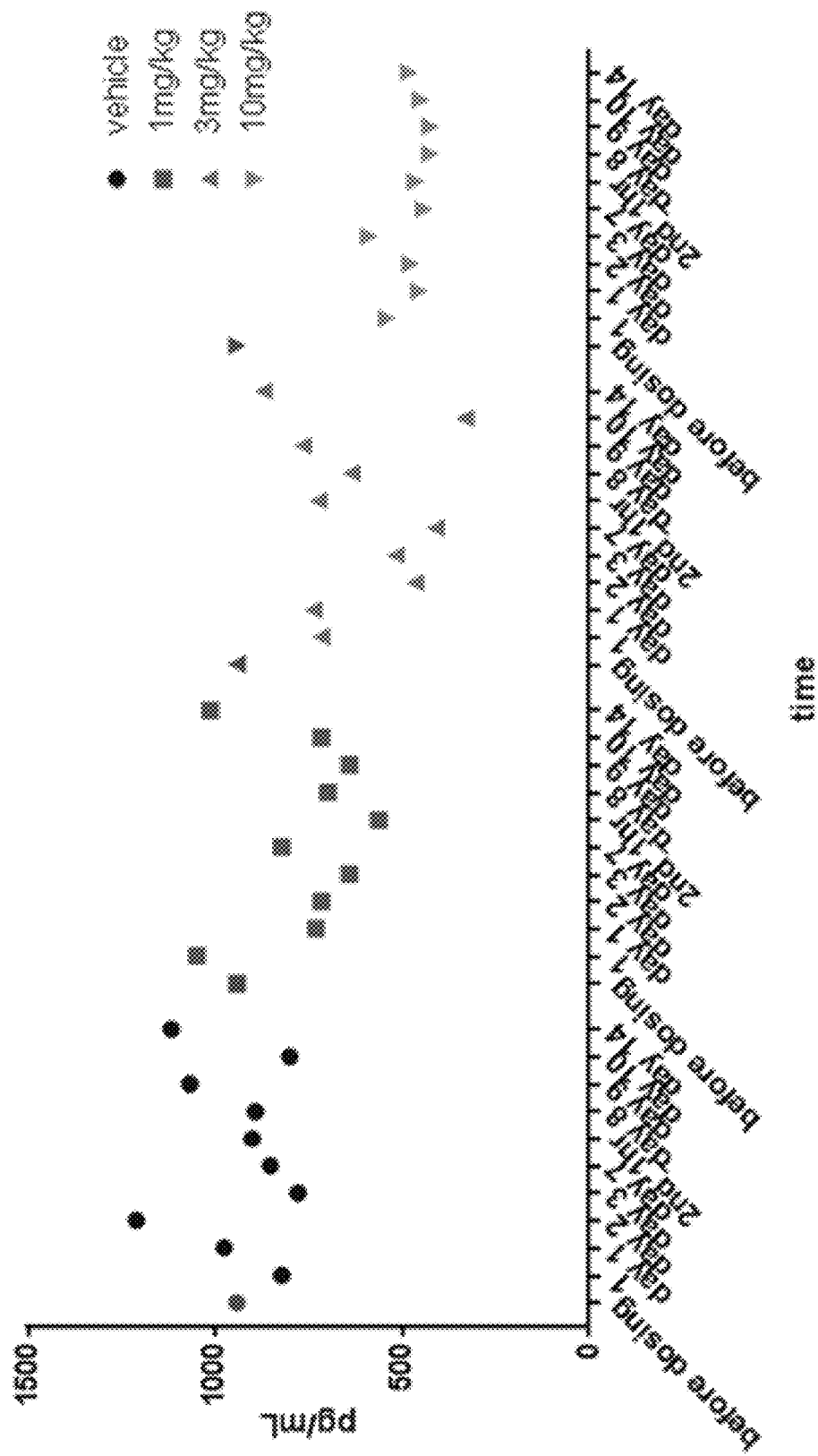
FIG. 8 is a graph showing a change in IL-8 level with time after treatment of the anti-c-Met antibody in conventional cancer cell line (EBC-1)-implanted mouse models.

Briefly, serum samples were taken in an amount of 100 μL from each of 3 mice per group according to time after antibody dosing (see FIG. 8). The serum samples from the same group were pooled, and quantitatively analyzed for IL-8 level using CBA method.

Figure 9:
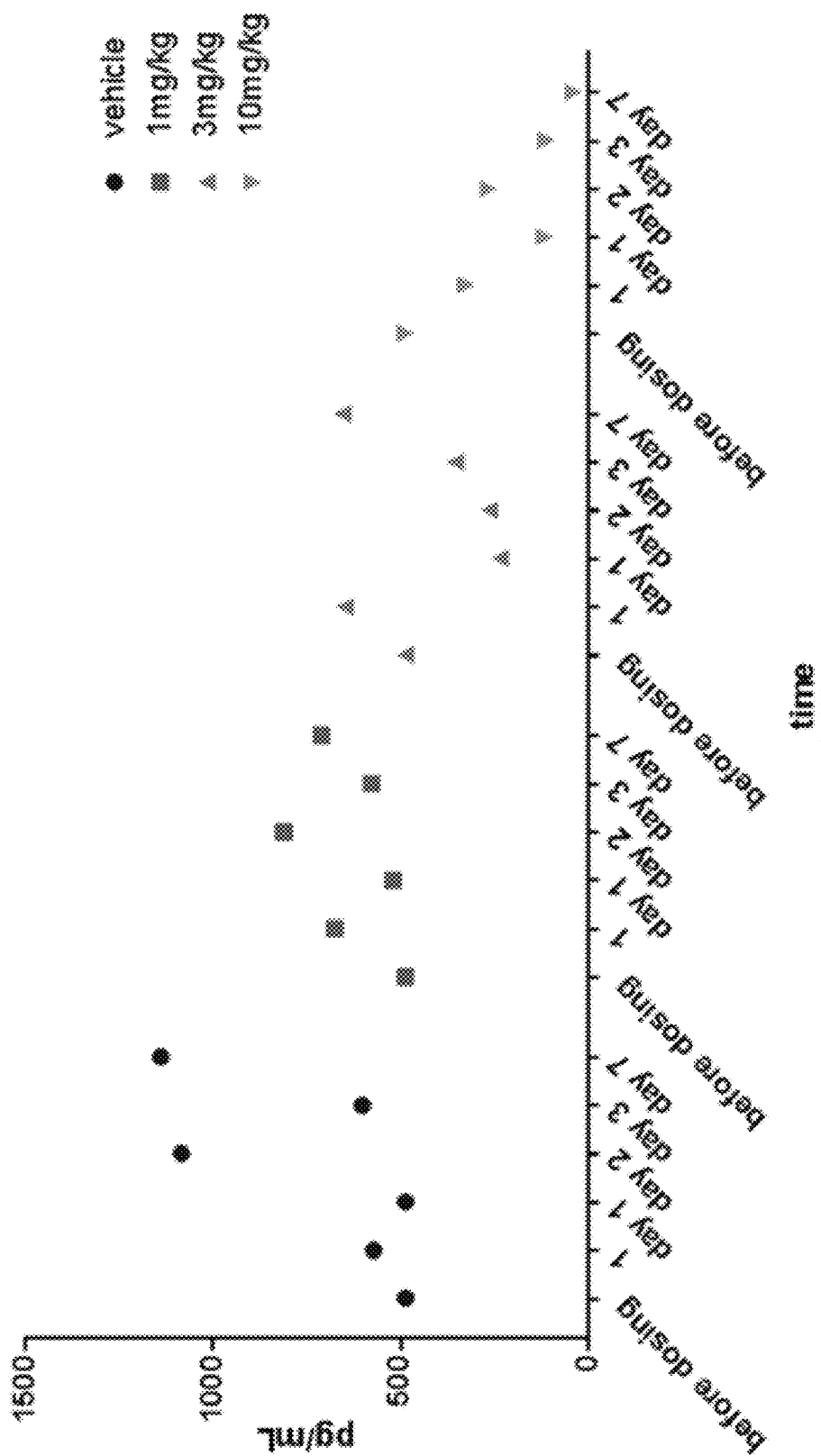
FIG. 9 is a graph showing a change in IL-8 level with time after treatment of the anti-c-Met antibody in conventional cancer cell line (Hs746T)-implanted mouse models.

The results are summarized in FIGS. 8 and 9 (wherein "1" between "before dosing" and "1 day" means "1 hour").

As can be seen in FIGS. 8 and 9, the serum IL-8 level was observed to decrease in a dose-dependent manner upon treatment with the anti-c-Met antibody, and was already lowered at 1 hr after treatment in the high-dose treatment group (10 mg/kg). At the same time, the tumor size was not significantly change in L3-1Y/IgG2 treated mice at this time point (1 hr after treatment). These data indicate that the change of serum IL-8 level shows a drug response in vivo xenograft models and it is not solely dependent on the tumor size. So, IL-8 can be used as an early marker indicative of in vivo responsiveness to an anti-c-Met antibody. Taken together, the data demonstrates that the responsiveness of IL-8 is not attributed simply to the change in tumor size and can be useful biomarker for c-Met targeted therapy.

1.4. Test of Efficacies of c-Met Inhibitors Other than Anti-c-Met Antibodies

It was verified whether or not the change in IL-8 level can be applicable to a monitoring of responsiveness to a c-Met targeting drug other than anti-c-Met antibodies, as a marker.

In particular, EBC-1 (human lung cancer cell line; Accession No. JCRB0820) and Hs746T (human stomach cancer cell line; Accession No. HTB-135), on which anti-c-Met antibody L3-1Y/IgG2 displays anticancer efficacies (anti-c-Met antibody responder groups), and Lovo (human colon cancer cell line; Accession No. CCL-229) and HT29 (human colon cancer cell line; Accession No. HTB-38), on which anti-c-Met antibody L3-1Y/IgG2 displays no anticancer efficacies (anti-c-Met antibody non-responder groups), were selected and cultured. The 4 cell lines were seeded on a 96 well plate at the same amount ($1\times10^4$ cells/well) and cultured for 24 hours (media: RPMI (Gibco, Invitrogen), culture conditions: 37° C., 5% $CO_2$). The cultured cells were treated with representative c-Met inhibitor, crizotinib (Selleck chemical) and PHA665752((R,Z)-5-(2,6-dichlorobenzylsulfonyl)-3-((3,5-dimethyl-4-(2-(pyrrolidin-1-ylmethyl)pyrrolidine-1-carbonyl)-1H-pyrrol-2-yl)methylene)indolin-2-one), respectively. For comparison, human control IgG (chrompure human IgG (009-000-003, JACKSON IMMUNORESEARCH LABS INC.)) as a control and anti-c-Met antibody L3-1Y/IgG2 (Reference Example) were used respectively. Each of the inhibitors (or antibody) was treated at 10-fold serial diluted concentrations from 1000 nM to 0.01 nM. 72 hours after the treatment, the level of IL-8 in cell culture of each treatment group was assayed by Cytometric Bead Array (CBA) method using BD Cytometric Bead Array kit (see Example 1.1.2). In addition, in order to verify the anticancer efficacy of the c-Met inhibitors, the cell proliferation (%) was measured at 72 hours after c-Met inhibitor treatment through Cell-Titer Glo (CTG) assay.

Figure 20:
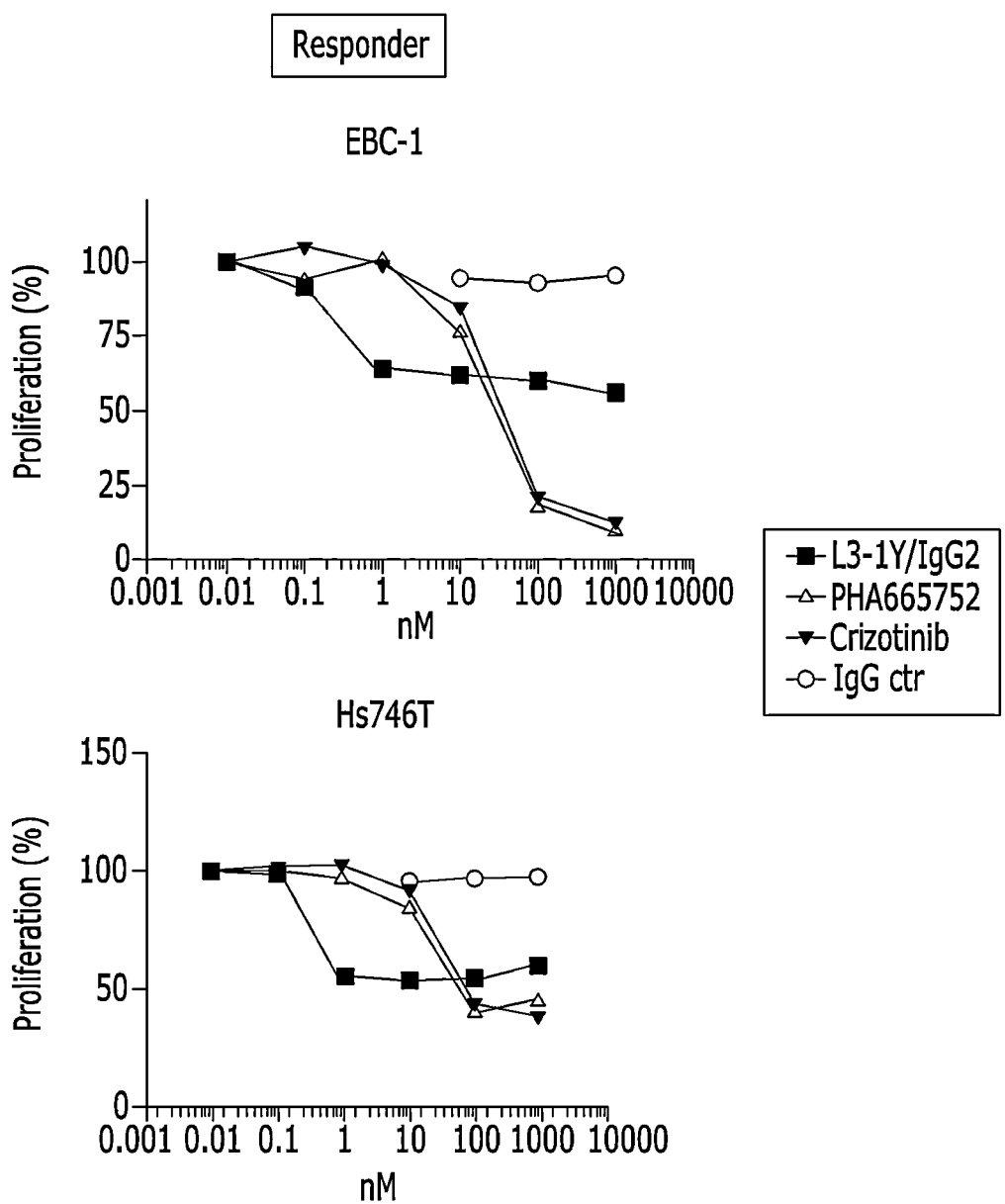
FIG. 20 contains graphs illustrating the responsiveness of anti-c-Met antibody responder cell lines to the treatment of other c-Met inhibitors; crizotinib and PHA665752.
Figure 21:
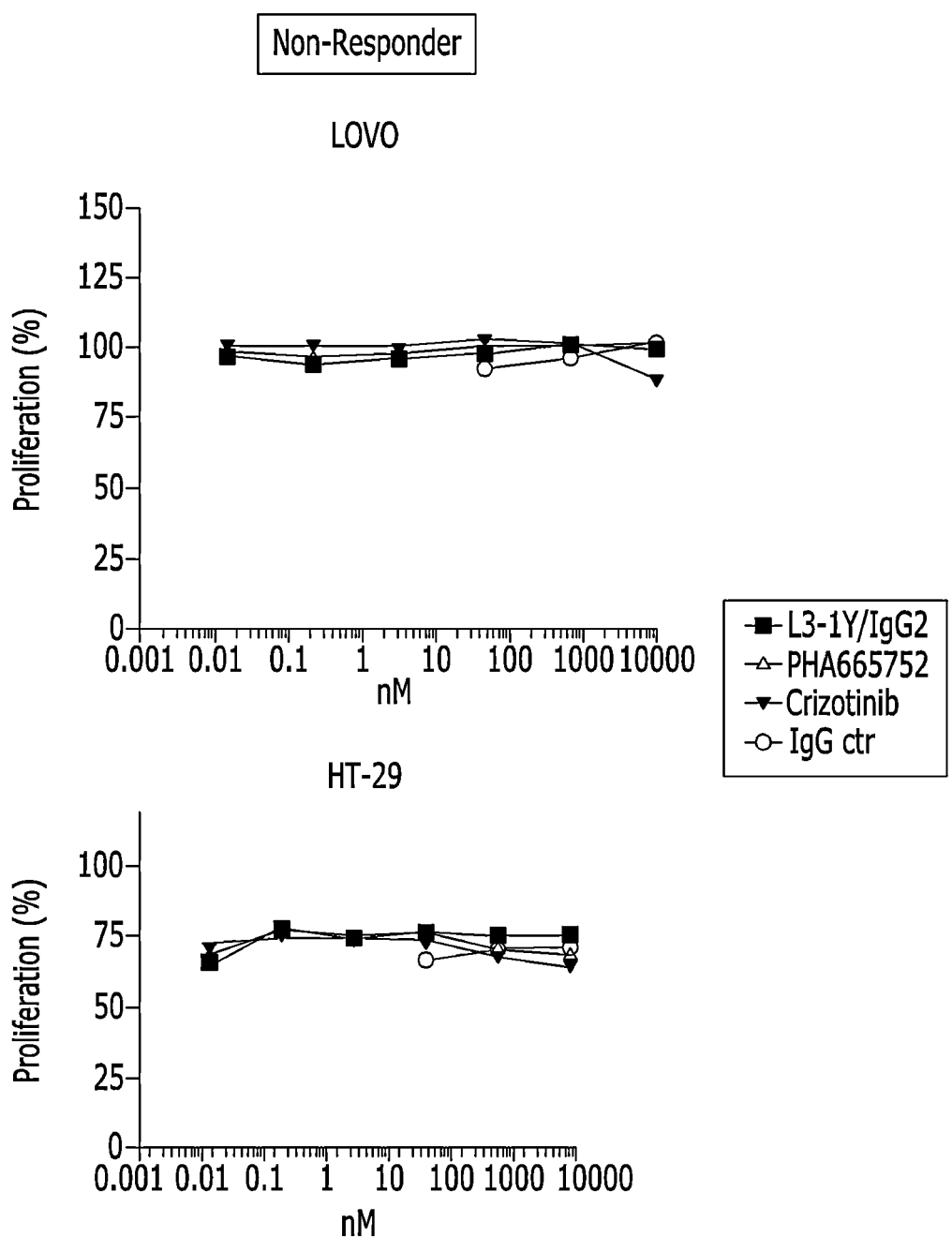
FIG. 21 contains graphs illustrating the responsiveness of anti-c-Met antibody non-responder cell lines to the treatment of other c-Met inhibitors; crizotinib and PHA665752.

The obtained results of cell proliferation (%) (i.e., results of CTG assay) at 72 hours were shown in FIG. 20 (anti-c-Met antibody responder groups) and FIG. 21 (anti-c-Met antibody non-responder groups). As shown in FIGS. 20 and 21, the profile of responsiveness to each c-Met inhibitor, crizotinib and PHA665752, is similar to that to anti-c-Met antibody L3-1Y/IgG2. That is, when crizotinib or PHA665752 was treated, the cell proliferation of L3-1Y/IgG2 responder groups, EBC-1 and Hs746T cell lines was significantly inhibited (decreased) at the inhibitor concentration of 10 nM or more (see FIG. 20), whereas the cell proliferation of L3-1Y/IgG2 non-responder groups, Lovo and HT29 cell lines displays no significant decrease (see FIG. 21).

Figure 22:
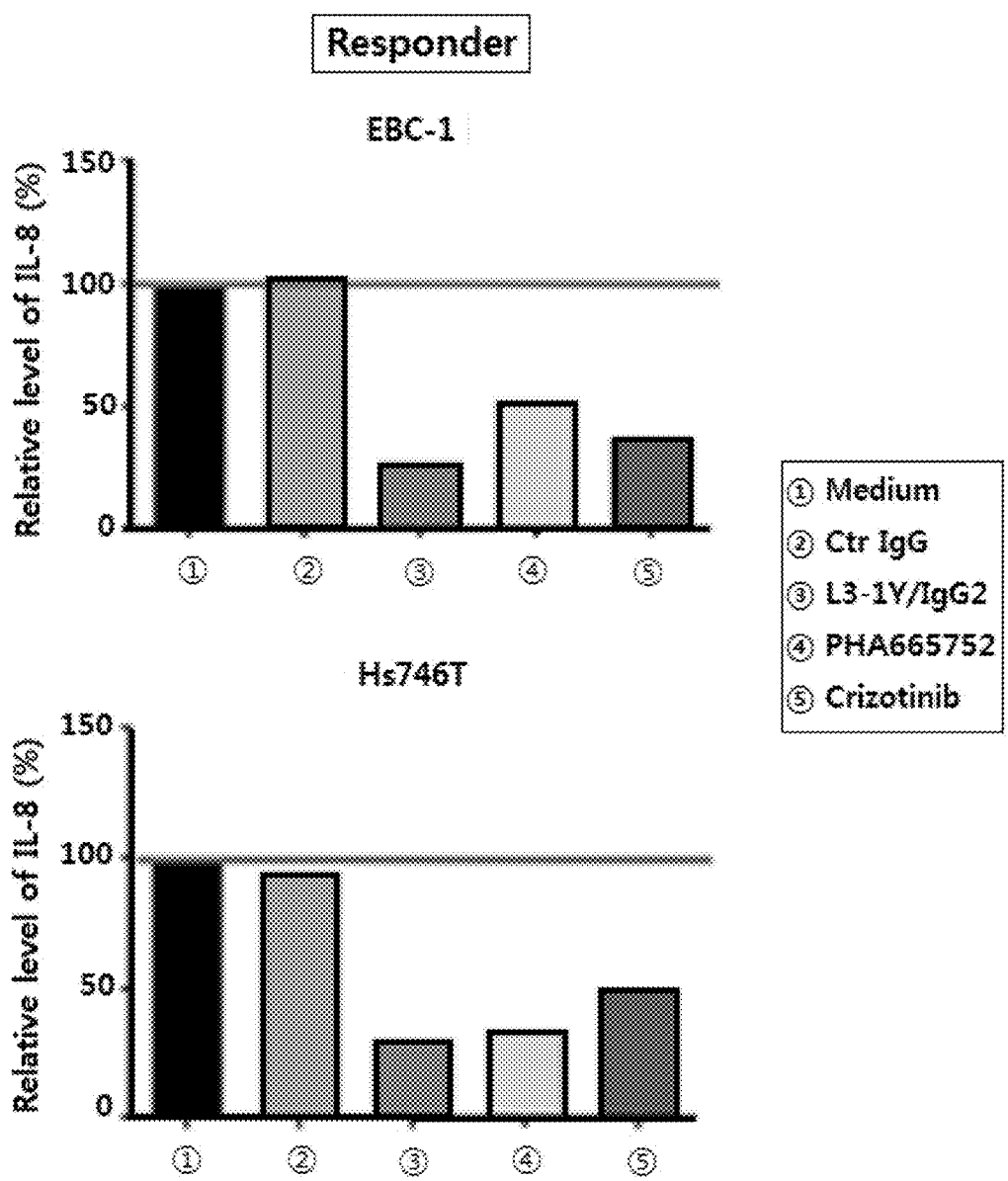
FIG. 22 contains graphs illustrating the relative levels of IL-8(%) in culture sup of the anti-c-Met antibody responder cell lines after treatment of various c-Met inhibitors, L3-1Y/IgG2, crizotinib and PHA665752.
Figure 23:
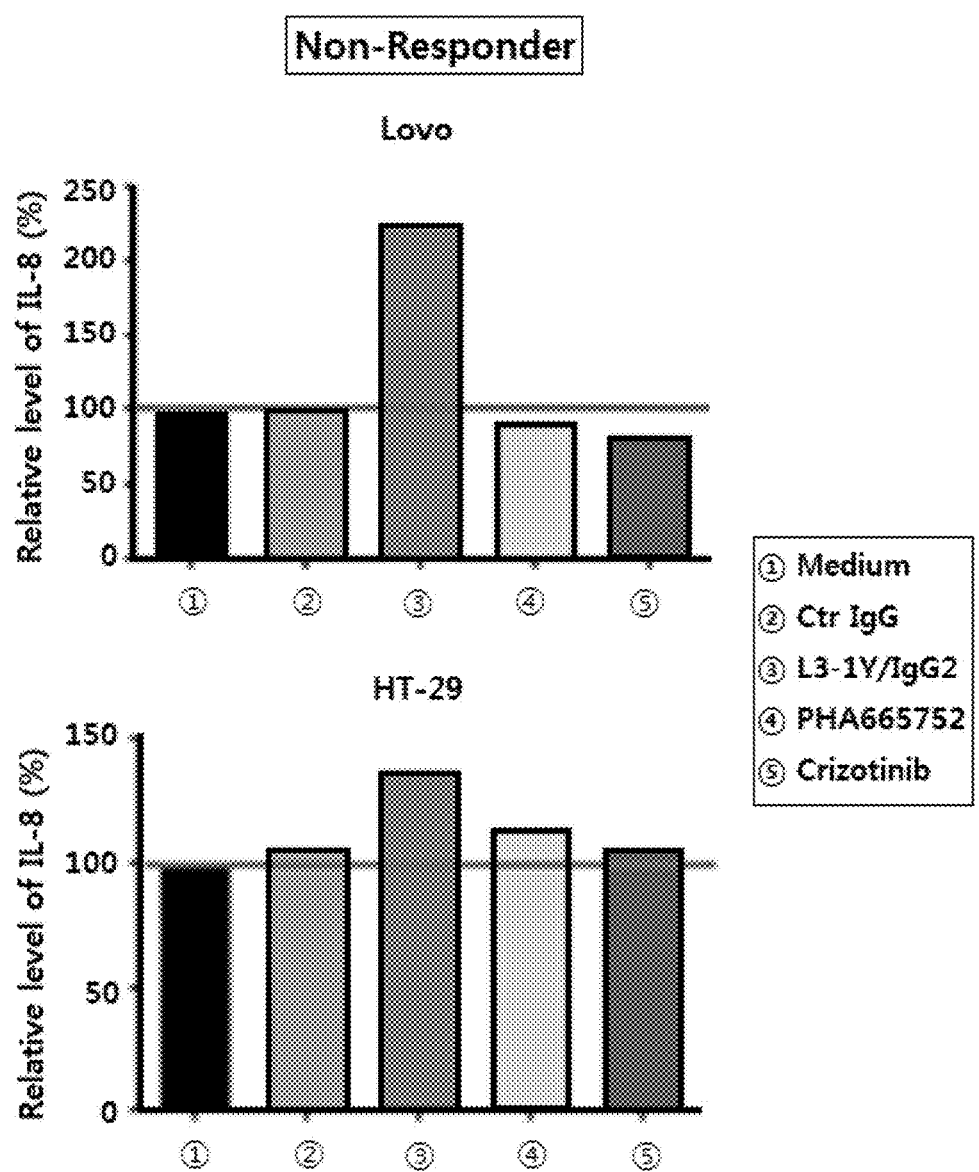
FIG. 23 contains graphs illustrating the relative levels of IL-8(%) in culture sup of the anti-c-Met antibody non-responder cell lines after treatment of various c-Met inhibitors, L3-1Y/IgG2, crizotinib and PHA665752.

In addition, at the concentration of 10 nM, from which the responsiveness to the inhibitors can be observed, the level of IL-8 in a cell culture of each treatment group was measured by Cytometric Bead Array (CBA) method using BD Cytometric Bead Array kit (see, Example 1.1.2), and the obtained results are shown in FIGS. 22 and 23 as relative ratio to the level of IL-8 in medium (100%). As shown in FIGS. 22 and 23, the level of IL-8 was significantly decreased in the responder groups, EBC-1 and Hs746T cell lines, which displayed significant decrease in cell proliferation, whereas any significant decrease in the level of IL-8 was not observed in the non-responder groups, Lovo and HT-29 cell lines.

These results indicate that the decrease in IL-8 level can also be useful as a maker for evaluation of the efficacy of not only anti-c-Met antibodies but also c-Met inhibitors other than anti-c-Met antibodies.

Example 2: Evaluation of Efficacy of Anti-c-Met Antibody Using bIG-H3

2.1. Selection of bIG-H3 as Pharmacodynamic Marker for Anti-c-Met Antibody

Proteins which showed a significant difference in the expression level between an anti-c-Met antibody-treated group and an untreated group responsive to the anti-c-Met antibody were selected as possible biomarkers for evaluating the efficacy of the anti-c-Met antibody, using an antibody array membrane capable of detecting 119 soluble receptors (a human soluble receptor array kit non-hematopoietic panel, cat# ARY012; R&D; alternatively, a human cytokine array kit (e.g., #ARY005; R&D) can be used).

Figure 10:
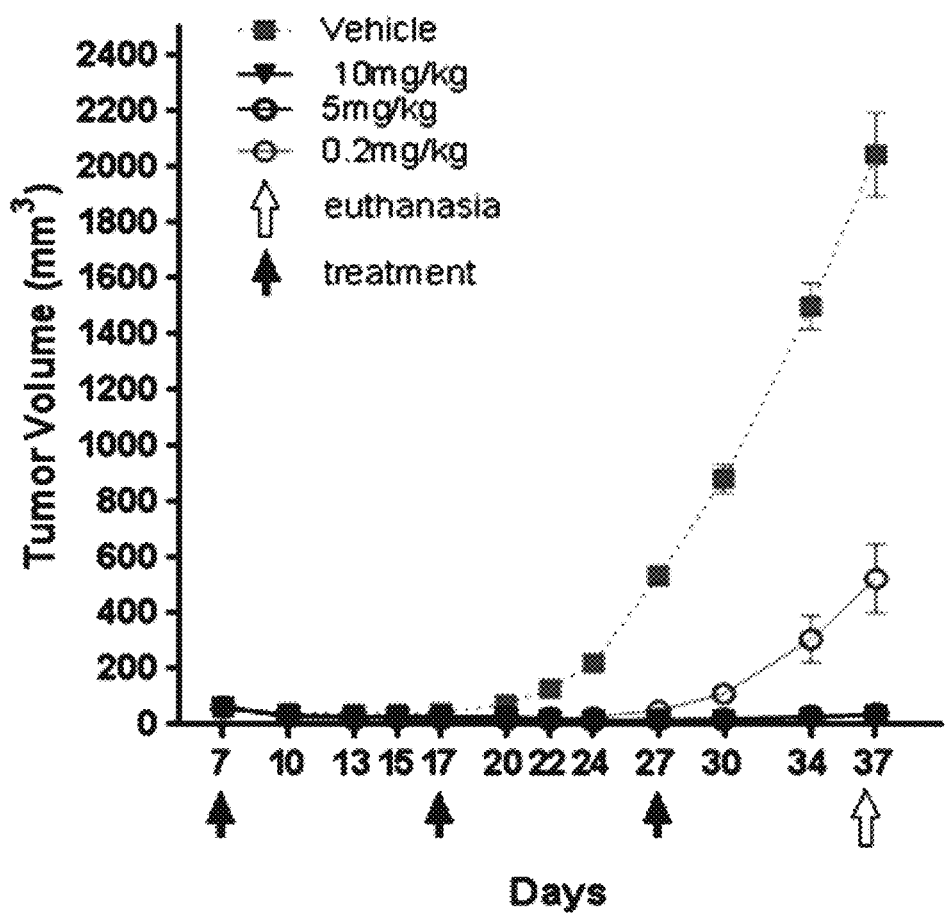
FIG. 10 is a graph showing a change in tumor size after treatment of the anti-c-Met antibody in U87MG-implanted mouse model.

In mouse models which were constructed with U87MG (Accession No. HTB-14) in the same manner as in Example 1.1.1, changes in tumor size with treatment with the anti-c-Met antibody L3-1Y/IgG2 were monitored. The results are shown in FIG. 10. As can be seen in FIG. 10, the anti-c-Met antibody L3-1Y/IgG2 exhibited anticancer activity in a dose-dependent manner in the U87MG-implanted mouse models.

Of the U87MG cells which were identified to respond to the anti-c-Met antibody, differences in protein expression level between anti-c-Met antibody-treated cells groups and untreated cells groups were investigated.

In this regard, serum samples taken from mouse models which were constructed with U87MG (Accession No. HTB-14) in the same manner as in Example 1.1.1 were incubated with the antibody array membrane (R&D, cat# ARY012) to examine responsiveness to the anti-c-Met antibody. In the membrane, 200 µl of the mouse serum was incubated for overnight at 4° C. with the buffer and the capture antibody, followed by developing the membrane in chemiluminescence immunoassay. The antibody L3-1Y/IgG2 was intravenously injected at a dose of 10 mg/ml every 7 days for 4 weeks from 7-10 days after implantation.

Figure 11:
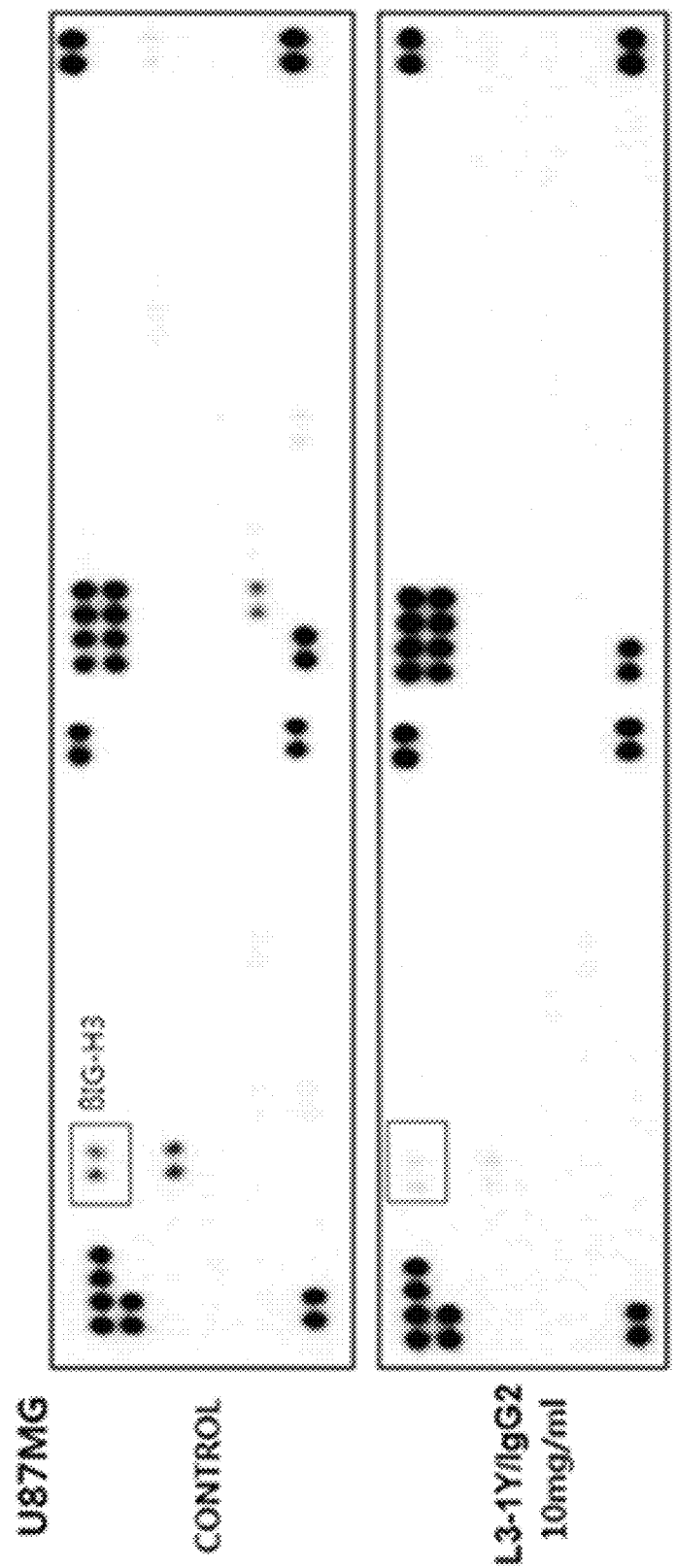
FIG. 11 shows a change in protein expression pattern in U87MG cells, as measured by a chemiluminescence immunoassay using protein array kit.

The results are depicted in FIG. 11. On the membrane, positive control dots appear at the corners and at middle regions while significant changes are detected as indicated by boxed dots. They were identified as bIG-H3. As compared to the control (PBS treated), L3-1Y/IgG2 significantly decreased the expression level of bIG-H3. Based on this finding, bIG-H3 is first suggested as a pharmacodynamic marker for anti-c-Met antibodies.

2.2. Evaluation of the Efficacy of Anti-c-Met Antibody in Cancer Cell-Implanted Mouse Model Using bIG-H3

2.2.1. Construction of Cancer Cell-Implanted Mouse Model

For use in assays for evaluating the efficacy of an anti-c-Met antibody, xenograft mouse models were prepared by implanting various cancer cell lines (anti-c-Met antibody non-responsive cell lines: Lovo (Accession No. CCL-229), HT-29 (Accession No. HTB-38), PC3 (Accession No. CRL-1435), BxPC3 (Accession No. CRL-1687), MDAMB231 (Accession No. HTB-26); anti-c-Met antibody responsive cell lines: Hs746T (Accession No. HTB-135), MKN45 (Accession No. RCB1001), EBC-1 (Accession No. JCRB0820), U87MG (Accession No. HTB-14), MHCC97H (Accession No. NB100-122)) to mice in the same manner as in Example 1.1.1.

Of the mouse models, Hs746T-, MKN45- and EBC-1-implanted mouse models were found to have responsiveness to the anti-c-Met antibody, as demonstrated in Example 1.1.2.

2.2.2. Evaluation of the Efficacy of Anti-c-Met Antibody in Cancer Cell-Implanted Mouse Model Using bIG-H3

To examine relationship between bIG-H3 level and responsiveness to anti-c-Met antibody, changes of serum bIG-H3 levels with treatment with an anti-c-Met antibody in cancer cell-implanted mouse models were monitored.

Briefly, serum samples taken from mouse models in a group were pooled, and quantitatively analyzed for bIG-H3 level using a bIG-H3 ELISA kit (R&D) in comparison with the control (injected with vehicle (PBS) only). More specifically, Whole blood was collected from the mouse models in a BD vacutainer SST™ tube. After collection of the whole blood, the tube was mixed by gently inverting for 5 times, and then, allowed to clot for 30 minutes at room temperature before centrifuging for 15 minutes at 1000×g to obtain serum. For individual ELISA assay, MIF (R&D, DMF00B) and IG-H3(R&D, DY2935) ELISA kit were used following manufacture's protocol. Briefly, 100 μL Assay Diluent RD1-53 was added to each well. The serum sample was added in coated plate at the amount of 50 μL per well, and then, incubated 2 hours at room temperature. After washing step, 200 ul of antibody conjugate was added to each well and incubated 2 hours and further incubated for 30 minutes after adding substrate solution. Wavelength at 450 nm was read using microplate reader.

Figure 12:
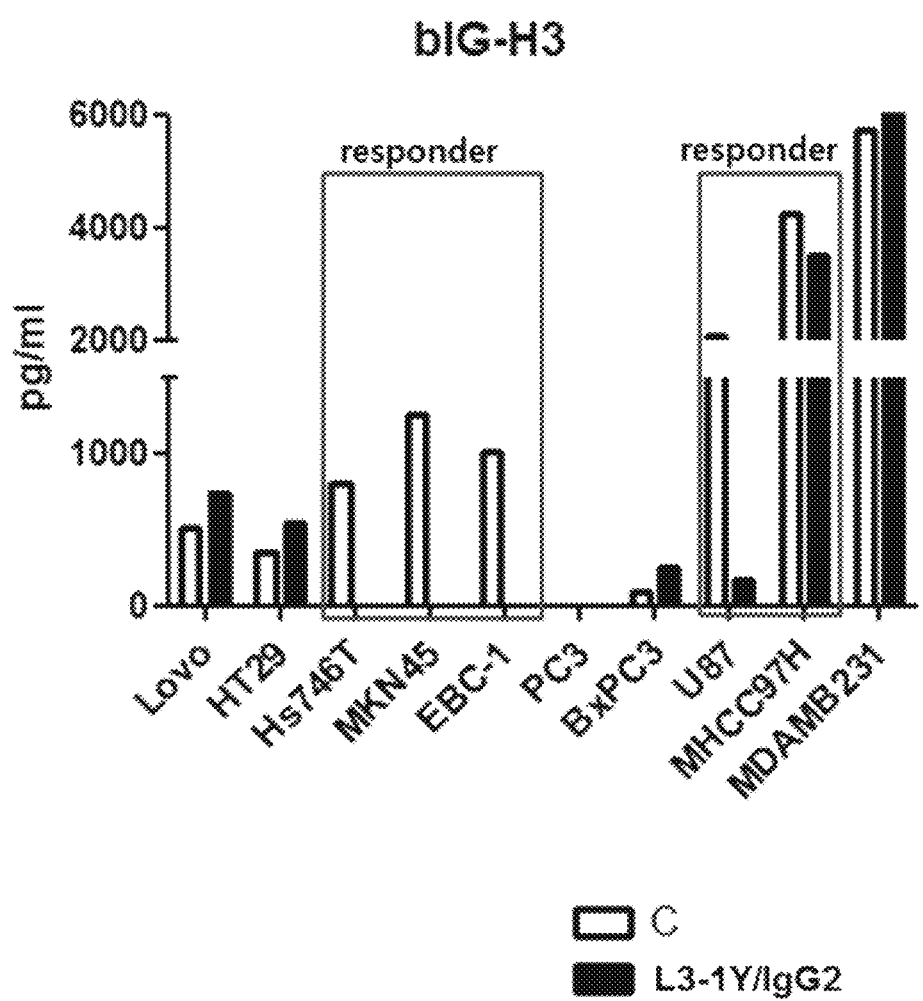
FIG. 12 is a graph showing a change in bIG-H3 level after treatment of the anti-c-Met antibody in serum from mouse models implanted with various cancer cells.

Results are depicted in FIG. 12. As is understood from the data of FIG. 12, the non-responder groups showed no significant differences or an increase in the bIG-H3 expression level upon treatment with L3-1Y/IgG2, compared to the non-treated group (injected with vehicle only, PBS) whereas the responder group significantly decreased in bIG-H3 expression level, compared to the untreated group, or expressed little bIG-H3. These data imply that a patient can be monitored for responsiveness to L3-1Y/IgG2, that is, the efficacy of L3-1Y/IgG2 by measuring the expression level of bIG-H3 in the patient treated with L3-1Y/IgG2.

2.3. Evaluation of Efficacy of Anti-c-Met Antibody in Mouse Model Implanted with Patient-Derived Tumor Tissues Using bIG-H3

2.3.1. Construction of Mouse Model Implanted with Patient-Derived Tumor Tissue

With reference to Example 1.2.1, patient-derived lung cancer cell-implanted mouse models LXFA297, LXFA526, LXFA623, LXFA983, LXFA1041, and LXFA1647 were constructed. Of them, LXFA526, LXFA623, and LXFA1647 were observed to be responsive to the anti-c-Met antibody as shown in Table 4.

2.3.2. Evaluation of Efficacy of Anti-c-Met Antibody in Mouse Model Implanted with Patient-Derived Tumor Tissues Using bIG-H3

To examine the relationship between bIG-H3 level and responsiveness to an anti-c-Met antibody, changes of serum bIG-H3 levels with treatment with an anti-c-Met antibody in patient-derived tumor tissues-implanted mouse models were monitored.

Briefly, serum samples taken from mouse models in a group were pooled, and quantitatively analyzed for bIG-H3 level using a bIG-H3 ELISA kit (R&D) in comparison with the control (injected with vehicle (PBS) only), in the same manner as in Example 2.2.2 (refer to Example 1.1.2).

Figure 13:
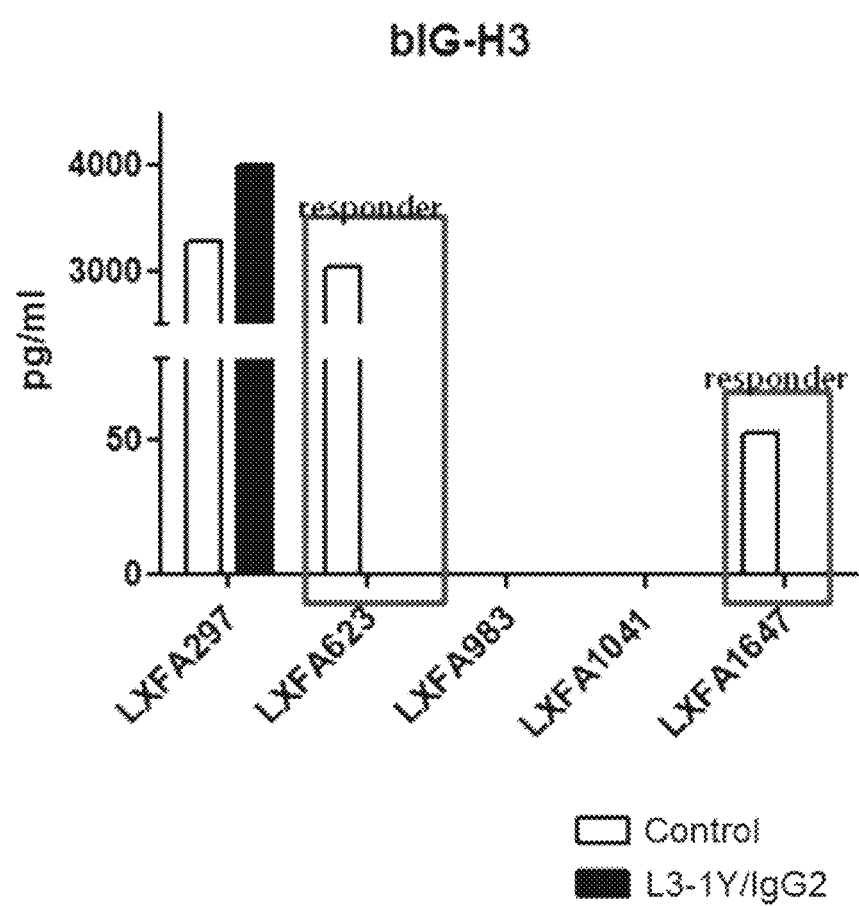
FIG. 13 is a graph showing a change in bIG-H3 level after treatment of the anti-c-Met antibody in serum from mouse models implanted with patient-derived tumor tissues.

Results are depicted in FIG. 13. As is understood from the data of FIG. 13, the non-responder groups showed no significant differences or an increase in the bIG-H3 expression level upon treatment with L3-1Y/IgG2, compared to the non-treated group (injected with vehicle only, PBS) whereas the responder group significantly decreased in bIG-H3 expression level, compared to the untreated group, or expressed little bIG-H3. These data imply that a patient can be monitored for responsiveness to L3-1Y/IgG2, that is, the efficacy of L3-1Y/IgG2 by measuring the expression level of bIG-H3 in the patient treated with L3-1Y/IgG2.

Cancer tissues isolated from L3-1Y/IgG2-treated or untreated groups of the animal models were homogenized and lysed in 500 μg of a lysis buffer (Roche). After centrifugation, the cell soup (cell lysate) was harvested and quantified. The cell soup was loaded in an amount corresponding to 1 ug of the total cell protein to plates of the bIG-H3 ELISA kit (R&D). The plates were previously coated with a capture antibody for bIG-H3. The HRP-conjugated detection antibody was applied to the plates before reading O.D 450.

Figure 14:
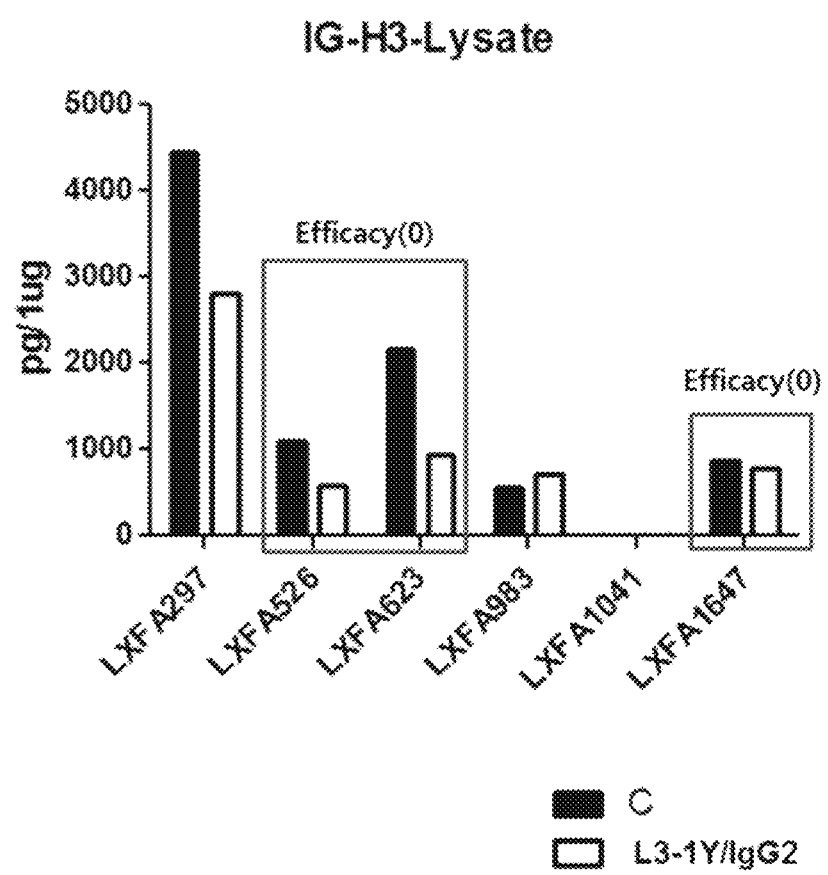
FIG. 14 is a graph showing a change in bIG-H3 level after treatment of the anti-c-Met antibody in cancer tissue lysates from mouse models implanted with patient-derived tumor tissues.

The results are depicted in FIG. 14. As can be seen in FIG. 14, it was also observed from the cell soup that the content of bIG-H3 in 1 μg of the total cell protein was remarkably reduced in the antibody-treated group of the responder, compared to the untreated group.

Example 3: Evaluation of Efficacy of Anti-c-Met Antibody Using MIF 3.1. Selection of MIF as Pharmacodynamic Marker for Anti-c-Met Antibody A protein which showed a significant difference in the expression level between an anti-c-Met antibody-treated group and an untreated group of the LXFA623 mouse model responsive to the anti-c-Met antibody (refer to Example 1.2.1 and Table 4) was selected as a marker for evaluating the efficacy of the anti-c-Met antibody, using an antibody array membrane capable of detecting 46 cytokines (R&D ARY005).

Briefly, 200 μl of each of serum samples taken from the antibody-treated group (L3-1Y/IgG2, 5 mg/kg) and the untreated group (PBS injected, control) of the LXFA623 mouse model were incubated overnight 4° C. with the buffer provided in the kit, followed by developing dots in chemiluminescence immunoassay. This experiment was performed with antibody array membrane (R&D ARY005).

The results are depicted in FIG. 15. On the membrane of FIG. 15, L3-1Y/IgG2 remarkably reduced the level of MIF, compared to the control (PBS injected), indicating that MIF can be used as a pharmacodynamic mark for anti-c-Met antibodies.

3.2. Evaluation of the Efficacy of Anti-c-Met Antibody in Cancer Cell-Implanted Mouse Model Using MIF In the same manner as in Example 2.2.1, xenograft mouse models were constructed by implanting various cancer cell lines (non-responder: Lovo (Accession No. CCL-229), HT-29 (Accession No. HTB-38), PC3 (Accession No. CRL-1435), BxPC3 (Accession No. CRL-1687), MDAMB231 (Accession No. HTB-26); responder: Hs746T (Accession No. HTB-135), MKN45 (Accession No. RCB1001), EBC-1 (Accession No. JCRB0820), U87MG (Accession No. HTB-14), MHCC97H (Accession No. NB100-122)).

To examine relationship between MIF level and responsiveness to anti-c-Met antibody, changes of MIF levels with treatment with an anti-c-Met antibody in cancer cell-implanted mouse models were monitored.

Briefly, serum samples taken from mouse models in each group, e.g., L3-1Y/IgG2-treated group or untreated group (PBS injected, control) of the xenograft animal models, were pooled, and quantitatively analyzed for MIF level using an MIF ELISA kit (R&D). The experiment was conducted according to the manufacturer's manual.

Figure 16:
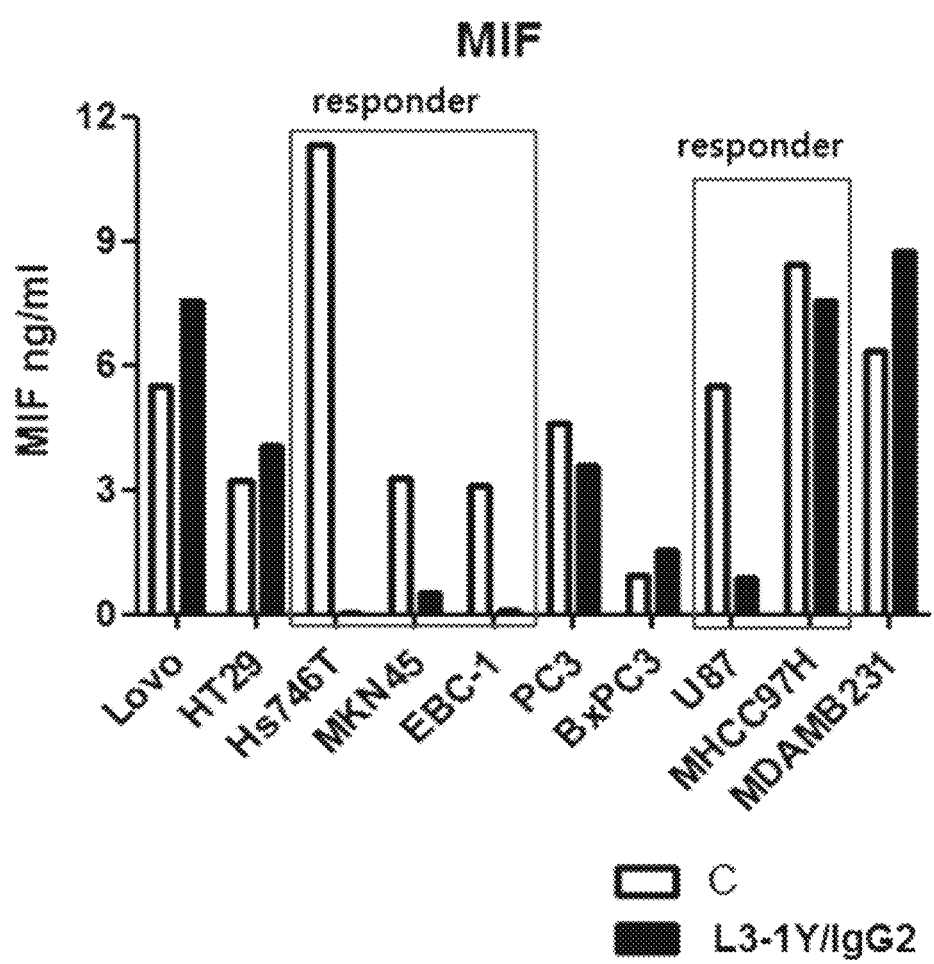
FIG. 16 is a graph showing a change in MIF level after treatment of the anti-c-Met antibody in serum samples from mouse models implanted with various cancer cell lines.

Results are depicted in FIG. 16. As is understood from the data of FIG. 16, the non-responder groups showed no significant differences or an increase in the MIF expression level upon treatment with L3-1Y/IgG2, compared to the untreated group (injected with vehicle only, PBS) whereas the responder group significantly decreased in MIF expression level, compared to the untreated group, or expressed little MIF. These data imply that a patient can be monitored for responsiveness to L3-1Y/IgG2, that is, the efficacy of L3-1Y/IgG2 by measuring the expression level of MIF in the patient treated with L3-1Y/IgG2.

3.3. Evaluation of Efficacy of Anti-c-Met Antibody in Mouse Model Implanted with Patient-Derived Tumor Tissues Using MIF With reference to Example 1.2.1, patient-derived lung cancer cell-implanted mouse models LXFA297, LXFA526, LXFA623, LXFA983, LXFA1041, and LXFA1647 were constructed. Of them, LXFA526, LXFA623, and LXFA1647 were observed to be responsive to the anti-c-Met antibody as shown in Table 4.

To examine the relationship between MIF level and responsiveness to an anti-c-Met antibody, changes of serum MIF levels with treatment with an anti-c-Met antibody in patient-derived tumor tissues-implanted mouse models were monitored.

Briefly, MIF levels were using an MIF ELISA kit in the same manner as in Example 3.2

Figure 17:
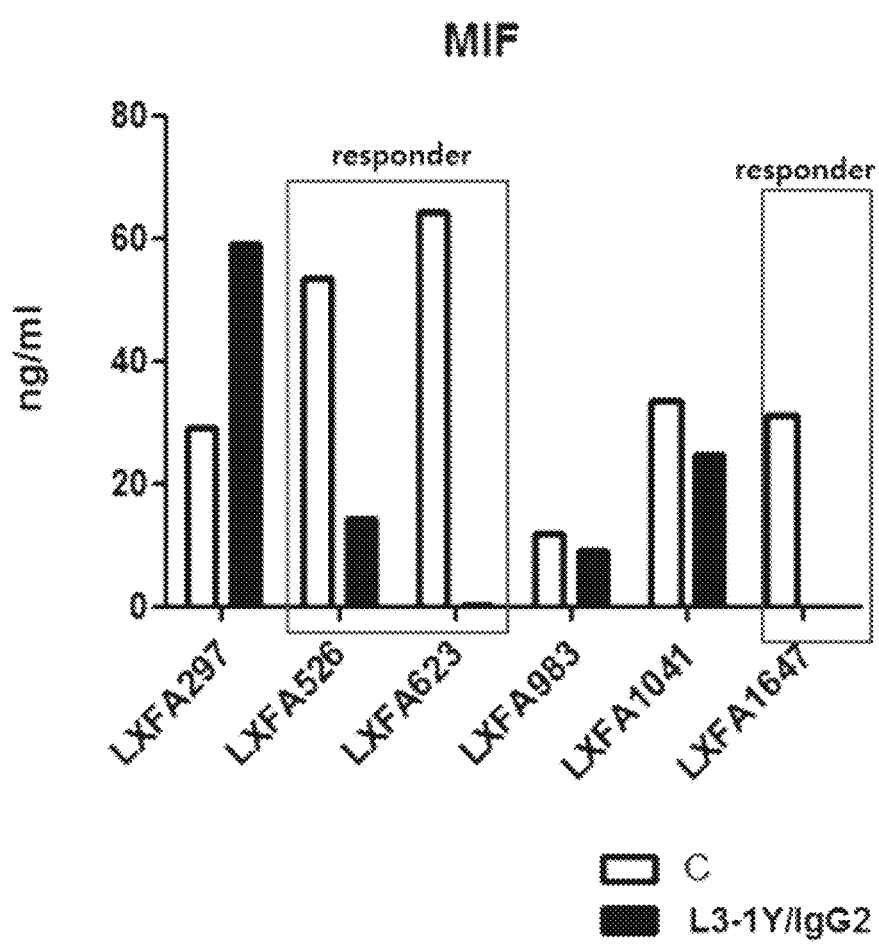
FIG. 17 is a graph showing a change in MIF level after treatment of the anti-c-Met antibody in serum samples from mouse models implanted with patient-derived tumor tissues.

Results are depicted in FIG. 17. As is understood from the data of FIG. 17, the non-responder groups showed no significant differences or an increase in the MIF expression level upon treatment with L3-1Y/IgG2, compared to the non-treated group (injected with vehicle only) whereas the responder group significantly decreased in MIF expression level, compared to the untreated group, or expressed little MIF. These data imply that a patient can be monitored for responsiveness to L3-1Y/IgG2, that is, the efficacy of L3-1Y/IgG2 by measuring the expression level of MIF in the patient treated with L3-1Y/IgG2.

Example 4: Prediction of Efficacy of Anti-c-Met Antibody Using RAS-RAF Mutation 4.1. Assay for Predicting Efficacy of Anti-c-Met Antibody in Mouse Model Implanted with Patient-Derived Tumor Tissue Using RAS-RAF Mutation 4.1.1. Construction of Mouse Model Implanted with Patient-Derived Tumor Tissue For use in predicting the efficacy of anti-c-Met antibodies, xenograft mouse models implanted with patient-derived tumor tissues were constructed.

Briefly female NMRI nude mice (Charles River or Harlan, 4-6 weeks old) were implanted s.c. with cancer tissues extracted from patients (LXFA: lung cancer, GXF: stomach cancer, RXF: kidney cancer, GXA: gastric cancer, LXFL: lung large cell carcinoma, OVXF: ovarian cancer, PAXF: pancreatic cancer, CXF: colon cancer). When the tumor grew to a volume of 80 to 200 mm$^3$, the mice were randomly divided into groups of 10. L3-1Y/IgG2 was injected i.v. at a dose of 5 mg/kg while PBS was used for a control group. On Day 0, 7, 14, 21, 28, and 35 after randomization, the antibody was administered. When the tumor volume reached 2000 mm$^3$, the mice were sacrificed and used in the following experiments.

4.1.2. Measurement of c-Met Expression Level in Patient-Derived Tumor Tissues-Implanted Mouse Model c-Met expression levels in the patient-derived cancer cell-implanted mouse models were measured using a Western blotting method.

Briefly, tumor tissues isolated from the animal models were homogenized and lysed in 500 µl of a lysis buffer (Roche). After centrifugation, the cell soup (cell lysate) was harvested and quantified. The cell soup was loaded in an amount corresponding to 10 µg of the total cell protein (SDS-PAGE), followed by exposure to the membrane (Cell Signal; including the antibody)

Figure 18:
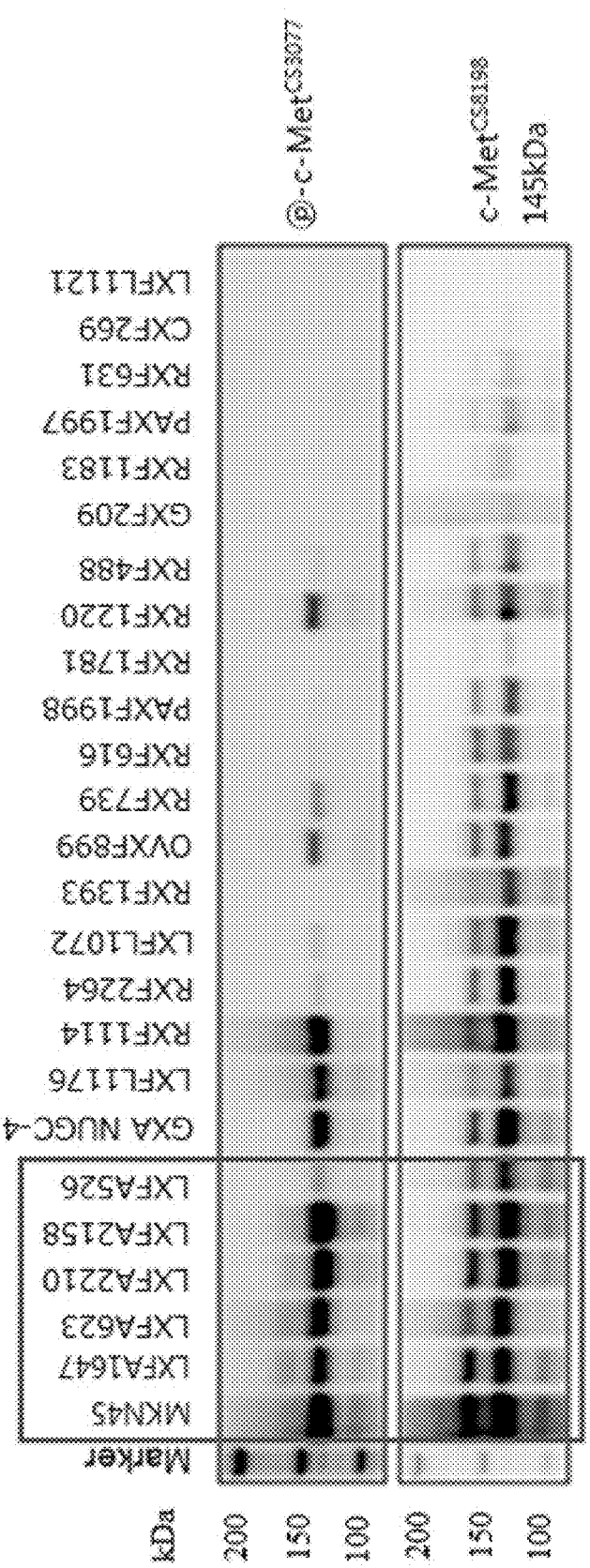
FIG. 18 shows c-Met protein expression levels in patient-derived cancer cell-implanted mouse models, as measured by Western blotting.

The results are depicted in FIG. 18. In FIG. 18, the models which developed c-Met bands can be classified as being responsive to L3-1Y/IgG2. However, LXFA2201 did not respond to L3-1Y/IgG2 due to its RAF mutation although the band was detected.

4.1.3. Determination of RAS-RAF Mutation and Responsiveness to Anti-c-Met Antibody in Patient-Derived Tumor Tissues-Implanted Mouse Model The patient-derived tumor tissues-implanted mouse models were examined for the presence of mutation of K-RAS and B-RAF, and for responsiveness to the anti-c-Met antibody.

DNA isolated from cancer cells was amplified by PCR using a Sequenom™ system including the primers to discriminate the wild-type from mutants. Mutants were detected mostly at G12V, G12C, Q61H, and G12C for K-RAS, and at G596R and D594A for B-RAF.

This experiment was carried out with reference to Example 1.2.1.

Results are summarized in FIG. 19 (efficacy of anti-c-Met antibody in LXFA 2201 and LXFA 2158 models; refer to Tables 4 and 5 for the other mouse models) and Table 6 (mutation of K-RAS and B-RAF in each mouse model). The level of c-Met in each mouse model was measured by Affymetrix array (Affymetrix GeneChip Human Genome U133 Plus 2.0 array; using the primer set "203510_at") according to the manufacturer's manual.

TABLE 6

| tumor model | L3-1Y/IgG2 EFFICACY | MET level (by Affymetrix) | K-RAS mutation | B-RAF mutation |
|---|---|---|---|---|
| LXFA 2201 | NO | 14,770 | wild type | Mutation G596R |
| LXFA 2158 | Efficacy | 14,750 | wild type | wild type |
| LXFA 1647 | Efficacy | 14,000 | wild type | wild type |
| LXFA 526 | Efficacy | 14,000 | wild type | wild type |
| LXFA 623 | Efficacy | 14,000 | wild type | wild type |
| LXFA 1041 | NO | 12,390 | Mutation (G12V) | wild type |
| LXFA 923 | NO | 12,250 | Mutation (G12C) | wild type |
| LXFA 1848 | NO | 12,150 | Mutation (Q61H) | wild type |
| LXFA 677 | NO | 12,060 | wild type | Mutation (D594A) |
| LXFA 983 | NO | 12,000 | Mutation (G12C) | wild type |

As can be seen in Table 6, when one or more mutations are present in K-RAS or B-RAF, the anti-c-Met antibody is not allowed to sufficiently its activity in spite of a high expression level of c-Met (e.g., LXFA 2201). This indicates that the presence or absence of mutations in K-RAS or B-RAF is a critical factor to predicting the efficacy of the anti-c-Met antibody.

4.2. Assay for Predicting Efficacy of Anti-c-Met Antibody in Cancer Cell Line Using RAS-RAF Mutation (In Vitro)

4.2.1. Preparation of Cancer Cell Line

NCI-H441 (HTB-114), NCI-H1993 (CRL-5909), NCI-H1373 (CRL-5866), A549 (CCL-185), HCC827 (CRL-2868), and EBC-1 (Accession No. JCRB0820) cells were seeded at a density of $1\times10^4$ cells/well to plates and incubated with the antibody L3-1Y/IgG2 (1 µg/ml) for 72 hrs. Cell growth was compared between antibody-treated and untreated groups.

4.2.2. Examination of Cancer Cell-Implanted Mouse Model for Presence of RAS-RAF Mutation and Responsiveness to Anti-c-Met Antibody The cancer cell lines were examined for the presence of mutations in K-RAS and B-RAF and responsiveness to anti-c-Met antibody.

Briefly, DNA isolated from the cancer cells was amplified using a Sequenom™ system including the primers to discriminate the wild-type from mutants. Mutations were detected mostly at G12V, G12C, and G12S for K-RAS, and at G596R and D594A for B-RAF.

Results are summarized in Table 7.

TABLE 7

| CELL LINE | L3-1Y/IgG2 EFFICACY | K-RAS mutation | B-RAF mutation |
|---|---|---|---|
| NCI-H441 | X | Mutation (G12V) | wild type |
| NCI-H1993 | Efficacy | wild type | wild type |
| NCI-H1373 | X | Mutation (G12C) | N.A |
| A549 | X | Mutation (G12S) | N.A |
| HCC827 | Efficacy | wild type | wild type |
| EBC1 | Efficacy | wild type | wild type |

(Efficacy: 30% or higher inhibition relative to the control,
N.A: not available)

As can be seen in Table 7, the anti-c-Met antibody can exert its anticancer activity in cancer models only when both K-RAS and B-RAF are wild-types.

Example 5: Prediction Accuracy of Each Marker 5.1. Test of In Vivo Efficacy of Antibody Fourteen (14) mouse xenograft models, which were subjected to subcutaneously grafting of patient derived tumor tissues (Non-small cell lung cancer: NSCLC), were examined by Oncotest GmbH (Germany).

To each of the 14 mouse xenograft models, L3-1Y/IgG2 and empty vehicle (control) were administered, respectively, and the size of the tumor tissues was measured to determine the responsiveness to the antibody.

When the tumor size in the mouse xenograft models reaches 100 mm³ or more, the mouse xenograft models were administered (iv) with L3-1Y/IgG2 (PBS buffer in case of control) at the amount of 5 mg/kg once a week for 6 weeks in total, and the tumor size reaches 2000 mm³ or more, the experiment was stopped.

The tumor size (mm³) was calculated by the following formula:

Tumor size (mm³)=(major axis*minor axis*minor axis)*½

The determination of responder (efficacy) group was conducted by ANOVA analysis where the hypothesis corresponding to p-value of 0.05 or less was excluded. That is, the hypothesis that the tumor size distribution is not changed in a drug (antibody)-administered group compared to non-administered group was subjected to ANOVA testing, and the group where p-value is more than 0.05 was determined as a non-responder (non-efficacy) group, and the group where p-value is 0.05 or less was determined as a responder (efficacy) group.

The obtained results for the responsiveness of the xenograft models to L3-1Y/IgG2 were summarized in Table 8:

TABLE 8

| | Responder (Efficacy) Group | Non-Responder (Non-Efficacy) Group |
|---|---|---|
| Samples | LXFA1647, LXFA2158, LXFA526, LXFA623 | LXFA1041, LXFA677, LXFA1848, LXFA2201, LXFA289, LXFA297, LXFA400, LXFA749, LXFA923, LXFA983 |

5.2. Test of Prediction Accuracy to the Efficacy of the Antibody

To the 14 mouse xenograft models were subjected to following 7 tests (see Examples 5.2.1 to 5.2.7). In each test, the prediction accuracy, prediction sensitivity, and prediction specificity were calculated as follows:

Prediction Accuracy (%)=[(TP+TN)/14]*100

Prediction Sensitivity (%)=(TP/the number of antibody efficacy positive (responder) models)*100

Prediction Specificity (%)=(TN/the number of antibody efficacy negative (non-responder) models)*100

[TP (true positive): the number of models that are determined as being efficacy positive in both antibody efficacy test (Example 5.2) and each test (one of Examples 5.2.1 to 5.2.7); and TN (true negative): the number of models that are determined as being efficacy negative in both antibody efficacy test (Example 5.2) and each test (one of Examples 5.2.1 to 5.2.7)]

The results of 7 tests are shown in Table 9 as below, wherein:

TP (true positive) refers to the case that is determined as being efficacy positive in both antibody efficacy test (Example 5.2) and each test (one of Examples 5.2.1 to 5.2.7);

TN (true negative) refers to the case that is determined as being efficacy negative in both antibody efficacy test (Example 5.2) and each test (one of Examples 5.2.1 to 5.2.7);

FP (false positive) refers to the case that is determined as being efficacy negative in antibody efficacy test (Example 5.2) but efficacy positive in each test (one of Examples 5.2.1 to 5.2.7); and FN (false negative) refers to the case that is determined as being efficacy positive in antibody efficacy test (Example 5.2) but efficacy negative in each test (one of Examples 5.2.1 to 5.2.7).

5.2.1. c-Met IHC: Ventana

Comparison Example

The mouse tumor tissues that have been subject to the experiment of Example 5.1 were extracted, and a part of them was used in preparing a formalin fixed paraffin embedded (FFPE) block. The prepared FFPE block was used for measuring the level of surface expression c-MET by Ventana MET IHC (immunohistochemistry) (using sp44 (Ventana, Catalog Number 790-4430), which is an assay used for a clinical trial (phase III) of metmab (Genentech); see US2013089541 A1) according to a standard protocol of the manufacturer.

5.2.3. Efficacy Prediction Using IL-8

The level of IL-8 in serum of each mouse xenograft model was quantified referring to Examples 1.1.2. The case, where the level of serum IL-8 is 500 pg/ml or more, was determined as a responder (efficacy or positive) group, and the case, where the level of serum IL-8 is less than 500 pg/ml, was determined as a non-responder (non-efficacy or negative) group.

5.2.4. Combination I

Examples 5.2.2 and 5.2.3

The results from Example 5.2.2 (efficacy prediction by the modified Ventana MET IHC) and Example 5.2.3 (efficacy prediction using IL-8) were combined to predict the efficacy of anti-c-Met antibody L3-1Y/IgG2. In particular, the case, where the IHC score according to the modified Ventana MET IHC assay of Example 5.2.2 is 2~3 and the serum IL-8 level according to Example 5.2.3 is 500 pg/ml or more, was determined as a responder (efficacy or positive) group, and the other case was determined as a non-responder (non-efficacy or negative) group.

The results from Examples 5.2.1, 5.2.2, 5.2.3, and 5.2.4 are summarized in Table 9, as below:

TABLE 9

| | | | c-Met IHC | | | | Combined |
|---|---|---|---|---|---|---|---|
| No | Model Name | in vivo efficacy | 1. Ventana (standard: 2+) | | 2. Modified SATT method (standard: 2+) | | Serum IL-8 3. serum level of IL-8 (vehicle group) (pg/mL) (standard: 500 pg/mL or more) | 4. Combined (modified Ventana 2+ AND IL-8 500 pg/mL or more) |
| 1 | LXFA297 | (—) | 3 | FP | 1 | TN* | 250.96 | TN* | TN |
| 2 | LXFA526 | moderate | 3 | TP | 3 | TP | 980.36 | TP | TP |
| 3 | LXFA623 | excellent | 3 | TP | 3 | TP | 22316.88 | TP | TP |
| 4 | LXFA983 | (—) | 3 | FP | 1 | TN* | 147.4 | TN* | TN |
| 5 | LXFA1041 | (—) | 3 | FP | 1 | TN* | 317.6 | TN* | TN |
| 6 | LXFA1647 | excellent | 3 | TP | 3 | TP | 962.88 | TP | TP |
| 1 | LXFA1848 | (—) | 3 | FP | 1 | TN* | 668.88 | FP | TN |
| 2 | LXFA2158 | excellent | 3 | TP | 3 | TP | 1921.76 | TP | TP |
| 3 | LXFA2201 | (—) | 3 | FP | 3 | FP | 1100.56 | FP | FP |
| 4 | LXFA289 | (—) | 3 | FP | 2 | FP | 444.64 | TN* | TN** |
| 5 | LXFA400 | (—) | 2 | FP | 1 | TN* | 1203.32 | FP | TN |
| 6 | LXFA677 | (—) | 3 | FP | 2 | FP | 607.08 | FP | FP |
| 7 | LXFA749 | (—) | 3 | FP | 2 | FP | 0 | TN* | TN** |
| 8 | LXFA923 | (—) | 3 | FP | 2 | FP | 138.6 | TN* | TN** |
| Prediction accuracy | | | 28.57% | | 64.29% | | 71.43% | 85.71% |
| Prediction sensitivity | | | 100% | | 100% | | 100% | 100% |
| Prediction specificity | | | 0% | | 50% | | 60% | 80% |

(*improved accuracy compared to "1"; and
**improved accuracy compared to "2")

The case, where the IHC score according to the Ventana MET IHC assay is 2~3, was determined as a responder (efficacy or positive) group.

5.2.2. Efficacy Prediction Using a Modified c-Met IHC

A modified Ventana MET IHC assay was performed, wherein the assay was identical to the Ventana MET IHC described Example 5.2.1, except that the Ventana antibody sp44 was used by 5/6 dilution. The case, where the IHC score according the modified Ventana MET IHC assay is 2~3, was determined as a responder (efficacy or positive) group.

5.2.5. Efficacy Prediction According to RAS-RAF Mutation

The 14 mouse xenograft models were subject to the experiment according to Example 4.1.3, to examine the presence or absence of K-RAS and/or B-RAF mutation. The case, where both of K-RAS and B-RAF are wild-type, was determined as a responder (efficacy or positive) group, and the case, where at least one of K-RAS and B-RAF is mutated, was determined as a non-responder (non-efficacy or negative) group.

5.2.6. Combination II

Examples 5.2.3 and 5.2.5

The results from Example 5.2.3 (efficacy prediction using IL-8) and Example 5.2.5 (efficacy prediction according to K-RAS and B-RAF mutation) were combined to predict the efficacy of anti-c-Met antibody L3-1Y/IgG2. In particular, the case, where the serum IL-8 level according to Example 5.2.3 is 500 pg/ml or more and both of K-RAS and B-RAF are wild-type, was determined as a responder (efficacy or positive) group, and the other case was determined as a non-responder (non-efficacy or negative) group.

5.2.7. Combination III

Examples 5.2.2, 5.23, and 5.2.5

The results from Example 5.2.2 (efficacy prediction by the modified Ventana MET IHC), Example 5.2.3 (efficacy prediction using IL-8), and Example 5.2.5 (efficacy prediction according to K-RAS and B-RAF mutation) were combined to predict the efficacy of anti-c-Met antibody L3-1Y/IgG2. In particular, the case, where when the IHC score according to the modified Ventana MET IHC assay of Example 5.2.2 is 2~3, the serum IL-8 level according to Example 5.2.3 is 500 pg/ml or more, and both of K-RAS and B-RAF are wild-type, the mouse xenograft model was determined as a responder (efficacy or positive) group, and the other case was determined as a non-responder (non-efficacy or negative) group.

The results from Examples 5.2.5, 5.2.6, and 5.2.7 are summarized in Table 10, as below:

nation of all of the modified c-MET IHC assay, IL-8 marker, and KRAS-BRAF mutation marker shows excellent prediction accuracy (100%).

While one or more embodiments of the present invention have been described with reference to the figures, it will be understood by those of ordinary skill in the art that various changes in form and details may be made therein without departing from the spirit and scope of the present invention as defined by the following claims.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification

TABLE 10

| No | Model Name | in vivo efficacy | KRAS-BRAF mutation | | 5. MUTATION | SAIT IHC+ Mutation 2 + 5 Modified SAIT 2+ AND mutation status | SAIT IHC+IL8+ Mutation 2 + 3 + 5. Modified SAIT 2+ AND mutation status AND serum IL-8 |
|---|---|---|---|---|---|---|---|
| | | | KRAS | BRAF | | | |
| 1 | LXFA297 | (—) | W | W | FP | TN | TN |
| 2 | LXFA526 | moderate | W | W | TP | TP | TP |
| 3 | LXFA623 | excellent | W | W | TP | TP | TP |
| 4 | LXFA983 | (—) | M(G12C) | W | TN | TN | TN |
| 5 | LXFA1041 | (—) | M(G12V) | W | TN | TN | TN |
| 6 | LXFA1647 | excellent | W | W | TP | TP | TP |
| 1 | LXFA1848 | (—) | M(Q61H) | W | TN | TN | TN |
| 2 | LXFA2158 | excellent | W | W | TP | TP | TP |
| 3 | LXFA2201 | (—) | W | M(G596R) | TN | TN | TN |
| 4 | LXFA289 | (—) | W | W | FP | FP | TN |
| 5 | LXFA400 | (—) | W | W | FP | TN | TN |
| 6 | LXFA677 | (—) | W | M(D594A) | TN | TN | TN |
| 7 | LXFA749 | (—) | W | W | FP | FP | TN |
| 8 | LXFA923 | (—) | M(G12C) | W | TN | TN | TN |
| Prediction accuracy = | | | 71.43% | | | 85.71% | 100% |
| Prediction sensitivity | | | 100% | | | 100% | 100% |
| Prediction specificity | | | 60% | | | 80% | 100% |

As shown in Tables 9 and 10, when the modified c-MET IHC assay, IL-8 marker, and KRAS-BRAF mutation marker are respectively used, the prediction accuracy is 64.29%, 71.43%, and 71.43%, respectively, which are all excellent compared to that of the control (Example 5.2.1; 28.57%). A combination of at least two of the modified c-MET IHC assay, IL-8 marker, and KRAS-BRAF mutation marker shows better prediction accuracy. In particular, the combias if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for selecting a subject suitable for the application of a c-Met inhibitor in cancer treatment, comprising:
    measuring the level of IL-8 in a serum sample from a patient having cancer;
    determining the presence of K-RAS and B-RAF mutations in a cancer tissue sample from the patient having cancer;
    measuring the level of c-Met expression in a cancer tissue sample from the patient having cancer;
    selecting the patient as the subject suitable for the application of a c-Met inhibitor when the level of IL-8 in the serum sample is about 500 pg/ml or higher, no K-RAS or B-RAF mutations are found in the cancer tissue sample, and c-Met is expressed in the cancer tissue sample; and
    administering the c-Met inhibitor to the selected patient.

2. The method of claim 1, wherein measuring the level of IL-8 comprises contacting the serum sample with an antibody or antigen-binding fragment thereof that specifically binds to IL-8.

3. The method of claim 2, wherein the antibody or antigen-binding fragment thereof that specifically binds to IL-8 is at least one selected from the group consisting of scFv, (scFv)2, scFv-Fc, Fab, Fab', and F(ab')2.

4. The method of claim 1, wherein the c-Met inhibitor is at least one selected from the group consisting of an anti- c-Met antibody or an antigen-binding fragment thereof, crizotinib, cabozantinib, foretinib, PHA-665752, SU11274, SGX-523, PF-04217903, EMD 1214063, golvatinib, INCB28060, MK-2461, tivantinib, NVP-BVU972, AMG458, BMS 794833, BMS 777607, MGCD-265, AMG-208, BMS-754807, JNJ-38877605, pharmaceutically acceptable salts thereof, rilotumumab, and combinations thereof, wherein the anti-c-Met antibody is selected from the group consisting of (1) an antibody recognizing or binding to a polypeptide comprising 5 to 19 contiguous amino acid residues within SEQ ID NO: 71 and wherein the polypeptide comprises at least SEQ ID NO: 73, (2) onartuzumab, and (3) LY2875358.

5. The method of claim 4, wherein the c-Met inhibitor comprises an anti-c-Met antibody or an antigen-binding fragment thereof that comprises: (a) a CDR-H1 comprising SEQ ID NO: 1, 22, 23, or 24; (b) a CDR-H2 comprising SEQ ID NO: 2, 25, or 26; (c) a CDR-H3 comprising SEQ ID NO: 3, 27, 28, or 85; (d) a CDR-L1 comprising SEQ ID NO: 10, 29, 30, 31, 32, 33, or 106, (e) a CDR-L2 comprising SEQ ID NO: 11, 34, 35, or 36, and (f) a CDR-L3 comprising SEQ ID NO: 12, 13, 14, 15, 16, 37, 86, or 89.

6. The method of claim 4, wherein the c-Met inhibitor comprises an anti-c-Met antibody or an antigen-binding fragment thereof that comprises: (a) a CDR-H1 comprising SEQ ID NO: 1; (b) a CDR-H2 comprising SEQ ID NO: 2; (c) a CDR-H3 comprising SEQ ID NO: 3; (d) a CDR-L1 comprising SEQ ID NO: 10, (e) a CDR-L2 comprising SEQ ID NO: 11, and (f) a CDR-L3 comprising SEQ ID NO: 12, 13, 14, 15, or 16.

\* \* \* \* \*